(12) United States Patent
Pasricha et al.

(10) Patent No.: US 8,071,652 B2
(45) Date of Patent: *Dec. 6, 2011

(54) METHOD OF TREATING IRRITABLE BOWEL SYNDROME

(75) Inventors: Pankaj Pasricha, Houston, TX (US);
Mohan Shenoy, Galveston, TX (US);
John Winston, League City, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 572 days.

This patent is subject to a terminal disclaimer.

(21) Appl. No.: 10/923,035

(22) Filed: Aug. 23, 2004

(65) Prior Publication Data

US 2005/0130189 A1 Jun. 16, 2005

Related U.S. Application Data

(60) Provisional application No. 60/496,716, filed on Aug. 21, 2003.

(51) Int. Cl.
*A61K 31/155* (2006.01)
(52) U.S. Cl. .......................... 514/634; 514/615; 514/617
(58) Field of Classification Search .................... None
See application file for complete search history.

(56) References Cited

U.S. PATENT DOCUMENTS

| | | | |
|---|---|---|---|
| 4,489,710 A | 12/1984 | Spitler | |
| 4,554,101 A | 11/1985 | Hopp | |
| 4,569,789 A | 2/1986 | Blattler et al. | |
| 4,625,014 A | 11/1986 | Senter et al. | |
| 4,638,045 A | 1/1987 | Kohn et al. | |
| 4,671,958 A | 6/1987 | Rodwell et al. | |
| 4,912,094 A | 3/1990 | Myers et al. | |
| 4,980,281 A | 12/1990 | Housey | |
| 5,057,540 A | 10/1991 | Kensil et al. | |
| 5,078,996 A | 1/1992 | Conlon, III et al. | |
| 5,151,254 A | 9/1992 | Arai et al. | |
| 5,266,464 A | 11/1993 | Housey | |
| 5,459,039 A | 10/1995 | Modrich et al. | |
| 5,498,531 A | 3/1996 | Jarrell | |
| 5,688,635 A | 11/1997 | Parker et al. | |
| 5,723,127 A | 3/1998 | Scott et al. | |
| 5,817,879 A | 10/1998 | Hirschmann et al. | |
| 5,877,007 A | 3/1999 | Housey | |
| 5,919,619 A | 7/1999 | Tullis | |
| 5,933,819 A | 8/1999 | Skolnick et al. | |
| 6,207,646 B1 | 3/2001 | Krieg et al. | |
| 6,420,119 B1 | 7/2002 | Polan et al. | |
| 6,596,747 B2 * | 7/2003 | Liu et al. | 514/374 |
| 2002/0022637 A1 * | 2/2002 | Li et al. | 514/307 |

FOREIGN PATENT DOCUMENTS

| | | |
|---|---|---|
| WO | WO 92/19265 | 11/1992 |
| WO | WO 97/24447 | 7/1997 |
| WO | WO 99/14346 | 3/1999 |
| WO | WO 00/18434 | 4/2000 |
| WO | WO 01/29058 | 4/2001 |

OTHER PUBLICATIONS

Borovikova, L., et al. "Role of Vagus Nerve Signaling in CNI-1493-Mediated Suppression of Acute Inflammation," 2000, Autonomic Neuroscience: Basic and Clinical, vol. 85, pp. 141-147.*
Al-chaer, E., et al., "A New Model of Chronic Visceral Hypersensitivity in Adult Rats Induced by Colon Irritation During Postnatal Development," Gastroenterology, 2000 vol. 119, pp. 1276-1285.*
Verdu, Elena, et al, "Irritable Bowel Syndrome," Best Practice & Research Clinical Gastroenterology, vol. 18, No. 2, pp. 315-321 (2004).*
The Merck Manual, 17th edition (1999), pp. 312-313.*
Marlow, S., et al., "Deficient Innervation Characterizes Intestinal Strictures in a Rat Model of Colitis," Experimental and Molecular Pathology, 80:54-66 (2006).
McKaig, B., et al., "Differential Expression of TGF-β Isoforms by Normal and Inflammatory Bowel Disease Intestinal Myofibroblasts," Am J Physiol Cell Physiol, 282:C172-C182 (2002).
Pucilowska, J., et al., "IGF-I and Procollagen α1(I) are Coexpressed in a Subset of Mesenchymal Cells in Active Chron's Disease," Am J. Physiol Gastrointest Liver Physiol, 279:G1307-G1322 (2000).

* cited by examiner

*Primary Examiner* — Phyllis G. Spivack
(74) *Attorney, Agent, or Firm* — Benjamin Adler

(57) ABSTRACT

A treatment to differentially regulate the expression of genes related to irritable bowel syndrome is provided.

1 Claim, 3 Drawing Sheets

SEQUENCE LISTING

<160> NUMBER OF SEQ ID NOS: 66

<210> SEQ ID NO 1
<211> LENGTH: 2236
<212> TYPE: DNA
<213> ORGANISM: Homo sapiens

<400> SEQUENCE: 1

```
cctcgccgca tccactctcc ggccggccgc ctgcccgccg cctcctccgt gcgcccgcca      60
gcctcgcccg cgccgtcacc atgagccagg cctactcgtc cagccagcgc gtgtcctcct     120
accgccgcac cttcggcggc gccccggtct tcccgctcgg ctccccgctg agctcgcccg     180
tgttcccgcg ggcgcctttc ggctctaagg gctcctccag ctcggtgacg tcccgcgtgt     240
accaggtgtc gcgcacgtcg ggaggggccg ggggcctggg gtcgctgcgg gccagccggc     300
tggggaccac ccgcacgccc tcctcctacg gcgcaggcga gctgctggac ttctcactgg     360
ccgacgcggt gaaccaggag tttctgacca cgcgcaccaa cgagaaggtg gagctgcagg     420
agctcaatga ccgttcgcca atctacatgg agaaggtgcg cttcctggag cagcagaacg     480
cgctcgccgc cgaagtgaac cggctcaagg gccgcgagcc gacgcgagtg gccgagctct     540
acgaggagga gctgcgggag ctgcggcgcc aggtggaggt gctcactaac cagcgcgcgc     600
gcgtcgacgt cgagcgcgac aacctgctcg acgacctgca gcggctcaag gccaagctgc     660
aggaggagat tcagttgaag gaagaagcag agaacaattt ggctgccttc cgagcggacg     720
tggatgcagc tactctagct cgcattgacc tggagcgcag aattgaatct ctcaacgagg     780
agatcgcgtt ccttaagaaa gtgcatgaag aggagatccg tgagttgcag gctcagcttc     840
aggaacagca ggtccaggtg gagatggaca tgtctaagcc agacctcact gccgccctca     900
gggatatccg ggctcagtat gagaccatcg cggctaagaa catttctgaa gctgaggagt     960
ggtacaagtc gaaggtgtca gacctgaccc aggcagccaa caagaacaac gacgccctgc    1020
gccaggccaa gcaggagatg atggaatacc gacaccagat ccagtcctac acctgcgaga    1080
ttgacgccct caagggcact aacgattccc tgatgaggca gatgcgggaa ttggaggacc    1140
gatttgccag tgaggccagt ggctaccagg acaacattgc acgcctggag gaggaaatcc    1200
ggcacctcaa ggatgagatg gcccgccatc tgcgcgagta ccaggacctg ctcaacgtga    1260
agatggccct ggatgtggag attgccacct accggaagct gctggaggga gaggagagcc    1320
ggatcaatct ccccatccag acctactctg ccctcaactt ccgagaaacc agccctgagc    1380
aaaggggttc tgaggtccat accaagaaga cggtgatgat caagaccatc gagacacggg    1440
atgggaggt cgtcagtgag gccacacagc agcagcatga agtgctctaa agacgagaga    1500
```

```
cccuctgcca ccagagaccg tcctcacccc tgtcctcact gctccctgaa gcccagcctt    1560
cttcatccca ggacaccaca cccagcctca gtcctccaaa tcacagcctc tgacccctcc    1620
tcactggcca tccctcgtgg tccccaacag cgacatagcc catccctgcc tggtcacagg    1680
catgccccgg ccacctctgc ggaccccagc tgtgagcctt ggctgttggc agtgagtgag    1740
cctggctctt gtgctggatg gagcccaggc gggagcggtg gccctgtccc tcccacctct    1800
gtgacctcag gcctacgctt tggctctgga gatagcccca gagcagggtg ttgggatact    1860
gcagggccag gactgagccc cgcagacctc cccagcccct agcccaggag agagaaagcc    1920
aggcaggtag cctgggggac tagccctgtg gagactgggg ggcttgaaat tgtccccgtg    1980
gtctcttact ttcctttccc cagcccaggg tggacttaga agcaggggc tacaagaggg     2040 aatccccgaa ggtgctggag gtgggagcag gagattgaga aggagagaaa gtgggtgaga    2100
tgctggagaa gagaggagag gagagaggca gagagcggtc tcaggctggt gggaggggcg    2160
cccacctccc cacgccctcc ccccccctgc tgcaggggct ctggagagaa acaataaaga    2220
gattcacaca caagcc                                                    2236

<210> SEQ ID NO 2
<211> LENGTH: 566
<212> TYPE: DNA
<213> ORGANISM: Homo sapiens

<400> SEQUENCE: 2
gccagaaccg gtggagcagc gacccctgag cagtgttctc tgtgctgagc ggcgggactg      60
agctgttgag ttagagccaa catgagtgag cgacaaggtg ctggggcaac caatggaaaa     120
gacaagacat ctggtgaaaa tgatggacag aagaaagttc aagaagaatt tgacattgac     180
atggatgcac cagagacaga acgtgcagcg gtggccattc agtctcagtt cagaaaattc     240
cagaagaaga aggctgggtc tcagtcctag tgggagaacc ccctcctagt ccacctgaaa     300
acaccaaatt caaccatcat ctgtcaagaa attaaaagaa caacacccta gagagaagtc     360
atccacacac aatccacaca cgcatagcaa acctccaatg catgtacaga aacctgtgat     420
atttataccc ttgtaggaag gtatagacaa tggaattgtg agtagcttaa tctctatgtt     480
tctctccatt ttcattcctc ctgcaactat tttccttgat gttgtaataa aatgaagtta     540
cgatgagtga attcaaaaaa aaaaaa                                          566

<210> SEQ ID NO 3
<211> LENGTH: 1433
<212> TYPE: DNA
<213> ORGANISM: Homo sapiens

<400> SEQUENCE: 3
attcggggcg agggaggagg aagaagcgga ggaggcggct cccgctcgca gggccgtgca      60
cctgcccgcc cgcccgctcg ctcgctcgcc cgccgcgccc cgctgccgac cgccagcatg     120
ctgccgagag tgggctgccc cgcgctgccc ctgccgccgc cgccgctgct gccgctgctg     180
ccgctgctgc tgctgctact gggcgcgagt ggcggcggcg gcggggcgcg cgcggaggtg     240
ctgttccgct gccgccctg cacacccgag cgcctggccg cctgcgggcc ccgccggtt     300 gcgccgcccg ccgcggtggc cgcagtggcc ggaggcgccc gcatgccatg cgcggagctc     360
gtccgggagc cgggctgcgg ctgctgctcg gtgtgcgccc ggctggaggg cgaggcgtgc     420
ggcgtctaca cccccgcgctg cggccagggg ctgcgctgct atcccccaccc gggctccgag     480 ctgccctgc aggcgctggt catgggcgag ggcacttgtg agaagcgccg ggacgccgag     540
```

| | |
|---|---|
| tatggcgcca gcccggagca ggttgcagac aatggcgatg accactcaga aggaggcctg | 600 |
| gtggagaacc acgtggacag caccatgaac atgttgggcg ggggaggcag tgctggccgg | 660 |
| aagcccctca agtcgggtat gaaggagctg gccgtgttcc gggagaaggt cactgagcag | 720 |
| caccggcaga tgggcaaggg tggcaagcat caccttggcc tggaggagcc caagaagctg | 780 |
| cgaccacccc ctgccaggac tccctgccaa caggaactgg accaggtcct ggagcggatc | 840 |
| tccaccatgc gccttccgga tgagcgggc cctctggagc acctctactc cctgcacatc | 900 |
| cccaactgtg acaagcatgg cctgtacaac ctcaaacagt gcaagatgtc tctgaacggg | 960 |
| cagcgtgggg agtgctggtg tgtgaacccc aacaccggga agctgatcca gggagccccc | 1020 |
| accatccggg gggaccccga gtgtcatctc ttctacaatg agcagcagga ggcttgcggg | 1080 |
| gtgcacaccc agcggatgca gtagaccgca gccagccggt gcctggcgcc cctgccccc | 1140 |
| gcccctctcc aaacaccggc agaaaacgga gagtgcttgg gtggtgggtg ctggaggatt | 1200 |
| ttccagttct gacacacgta tttatatttg aaaagagacc agcaccgagc tcggcacctc | 1260 |
| cccggcctct ctcttcccag ctgcagatgc cacacctgct ccttcttgct ttccccgggg | 1320 |
| gaggaagggg gttgtggtcg gggagctggg gtacaggttt ggggaggggg aagagaaatt | 1380 |
| tttatttttg aacccctgtg tcccttttgc ataagattaa aggaaggaaa agt | 1433 |

<210> SEQ ID NO 4
<211> LENGTH: 4670
<212> TYPE: DNA
<213> ORGANISM: Homo sapiens

<400> SEQUENCE: 4

| | |
|---|---|
| gcactcgctg gaaagcggct ccgagccagg ggctattgca aagccagggt gcgctaccgg | 60 |
| acggagaggg gagagccctg agcagagtga gcaacatcgc agccaaggcg gaggccgaag | 120 |
| aggggcgcca ggcaccaatc tccgcgttgc ctcagcccg gaggcgcccc agagcgcttc | 180 |
| ttgtcccagc agagccactc tgcctgcgcc tgcctctcag tgtctccaac tttgcgctgg | 240 |
| aagaaaaact tccgcgcgcg cggcagaact gcagcgcctc cttttagtga ctccgggagc | 300 |
| ttcggctgta gccggctctg cgcgcccttc caacgaataa tagaaattgt taattttaac | 360 |
| aatccagagc aggccaacga ggctttgctc tcccgacccg aactaaaggt ccctcgctcc | 420 |
| gtgcgctgct acgagcggtg tctcctgggg ctccaatgca gcgagctgtg cccgaggggt | 480 |
| tcggaaggcg caagctgggc agcgacatgg ggaacgcgga gcgggctccg ggtctcggga | 540 |
| gctttgggcc cgtacccacg ctgctgctgc tcgccgcggc gctactggcc gtgtcggacg | 600 |
| cactcgggcg cccctccgag gaggacgagg agctagtggt gccggagctg agcgcgccc | 660 |
| cgggacacgg gaccacgcgc ctccgcctgc acgcctttga ccagcagctg gatctggagc | 720 |
| tgcggcccga cagcagcttt ttggcgcccg gcttcacgct ccagaacgtg gggcgcaaat | 780 |
| ccgggtccga gacgccgctt ccggaaaccg acctggcgca ctgcttctac tccggcaccg | 840 |
| tgaatggcga tcccagctcg gctgccgccc tcagcctctg cgaggcgtg gcggcgcct | 900 |
| tctacctgct gggggaggcg tatttcatcc agccgctgcc cgccgccagc gagcgcctcg | 960 |
| ccaccgccgc cccaggggag aagccgccgg caccactaca gttccaccctc ctgcggcgga | 1020 |
| atcggcaggg cgacgtcggc ggcacgtgcg gggtcgtgga cgacgagccc cggccgactg | 1080 |
| ggaaagcgga gaccgaagac gaggacgaag ggactgaggg cgaggacgaa ggggctcagt | 1140 |
| ggtcgccgca ggacccggca ctgcaaggcg taggacagcc cacaggaact ggaagcataa | 1200 |
| gaaagaagcg atttgtgtcc agtcaccgct atgtggaaac catgcttgtg gcagaccagt | 1260 |

```
cgatggcaga attccacggc agtggtctaa agcattacct tctcacgttg ttttcggtgg    1320
cagccagatt gtacaaacac cccagcattc gtaattcagt tagcctggtg gtggtgaaga    1380
tcttggtcat ccacgatgaa cagaaggggc cggaagtgac ctccaatgct gccctcactc    1440
tgcggaactt ttgcaactgg cagaagcagc acaacccacc cagtgaccgg gatgcagagc    1500
actatgacac agcaattctt ttcaccagac aggacttgtg tgggtcccag acatgtgata    1560
ctcttgggat ggctgatgtt ggaactgtgt gtgatccgag cagaagctgc tccgtcatag    1620
aagatgatgg tttacaagct gccttcacca cagcccatga attaggccac gtgtttaaca    1680
tgccacatga tgatgcaaag cagtgtgcca gccttaatgg tgtgaaccag gattcccaca    1740
tgatggcgtc aatgctttcc aacctggacc acagccagcc ttggtctcct tgcagtgcct    1800
acatgattac atcatttctg gataatggtc atggggaatg tttgatggac aagcctcaga    1860
atcccataca gctcccaggc gatctccctg gcacctcgta cgatgccaac cggcagtgcc    1920
agtttacatt tggggaggac tccaaacact gccccgatgc agccagcaca tgtagcacct    1980
tgtggtgtac cggcacctct ggtggggtgc tggtgtgtca aaccaaacac ttcccgtggg    2040
cggatggcac cagctgtgga agggaaat ggtgtatcaa cggcaagtgt gtgaacaaaa    2100
ccgacagaaa gcattttgat acgccttttc atggaagctg gggaatgtgg gggccttggg    2160
gagactgttc gagaacgtgc ggtggaggag tccagtacac gatgagggaa tgtgacaacc    2220
cagtcccaaa gaatggaggg aagtactgtg aaggcaaacg agtgcgctac agatcctgta    2280
accttgagga ctgtccagac aataatggaa aaacctttag agaggaacaa tgtgaagcac    2340
acaacgagtt ttcaaaagct tcctttggga gtgggcctgc ggtggaatgg attcccaagt    2400
acgctggcgt ctccaccaaag gacaggtgca agctcatctg ccaagccaaa ggcattggct    2460
acttcttcgt tttgcagccc aaggttgtag atggtactcc atgtagccca gattccacct    2520
ctgtctgtgt gcaaggacag tgtgtaaaag ctggttgtga tcgcatcata gactccaaaa    2580
agaagtttga taaatgtggt gtttgcgggg gaaatggatc tacttgtaaa aaaatatcag    2640
gatcagttac tagtgcaaaa cctggatatc atgatatcat cacaattcca actggagcca    2700
ccaacatcga agtgaaacag cggaaccaga ggggatccag gaacaatggc agctttcttg    2760
ccatcaaagc tgctgatggc acatatattc ttaatggtga ctacactttg tccacctag    2820 agcaagacat tatgtacaaa ggtgttgtct tgaggtacag cggctcctct gcggcattgg    2880
aaagaattcg cagctttagc cctctcaaag agccctgac catccaggtt cttactgtgg    2940
gcaatgccct tcgacctaaa attaaataca cctacttcgt aaagaagaag aaggaatctt    3000
tcaatgctat cccccacttttt tcagcatggg tcattgaaga gtggggcgaa tgttctaagt    3060
catgtgaatt gggttggcag agaagactgg tagaatgccg agacattaat ggacagcctg    3120
cttccgagtg tgcaaaggaa gtgaagccag ccagcaccag accttgtgca gaccatccct    3180 gccccccagtg gcagctgggg gagtggtcat catgttctaa gacctgtggg aagggttaca    3240
aaaaaagaag cttgaagtgt ctgtcccatg atggaggggt gttatctcat gagagctgtg    3300
atcctttaaa gaaacctaaa catttcatag acttttgcac aatggcagaa tgcagttaag    3360
tggtttaagt ggtgttagct ttgagggcaa ggcaaagtga ggaagggctg gtgcagggaa    3420
agcaagaagg ctggagggat ccagcgtatc ttgccagtaa ccagtgaggt gtatcagtaa    3480
ggtgggatta tgggggtaga tagaaaagga gttgaatcat cagagtaaac tgccagttgc    3540 aaattttgata ggatagttag tgaggattat taacctctga gcagtgatat agcataataa    3600
agccccgggc attattatta ttatttcttt tgttacatct attacaagtt tagaaaaaac    3660
```

| | |
|---|---|
| aaagcaattg tcaaaaaaag ttagaactat tacaacccct gtttcctggt acttatcaaa | 3720 |
| tacttagtat catgggggtt gggaaatgaa aagtaggaga aaagtgagat tttactaaga | 3780 |
| cctgttttac tttacctcac taacaatggg gggagaaagg agtacaaata ggatctttga | 3840 |
| ccagcactgt ttatggctgc tatggtttca gagaatgttt atacattatt tctaccgaga | 3900 |
| attaaaactt cagattgttc aacatgagag aaaggctcag caacgtgaaa taacgcaaat | 3960 |
| ggcttcctct ttcctttttt ggaccatctc agtctttatt tgtgtaattc attttgagga | 4020 |
| aaaaacaact ccatgtattt attcaagtgc attaaagtct acaatggaaa aaagcagtg | 4080 |
| aagcattaga tgctggtaaa agctagagga gacacaatga gcttagtacc tccaacttcc | 4140 |
| tttctttcct accatgtaac cctgctttgg gaatatggat gtaaagaagt aacttgtgtc | 4200 |
| tcatgaaaat cagtacaatc acacaaggag gatgaaacgc cggaacaaaa atgaggtgtg | 4260 |
| tagaacaggg tcccacaggt ttggggacat tgagatcact tgtcttgtgg tggggaggct | 4320 |
| gctgagggt agcaggtcca tctccagcag ctggtccaac agtcgtatcc tggtgaatgt | 4380 |
| ctgttcagct cttctgtgag aatatgattt tttccatatg tatatagtaa aatatgttac | 4440 |
| tataaattac atgtacttta taagtattgg tttgggtgtt ccttccaaga aggactatag | 4500 |
| ttagtaataa atgcctataa taacatattt attttatac atttatttct aatgaaaaaa | 4560 |
| acttttaaat tatatcgctt ttgtggaagt gcatataaaa tagagtattt atacaatata | 4620 |
| tgttactaga aataaagaa cacttttgga aaaaaaaaa aaaaaaaaaa | 4670 |

<210> SEQ ID NO 5
<211> LENGTH: 3360
<212> TYPE: DNA
<213> ORGANISM: Homo sapiens

<400> SEQUENCE: 5

| | |
|---|---|
| cattttactt atggaaaaca gtgtggcata ttctgctgag cttcgccctg gaagaagcct | 60 |
| cttttataca tctcttcagg gaagagagaa gcaatgggca tgttagtata caatgatcac | 120 |
| agccacgcag gcctgcaagc tgccttttgg acaggctgtt gactgccgtt ccaattagct | 180 |
| gattggagaa tgtggaatgc agagtgataa tgctgcatat ctgctatcag gcagcagcaa | 240 |
| aggttttgt cttgggaagg caagcttttcc ctgcaatatt atctcagcag ctccctagct | 300 |
| gcttaccctg aaaacgaggg atccaaacgg agggtgttgc actctgctaa cgctggtcct | 360 |
| gtgcgtggct gtggcatatg agcggcaggt ctgaaaaagc aggtgtgtgc tgggacgggc | 420 |
| actggactgg aacgcaggcg gacgctctcg ggtttacctg cttcctgtta acagattgtg | 480 |
| ggctcccagg gcatatgtct gcacgctgag gccgaggcgg agaagggct tcctgagcgt | 540 |
| cccagtacac tgacagagac acttggattg gacttaatct taaacctctg gagttcaaga | 600 |
| ccttttaaaa agggctaaat aaacaatctc tacatgtaaa aggccactga ctcctacttc | 660 |
| ctctgtatag agcaactgtt gaactcagct gcctgtagga aaactgaaga ctttaataac | 720 |
| aaactctcca aggtgaaaat gaacacaggg cgtgattctc agtcaccaga ctcacaaaag | 780 |
| gttttagaag cgttcgacca aacctacaag ataaagatc accaactcag agccagataa | 840 |
| cagtgaatgg aaactcagga ggtgccgtga gtcccatgag ttactatcag aggccgtttt | 900 |
| cccccctcggc atattctctc ccagcctcac tcaactccag cattgtcatg cagcacggca | 960 |
| catccctcga ttccacagac acatatcccc agcatgcgca gtctctggat ggcaccacca | 1020 |
| gcagctctat cccctgtac cgatcctcag aggaagagaa gagagtgaca gtcatcaaag | 1080 |
| ccccgcatta cccagggatc gggcccgtgg atgaatccgg aatccccaca gcaattagaa | 1140 |

-continued

```
cgacagtcga ccggcccaag gactggtaca agacgatgtt taagcaaatt cacatggtgc    1200
acaagccgga tgatgacaca gacatgtata atactcctta tacatacaat gcaggtctgt    1260
acaacccacc ctacagtgct cagtcacacc ctgctgcaaa gacccaaacc tacagacctc    1320
tttccaaaag ccactccgac aacagcccca atgcctttaa ggatgcgtcc tccccagtgc    1380
ctcccccaca tgttccacct ccagtcccgc cgcttcgacc aagagatcgg tcttcaacag    1440
aaaagcatga ctgggatcct ccagacagaa aagtggacac aagaaaattt cggtctgagc    1500
caaggagtat ttttgaatat gaacctggca agtcatcaat tcttcagcat gaaagaccaa    1560
ctgatcgcat aaatccagat gacatagatt tagaaaatga gccctggtat aaattctttt    1620
cagaactgga gtttggacgc ccgcctccta aaaagcctct ggactatgtt caagatcatt    1680
cttctggtgt tttcaatgag gcctccttgt atcagtcctc tatagacaga agcctggaaa    1740
gacccatgag ttctgcaagc atggccagtg acttcaggaa gcggaggaag agcgagcctg    1800
cagtgggtcc accacggggc ttgggagatc aaagtgcgag caggactagc ccaggccgag    1860
tggacctccc aggatcaagc accactctta caaagtcttt cactagctct tctccttctt    1920
ccccatcaag agcaaaagac cgtgagtccc ctagaagtta ctcatccact ttgactgaca    1980
tggggagaag tgcaccaagg gaaagaagag gaactccaga aaagagaaa ttgcctgcaa     2040
aagctgttta tgattttaag gctcagacat ctaaggagtt gtcatttaag aaggagata     2100
ctgtctacat cctcaggaaa attgatcaaa attggtatga gggagaacac cacgggagag    2160
tgggcatctt cccgatctca tacgtagaga aactcacacc tcctgagaaa gcacagcctg    2220
caagaccacc tccgccagcc cagcccggag aaatcggaga agctatagcc aaatacaact    2280
tcaacgcaga cacaaatgtg gagctgtcac tgagaaaggg agatagagtt attcttctta    2340
aaagagttga tcaaaactgg tatgaaggta aaatcccagg aaccaacaga caaggcatct    2400
tccctgtttc ctatgtggag gtcgtcaaga agaacacaaa aggtgctgag gactaccctg    2460
accctccaat accccacagc tattctagtg ataggattca cagcttgagc tcaaataagc    2520
cacagcgtcc tgtgtttact catgaaaata ttcaaggtgg gggggaaccg tttcaggctc    2580
tgtataacta tactcccagg aatgaagatg agctggagct cagagaaagt gatgtcattg    2640
atgtcatgga aaagtgtgat gacggctggt tgtgggggac ctcaagaaga accaaattct    2700
ttggtacttt ccccggaaac tacgtcaaga ggctgtgaat tgcgctccct ccttctgtag    2760
aggccgcctg ccagccatgc acctgcgtca acgcgcctga acacccgc gggcctcccg     2820
ttgtcatgcc ttacggtttc caatgcgccg tcaccatctc cacctgccac caaaccacca    2880
gcagagtagc cgccgctgct gtgagcctgg ggacgacatg gcaggctggt cccccctccgt   2940
gaaagtgtgg attcctactt cctgctctaa gctttgacac gtcaaaatgt gggatcagaa    3000
agaaaaaaat catgatattt aaaaatggtc aaatatttga ggcaaaaaaa aaaaaaaaa     3060
gtgtctccag gaggctgtcc agcctcgtgg ctccatttca acatctcccc ccaggcgatg    3120
ttctccccca agacgaccag aaaattgttt attggggaat gctgtggttt gcattttcat    3180
attcttcgct tggcagtgtg tattcttttc acaagtttgc ctagtgtctt ggtttacaca    3240
atatgacaac tgtaactgta ctttagctat tgtttgcctg cacatacatg ttgtaatatg    3300
cacagtgatt acaaccttta aagcaagagg aggcgagtta atttggatga gtgtgatttt    3360
```

<210> SEQ ID NO 6
<211> LENGTH: 724
<212> TYPE: DNA
<213> ORGANISM: Homo sapiens

<400> SEQUENCE: 6

```
gtagccggac cctttgcctt cgccactgct cagcgtctgc acatccctac aatggctaaa      60
acagcaatgg cctacaagga aaaaatgaag gagctgtcca tgctgtcact gatctgctct     120
tgcttttacc cggaacctcg caacatcaac atctatactt cgatgatat ggaagtgaag      180
caaatcaaca aacgtgcctc tggccaggct tttgagctga tcttgaagcc accatctcct     240
atctcagaag ccccacgaac tttagcttct ccaaagaaga aagacctgtc cctggaggag     300
atccagaaga aactggaggc tgcagaggaa agaagaaagt ctcaggaggc ccaggtgctg     360
aaacaattgg cagagaagag ggaacacgag cgagaagtcc ttcagaaggc tttggaggag     420
aacaacaact tcagcaagat ggcggaggaa aagctgatcc tgaaaatgga acaaattaag     480
gaaaaccgtg aggctaatct agctgctatt attgaacgtc tgcaggaaaa ggagaggcat     540
gctgcggagg tgcgcaggaa caaggaactc caggttgaac tgtctggctg aagcaaggga     600
gggtctggca cgccccacca atagtaaatc cccctgccta tattataatg gatcatgcga     660
tatcaggatg gggaatgtat gacatggttt aaaaagaact cattataaaa aaaaaaaaa     720
aaaa                                                                  724
```

<210> SEQ ID NO 7
<211> LENGTH: 2961
<212> TYPE: DNA
<213> ORGANISM: Homo sapiens

<400> SEQUENCE: 7

```
aagagatgat ttctccatcc tgaacgtgca gcgagcttgt caggaagatc ggaggtgcca      60
agtagcagag aaagcatccc ccagctctga cagggagaca gcacatgtct aaggcccaca    120
agccttggcc ctaccggagg agaagtcaat tttcttctcg aaaatacctg aaaaaagaaa    180
tgaattcctt ccagcaacag ccaccgccat tcggcacagt gccaccacaa atgatgtttc    240
ctccaaactg gcaggggggca gagaaggacg ctgcttttcct cgccaaggac ttcaactttc   300
tcactttgaa caatcagcca ccaccaggaa acaggagcca accaagggca atggggcccg    360
agaacaacct gtacagccag tacgagcaga aggtgcgccc ctgcattgac ctcatcgact    420
ccctgcgggc tctgggtgtg gagcaggacc tggccctgcc agccatcgcc gtcatcgggg    480
accagagctc gggcaagagc tctgtgctgg aggcactgtc aggagtcgcg cttcccagag    540
gcagcggaat cgtaaccagg tgtccgctgg tgctgaaact gaaaaagcag ccctgtgagg    600
catgggccgg aaggatcagc taccggaaca ccgagctaga gcttcaggac cctggccagg    660
tggagaaaga gatacacaaa gcccagaacg tcatggccgg aatggccgg ggcatcagcc     720
atgagctcat cagcctggag atcacctccc ctgaggttcc agacctgacc atcattgacc    780
ttcccggcat caccagggtg gctgtggaca ccagccccg agacatcgga ctgcagatca    840
aggctctcat caagaagtac atccagaggc agcagacgat caacttggtg gtggttccct    900
gtaacgtgga cattgccacc acggaggcgc tgagcatggc ccatgaggtg acccggaag    960
gggacaggac catcggtatc ctgaccaaac cagatctaat ggcagggc actgagaaaa    1020
gcgtcatgaa tgtggtgcgg aacctcacgt accccctcaa gaagggctac atgattgtga   1080
agtgccgggg ccagcaggag atcacaaaca ggctgagctt ggcagaggca accaagaaag   1140
aaattacatt cttttcaaaca catccatatt tcagagttct cctggaggag gggtcagcca   1200
cggttccccg actggcagaa agacttacca ctgaactcat catgcatatc caaaaatcgc   1260
tcccgttgtt agaaggacaa ataagggaga gccaccagaa ggcgaccgag gagctgcggc   1320
```

```
gttgcgggc tgacatcccc agccaggagg ccgacaagat gttctttcta attgagaaaa    1380
tcaagatgtt taatcaggac atcgaaaagt tagtagaagg agaagaagtt gtaagggaga    1440
atgagacccg tttatacaac aaaatcagag aggattttaa aaactgggta ggcatacttg    1500
caactaatac ccaaaaagtt aaaaatatta tccacgaaga agttgaaaaa tatgaaaagc    1560
agtatcgagg caaggagctt ctgggatttg tcaactacaa gacatttgag atcatcgtgc    1620
atcagtacat ccagcagctg gtggagcccg cccttagcat gctccagaaa gccatggaaa    1680
ttatccagca agcttttcatt aacgtggcca aaaacatttt tggcgaattt ttcaacctta    1740
accaaactgt tcagagcacg attgaagaca taaaagtgaa acacacagca aaggcagaaa    1800
acatgatcca acttcagttc agaatggagc agatggtttt ttgtcaagat cagatttaca    1860
gtgttgttct gaagaaagtc cgagaagaga ttttaaccc tctggggacg ccttcacaga    1920
atatgaagtt gaactctcat tttcccagta atgagtcttc ggtttcctcc tttactgaaa    1980
taggcatcca cctgaatgcc tacttcttgg aaaccagcaa acgtctcgcc aaccagatcc    2040 cattataat tcagtatttt atgctccgag agaatggtga ctccttgcag aaagccatga    2100
tgcagatact acaggaaaaa aatcgctatt cctggctgct tcaagagcag agtgagaccg    2160
ctaccaagag aagaatcctt aaggagagaa tttaccggct cactcaggcg cgacacgcac    2220
tctgtcaatt ctccagcaaa gagatccact gaagggcggc gatgcctgtg gttgttttct    2280
tgtgcgtact cattcattct aaggggagtc ggtgcaggat gccgcttctg ctttggggcc    2340
aaactcttct gtcactatca gtgtccatct ctactgtact ccctcagcat cagagcatgc    2400 atcagggtc cacacaggct cagctctctc caccacccag ctcttccctg accttcacga    2460
agggatggct ctccagtcct tgggtcccgt agcacacagt tacagtgtcc taagatactg    2520
ctatcattct tcgctaattt gtatttgtat tcccttcccc ctacaagatt atgagacccc    2580 agaggggaa ggtctgggtc aaattcttct tttgtatgtc cagtctcctg cacagcacct    2640
gcagcattgt aactgcttaa taaatgacat ctcactgaac gaatgagtgc tgtgtaagtg    2700
atggagatac ctgaggctat tgctcaagcc caggccttgg acattttagtg actgttagcc    2760 ggtccctttc agatccagtg gccatgcccc ctgcttccca tggttcactg tcattgtgtt    2820
tcccagcctc tccactcccc cgccagaaag gagcctgagt gattctcttt tcttcttgtt    2880
tccctgatta tgatgagctt ccattgttct gttaagtctt gaagaggaat ttaataaagc    2940
aaagaaactt tttaaaaacg t                                              2961
```

<210> SEQ ID NO 8
<211> LENGTH: 1890
<212> TYPE: DNA
<213> ORGANISM: Homo sapiens

<400> SEQUENCE: 8

```
ggcacccagg gtccggcctg cgccttcccg ccaggcctgg acactggttc aacacctgtg     60
acttcatgtg tgcgcgccgg ccacacctgc agtcacacct gtagccccct ctgccaagag    120
atccataccg aggcagcgtc ggtggctaca agccctcagt ccacacctgt ggacacctgt    180
gacacctggc cacacgacct gtggccgcgg cctggcgtct gctgcgacag gagcccttac    240
ctcccctgtt ataacccctg accgccacct aactgcccct gcagaaggag caatggcctt    300
ggctcctgag agggcagccc cacgcgtgct gttcggagag tggctccttg gagagatcag    360
cagcggctgc tatgaggggc tgcagtggct ggacgaggcc cgcacctgtt ccgcgtgcc    420 ctggaagcac ttcgcgcgca aggacctgag cgaggccgac gcgcgcatct tcaaggcctg    480
```

```
ggctgtggcc cgcggcaggt ggccgcctag cagcagggga ggtggcccgc ccccgaggc    540 tgagactgcg gagcgcgccg gctggaaaac caacttccgc tgcgcactgc gcagcacgcg    600
tcgcttcgtg atgctgcggg ataactcggg ggacccggcc gacccgcaca aggtgtacgc    660
gctcagccgg gagctgtgct ggcgagaagg cccaggcacg gaccagactg aggcagaggc    720
ccccgcagct gtcccaccac cacagggtgg gcccccaggg ccattcttgg cacacacaca    780
tgctggactc caagccccag gcccctcccc tgcccagct ggtgacaagg gggacctcct     840
gctccaggca gtgcaacaga gctgcctggc agaccatctg ctgacagcgt catgggggc     900 agatccagtc ccaaccaagg ctcctggaga gggacaagaa gggcttcccc tgactggggc    960
ctgtgctgga ggcccagggc tccctgctgg ggagctgtac gggtgggcag tagagacgac   1020
ccccagcccc gggcccagc  ccgcggcact aacgacaggc gaggccgcgg ccccagagtc   1080
cccgcaccag gcagagccgt acctgtcacc ctccccaagc gcctgcaccg cggtgcaaga   1140
gcccagccca ggggcgctgg acgtgaccat catgtacaag ggccgcacgg tgctgcagaa   1200
ggtggtggga cacccgagct gcacgttcct atacggcccc ccagacccag ctgtccgggc   1260
cacagacccc cagcaggtag cattcccag  ccctgccgag ctcccggacc agaagcagct   1320
gcgctacacg gaggaactgc tgcggcacgt ggcccctggg ttgcacctgg agcttcgggg   1380
gccacagctg tgggcccggc gcatgggcaa gtgcaaggtg tactgggagg tgggcggacc   1440
cccaggctcc gccagcccct caccccagc  ctgcctgctg cctcggaact gtgacacccc   1500
catcttcgac ttcagagtct tcttccaaga gctggtggaa ttcccgggcac ggcagcgccg  1560 tggctcccca cgctatacca tctacctggg cttcgggcag gacctgtcag ctgggaggcc   1620
caaggagaag agcctggtcc tggtgaagct ggaaccctgg ctgtgccgag tgcacctaga   1680
gggcacgcag cgtgagggtg tgtcttccct ggatagcagc agcctcagcc tctgcctgtc   1740
cagcgccaac agcctctatg acgacatcga gtgcttcctt atggagctgg agcagccgc    1800 ctagaaccca gtctaatgag aactccagaa agctggagca gcccacctag agctggccgc   1860
ggccgcccag tctaataaaa agaactccag                                    1890
```

<210> SEQ ID NO 9
<211> LENGTH: 2595
<212> TYPE: DNA
<213> ORGANISM: Homo sapiens

<400> SEQUENCE: 9

```
tcatattagt gcatttcttt gcagaggtta cctcttttc ttgtctctcg tcaggtctct      60
gacattgaca gagcctggac gttggaggaa gccccaggac gttggagggg taaagtaaaa    120
gtccacagtt accgtgagag aaaaaagagg gagaaagcag tgcagccaaa ctcggaagaa    180
aagagaggag gaaaaggact cgactttcac attggaacaa ccttcttcc agtgctaaag     240 gatctctgat ctggggaaca caccctgga catggctcca gagatcaact tgccgggccc     300
aatgagcctc attgataaca ctaaagggca gctggtggtg aatccagaag ctctgaagat    360
cctatctgca attacgcagc ctgtggtggt ggtggcgatt gtgggcctct atcgcacagg    420
caaatcctac ctgatgaaca agctggctgg gaagaaaaac ggcttctctc taggctccac    480
agtgaagtct cacaccaagg gaatctggat gtggtgtgtg cctcatccca agaagccaga    540
acacacccta gttctgctcg acactgaggg cctgggagat atagagaagg gtgacaatga    600
gaatgactcc tggatctttg ccttggccat cctcctgagc agcaccttcg tgtacaatag    660
catgggaacc atcaaccagc aggccatgga ccaacttcac tatgtgacag agctgacaga    720
```

```
tcgaatcaag gcaaactcct cacctggtaa caattctgta gacgactcag ctgactttgt    780 gagcttttt ccagcatttg tgtggactct cagagatttc accctggaac tggaagtaga     840
tggagaaccc atcactgctg atgactactt ggagctttcg ctaaagctaa gaaaaggtac    900
tgataagaaa agtaaaagct ttaatgatcc tcggttgtgc atccgaaagt tcttccccaa    960
gaggaagtgc ttcgtcttcg attggcccgc tcctaagaag taccttgctc acctagagca   1020
gctaaaggag gaagagctga accctgattt catagaacaa gttgcagaat tttgttccta   1080
catcctcagc cattccaatg tcaagactct ttcaggtggc attccagtca atgggcctcg   1140
tctagagagc ctggtgctga cctacgtcaa tgccatcagc agtggggatc taccctgcat   1200
ggagaacgca gtcctggcct tggcccagat agagaactca gccgcagtgg aaaaggctat   1260
tgcccactat gaacagcaga tgggccagaa ggtgcagctg cccacggaaa ccctccagga   1320
gctgctggac ctgcacaggg acagtgagag agaggccatt gaagtcttca tgaagaactc   1380
tttcaaggat gtggaccaaa tgttccagag gaaattaggg gcccagttgg aagcaaggcg   1440
agatgacttt tgtaagcaga attccaaagc atcatcagat tgttgcatgg ctttacttca   1500
ggatatattt ggccctttag aagaagatgt caagcaggga acattttcta aaccaggagg   1560
ttaccgtctc tttactcaga agctgcagga gctgaagaat aagtactacc aggtgccaag   1620
gaaggggata caggccaaag aggtgctgaa aaaatatttg gagtccaagg aggatgtggc   1680
tgatgcactt ctacagactg atcagtcact ctcagaaaag gaaaaagcga ttgaagtgga   1740
acgtataaag gctgaatctg cagaagctgc aagaaaatg ttggaggaaa tacaaaagaa    1800
gaatgaggag atgatggaac agaaagagaa gagttatcag aacatgtga aacaattgac     1860 tgagaagatg gagagggaca gggcccagtt aatggcagag caagagaaga ccctcgctct   1920
taaacttcag gaacaggaac gccttctcaa ggagggattc gagaatgaga gcaagagact   1980
tcaaaaagac atatgggata tccagatgag aagcaaatca ttggagccaa tatgtaacat   2040
actctaaaag tccaaggagc aaaatttgcc tgtccagctc cctctcccca agaaacaaca   2100
tgaatgagca acttcagagt gtcaaacaac tgccattaaa cttaactcaa aatcatgatg   2160 catgcattt tgttgaacca taaagttttgc aaagtaaagg ttaagtatga ggtcaatgtt    2220
ttacctacag agcaattcaa ctcatgctta tttatagtac taactttaa tatgatcttt     2280 aactaaatcc tatatttgaa atcatacaca aggactcaag agagatattg tgtaactagg   2340
atgcattttc caatgagata tcttgcagtt tctgttctgg gtagattttt ttctctcata   2400
tgcaccaccc ttactgtata ttcagtccta tactcttatt cagggattta actatggtcg   2460
tagcataggg ctgaagtgtt gtgaatatga tgaaaatgtg atgagaccaa acaaaccatg   2520
gggcacagta gagcatcact cctgccaagt ggtctttgta tggcatgctg gctgcaaata   2580
aaggagatct gggac                                                    2595

<210> SEQ ID NO 10
<211> LENGTH: 2459
<212> TYPE: DNA
<213> ORGANISM: Homo sapiens

<400> SEQUENCE: 10
tccttcactg aggagccaga gggaatcaat tccccaagct gggttgagga gaacaggaga     60
tggagaaagc aagtggaaga cagtccattg ctctgtccac agtggagact ggcacagtga    120 acccgggggct ggagctcatg gaaaagaag tagagcctga gggaagcaag aggactgacg     180
cacaaggaca cagcctgggg gatggactgg gcccttccac ttaccagagg aggagtcggt    240
```

```
ggcctttcag caaagcaaga agtttctgca aaacacacgc cagattgttc aagaagatcc      300
tgttgggcct gttgtgtttg gcctatgctg cctatctcct ggcagcttgc atcttgaatt      360
tccagagggc actggccttg tttgtcatca cctgcttggt gatctttgtc ctggttcact      420 cgttttttgaa aaagctcctg gcaaaaaat taacaagatg tctgaagccc tttgaaaact      480
cccgcctgag gctttggacg aaatgggtgt ttgcaggagt ctccttggtt ggccttatac      540
tgtggttggc tttagacaca gcccaaaggc cagagcagct gatccccttt gcaggaatct      600
gcatgttcat cctatcctc tttgcctgct ccaaacacca cagcgcagtg tcctggagga      660
cagtgttttc gggcctaggt cttcaatttg tctttgggat cttggtcatc agaactgatc      720
ttggatatac tgtatttcag tggctgggag agcaggtcca gattttcctg aactacactg      780
tggccggctc cagttttgtc tttggggata cactggtcaa ggatgtcttt gcttttcagg      840
ccttaccaat catcattttc tttggatgtg tggtgtccat tctctactac ctgggcctgg      900
tgcaatgggt agttcagaag gtcgcctggt ttttacaaat cactatgggc accactgcta      960
cagagaccct ggctgtggca ggaaacatct ttgtgggtat gacagaggca cctctgctca     1020
tccgtcccta ccttggggac atgacactct ctgaaatcca tgcggtgatg actgagggt      1080 ttgccaccat ttctggcact gtgctggagc ccttcatagc ctttgggtt gatgcatcat      1140 ccctgatttc tgcctctgtg atggccgccc cttgtgctct cgcctcatca aagctagcgt     1200
atccggaagt ggaggagtcc aagttcaaga gtgaggaggg ggtaaagctg ccccgtggga     1260
aggagaggaa tgtcctggaa gctgccagca acggagccgt agatgccata ggccttgcta     1320
ctaatgtagc agccaacctg attgcctttt ggctgtgtt ggccttcatc aatgctgccc     1380
tctcctggct gggggaattg gtggacatac aggggctcac tttccaggtc atctgctcct     1440
atctcctaag gcccatggtt ttcatgatgg gtgtagagtg gacagactgt ccaatggtgg     1500
ctgagatggg gggaatcaag ttcttcataa atgagtttgt ggcttatcag caactgtctc     1560
aatacaagaa caaacgtctc tctggaatgg aggagtggat tgagggagag aaacagtgga     1620
tttctgtgag agctgaaatc attacaacat tttcactctg tggatttgcc aatcttagtt     1680
ccataggaat cacacttgga ggcttgacat caatagtacc tcaccggaag agtgacttgt     1740
ccaaggttgt ggtcagggcc ctcttcacag gggcctgtgt atcccttatc agtgcctgta     1800
tggcaggaat cctctatgtc cccagggag ctgaagctga ctgtgtctcc ttcccaaaca     1860
caagtttcac caatagaacc tatgagacct acatgtgctg cagagggctc tttcagagta     1920
cttctctgaa tggcaccaac cctccttctt tttctggtcc ctgggaagat aaggagttca     1980
gtgctatggc ccttactaac tgctgtggat tctacaacaa taccgtctgt gcctaaggct     2040
gcttgatcta tttctataac agttttgatc ttaaaagctt tgtgattgca aaggtgttta     2100
tgtactcagg gtgcccacaa ctcactcacc aagatgttta acagtaagta acagtaaatg     2160
taaaagattc attttgggcc gggctcagtg gctcacgcct gtaatcccag cgctttggga     2220
ggccgaggcg gcggatcgc agggtcagga gatcgagacc atcctggcta acacggtgaa     2280
accccgtctc tactaaaggt acaaaaaatt ggccgggagt ggtgtcgggc gactgtagtc     2340
ccagctactc gcgagactga ggcaggagaa tggcgtgaat ccgggaggcg gagcttgcag     2400
cgagccggga tcgcgccact gtactccagc ctgggtgaca gagcgagact ctgtctcag      2459
```

<210> SEQ ID NO 11
<211> LENGTH: 3972
<212> TYPE: DNA
<213> ORGANISM: Homo sapiens

<400> SEQUENCE: 11

```
gctgccgccg ccgcgcccgg gcgcacccgc ccgctcgctg tcccgcgcac cccgtagcgc      60
ctcgggctcc cgggccggac agaggagcca gcccggtgcg cccctccacc tcctgctcgg     120
ggggctttaa tgagacaccc accgctgctg tggggccggc ggggagcagc accgcgacgg     180
ggaccgggc tgggcgctgg agccagaatc ggaaccacga tgtgactccg ccgccgggga     240
cccgtgaggt ttgtgtggac cccgagttcc accaggtgag aagagtgatg accatccttt     300
tccttactat ggttatttca tactttggtt gcatgaaggc tgcccccatg aaagaagcaa     360
acatccgagg acaaggtggc ttggcctacc caggtgtgcg gacccatggg actctggaga     420
gcgtgaatgg gcccaaggca ggttcaagag gcttgacatc attggctgac actttcgaac     480
acgtgataga agagctgttg gatgaggacc agaaagttcg gcccaatgaa gaaaacaata     540
aggacgcaga cttgtacacg tccagggtga tgctcagtag tcaagtgcct ttggagcctc     600
ctcttctctt tctgctggag gaatacaaaa attacctaga tgctgcaaac atgtccatga     660
gggtccggcg ccactctgac cctgcccgcc gaggggagct gagcgtgtgt gacagtatta     720
gtgagtgggt aacggcggca gacaaaaaga ctgcagtgga catgtcgggc gggacggtca     780
cagtccttga aaaggtccct gtatcaaaag ccaactgaa gcaatacttc tacgagacca     840
agtgcaatcc catgggttac acaaaagaag gctgcagggg catagacaaa aggcattgga     900
actcccagtg ccgaactacc cagtcgtacg tgcgggccct taccatggat agcaaaaaga     960
gaattggctg gcgattcata aggatagaca cttcttgtgt atgtacattg accattaaaa    1020
ggggaagata gtggatttat gttgtataga ttagattata ttgagacaaa aattatctat    1080
ttgtatatat acataacagg gtaaattatt cagttaagaa aaaataatt ttatgaactg    1140
catgtataaa tgaagtttat acagtacagt ggttctacaa tctatttatt ggacatgtcc    1200
atgaccagaa gggaaacagt catttgcgca caacttaaaa agtctgcatt acattccttg    1260
ataatgttgt ggtttgttgc cgttgccaag aactgaaaac ataaaaagtt aaaaaaaata    1320
ataaattgca tgctgcttta attgtgaatt gataataaac tgtcctcttt cagaaaacag    1380
aaaaaaaaca cacacacaca caacaaaaat ttgaaccaaa acattccgtt tacatttag    1440
acagtaagta tcttcgttct tgttagtact atatctgttt tactgctttt aacttctgat    1500
agcgttggaa ttaaaacaat gtcaaggtgc tgttgtcatt gctttactgg cttaggggat    1560
gggggatggg gggtatattt ttgtttgttt tgtgttttt tttcgtttgt ttgttttgtt    1620
ttttagttcc cacagggagt agagatgggg aaagaattcc tacaatatat attctggctg    1680
ataaaagata catttgtatg ttgtgaagat gtttgcaata tcgatcagat gactagaaag    1740
tgaataaaaa ttaaggcaac tgaacaaaaa aatgctcaca ctccacatcc cgtgatgcac    1800
ctcccaggcc ccgctcattc tttgggcgtt ggtcagagta agctgctttt gacgaagga    1860
cctatgtttg ctcagaacac attctttccc cccctccccc tctggtctcc tctttgtttt    1920
gttttaagga agaaaaatca gttgcgcgtt ctgaaatatt ttaccactgc tgtgaacaag    1980
tgaacacatt gtgtcacatc atgacactcg tataagcatg gagaacagtg atttttttt    2040
agaacagaaa acaacaaaaa ataacccaa aatgaagatt attttttatg aggagtgaac    2100
atttgggtaa atcatggcta agcttaaaaa aaactcatgg tgaggcttaa caatgtcttg    2160
taagcaaaag gtagagccct gtatcaaccc agaaacacct agatcagaac aggaatccac    2220
attgccagtg acatgagact gaacagccaa atggaggcta tgtggagttg gcattgcatt    2280
taccggcagt gcgggaggaa tttctgagtg gccatcccaa ggtctaggtg gaggtggggc    2340
```

```
atggtatttg agacattcca aaacgaaggc ctctgaagga cccttcagag gtggctctgg    2400
aatgacatgt gtcaagctgc ttggacctcg tgctttaagt gcctacatta tctaactgtg    2460
ctcaagaggt tctcgactgg aggaccacac tcaagccgac ttatgcccac catcccacct    2520
ctggataatt ttgcataaaa ttggattagc ctggagcagg ttgggagcca aatgtggcat    2580
ttgtgatcat gagattgatg caatgagata gaagatgttt gctacctgaa cacttattgc    2640
tttgaaacta gacttgagga aaccagggtt tatcttttga gaacttttgg taagggaaaa    2700
gggaacagga aaagaaaccc caaactcagg ccgaatgatc aaggggaccc ataggaaatc    2760
ttgtccagag acaagacttc gggaaggtgt ctggacattg agaacaccaa gacttgaagg    2820
tgccttgctc aatggaagag gccaggacag agctgacaaa attttgctcc ccagtgaagg    2880
ccacagcaac cttctgccca tcctgtctgt tcatggagag ggtccctgcc tcacctctgc    2940
cattttgggt taggagaagt caagttggga gcctgaaata gtggttcttg gaaaaatgga    3000
tccccagtga aaactagagc tctaagccca ttcagcccat ttcacacctg aaaatgttag    3060
tgatcaccac ttggaccagc atccttaagt atcagaaagc cccaagcaat tgctgcatct    3120
tagtagggtg agggataagc aaaagaggat gttcaccata acccaggaat gaagatacca    3180
tcagcaaaga atttcaattt gttcagtctt tcatttagag ctagtctttc acagtaccat    3240 ctgaataccct ctttgaaaga aggaagactt tacgtagtgt agatttgttt tgtgttgttt    3300
gaaaatatta tcttttgtaat tattttaaat atgtaaggaa tgcttggaat atctgctata    3360
tgtcaacttt atgcagcttc cttttgaggg acaaatttaa aacaaacaac ccccatcac    3420 aaacttaaag gattgcaagg gccagatctg ttaagtggtt tcataggaga cacatccagc    3480
aattgtgtgg tcagtggctc ttttacccaa taagatacat cacagtcaca tgcttgatgg    3540
tttatgttga cctaagattt attttgttaa aatctctctc tgttgtgttc gttcttgttc    3600
tgttttgttt tgtttttttaa agtcttgctg tggtctcttt gtggcagaag tgtttcatgc    3660
atggcagcag gcctgttgct tttttatggc gattcccatt gaaaatgtaa gtaaatgtct    3720
gtggccttgt tctctctatg gtaaagatat tattcaccat gtaaaacaaa aaacaatatt    3780
tattgtattt tagtatattt ataaattat gttattgaaa aaaattggca ttaaaactta    3840
accgcatcag aacctattgt aaatacaagt tctatttaag tgtactaatt aacatataat    3900
atatgtttta aatatagaat ttttaatgtt tttaaatata ttttcaaagt acataaaaaa    3960
aaaaaaaaaa aa                                                       3972
```

<210> SEQ ID NO 12
<211> LENGTH: 4784
<212> TYPE: DNA
<213> ORGANISM: Homo sapiens

<400> SEQUENCE: 12

```
gaggcgacac tgagtctcca agtccggaga ggtgcccgag ggaaagaggg cggcagctaa      60
actggtcctg gagagaagcc ccttccgccc ctctcctcag ccagcatgtc ccggactccg     120
ccgctcctca gtccgcgcgg tggggacccc gggccgtggc ggccggcgca gccctgacgg     180
gttgcgaacc aggggcgccc cgaacgcggg gggttggggt ctgggagcgc gagcggccgc     240
tacggtacga gcggggtgtg ctgagtcccg tggccacccc cggccccagc catgaggagg     300
gacgagcgag acgccaaagc catgcggtcc ctgcagccgc cggatggggc cggctcgccc     360
cccgagagtc tgaggaacgg ctacgtgaag agctgcgtga gccccttgcg gcaggaccct     420
ccgcgcggct tcttcttcca cctctgccgc ttctgcaacg tggagctgcg gccgccgccg     480
```

```
gcctctcccc agcagccgcg gcgctgctcc cccttctgcc gggcgcgcct ctcgctgggc    540
gccctggctg cctttgtcct cgccctgctg ctgggcgcgg aacccgagag ctgggctgcc    600
ggggccgcct ggctgcggac gctgctgagc gtgtgttcgc acagcttgag cccctcttc    660 agcatcgcct gtgccttctt cttcctcacc tgcttcctca cccggaccaa gcggggaccc    720
ggcccgggcc ggagctgcgg ctcctggtgg ctgctggcgc tgcccgcctg ctgttacctg    780
ggggacttct tggtgtggca gtggtggtct tggccttggg gggatggcga cgcagggtcc    840
gcggccccgc acacgccccc ggaggcggca gcgggcaggt tgctgctggt gctgagctgc    900
gtagggctgc tgctgacgct cgcgcacccg ctgcggctcc ggcactgcgt tctggtgctg    960
ctcctggcca gcttcgtctg gtgggtctcc ttcaccagcc tcgggtcgct gccctccgcc   1020
ctcaggccgc tgctctccgg cctggtgggg ggcgctggct gcctgctggc cctggggttg   1080
gatcacttct ttcaaatcag ggaagcgcct cttcatcctc gactgtccag tgccgccgaa   1140
gaaaaagtgc tgtgatccg accccggagg aggtccagct gcgtgtcgtt aggagaaact   1200
gcagccagtt actatggcag ttgcaaaata ttcaggagac cgtcgttgcc ttgtatttcc   1260
agagaacaga tgattctttg ggattgggac ttaaaacaat ggtataagcc tcattatcaa   1320
aattctggag gtggaaatgg agttgatctt tcagtgctaa atgaggctcg caatatggtg   1380
tcagatcttc tgactgatcc aagccttcca ccacaagtca tttcctctct acggagtatt   1440
agtagcttaa tgggtgcttt tcaggttcc tgtaggccaa agattaatcc tctcacacca   1500
tttcctggat tttaccctg ttctgaaata gaggacccag ctgagaaagg ggatagaaaa   1560
cttaacaagg gactaaatag gaatagtttg ccaactccac agctgaggag aagctcagga   1620
acttcaggat tgctacctgt tgaacagtct tcaaggtggg atcgtaataa tggcaaaagg   1680
cctcaccaag aatttggcat ttcaagtcaa ggatgctatc taaatgggcc ttttaattca   1740
aatctactga ctatcccgaa gcaaaggtca tcttctgtat cactgactca ccatgtaggt   1800
ctcagaagag ctggtgtttt gtccagtctg agtcctgtga attcttccaa ccatggacca   1860
gtgtctactg gctctctaac taatcgatca cccatagaat ttcctgatac tgctgatttt   1920
cttaataagc caagcgttat cttgcagaga tctctgggca atgcacctaa tactccagat   1980
ttttatcagc aacttagaaa ttctgatagc aatctgtgta acagctgtgg acatcaaatg   2040
ctgaaatatg tttcaacatc tgaatcagat ggtacagatt gctgcagtgg aaaatcaggt   2100
gaagaagaaa acattttctc gaaagaatca ttcaaactta tggaaactca acaagaagag   2160
gaaacagaga agaaagacag cagaaaatta tttcaggaag gtgataagtg gctaacagaa   2220
gaggcacaga gtgaacagca aacaaatatt gaacaggaag tatcactgga cctgattta   2280 gtagaagagt atgactcatt aatagaaaag atgagcaact ggaatttcc aattttgaa   2340 cttgtagaaa agatgggaga gaaatcagga aggattctca gtcaggttat gtataccta   2400 tttcaagaca ctggtttatt ggaaatattt aaaattccca ctcaacaatt tatgaactat   2460
tttcgtgcat tagaaaatgg ctatcgagac attccttatc acaatcgtat acatgccaca   2520
gatgtgctac atgcagtttg gtatctgaca acacggccag ttcctggctt acagcagatc   2580
cacaatggtt gtgaacagg aaatgaaaca gattctgatg gtagaattaa ccatgggcga   2640
attgcttata tttcttcgaa gagctgctct aatcctgatg agagttatgg ctgcctgtct   2700
tcaaacattc ctgcattaga attgatggct ctatacgtgg cagctgccat gcatgattat   2760
gatcacccag ggaggacaaa tgcatttcta gtggctacaa tgcccctca ggcagtttta   2820 tacaatgaca gatctgttct ggaaaatcat catgctgcgt cagcttggaa tctatatctt   2880
```

```
tctcgcccag aatacaactt ccttcttcat cttgatcatg tggaattcaa gcgctttcgt    2940 ttttagtca ttgaagcaat ccttgctacg gatcttaaaa agcattttga ttttctcgca     3000
gaattcaatg ccaaggcaaa tgatgtaaat agtaatggca tagaatggag taatgaaaat    3060
gatcgcctct tggtatgcca ggtgtgcatc aaactggcag atataaatgg cccagcaaaa    3120
gttcgagact tgcatttgaa atggacagaa ggcattgtca atgaatttta tgagcaggga    3180
gatgaagaag caaatcttgg tctgcccatc agtccattca tggatcgttc ttctcctcaa    3240
ctagcaaaac tccaagaatc ttttatcacc cacatagtgg gtcccctgtg taactcctat    3300
gatgctgctg gtttgctacc aggtcagtgg ttagaagcag aagaggataa tgatactgaa    3360
agtggtgatg atgaagacgg tgaagaatta gatacagaag atgaagaaat ggaaaacaat    3420
ctaaatccaa aaccaccaag aaggaaaagc agacggcgaa tattttgtca gctaatgcac    3480
cacctcactg aaaaccacaa gatatggaag gaaatcgtag aggaagaaga aaaatgtaaa    3540
gctgatggga ataaactgca ggtggagaat tcctccttac ctcaagcaga tgagattcag    3600
gtaattgaag aggcagatga agaggaatag cgacagtttg agtaaaagaa aagtcatatt    3660
gaagaagccc agagggttgt gcccaggggc agaaatcatt gcctagtgtt caccggctga    3720
ctctcaactg accattccca tgtggacagg ccttaatact gtgagaggat ccttgctctg    3780
ctggcagttt cccactccta tgcactttca caggaactag aaaactattc ttaaaccaaa    3840 ataccatcc gtgttgaccc atgttgcaga gcccttactt aaatccttca ctggtgtatg     3900
aatactttgt cataatgctg ctttgctggg tagtgagctc ttattttca ctgggggtca    3960 gctataacta aaaactcaag tgacatattt cagttaccaa agtggccagg aacttttgc    4020 ttttatgaaa atagattcat attgtatttc ccagtgtgtc ttttatgtct ttgaatgttt    4080
tggagaaaag tctatgcctg tctaaaatg aatccagtgt tgcctttctg agggatttct     4140
gctcaatgca atacactgtt cagtgctatt ctcccagcta ggtttatcca tgaaggactg    4200
agtgaccttt gttgtattta acaaaatcca ggtgcatcaa tttctgatgc tttttactat    4260
tgtgtattat ctactatgtg tgttttattt ctgctgagag tattcaggtt tgccatggac    4320
atcagaagtt tgaattccag tcttatctta tgttccatgg ctgaatttta aagctgttta    4380
ggtttaacaa tgaagggatt tattctttag tcaaaattgt tgtttttact ctagctcagg    4440
attcgtattt ttaaagattt agttaatata aacacagcac agatttgtca gaagaaaaa    4500 aatttgctgt aataccaaaa ctaacctcat caaagataca gaaaaaaga aatatagtga    4560 gccctaaagg acacatacat tgaataaata attggaacat gtggttatct ttagatccac    4620
atcttagctg tcatttgttc actctaaaac tgatgttcat cttcctgtta atttccctct    4680
gcctaaagag tacatgacag aaatgaccta tcactactta ttatttctga agcctaactg    4740
caagagtgat ttcttgagaa caagtaaaga actggctcgt gccg                    4784
```

<210> SEQ ID NO 13
<211> LENGTH: 2710
<212> TYPE: DNA
<213> ORGANISM: Homo sapiens

<400> SEQUENCE: 13

```
gcaggcatcg tctcctccgg tctcacagct accccgggct ggagcgtggg gagggggtaa     60
gggagccagc caactcgggg aaacttcgtt gccagagatg actggggttt tcgggctttc    120
ccagccttcc catgccgggc cacacggcat tcattaaagt ggtggggcaa ctattggtgc    180
gctccagccg ggcaggtttt gagctgcaga gacccgtgcc cggtagcagc gctttgccac    240
```

```
cgagtgcacc caggacgcag tggccgccag cccgggtctc ctgctggggg ccggcgagtg    300
cagggagact ttgcgccacg atgttttgtt ttcctgccgc aggaacgcta ggcagtctct    360
ttccaccaga cttaacccgc ctgaagcaat agccatggaa gttgcggcgg cacagaggga    420
gacagaaccg cttggagcgg catctttctt ggatgttttt tctctacaca gacttctttc    480
tttccttggt ggccgttccc gcagcagcac cggtgtgcca gcccaagagc gccactaacg    540
ggcaaccccc ggctccggct ccgactccaa ctccgcgcct gtccatttcc tcccgagcca    600
cagtggtagc caggatggaa ggcacctccc aaggggcttg cagaccgtc atgaagtgga     660 agacggtggt tgccatcttt gtggttgtgg tggtctacct tgtcactggc ggtcttgtct    720
tccgggcatt ggagcagccc tttgagagca gccagaagaa taccatcgcc ttggagaagg    780
cggaattcct gcgggatcat gtctgtgtga gcccccagga gctggagacg ttgatccagc    840
atgctcttga tgctgacaat gcgggagtca gtccaatagg aaactcttcc aacaacagca    900
gccactggga cctcggcagt gccttttcct ttgctggaac tgtcattacg accatagggt    960 atggggaatat tgctccgagc actgaaggag gcaaaatctt ttgtatttta tatgccatct   1020
ttggaattcc actctttggt ttcttattgg ctggaattgg agaccaactt ggaaccatct   1080
ttgggaaaag cattgcaaga gtggagaagg tctttcgaaa aaagcaagtg agtcagacca   1140
agatccgggt catctcaacc atcctgttca tcttggccgg ctgcattgtg tttgtgacga   1200
tccctgctgt catctttaag tacatcgagg gctggacggc cttggagtcc atttactttg   1260
tggtggtcac tctgaccacg gtgggctttg gtgattttgt ggcaggggga aacgctggca   1320
tcaattatcg ggagtggtat aagcccctag tgtggttttg gatccttgtt ggccttgcct   1380
actttgcagc tgtcctcagt atgatcgagg attggctacg ggttctgtcc aaaaagacaa   1440 agaagaggt gggtgaaatc aaggcccatg cggcagagtg aaggccaat gtcacggctg     1500 agttccggga cacggcga aggctcagcg tggagatcca cgataagctg cagcgggcgg     1560
ccaccatccg cagcatggag cgccggcggc tgggcctgga ccagcgggcc cactcactgg   1620
acatgctgtc ccccgagaag cgctctgtct ttgctgccct ggacaccggc cgcttcaagg   1680
cctcatccca ggagagcatc aacaaccggc ccaacaacct gcgcctgaag gggccggagc   1740
agctgaacaa gcatgggcag ggtgcgtccg aggacaacat catcaacaag ttcgggtcca   1800
cctccagact caccaagagg aaaaacaagg acctcaaaaa gaccttgccc gaggacgttc   1860
agaaaatcta caagaccttc cggaattact ccctggacga ggagaagaaa gaggaggaga   1920
cggaaaagat gtgtaactca gacaactcca gcacagccat gctgacggac tgtatccagc   1980
agcacgctga gttggagaac ggaatgatac ccacggacac caaagaccgg gagccggaga   2040
acaactcatt acttgaagac agaaactaaa tgtgaaggac attggtcttg gactgagcgt   2100
tgtgtgtgtg tgtgtgtgtg tgtttttaat attcacactg agacatgtgc cttaaacaga   2160
ctttttagtc caaaattaca tagcattgaa gaatatattt cactgtgcca taaacaactg   2220
aaagcttgct ctgccaaaag gaatcagaga acaagaactt catttcagat agcaaacgca   2280
ggacacacca agagtgtccg tgcacgtagc cggttctggc cgtacatgtt aagggcattt   2340
cagtggcagt gctgtacccc tgggcagtgc tacctgggca cacgtagaa caagggcagc   2400 tattccttag accagcctcc tgaaagaaac aggtgtgtct ttttagtgga gtcgtagtaa   2460
tatgtgcaca cacagaaggg gacctgattg ggtgggagct ggttatgtgt aactagcgtt   2520
ggagttgaca ttttgcatg tgctctgagc ttgaattttg ataccaacca ttcagtgcat    2580
catacctagt cttttctatgc tccaaatgaa tgtctgtggg gacctgagag cacctggaat   2640
```

```
ttgttggaag cagatcagag cacacgtacg aaaaggtgca attgcttttc tcatgacaaa   2700
agaaaaaaaa                                                          2710

<210> SEQ ID NO 14
<211> LENGTH: 2391
<212> TYPE: DNA
<213> ORGANISM: Homo sapiens

<400> SEQUENCE: 14
atgctgcgag gcggacggcg cgggcagctt ggctggcaca gctgggctgc ggggccgggc     60
agcctgctgg cttggctgat actggcatct gcgggcgccg caccctgccc cgatgcctgc    120
tgcccccacg gctcctcggg actgcgatgc acccggatg gggccctgga tagcctccac     180
cacctgcccg gcgcagagaa cctgactgag ctctacatcg agaaccagca gcatctgcag    240
catctggagc tccgtgatct gaggggcctg ggggagctga aaacctcac catcgtgaag     300 agtggtctcc gtttcgtggc gccagatgcc ttccatttca ctcctcggct cagtcgcctg    360
aatctctcct tcaacgctct ggagtctctc tcctggaaaa ctgtgcaggg cctctcctta    420
caggaactgg tcctgtcggg gaaccctctg cactgttctt gtgccctgcg ctggctacag    480
cgctgggagg aggagggact gggcggagtg cctgaacaga agctgcagtg tcatgggcaa    540
gggcccctgg cccacatgcc caatgccagc tgtggtgtgc ccacgctgaa ggtccaggtg    600
cccaatgcct cggtggatgt gggggacgac gtgctgctgc ggtgccaggt ggaggggcgg    660
ggcctggagc aggccggctg gatcctcaca gagctggagc agtcagccac ggtgatgaaa    720
tctgggggtc tgccatccct ggggctgacc ctggccaatg tcaccagtga cctcaacagg    780
aagaacgtga cgtgctgggc agagaacgat gtgggccggg cagaggtctc tgttcaggtc    840
aacgtctcct tcccggccag tgtgcagctg cacacggcgg tggagatgca ccactggtgc    900
atccccttct ctgtggatgg gcagccgca ccgtctctgc gctggctctt caatggctcc    960
gtgctcaatg agaccagctt catcttcact gagttcctgg agccggcagc caatgagacc   1020
gtgcggcacg ggtgtctgcg cctcaaccag cccacccacg tcaacaacgg caactacacg   1080
ctgctggctg ccaacccctt cggccaggcc tccgcctcca tcatggctgc cttcatggac   1140 aacccctttcg agttcaaccc cgaggacccc atccctgtct ccttctcgcc ggtgacact    1200 aacagcacat ctggagaccc ggtggagaag aaggacgaaa caccttttgg ggtctcggtg   1260
gctgtgggcc tggccgtctt tgcctgcctc ttccttttcta cgctgctcct tgtgctcaac   1320
aaatgtggac ggagaaacaa gtttgggatc aaccgcccgg ctgtgctggc tccagaggat   1380
gggctggcca tgtccctgca tttcatgaca ttgggtggca gctccctgtc ccccaccgag   1440
ggcaaaggct ctgggctcca aggccacatc atcgagaacc cacaatactt cagtgatgcc   1500
tgtgttcacc acatcaagcg ccgggacatc gtgctcaagt gggagctggg ggagggcgcc   1560
tttgggaagg tcttccttgc tgagtgccac aacctcctgc tgagcagga caagatgctg   1620 gtggctgtca aggcactgaa ggaggcgtcc gagagtgctc ggcaggactt ccaacgtgag   1680
gctgagctgc tcaccatgct gcagcaccag cacatcgtgc gcttcttcgg cgtctgcacc   1740
gagggccgcc ccctgctcat ggtcttcgag tatatgcggc acgggaccct caaccgcttc   1800
ctccgatccc atggacccga tgccaagctg ctggctggtg gggaggatgt ggctccaggc   1860
cccctgggtc tggggcagct gctggccgtg gctagccagg tcgctgcggg gatggtgtac   1920
ctggcgggtc tgcattttgt gcaccgggac ctggccacac gcaactgtct agtgggccag   1980
ggactggtgg tcaagattgg tgattttggc atgagcaggg atatctacag caccgactat   2040
```

| | |
|---|---:|
| taccgtgtgg gaggccgcac catgctgccc attcgctgga tgccgcccga gagcatcctg | 2100 |
| taccgtaagt tcaccaccga gagcgacgtg tggagcttcg gcgtggtgct ctgggagatc | 2160 |
| ttcacctacg gcaagcagcc ctggtaccag ctctccaaca cggaggcaat cgactgcatc | 2220 |
| acgcagggac gtgagttgga gcggccacgt gcctgcccac cagaggtcta cgccatcatg | 2280 |
| cggggctgct ggcagcggga gccccagcaa cgccacagca tcaaggatgt gcacgcccgg | 2340 |
| ctgcaagccc tggcccaggc acctcctgtc tacctggatg tcctgggcta g | 2391 |

<210> SEQ ID NO 15
<211> LENGTH: 4909
<212> TYPE: DNA
<213> ORGANISM: Homo sapiens

<400> SEQUENCE: 15

| | |
|---|---:|
| tagacgcacc ctctgaagat ggtgactccc tcctgagaag ctggacccct tggtaaaaga | 60 |
| caaggccttc tccaagaaga atatgaaagt gttactcaga cttatttgtt tcatagctct | 120 |
| actgatttct tctctggagg ctgataaatg caaggaacgt gaagaaaaaa taattttagt | 180 |
| gtcatctgca aatgaaattg atgttcgtcc ctgtcctctt aacccaaatg aacacaaagg | 240 |
| cactataact tggtataaag atgacagcaa gacacctgta tctacagaac aagcctccag | 300 |
| gattcatcaa cacaaagaga aactttggtt tgttcctgct aaggtggagg attcaggaca | 360 |
| ttactattgc gtggtaagaa attcatctta ctgcctcaga attaaaataa gtgcaaaatt | 420 |
| tgtggagaat gagcctaact tatgttataa tgcacaagcc atatttaagc agaaactacc | 480 |
| cgttgcagga gacggaggac ttgtgtgccc ttatatggag ttttttaaaa atgaaaataa | 540 |
| tgagttacct aaattacagt ggtataagga ttgcaaacct ctacttcttg acaatataca | 600 |
| ctttagtgga gtcaaagata ggctcatcgt gatgaatgtg gctgaaaagc atagagggaa | 660 |
| ctatacttgt catgcatcct acacatactt gggcaagcaa tatcctatta cccgggtaat | 720 |
| agaatttatt actctagagg aaaacaaacc cacaaggcct gtgattgtga gcccagctaa | 780 |
| tgagacaatg gaagtagact tgggatccca gatacaattg atctgtaatg tcaccggcca | 840 |
| gttgagtgac attgcttact ggaagtggaa tgggtcagta attgatgaag atgacccagt | 900 |
| gctaggggaa gactattaca gtgtggaaaa tcctgcaaac aaaagaagga gtaccctcat | 960 |
| cacagtgctt aatatatcgg aaattgaaag tagattttat aaacatccat ttacctgttt | 1020 |
| tgccaagaat acacatggta tagatgcagc atatatccag ttaatatatc cagtcactaa | 1080 |
| tttccagaag cacatgattg gtatatgtgt cacgttgaca gtcataattg tgtgttctgt | 1140 |
| tttcatctat aaaatcttca agattgacat tgtgctttgg tacagggatt cctgctatga | 1200 |
| ttttctccca ataaaagctt cagatggaaa gacctatgac gcatatatac tgtatccaaa | 1260 |
| gactgttggg gaagggtcta cctctgactg tgatatttttt gtgtttaaag tcttgcctga | 1320 |
| ggtcttggaa aaacagtgtg gatataagct gttcatttat ggaagggatg actacgttgg | 1380 |
| ggaagacatt gttgaggtca ttaatgaaaa cgtaaagaaa agcagaagac tgattatcat | 1440 |
| tttagtcaga gaaacatcag gcttcagctg gctgggtggt tcatctgaag agcaaatagc | 1500 |
| catgtataat gctcttgttc aggatggaat taaagttgtc ctgcttgagc tggagaaaat | 1560 |
| ccaagactat gagaaaatgc cagaatcgat taaattcatt aagcagaaac atggggctat | 1620 |
| ccgctggtca ggggacttta cacagggacc acagtctgca agacaaggt tctggaagaa | 1680 |
| tgtcaggtac cacatgccag tccagcgacg gtcaccttca tctaaacacc agttactgtc | 1740 |
| accagccact aaggagaaac tgcaaagaga ggctcacgtg cctctcgggt agcatggaga | 1800 |

```
agttgccaag agttctttag gtgcctcctg tcttatggcg ttgcaggcca ggttatgcct    1860
catgctgact tgcagagttc atggaatgta actatatcat cctttatccc tgaggtcacc    1920
tggaatcaga ttattaaggg aataagccat gacgtcaata gcagcccagg gcacttcaga    1980
gtagagggct tgggaagatc ttttaaaaag gcagtaggcc cggtgtggtg gctcacgcct    2040
ataatcccag cactttggga ggctgaagtg ggtggatcac cagaggtcag gagttcgaga    2100
ccagcccagc caacatggca aaccccatc tctactaaaa atacaaaaat gagctaggca     2160
tggtggcaca cgcctgtaat cccagctaca cctgaggctg aggcaggaga attgcttgaa    2220
ccggggagac ggaggttgca gtgagccgag tttgggccac tgcactctag cctggcaaca    2280
gagcaagact ccgtctcaaa aaagggcaa taaatgccct ctctgaatgt ttgaactgcc      2340
aagaaaaggc atggagacag cgaactagaa gaaagggcaa gaaggaaata gccaccgtct    2400
acagatggct tagttaagtc atccacagcc caagggcggg gctatgcctt gtctggggac    2460
cctgtagagt cactgaccct ggagcggctc tcctgagagg tgctgcaggc aaagtgagac    2520
tgacacctca ctgaggaagg gagacatatt cttggagaac tttccatctg cttgtatttt    2580
ccatacacat ccccagccag aagttagtgt ccgaagaccg aattttattt tacagagctt    2640
gaaaactcac ttcaatgaac aaagggattc tccaggattc caaagtttg aagtcatctt      2700 agctttccac aggaggggaga gaacttaaaa aagcaacagt agcagggaat tgatccactt    2760
cttaatgctt tcctccctgg catgaccatc ctgtcctttg ttattatcct gcattttacg    2820
tctttggagg aacagctccc tagtggcttc ctccgtctgc aatgtcccttt gcacagccca    2880 cacatgaacc atccttccca tgatgccgct cttctgtcat cccgctcctg ctgaaacacc    2940
tcccaggggc tccacctgtt caggagctga agcccatgct ttcccaccag catgtcactc    3000
ccagaccacc tccctgccct gtcctccagc ttcccctcgc tgtcctgctg tgtgaattcc    3060
caggttggcc tggtggccat gtcgcctgcc cccagcactc ctctgtctct gctcttgcct    3120
cgacccttcc tcctcctttg cctaggaggc cttctcgcat tttctctagc tgatcagaat    3180
tttaccaaaa ttcagaacat cctccaattc cacagtctct gggagacttt ccctaagagg    3240
cgacttcctc tccagccttc tctctctggt caggcccact gcagagatgg tggtgagcac    3300
atctgggagg ctggtctccc tccagctgga attgctgctc tctgagggag aggctgtggt    3360
ggctgtctct gtccctcact gccttccagg agcaatttgc acatgtaaca tagatttatg    3420
taatgcttta tgtttaaaaa cattccccaa ttatcttatt taattttgc aattattcta     3480 attttatata tagagaaagt gacctatttt ttaaaaaat cacactctaa gttctattga     3540
acctaggact tgagcctcca tttctggctt ctagtctggt gttctgagta cttgatttca    3600
ggtcaataac ggtccccct cactccacac tggcacgttt gtgagaagaa atgacatttt      3660
gctaggaagt gaccgagtct aggaatgctt ttattcaaga caccaaattc caaacttcta    3720
aatgttggaa ttttcaaaaa ttgtgtttag attttatgaa aaactcttct actttcatct    3780
attctttccc tagaggcaaa catttcttaa aatgtttcat tttcattaaa aatgaaagcc    3840
aaatttatat gccaccgatt gcaggacaca agcacagttt taagagttgt atgaacatgg    3900
agaggacttt tggttttat atttctcgta tttaatatgg gtgaacacca acttttattt     3960
ggaataataa ttttcctcct aaacaaaaac acattgagtt taagtctctg actcttgcct    4020
ttccacctgc tttctcctgg gcccgctttg cctgcttgaa ggaacagtgc tgttctggag    4080
ctgctgttcc aacagacagg gcctagcttt catttgacac acagactaca gccagaagcc    4140
catggagcag ggatgtcacg tcttgaaaag cctattagat gttttacaaa tttaattttg    4200
```

| | |
|---|---|
| cagattattt tagtctgtca tccagaaaat gtgtcagcat gcatagtgct aagaaagcaa | 4260 |
| gccaatttgg aaacttaggt tagtgacaaa attggccaga gagtgggggt gatgatgacc | 4320 |
| aagaattaca agtagaatgg cagctggaat ttaaggaggg acaagaatca atggataagc | 4380 |
| gtgggtggag gaagatccaa acagaaaagt gcaaagttat tccccatctt ccaagggttg | 4440 |
| aattctggag gaagaagaca cattcctagt tccccgtgaa cttcctttga cttattgtcc | 4500 |
| ccactaaaac aaaacaaaaa acttttaatg ccttccacat taattagatt ttcttgcagt | 4560 |
| tttttatgg cattttttta aagatgccct aagtgttgaa gaagagtttg caaatgcaac | 4620 |
| aaaatattta attaccggtt gttaaaactg gtttagcaca atttatattt tccctctctt | 4680 |
| gcctttctta tttgcaataa aaggtattga gccattttt aaatgacatt tttgataaat | 4740 |
| tatgtttgta ctagttgatg aaggagtttt ttttaacctg tttatataat tttgcagcag | 4800 |
| aagccaaatt ttttgtatat taaagcacca aattcatgta cagcatgcat cacggatcaa | 4860 |
| tagactgtac ttattttcca ataaaatttt caaactttgt actgttaaa | 4909 |

<210> SEQ ID NO 16
<211> LENGTH: 3599
<212> TYPE: DNA
<213> ORGANISM: Homo sapiens

<400> SEQUENCE: 16

| | |
|---|---|
| ggcccctgcg cccttcctgg gatcactccg actgccccgc gcctctgcca actcctctgg | 60 |
| accctcgcgg ccgtgggcag cggctgccgc gcctgtctgc ccgagggagg accttcgcct | 120 |
| ctgcatttgt ccagtaactc tggctgtgcc ggatactgct tgggtaaaac gggcacccca | 180 |
| ggaacatggc agacgaagat ctcatcttcc gcctggaagg cgttgatggc ggccagtccc | 240 |
| cccgagctgg ccatgatggt gattctgatg gggacagcga cgatgaggaa ggttacttca | 300 |
| tctgccccat cacggatgac ccaagctcga accagaatgt caattccaag gttaataagt | 360 |
| actacagcaa cctaacaaaa agtgagcggt atagctccag cgggtccccg gcaaactcct | 420 |
| tccacttcaa ggaagcctgg aagcacgcaa tccagaaggc caagcacatg cccgaccct | 480 |
| gggctgagtt ccacctggaa gatattgcca ccgaacgtgc tactcgacac aggtacaacg | 540 |
| ccgtcaccgg ggaatggctg gatgatgaag ttctgatcaa gatggcatct cagcccttcg | 600 |
| gccgaggagc aatgagggag tgcttccgga cgaagaagct ctccaacttc ttgcatgccc | 660 |
| agcagtggaa gggcgcctcc aactacgtgg cgaagcgcta catcgagccc gtagaccggg | 720 |
| atgtgtactt tgaggacgtg cgtctacaga tggaggccaa gctctggggg gaggagtata | 780 |
| atcggcacaa gccccccaag caggtggaca tcatgcagat gtgcatcatc gagctgaagg | 840 |
| acagaccggg caagcccctc ttccacctgg agcactacat cgagggcaag tacatcaagt | 900 |
| acaactccaa ctctggcttt gtccgcgatg acaacatccg cctgacgccg caggccttca | 960 |
| gccacttcac ttttgagcgt tccggccatc agctgatagt ggtggacatc cagggagttg | 1020 |
| gggatctcta cactgaccca cagatccaca cggagacggg cactgacttt ggagacggca | 1080 |
| acctaggtgt ccgcgggatg cgcgctcttc tctactctca tgcctgcaac cggatttgcg | 1140 |
| agagcatggg ccttgctccc tttgacctct cgccccggga gagggatgca gtgaatcaga | 1200 |
| acaccaagct gctgcaatca gccaagacca tcttgagagg aacagaggaa aaatgtggga | 1260 |
| gccccgagt aaggaccctc tctgggagcc ggccacccct gctccgtccc ctttcagaga | 1320 |
| actctgagca cgagaacatg agcgacgtga ccttcgactc tctcccttct tccccatctt | 1380 |
| cggccacacc acacagccag aagctagacc acctccattg gccagtgttc agtgacctcg | 1440 |

```
ataacatggc atccagagac catgatcatc tagacaacca ccgggagtct gagaatagtg    1500
gggacagcgg ataccccagt gagaagcggg gtgagctgga tgaccctgag ccccgagaac    1560
atggccactc atacagtaat cggaagtacg agtctgacga agacagcctg ggcagctctg    1620
gacgggtatg tgtagagaag tggaatctcc tcaactcctc ccgcctccac ctgccgaggg    1680
cttcggccgt ggccctggaa gtgcaaaggc ttaatgctct ggacctcgaa agaaaatcg    1740
ggaagtccat tttggggaag gtccatctgg ccatggtgcg ctaccacgag ggtgggcgct    1800
tctgcgagaa gggcgaggag tgggaccagg agtcggctgt cttccacctg agcacgcag    1860
ccaacctggg cgagctggag gccatcgtgg gcctgggact catgtactcg cagttgcctc    1920
atcacatcct agccgatgtc tctctgaagg agacagaaga gaacaaaacc aaaggatttg    1980
attacttact aaaggccgct gaagctggcg acaggcagtc catgatccta gtggcgcgag    2040
cttttgactc tggccagaac ctcagcccgg acaggtgcca agactggcta gaggccctgc    2100
actggtacaa cactgccctg gagatgacgg actgtgatga gggcggtgag tacgacggaa    2160
tgcaggacga gccccggtac atgatgctgg ccagggaggc cgagatgctg ttcacaggag    2220
gctacgggct ggagaaggac ccgcagagat caggggactt gtatacccag gcagcagagg    2280
cagcgatgga agccatgaag ggccgactgg ccaaccagta ctaccaaaag gctgaagagg    2340
cctgggccca gatggaggag taaccaggaa atcactgcc ggctagtccc aagcaaacgg    2400
gctaggagga aagattaaaa aaacaacaac aacaacttat ttagtttggg gaggggaagc    2460
attttttaagt gtgttgtaaa atcaaatttt atatttcatt ttttgactct tgaaaaatgt    2520
ctttgctcct tggcagctac cagcagagac tctatagctg tctcttaggg cagtattttg    2580
gggaagtggg gcttgaagaa gcagcctaat gaaccaacat accgttttgt gtgtggtttt    2640
ttttgtttgt ttgtttgttt gttttgagac agagtcttgc tctgtcaccc aggctggagt    2700
gcagtgacat gatcttagct cactgcaacc tccgcctcct gggttcaagt gattctcctg    2760
cctcagcctc ccaagtagct gggattactg gtgcacacca ccacactcag ctaattttg    2820
catttttagt agagatgggg tttcaccatg ttggccaggc tggtctcgaa ctcctggact    2880
taagtgagcc tcccgcctca gtctcccaaa gcgctgggat tacaggcagg agccactgag    2940
cccagccaag acttcagtgt tgactgcttt ggaggcacaa acccatgcaa gcgttagttc    3000
caaagttcag tgtgtacc ctaaatgaaca atgaagcagg taaaattacc cttgaaaaaa    3060
atcccttgga ccacccataa atgacagtga cttttcaat atggactcat catagccagt    3120
tttccttttg aagttggaac tgatcaccct tttgtcatct gtaccagatc agtagttggc    3180
ttgtgttaca ttttgtgtgt gtgtgtgcgt gttttaaacc agtgcatata aattgtatgt    3240
taaatgtaag taactttaag ttgacttatc tcttcacagt aatcaagcct cacgtaattc    3300
atgctttta aattcagcca gcccccctc tctgaaattt tattatgtaa ataatttgtg    3360
ttccctgatc actcgtttaa gttcttagtt gtatgtcatc tcttctctag caggaattgg    3420
caaactttt tgtaaagggg tagaaagtga agatttagg ctttgcaggc catatagcct    3480
ctgctgcaaa tgctcagccc tgctgttgta atgtaaaagc tgccacagac actacatgaa    3540
cacgaatgag tgtggctggt gttccaataa aactttattt acacaaaaaa aaaaaaaaa    3599
```

<210> SEQ ID NO 17
<211> LENGTH: 1288
<212> TYPE: DNA
<213> ORGANISM: Homo sapiens

<400> SEQUENCE: 17

```
acaccagccc tcagtcactg ggagaagaac ctctcatacc ctcggtgctc cagtccccag    60
ctcactcagc cacacacacc atgtgtgaag aggagaccac cgcgctcgtg tgtgacaatg   120
gctctggcct gtgcaaggca ggcttcgcag gagatgatgc ccccgggct gtcttcccct   180 ccattgtggg ccgccctcgc caccagggtg tgatggtggg aatgggccag aaagacagct   240
atgtggggga tgaggctcag agcaagcgag ggatcctaac tctcaaatac cccattgaac   300
acggcatcat caccaactgg gatgacatgg agaagatctg gcaccactcc ttctacaatg   360
agctgcgtgt agcacctgaa gagcacccca ccctgctcac agaggctccc ctaaatccca   420
aggccaacag ggaaaagatg acccagatca tgtttgaaac cttcaatgtc cctgccatgt   480
acgtcgccat tcaagctgtg ctctccctct atgcctctgg ccgcacgaca ggcatcgtcc   540
tggattcagg tgatggcgtc acccacaatg tccccatcta tgaaggctat gccctgcccc   600
atgccatcat gcgcctggac ttggctggcc gtgacctcac ggactacctc atgaagatcc   660
tcacagagag aggctattcc tttgtgacca cagctgagag agaaattgtg cgagacatca   720
aggagaagct gtgctatgtg gccctggatt ttgagaatga gatggccaca gcagcttcct   780
cttcctccct ggagaagagc tatgagctgc agatgggca ggttatcacc attggcaatg   840
agcgcttccg ctgccctgag accctcttcc agccttcctt tattggcatg gagtccgctg   900
gaattcatga caacctac aattccatca tgaagtgtga cattgacatc cgtaaggact   960
tatatgccaa caatgtcctc tctggggca ccaccatgta ccctggcatt gctgacagga  1020
tgcagaagga gatcacagcc ctggccccca gcaccatgaa gatcaagatt attgctcccc  1080
cagagcggaa gtactcagtc tggatcgggg gctctatcct ggcctctctc tccaccttcc  1140
agcagatgtg gatcagcaag cctgagtatg atgaggcagg ccctccatt gtccacagga  1200 agtgcttcta agtcagaac aggttctcca aggatcccct cgagactact ctgttaccag  1260
tcatgaaaca ttaaaaccta caagcctt                                    1288

<210> SEQ ID NO 18
<211> LENGTH: 6861
<212> TYPE: DNA
<213> ORGANISM: Homo sapiens

<400> SEQUENCE: 18
gcctgggagg tgcgtcagat ccgagctcgc catccagttt cctctccact agtcccccca    60
gttggagatc tgggaccaac aaggcaccat ggcgcagaag ggccaactca gtgacgatga   120
gaagttcctc tttgtggaca aaaacttcat caacagccca gtggcccagg ctgactgggc   180
cgccaagaga ctcgtctggg tcccctcgga gaagcagggc ttcgaggcag ccagcattaa   240
ggaggagaag ggggatgagg tggttgtgga gctggtggag aatggcaaga aggtcacggt   300
tgggaaagat gacatccaga agatgaaccc acccaagttc tccaaggtgg aggacatggc   360
ggagctgacg tgcctcaacg aagcctccgt gctacacaac ctgagggagc ggtacttctc   420
agggctaata tatacgtact ctggcctctt ctgcgtggtg gtcaacccct ataaacacct   480
gcccatctac tcggagaaga tcgtcgacat gtacaagggc aagaagagggc acgagatgcc   540 gcctcacatc tacgccatcg cagacacggc ctaccggagc atgcttcaag atcgggagga   600
ccagtccatt ctatgcacag gcgagtctgg agccggaaa accgaaaaca ccaagaaggt   660
cattcagtac ctggccgtgg tggcctcctc ccacaagggc aagaaagaca caagtatcac   720
gggagagctg gaaaagcagc ttctacaagc aaacccgatt ctggaggctt cggcaacgc   780 caaaacagtg aagaacgaca actcctcacg attcggcaaa ttcatccgca tcaacttcga   840
```

```
cgtcacgggt tacatcgtgg gagccaacat tgagacctat ctgctagaaa aatcacgggc    900
aattcgccaa gccagagacg agaggacatt ccacatcttt tactacatga ttgctggagc    960
caaggagaag atgagaagtg acttgctttt ggagggcttc aacaactaca ccttcctctc   1020
caatggcttt gtgcccatcc cagcagccca ggatgatgag atgttccagg aaaccgtgga   1080
ggccatggca atcatgggtt tcagcgagga ggagcagcta tccatattga aggtggtatc   1140
atcggtcctg cagcttggaa atatcgtctt caagaaggaa agaaacacag accaggcgtc   1200
catgccagat aacacagctg ctcagaaagt ttgccacctc atgggaatta atgtgacaga   1260
tttcaccaga tccatcctca ctcctcgtat caaggttggg cgagatgtgg tacagaaagc   1320
tcagacaaaa gaacaggctg actttgctgt agaggctttg gccaaggcaa catatgagcg   1380
ccttttccgc tggatactca cccgcgtgaa caaagccctg gacaagaccc atcggcaagg   1440
ggcttccttc ctggggatcc tggatatagc tggatttgag atctttgagg tgaactcctt   1500
cgagcagctg tgcatcaact acaccaacga gaagctgcag cagctcttca accacaccat   1560
gttcatcctg gagcaggagg agtaccagcg cgagggcatc gagtggaact tcatcgactt   1620
tgggctggac ctacagccct gcatcgagct catcgagcga ccgaacaacc ctccaggtgt   1680
gctggccctg ctggacgagg aatgctggtt ccccaaagcc acggacaagt ctttcgtgga   1740
gaagctgtgc acggagcagg gcagccaccc caagttccag aagcccaagc agctcaagga   1800
caagactgag ttctccatca tccattatgc tgggaaggtg gactataatg cgagtgcctg   1860
gctgaccaag aatatggacc cgctgaatga caacgtgact ccctgctca atgcctcctc   1920
cgacaagttt gtggccgacc tgtggaagga cgtggaccgc atcgtgggcc tggaccagat   1980
ggccaagatg acggagagct cgctgcccag cgcctccaag accaagaagg gcatgttccg   2040
cacagtgggg cagctgtaca aggagcagct gggcaagctg atgaccacgc tacgcaacac   2100
cacgcccaac ttcgtgcgct gcatcatccc caaccacgag aagaggtccg gcaagctgga   2160
tgcgttcctg gtgctggagc agctgcggtg caatggggtg ctggaaggca ttcgcatctg   2220
ccggcagggc ttccccaacc ggatcgtctt ccaggagttc cgccaacgct acgagatcct   2280
ggcggcgaat gccatcccca aggcttcat ggacgggaag caggcctgca ttctcatgat   2340
caaagccctg gaacttgacc ccaacttata caggataggg cagagcaaaa tcttcttccg   2400
aactggcgtc ctggcccacc tagaggagga gcgagatttg aagatcaccg atgtcatcat   2460
ggccttccag gcgatgtgtc gtggctactt ggccagaaag cttttgcca agaggcagca   2520
gcagctgacc gccatgaagg tgattcagag gaactgcgcc gcctacctca agctgcggaa   2580
ctggcagtgg tggaggcttt tcaccaaagt gaagccactg ctgcaggtga cacggcagga   2640
ggaggagatg caggccaagg aggatgaact gcagaagacc aaggagcggc agcagaaggc   2700
agagaatgag cttaaggagc tggaacagaa gcactcgcag ctgaccgagg agaagaacct   2760
gctacaggaa cagctgcagg cagagacaga gctgtatgca gaggctgagg agatgcgggt   2820
gcggctggcg gccaagaagc aggagctgga ggagatactg catgagatgg aggcccgcct   2880
ggaggaggag gaagacaggg gccagcagct acaggctgaa aggaagaaga tggcccagca   2940
gatgctggac cttgaagaac agctggagga ggaggaagct gccaggcaga gctgcaact   3000
tgagaaggtc acggctgagg ccaagatcaa gaaactggag gatgagatcc tggtcatgga   3060
tgatcagaac aataaactat caaaagaacg aaaactcctt gaggagagga ttagtgactt   3120
aacgacaaat cttgcagaag aggaagaaaa ggccaagaat cttaccaagc tgaaaaacaa   3180
gcatgaatct atgatttcag aactggaagt gcggctaaag aaggaagaga agagccgaca   3240
```

```
ggagctggag aagctgaaac ggaagctgga gggtgatgcc agcgacttcc acgagcagat   3300
cgctgacctc caggcgcaga tcgcagagct caagatgcag ctggccaaga aggaggagga   3360
gctgcaggcg gccctggcca ggcttgacga tgaaatcgct cagaagaaca atgccctgaa   3420
gaagatccgg gagctggagg ccacatctc agacctccag gaggacctgg actcagagcg   3480
ggccgccagg aacaaggctg aaaagcagaa gcgagacctc ggcgaggagc tggaggccct   3540
aaagacagag ctggaagaca cactggacag cacagccact cagcaggagc tcagggccaa   3600
gagggagcag gaggtgacgg tgctgaagaa ggccctggat gaagagacgc ggtcccatga   3660
ggctcaggtc caggagatga ggcagaaaca cgcacaggcg gtggaggagc tcacagagca   3720
gcttgagcag ttcaagaggg ccaaggcgaa cctagacaag aataagcaga cgctggagaa   3780
agagaacgca gacctggccg gggagctgcg ggtcctgggc caggccaagc aggaggtgga   3840
acataagaag aagaagctgg aggcgcaggt gcaggagctg cagtccaagt gcagcgatgg   3900
ggagcgggcc cggcggagc tcaatgacaa agtccacaag ctgcagaatg aagttgagag   3960
cgtcacaggg atgcttaacg aggccgaggg gaaggccatt aagctggcca aggacgtggc   4020
gtccctcagt tccagctcc aggacaccca ggagctgctt caagaagaaa cccggcagaa   4080
gctcaacgtg tctacgaagc tgcgccagct ggaggaggag cggaacagcc tgcaagacca   4140
gctggacgag gagatggagg ccaagcagaa cctggacgc acatctcca ctctcaacat   4200 ccagctctcc gactcgaaga gaagctgca ggactttgcc agcaccgtgg aagctctgga   4260
agaggggaag aagaggttcc agaaggagat cgagaacctc acccagcagt acgaggaaa   4320 ggcggccgct tatgataaac tggaaaagac caagaacagg cttcagcagg agctggacga   4380
cctggttgtt gatttggaca accagcggca actcgtgtcc aacctggaaa agaagcagag   4440
gaaatttgat cagttgttag ccgaggagaa aaacatctct tccaaatacg cggatgagag   4500
ggacagagct gaggcagaag ccagggagaa ggaaaccaag gccctgtccc tggctcgggc   4560
ccttgaagag gccttggaag ccaaagagga actcgagcgg accaacaaaa tgctcaaagc   4620
cgaaatggaa gacctggtca gctccaagga tgacgtgggc aagaacgtcc atgagctgga   4680
gaagtccaag cgggccctgg agacccagat ggaggagatg aagacgcagc tggaagagct   4740
ggaggacgag ctgcaagcca cggaggacgc caaactgcgg ctggaagtca acatgcaggc   4800
gctcaagggc cagttcgaaa gggatctcca agcccgggac gagcagaatg aggagaagag   4860
gaggcaactg cagagacagc ttcacgagta tgagacggaa ctggaagacg agcgaaagca   4920
acgtgccctg gcagctgcag caaagaagaa gctggaaggg gacctgaaag acctggagct   4980
tcaggccgac tctgccatca aggggaggga ggaagccatc aagcagctac gcaaactgca   5040
ggctcagatg aaggactttc aaagagagct ggaagatgcc cgtgcctcca gagatgagat   5100
ctttgccaca gccaaagaga atgagaagaa agccaagagc ttggaagcag acctcatgca   5160
gctacaagag gacctcgccg ccgctgagag ggctcgcaaa caagcggacc tcgagaagga   5220
ggaactggca gaggagctgg ccagtagcct gtcgggaagg aacgcactcc aggacgagaa   5280
gcgccgcctg gaggcccgga tcgcccagct ggaggaggag ctgaggagg gcagggcaa   5340 catggaggcc atgagcgacc gggtccgcaa agccacacag caggccgagc agctcagcaa   5400
cgagctggcc acagagcgca gcacggccca gaagaatgag agtgccccgg cagcagctcga   5460 gcggcagaac aaggagctcc ggagcaagct ccacgagatg gagggggccg tcaagtccaa   5520
gttcaagtcc accatcgcgg cgctggaggc caagattgca cagctggagg agcaggtcga   5580
gcaggaggcc agagagaaac aggcggccac caagtcgctg aagcagaaag acaagaagct   5640
```

| | |
|---|---|
| gaaggaaatc ttgctgcagg tggaggacga gcgcaagatg gccgagcagt acaaggagca | 5700 |
| ggcagagaaa ggcaatgcca gggtcaagca gctcaagagg cagctggagg aggcagagga | 5760 |
| ggagtcccag cgcatcaacg ccaaccgcag gaagctgcag cgggagctgg atgaggccac | 5820 |
| ggagagcaac gaggccatgg gccgcgaggt gaacgcactc aagagcaagc tcaggcgagg | 5880 |
| aaacgagacc tctttcgttc cttctagaag gtctggagga cgtagagtta ttgaaaatgc | 5940 |
| agatggttct gaggaggaaa cggacactcg agacgcagac ttcaatggaa ccaaggccag | 6000 |
| tgaataagca actttctaca gttttgcacc acggcaagaa aaccaaaaac caaaacaaac | 6060 |
| aaacaaaaaa aacccaacaa caacccagaa caaagcaaaa cccagcagac tgtacttagc | 6120 |
| attgtctaaa tccattctca aattccaaat atcacagaca cccctcacac aaggaatata | 6180 |
| aaaaccacca ccctccagcc tgggcaacgt agtaaaacct catctataca agaatttaaa | 6240 |
| aataagctgg gcgtggtggt acacacctgt ggtcccagct actagggagg ctgagccagg | 6300 |
| aagaacgctc cagcccagga cttcgaggct gcaatgagct ataattgcat cattgcactc | 6360 |
| cagcctgggc aacagagacc ctgtctcaac caccaccacc accaccaccc ctactacccc | 6420 |
| tgtattcaag gtaaaaattg aagtttgtat gatgtaagag atgagaaaaa cccaacagga | 6480 |
| aacacagaca catcctccag ttctatcaat ggattgtgca gacactgagt ttttagaaaa | 6540 |
| acatatccac ggtaaccggt ccctggcaat tctgtttaca tgaaatgggg agaaagtcac | 6600 |
| cgaaatgggt gccgccggcc cccactccca attcattccc taacctgcaa accttttccaa | 6660 |
| cttctcacgt caggcctttg agaattcttt cccctctcc tggtttccac acctcagaca | 6720 |
| cgcacagttc accaagtgcc ttctgtagtc acatgaattg aaaaggagac gctgctccca | 6780 |
| cggaggggag caggaatgct gcactgttta caccctgact gtgcttaaaa acacttttcac | 6840 |
| taataaatgg ttataaatca c | 6861 |

<210> SEQ ID NO 19
<211> LENGTH: 1243
<212> TYPE: DNA
<213> ORGANISM: Homo sapiens

<400> SEQUENCE: 19

| | |
|---|---|
| ggacgcaacc atctgcggaa aggatagggg ggaggaagac ttaacactgc aacaacaggt | 60 |
| acaaaaaaga aggaaactca gtaacaggac ccagaggacc attatatatt gctctatatt | 120 |
| ctaggtcgcc cactttacac ttccttctca tgcacttggt caataccacg cccgctgacc | 180 |
| acactggcga cttccctctc tgtcgcccct ccgtgaagtc agacccactc tgcgggccaa | 240 |
| gaaaggtgac cgggcttcct tccggcttgc taagcagagg ccggaagcgg tggtttttag | 300 |
| cggctctctg ggtagcaggg tggtgtgata gcggcagcga ggggctcgga gaggtgctcg | 360 |
| gattctcgta gctgtgccgg gacttaacca ccaccatgtc gagcaaaaga acaaagacca | 420 |
| agaccaagaa gcgccctcag cgtgcaacat ccaatgtgtt tgctatgttt gaccagtcgc | 480 |
| agattcagga gttcaaagag gccttcaaca tgattgatca gaacagagat ggtttcatcg | 540 |
| acaaggaaga tttgcatgat atgcttgctt cattggggaa gaatccaact gatgagtatc | 600 |
| tagatgccat gatgaatgag gctccaggcc ccatcaattt caccatgttc ctcaccatgt | 660 |
| ttggtgagaa gttaaatggc acagatcctg aagatgtcat cagaaatgcc tttgcttgct | 720 |
| ttgatgaaga agcaactggc accatacagg aagattactt gagagagctg ctgacaacca | 780 |
| tgggggatcg gtttacagat gaggaagtgg atgagctgta cagagaagca cctattgata | 840 |
| aaaaggggaa tttcaattac atcgagttca cacgcatcct gaaacatgga gccaaagaca | 900 |

```
aagatgactg aaataacttc aaattccagc caaacgttcc ttgttgccac tttgggtatt    960
ctgagatttt ctcttgcatg cccttagctt tacagctttt gcattcctg ttgtatttat   1020 tctcagccat tttgggcata tgtatcttta taatcagact ggaaacggga ctttctatta   1080
atatcatttt cagaataaaa aataggataa tttaacctac cagcccttct cccccaataa   1140
ctgtggtcta tacagagtca atatatttt tcggagaaag ttattcgctc gattttttct    1200
gaatcataat taaactttat gataaaataa aaaaaaaaaa aaa                    1243

<210> SEQ ID NO 20
<211> LENGTH: 878
<212> TYPE: DNA
<213> ORGANISM: Homo sapiens

<400> SEQUENCE: 20
aggaagtgtc ggcgccgcca ctgtccggcc acagcctaac gctcttcgct gtcgtttgcg     60
gtctcggcag ggcgccccg ttctggtgtt tggcgtcgga attaaacaac caccatgtcg    120
agcaaaaagg caaagaccaa gaccaccaag aagcgccctc agcgtgcaac atccaatgtg    180
tttgccatgt tgaccagtc acagattcag gagttcaaag aggccttcaa catgattgat    240
cagaacagag atggcttcat cgacaaggaa gatttgcatg atatgcttgc ttctctaggg    300
aagaatccca ctgatgcata ccttgatgcc atgatgaatg aggccccagg gccaatcaat    360
ttcaccatgt tcctgaccat gtttggtgag aagttaaatg gcacagatcc tgaagatgtc    420
atcagaaacg cctttgcttg ctttgatgaa gaagcaacag gtaccattca ggaagattac    480
ctaagagagc tgctgacaac catgggggat cggtttacag atgaggaagt ggatgagctg    540
tacagagaag cacctattga caaaaagggg aatttcaatt acatcgagtt cacacgcatc    600
ctgaaacatg gagccaaaga caaagatgac tgaaagaact ttagctaaaa tcttccagtt    660
acattgtctt actctctttt acttctcaga cacttccccc accctcatag aacctgttgc    720
atgcaactta gtttcacagc tttgcctctt cttttgatg tatttattcc agacctttct    780
gccacttagc acttgtataa tcagactgga atgggatg agggtgtaaa ttgtattgaa     840
aaagatcgcg aataaaaatc aacaaagtgt gaaagccc                          878

<210> SEQ ID NO 21
<211> LENGTH: 1681
<212> TYPE: DNA
<213> ORGANISM: Homo sapiens

<400> SEQUENCE: 21
agttggaggg aggcagggaa tctggcttga ttggcgtgct gagacgcacc tggcgcaacc     60
ctcccttctg aatcgaagtt caagtcccgc ggacactgca accatgaagg agagacgggc    120
cccccagcca gtcgtggcca gatgtaagct cgttctggtc ggggacgtgc agtgtgggaa    180
gaccgcgatg ttgcaagtgt tagcgaagga ttgctatcca gagacctatg tgcccaccgt    240
gttcgaaaat tacacagcct gtttggagac agaggaacag agggtggagc ttagtctctg    300 ggataccttca ggatctccct actacgataa tgtccgtcca ctctgctaca gcgactcgga    360
tgcagtatta ctatgttttg acatcagccg tccagagaca gtggacagcg cactcaagaa    420
gtggaggaca gaaatcctag attattgtcc cagcacccgc gttttgctca ttggctgcaa    480
gacagacctg cgaacagacc tgagtactct gatggagctg tcccaccaga agcaggcgcc    540 catctccctat gagcagggtt gtgcaatagc aaagcagctg ggtgcagaaa tctacctgga    600
aggctcagct ttcacctcag aaaagagcat ccacagcatc tttcggacgg catccatgct    660
```

```
gtgtctgaac aagcctagcc cactgcccca gaagagccct gtccgaagcc tctccaaacg    720
actgctccac ctccccagtc gctctgaact catctcttct accttcaaga aggaaaaggc    780
caaaagctgt tccattatgt gaagtggaaa ttggagggg gagacaaccc cctacttcct     840 cccttgggt gcagaggcac ggggagaggg aggatgagac aatttaggac actggacatg    900
agtttttcag atggccacgg tgagggcttg gaaggagaca ggaatggggc gaggaaggag    960
ccaggcccgg catgaggacc tgacgctgag agagaaccat catacccaa gccaggcact    1020 agattttgga gggggcgact accccagtgc ccccccgct ccagaggaag gaaagctgtg     1080
ggggacgggg ggcatgctgg cctcatgggc ttggggcct acagcagcct caccttcagc    1140
ttcatgcctc ttccacacag cgtttccatg caggtcaggg gatgggaggg gtccctgagc    1200
ccttcccttc ccctctaagg aggcagcaac ggagagtggg gaagtggagc ggcagctccc    1260
ttggggcctt agcccaggtg cttcgtaact gcaatcggaa gtgcaggggc tggtcagagc    1320
caatgagaag gaaacctcat ctttgcatag cccatgcctc atgagaggt gacatcatac     1380 attcacatgc ttctcaccta gtccccagg gtccaaggga gaagcccag accccttct      1440 cttgcagagt gtgggggtgg tggtgctgca ggggcagggc tgggtgggg tcaccagact     1500 ttttctgccc ttagggtagt acagctggca tttgtttat agactcttgt ctttggaatt    1560
ggggggaggg gggagtgtt tcaatctgtt atatgttctg tgtttaatga agaaaaccta     1620
tttattaatg aaaaatataa tacatataaa gaaaaaaaaa aaaagaaaaa aaaaaaaaa    1680 a                                                                   1681

<210> SEQ ID NO 22
<211> LENGTH: 865
<212> TYPE: DNA
<213> ORGANISM: Homo sapiens

<400> SEQUENCE: 22
ctcaaacacc gcctgctaaa ataccccgac tggaggagca taaaagcgca gccgagccca     60
gcgccccgca cttttctgag cagacgtcca gagcagagtc agccagcatg accgagcgcc    120
gcgtcccctt ctcgctcctg cgggcccca gctgggaccc cttccgcgac tggtacccgc     180
atagccgcct cttcgaccag gccttcgggc tgccccggct gccggaggag tggtcgcagt    240
ggttaggcgg cagcagctgg ccaggctacg tgcgcccccc gccccccgcc gccatcgaga    300
gccccgcagt ggccgcgccc gcctacagcc gcgcgctcag ccggcaactc agcagcgggg    360
tctcggagat ccggcacact gcggaccgct ggcgcgtgtc cctggatgtc aaccacttcg    420
ccccggacga gctgacggtc aagaccaagg atggcgtggt ggagatcacc ggcaagcacg    480
aggagcggca ggacgagcat ggctacatct cccggtgctt cacgcggaaa tacacgctgc    540
cccccggtgt ggaccccacc caagtttcct cctccctgtc ccctgagggc acactgaccg    600
tggaggcccc catgcccaag ctagccacgc agtccaacga gatcaccatc ccagtcacct    660
tcgagtcgcg ggcccagctt gggggcccag aagctgcaaa atccgatgag actgccgcca    720
agtaaagcct tagcctggat gcccacccct gctgccgcca ctggctgtgc ctcccccgcc    780
acctgtgtgt tcttttgata catttatctt ctgttttct caaataaagt tcaaagcaac    840
cacctgtaaa aaaaaaaaaa aaaaa                                         865

<210> SEQ ID NO 23
<211> LENGTH: 3890
<212> TYPE: DNA
<213> ORGANISM: Homo sapiens
```

<400> SEQUENCE: 23

```
gcacctgggc acctgggcag ccgccgcggc gctggctaga cgtgcgcgat ggagggcgac      60
ggcgggaccc catgggccct ggcgctgctg cgcaccttcg acgcgggcga gttcacgggc     120
tgggagaagg tgggctcggg cggcttcggg caggtgtaca aggtgcgcca tgtccactgg     180
aagacctggc tggccatcaa gtgctcgccc agcctgcacg tcgacgacag ggagcgcatg     240
gagcttttgg aagaagccaa gaagatggag atggccaagt tcgctacat cctgcctgtg      300
tatggcatct gccgcgaacc tgtcggcctg gtcatggagt acatggagac gggctccctg     360
gaaaagctgc tggcttcgga gccattgcca tgggatctcc ggttccgaat catccacgag     420
acggcggtgg gcatgaactt cctgcactgc atggccccgc cactcctgca cctggacctc     480
aagcccgcga acatcctgct ggatgccac taccacgtca agatttctga ttttggtctg      540
gccaagtgca acgggctgtc ccactcgcat gacctcagca tggatggcct gtttggcaca     600
atcgcctacc tccctccaga gcgcatcagg agaagagcc ggctcttcga caccaagcac      660
gatgtataca gctttgcgat cgtcatctgg ggcgtgctca cacagaagaa gccgtttgca     720
gatgagaaga acatcctgca catcatggtg aaggtggtga agggccaccg ccccgagctg     780
ccgcccgtgt gcagagcccg gccgcgcgcc tgcagccacc tgatacgcct catgcagcgg     840
tgctggcagg gggatccgcg agttaggccc accttccaag aaattacttc tgaaaccgag     900
gacctgtgtg aaaagcctga tgacgaagtg aaagaaactg ctcatgatct ggacgtgaaa     960
agccccccgg agcccaggag cgaggtggtg cctgcgaggc tcaagcgggc ctctgccccc    1020
accttcgata cgactacag cctctccgag ctgctctcac agctggactc tggagtttcc     1080
caggctgtcg agggccccga ggagctcagc cgcagctcct ctgagtccaa gctgccatcg    1140
tccggcagtg ggaagaggct ctcggggtg tcctcggtgg actccgcctt ctcttccaga     1200
ggatcactgt cgctgtcctt tgagcgggaa ccttcaacca gcgatctggg caccacagac    1260
gtccagaaga agaagcttgt ggatgccatc gtgtccgggg acaccagcaa actgatgaag    1320
atcctgcagc gcaggacgt ggacctggca ctggacagcg tgccagcct gctgcacctg      1380
gcggtggagg ccgggcaaga ggagtgcgcc aagtggctgc tgctcaacaa tgccaaccc      1440
aacctgagca accgtagggg ctccacccg ttgcacatgg ccgtggagag gagggtgcgg      1500
ggtgtcgtgg agctcctgct ggcgcggaag atcagtgtca acgccaagga tgaggaccag    1560
tggacagccc tccactttgc agcccagaac ggggacgagt ctagcacacg gctgctgttg    1620
gagaagaacg cctcggtcaa cgaggtggac tttgagggcc ggacgcccat gcacgtggcc    1680
tgccagcacg gcaggagaa tatcgtgcgc atcctgctgc gccgaggcgt ggacgtgagc    1740
ctgcagggca aggatgcctg gctgccactg cactacgctg cctggcaggg ccacctgccc    1800
atcgtcaagc tgctggccaa gcagccgggg gtgagtgtga acgcccagac gctggatggg    1860
aggacgccat tgcacctggc cgcacagcgc gggcactacc gcgtggcccg catcctcatc    1920
gacctgtgct ccgacgtcaa cgtctgcagc ctgctggcac agacacccct gcacgtggcc    1980
gcggagacgg ggcacacgag cactgccagg ctgctcctgc atcggggcgc tggcaaggag    2040
gccatgacct cagacggcta caccgctctg caccctggctg cccgcaacgg acacctggcc    2100
actgtcaagc tgcttgtcga ggagaaggcc gatgtgctgg cccggggacc cctgaaccag    2160
acggcgctgc acctggctgc cgcccacggg cactcggagg tggtggagga gttggtcagc    2220
gccgatgtca ttgacctgtt cgacgagcag gggctcagcg cgctgcacct ggccgcccag    2280
ggccggcacg cacagacggt ggagactctg ctcaggcatg gggcccacat caacctgcag    2340
```

```
agcctcaagt tccagggcgg ccatggcccc gccgccacgc tcctgcggcg aagcaagacc    2400
tagctggctg cctgcggaga ccgggggtcc acgtggggct cttgtcctgt cctgtgttcc    2460
tcgtggggat ggaacgatcc tgcgtggggc cctgttgtgg cttacctaaa tgttaaccaa    2520
gcagaggtga catggtgcca tcaggaggcg gctgctgctg accggagtgt ccctccagg     2580 tgaagctggc tcaggtgcac atgcccgctc catcatcgat ctaggcacct gctgtctgaa    2640
gggaccgtgg gtcagaatca tttcgttgtg ctcctaatgg gtcgctgagg ctggtctctc    2700
agtgatgaag ccccaggcgt ggaagcatcc actctctcct gaggcgagcc accttgggtt    2760
gctggagctc accagtcttg agggaggtgc aggggaaact gtgtttttta tcttcataca    2820
tgacggtggg cagagaggcc tgtcttaaag tttccatgga attgttttat aaaatatctt    2880
aagagatgaa taccttatca gctgttgctt gaaacctgtt aaaaatgttc ataacattgg    2940
atagtctagt ctctaaatga tgactaagta gtggggttgg ctttgaaaac aatgttttat    3000
gcaacaagga acgaatggta gcagccagct ttgcggggcg tatgtgtggc cagctcttaa    3060
ccattccagt ctattacttg ggtgagtcct tgtggacaac cacacacacg tgcccacatg    3120
gtactagctg ccgttcgttt ctcgttgcct aagatgtttt ggcaactcta gagccacagg    3180
cctaagtcat taaaaaattc tcccttttgta acctcagtgc tggggactga ggcgagcccc    3240
ctcaggtcgc tggagtgcac cagtcttggg aagaggtgc aggagaagct gtgttttta    3300 tctccacacg cagtatgaag ataaaattac atagtattac ctagacatag acagtattac    3360
ctaggtagat gcactgctca cctgcgccct tcccagctct cattttttgtt aggtgatttg    3420 ggatagggat agtgttttgg ggtatggggg gagtgtttct gacctgcttt gcagacgtgc    3480
ctccgcacct cagcagtttg gggtgtggcc ccagggcggt tcttggatgt aaagatgtg     3540 gccatctagc ctcgtaactt cactgtcacc tgtgtcccat agggtgcctt ctgaatactg    3600
ttattagaat aagtttgttg cagaacgtga ccctgcgtgc aaacatgtac cgtggcctgg    3660
tatatgatag agattgatat taatgtacca tgtatgttaa tgtgaatctg tgggcaggat    3720
acttttccat ggcaggaaat atccaagctg ttgaaactgg ctatgtttta atatgcctca    3780
ttgtgccttt actgttgtgt ggactgcgtg agggacaaga agttccattt gatgtcaata    3840
aagcaaagta cttgcctact ttttttgaagc tgaaaaaaaa aaaaaaaaaa              3890
```

<210> SEQ ID NO 24
<211> LENGTH: 894
<212> TYPE: DNA
<213> ORGANISM: Homo sapiens

<400> SEQUENCE: 24

```
cgtcatacgc agcgcccttt gtgacaccag ggccctggtg ctttaactag ggcgttggga     60
cctgttgccc acacagaccg ccctgcagtt tcagactgga gggcggtgga cggctactca    120
gcggcccaac tctctcgcag cccttctctc cgcaaaatgt cagcctccac ctcctcgcac    180
cggcccatca gggggatcct gaaaacaaa agctcgtcgg gttcctcggt ggcgacttcc     240
ggtcagcagt ctggagggac tattcaagat gtgaagagaa agaaatccca aaagtgggac    300
gaatcaagca tccttgcggc acaccgcgca acgtacagag attacgattt aatgaaggca    360
aatgagcccg gcacttccta catgagtgtg caagataatg ggaagattc agtgcgcgat     420 gtcgaaggag aagattcagt gcgtggtgtc gaaggaaagg aagccaccga tgcttccgac    480
cacagctgtg aggtggacga gcaagagagc agtgaggcct acatgagaaa aatcctcctc    540
cacaaacagg agaaaaagcg gcagttcgaa atgagaagaa ggcttcacta caacgaagaa    600
```

```
ttgaacatca aattagctag acaattaatg tggaaagagc tacaaagtga agataatgaa    660
aacgaagaaa cgccacaagg cacgaacgaa gagaagactg ctgcggaaga atcagaggaa    720
gctcctctga ccggtggact gcaaacccag tcatgcgacc cttagaagat gcctgcttca    780
cccttgcaat tgtttgtgaa tatgtgacgc ttagaagata tctgcttcac ccttgcaatt    840
gtttgtgaaa tacaaacctt gttactgtaa aaaaaaaaaa aaaaaaaaaa aaaa          894
```

<210> SEQ ID NO 25
<211> LENGTH: 1574
<212> TYPE: DNA
<213> ORGANISM: Homo sapiens

<400> SEQUENCE: 25

```
tcaccacggc ggcagccctt taaaccctc acccagccag cgccccatcc tgtctgtccg      60
aacccagaca caagtcttca ctccttcctg cgagccctga ggaagccttg tgagtgcatt    120
ggctggggct tggagggaag ttgggctgga gctggacagg agcagtgggt gcatttcagg    180
caggctctcc tgaggtccca ggcgccagct ccagctccct ggctagggaa acccacccctc   240 tcagtcagca tgggggccca agctccaggc agggtgggct ggatcactag cgtcctggat    300
ctctctcaga ctgggcagcc ccgggctcat tgaaatgccc cggatgactt ggctagtgca    360
gaggaattga tggaaaccac cggggtgaga gggaggctcc ccatctcagc cagccacatc    420
cacaaggtgt gtgtaagggt gcaggcgccg ccggttagg ccaaggctct actgtctgtt     480 gccccctccag gagaacttcc aaggagcttt cccagacat ggccaacaag ggtccttcct    540
atggcatgag ccgcgaagtg cagtccaaaa tcgagaagaa gtatgacgag gagctggagg   600
agcggctggt ggagtggatc atagtgcagt gtggccctga tgtgggccgc ccagaccgtg    660
ggcgcttggg cttccaggtc tggctgaaga atggcgtgat tctgagcaag ctggtgaaca    720
gcctgtaccc tgatggctcc aagccggtga aggtgcccga gaacccaccc tccatggtct    780
tcaagcagat ggagcaggtg gctcagttcc tgaaggcggc tgaggactat ggggtcatca    840
agactgacat gttccagact gttgacctct ttgaaggcaa agacatggca gcagtgcaga    900
ggaccctgat ggctttgggc agcttggcag tgaccaagaa tgatgggcac taccgtggag   960
atcccaactg gttatgaag aaagcgcagg agcataagag ggaattcaca gagagccagc    1020
tgcaggaggg aaagcatgtc attggccttc agatgggcag caacagaggg gcctcccagg   1080
ccggcatgac aggctacgga cgacctcggc agatcatcag ttagagcgga gagggctagc    1140
cctgagcccg gccctccccc agctccttgg ctgcagccat cccgcttagc ctgcctcacc    1200
cacacccgtg tggtaccttc agccctggcc aagctttgag gctctgtcac tgagcaatgg    1260
taactgcacc tgggcagctc ctccctgtgc ccccagcctc agcccaactt cttacccgaa    1320
agcatcactg ccttggcccc tccctcccgg ctgcccccat cacctctact gtctcctccc    1380
tgggctaagc aggggagaag cgggctgggg gtagcctgga tgtgggccaa gtccactgtc    1440
ctccttggcg gcaaaagccc attgaagaag aaccagccca gcctgccccc tatcttgtcc    1500
tggaatattt ttggggttgg aactcaaaaa aaaaaaaaaa aaatcaatct tttctcaaaa   1560
aaaaaaaaaa aaaa                                                     1574
```

<210> SEQ ID NO 26
<211> LENGTH: 3700
<212> TYPE: DNA
<213> ORGANISM: Homo sapiens

<400> SEQUENCE: 26

```
agccgccgcc acccgccgcg cccgacaccc gggaggcccc gccagcccgc gggagaggcc    60
cagcgggagt cgcggaacag caggcccgag cccaccgcgc cgggccccgg acgccgcgcg   120
gaaaagatga atttacaacc aattttctgg attggactga tcagttcagt ttgctgtgtg   180
tttgctcaaa cagatgaaaa tagatgttta aaagcaaatg ccaaatcatg tggagaatgt   240
atacaagcag ggccaaattg tgggtggtgc acaaattcaa cattttaca ggaaggaatg    300 cctacttctg cacgatgtga tgatttagaa gccttaaaaa agaagggttg ccctccagat   360
gacatagaaa atcccagagg ctccaaagat ataagaaaa ataaaaatgt aaccaaccgt    420
agcaaaggaa cagcagagaa gctcaagcca gaggatatta ctcagatcca accacagcag   480
ttggttttgc gattaagatc aggggagcca cagacattta cattaaaatt caagagagct   540
gaagactatc ccattgacct ctactacctt atggacctgt cttactcaat gaaagacgat   600
ttggagaatg taaaaagtct tggaacagat ctgatgaatg aaatgaggag gattacttcg   660
gacttcagaa ttggatttgg ctcatttgtg aaaagactg tgatgcctta cattagcaca    720
acaccagcta agctcaggaa cccttgcaca agtgaacaga actgcaccag cccatttagc   780
tacaaaaatg tgctcagtct tactaataaa ggagaagtat ttaatgaact tgttggaaaa   840
cagcgcatat ctggaaattt ggattctcca gaaggtggtt tcgatgccat catgcaagtt   900
gcagtttgtg atcactgat tggctggagg aatgttacac ggctgctggt gttttccaca    960
gatgccgggt ttcactttgc tggagatggg aaacttggtg gcattgtttt accaaatgat  1020
ggacaatgtc acctggaaaa taatatgtac acaatgagcc attattatga ttatccttct  1080
attgctcacc ttgtccagaa actgagtgaa aataatattc agacaatttt tgcagttact  1140
gaagaatttc agcctgttta caaggagctg aaaaacttga tccctaagtc agcagtagga  1200
acattatctg caaattctag caatgtaatt cagttgatca ttgatgcata caattccctt  1260
tcctcagaag tcattttgga aaacggcaaa ttgtcagaag gagtaacaat aagttacaaa  1320
tcttactgca agaacggggt gaatggaaca ggggaaaatg gaagaaaatg ttccaatatt  1380
tccattggag atgaggttca atttgaaatt agcataactt caaataagtg tccaaaaaag  1440
gattctgaca gctttaaaat taggcctctg ggctttacgg aggaagtaga ggttattctt  1500
cagtacatct gtgaatgtga atgccaaagc gaaggcatcc ctgaaagtcc caagtgtcat  1560
gaaggaaatg ggacatttga gtgtggcgcg tgcaggtgca atgaagggcg tgttggtaga  1620
cattgtgaat gcagcacaga tgaagttaac agtgaagaca tggatgctta ctgcaggaaa  1680
gaaaacagtt cagaaatctg cagtaacaat ggagagtgcg tctgcggaca gtgtgtttgt  1740
aggaagaggg ataatacaaa tgaaatttat tctggcaaat tctgcgagtg tgataatttc  1800
aactgtgata gatccaatgg cttaatttgt ggaggaaatg gtgtttgcaa gtgtcgtgtg  1860
tgtgagtgca acccccaacta cactggcagt gcatgtgact gttcttttgga tactagtact  1920 tgtgaagcca gcaacggaca gatctgcaat ggccggggca tctgcgagtg tggtgtctgt  1980
aagtgtacag atccgaagtt tcaagggcaa acgtgtgaga tgtgtcagac ctgccttggt  2040
gtctgtgctg agcataaaga atgtgttcag tgcagagcct tcaataaagg agaaaagaaa  2100
gacacatgca cacaggaatg ttcctatttt aacattacca aggtagaaag tcgggacaaa  2160
ttaccccagc cggtccaacc tgatcctgtg tcccattgta aggagaagga tgttgacgac  2220
tgttggttct attttacgta ttcagtgaat gggaacaacg aggtcatggt tcatgttgtg  2280
gagaatccag agtgtcccac tggtccagac atcattccaa ttgtagctgg tgtggttgct  2340
ggaattgttc ttattggcct tgcattactg ctgatatgga agcttttaat gataattcat  2400
```

| | |
|---|---|
| gacagaaggg agtttgctaa atttgaaaag gagaaaatga atgccaaatg ggacacgggt | 2460 |
| gaaaatccta tttataagag tgccgtaaca actgtggtca atccgaagta tgagggaaaa | 2520 |
| tgagtactgc ccgtgcaaat cccacaacac tgaatgcaaa gtagcaattt ccatagtcac | 2580 |
| agttaggtag ctttagggca atattgccat ggttttactc atgtgcaggt tttgaaaatg | 2640 |
| tacaatatgt ataatttta aaatgtttta ttattttgaa aataatgttg taattcatgc | 2700 |
| cagggactga caaaagactt gagacaggat ggttattctt gtcagctaag gtcacattgt | 2760 |
| gccttttga ccttttcttc ctggactatt gaaatcaagc ttattggatt aagtgatatt | 2820 |
| tctatagcga ttgaaagggc aatagttaaa gtaatgagca tgatgagagt ttctgttaat | 2880 |
| catgtattaa aactgattt tagctttaca aatatgtcag tttgcagtta tgcagaatcc | 2940 |
| aaagtaaatg tcctgctagc tagttaagga ttgttttaaa tctgttattt tgctatttgc | 3000 |
| ctgttagaca tgactgatga catatctgaa agacaagtat gttgagagtt gctggtgtaa | 3060 |
| aatacgtttg aaatagttga tctacaaagg ccatgggaaa aattcagaga gttaggaagg | 3120 |
| aaaaaccaat agctttaaaa cctgtgtgcc attttaagag ttacttaatg tttggtaact | 3180 |
| tttatgcctt cactttacaa attcaagcct tagataaaa aaccgagcaa ttttctgcta | 3240 |
| aaaagtcctt gatttagcac tatttacata caggccatac tttacaaagt atttgctgaa | 3300 |
| tggggacctt ttgagttgaa tttatttat tattttatt ttgtttaatg tctggtgctt | 3360 |
| tctatcacct cttctaatct tttaatgtat ttgtttgcaa ttttggggta agactttttt | 3420 |
| atgagtactt tttcttgaa gttttagcgg tcaatttgcc tttttaatga acatgtgaag | 3480 |
| ttatactgtg gctatgcaac agctctcacc tacgcgagtc ttactttgag ttagtgccat | 3540 |
| aacagaccac tgtatgttta cttctcacca tttgagttgc ccatcttgtt tcacactagt | 3600 |
| cacattcttg tttaagtgc ctttagtttt aacagttcac tttttacagt gctatttact | 3660 |
| gaagttattt attaaatatg cctaaaatac ttaaatcgga | 3700 |

<210> SEQ ID NO 27
<211> LENGTH: 6407
<212> TYPE: DNA
<213> ORGANISM: Homo sapiens

<400> SEQUENCE: 27

| | |
|---|---|
| agtctgcggg cctccggggc tgcggcgagg ccggagcgtc gcggcggaga ggacgagacc | 60 |
| gggacaagac cagggcagga gggagccggc cagccgcgag aaccccgcac gcccggcaag | 120 |
| atgctgtcct tgcggctgca gacgggcccc gagaaggccg agctccagga gctcaacgcc | 180 |
| cggctctatg actacgtgtg tcgggtgcgg gagctggagc gcgaaaacct actcctggag | 240 |
| gaggagctgc gcgccggcg cgggcgagag ggcctgtggg ccgaggggca ggcccgctgc | 300 |
| gccgaggagg cgcgcagctt gcggcagcag ctggacgagc tgagctgggc cactgcgctg | 360 |
| gcggagggcg agcgggacgc tctgcggcgc gagctgcggg agctgcagcg cctggatgcg | 420 |
| gaggagcgcg ccgcccgcgg ccgcctggac gccgagctgg gtgcgcagca gcgcgagctg | 480 |
| caggaggcgc tgggcgcgcg cgccgccctc gaggcgctgc tgggccgact gcaggccgag | 540 |
| cgccgaggcc tcgacgcggc ccacgaacgc gacgtgaggg agctgcgcgc gcgcgccgcc | 600 |
| agccttacca tgcatttccg cgcccgcgcc accggcccg ccgcgccgcc gccacgcctg | 660 |
| cgggaggtgc acgacagcta cgcactgctg gtggccgagt cgtggcggga gacggtgcag | 720 |
| ctgtacgagc acgaggtgcg cgagctggag gaggcgctgc ggcgcggcca ggagagcaga | 780 |
| ctccaggcgg aggaagagac gcggctgtgc gcgcaggagg cagaggcgct gcggcgcgag | 840 |

```
gcgctcgggt tggagcagct gcgcgcgcgg ctggaggacg cgctgctgcg gatgcgcgag    900
gagtacggga tacaggccga ggagcggcag agagtgattg actgcctgga ggatgagaag    960
gcaacccctca ccttggccat ggctgactgg ctgcgggact atcaggacct cctgcaggtg   1020
aagaccggcc tcagtttgga ggtggcgacc taccgggcct tattggaagg agaaagtaat   1080
ccagagatag tgatctgggc tgagcacgtt gaaaacatgc cgtcagaatt cagaaacaaa   1140
tcctatcact ataccgactc actactacag agggaaaatg aaaggaatct attttcaagg   1200
cagaaagcac ctttggcaag tttcaatcac agctcggcac tgtattctaa cctgtcaggg   1260
caccgtggat ctcagacggg cacatctatt ggaggtgatg ccagaagagg cttcttgggc   1320
tcgggatatt cttcctcggc cactacccag caggaaaact catacggaaa agccgtcagc   1380
agtcaaacca acgtcagaac tttctctcca acctatggcc ttttaagaaa tactgaggct   1440
caagtgaaaa cattccctga cagaccaaaa gccggagata caaggaggt ccccgtttac    1500
ataggtgaag attccacaat tgcccgcgag tcgtaccggg atcgccgaga caaggtggca   1560
gcaggtgctt cggaaagcac acggtcaaat gagaggaccg tcattctggg aaagaaaaca   1620
gaagtgaaag ccacgaggga gcaagaaaga aacagaccag aaaccatccg aacaaagcca   1680
gaagagaaaa tgttcgattc taaagagaag gcttccgagg agagaaacct aagatgggaa   1740
gaattgacaa agttagataa ggaagcgaga cagagagaaa gccagcagat gaaggagaag   1800
gctaaggaga aggactcact gaaggagaag agtgtgcgag agagagaggt gccgattagt   1860
ctagaagtat cccaggacag aagagcagag gtgtccccga aaggtttgca gacgcctgtg   1920
aaggatgctg gtggtgggac cggtagagag gcagaagcaa gagagctacg gttcaggttg   1980
ggcaccagtg atgccactgg ttctctgcaa ggcgattcca tgacagaaac cgtagcagaa   2040
aacatcgtta ccagtatcct gaagcagttc actcagtctc cagagacaga agcatctgct   2100
gattcttttc cagacacaaa agtcacttac gtggacagga aagagcttcc tggggaaagg   2160
aaaacaaaga ctgaaatact tgtggagtct aaactgactg aggatgttga tgtttccgat   2220
gaagctggcc tggactacct ttttaagcaag gatattaagg aagtgggggct gaaaggcaag   2280
tcagccgagc agatgatagg agacatcatc aacctcggcc tgaaagggag ggagggagga   2340
gcaaaggtcg tcaacgtgga gatcgtggag gagcccgtga gttatgtcag cggggagaag   2400
ccggaggagt tttccgtccc attcaaagtg gaggaggtcg aagatgtgtc gccaggcccc   2460
tgggggttgg ttaaggagga ggaaggttat ggagaaagcg atgtcacatt ctcagttaat   2520
cagcatcgaa ggaccaagca gcctcaggag aacacgactc acgtggaaga agtgacagag   2580
gcaggtgatt cagagggcga gcagagttat tttgtgtcca ctccagatga acaccccggg   2640
gggcacgaca gagatgacgg ctcggtgtac gggcagatcc acatcgagga ggaatccacc   2700
atcaggtact cttggcagga tgaaatcgtg cagggactc gaaggaggac acagaaggac   2760
ggtgcagtgg gcgagaaggt tgtgaagccc ttggatgtcc cagcgccctc tctggagggg   2820
gacctgggtt ccactcactg gaaagaacaa gctagaagcg gtgaatttca tgccgaaccc   2880
acagtcattg aaaaagaaat taaaataccc cacgaattcc acacctccat gaagggcatc   2940
tcctccaagg agccccggca gcagctggtg gaagtcatcg ggcagctgga ggaaaccctt   3000
cccgagcgca tgggggagga gctgtccgcc ctcaccagag aggggcaggg tgggccgggg   3060
agcgtttccg tggatgtcaa gaaggtccag ggtgctggtg gcagttccgt gaccctggtt   3120
gctgaagtca acgtctcaca aactgtggat gccgatcggt tagacctgga ggaggtgagc   3180
aaagatgagg ccagtgagat ggagaaggct gtggagtcgg tggttcggga gagcctgagc   3240
```

```
aggcaacgca gcccagcgcc tggcagccca gatgaggaag gtggagcgga ggccccggct   3300
gctggcattc gctttaggcg ttgggccacc cgggagctgt acatcccttc aggcgagagc   3360
gaggttgctg gtggggcctc tcacagctcg ggacagcgca ctccccaggg cccagtgtcg   3420
gccactgtgg aggtcagcag ccccacaggc tttgcccagt cacaggtgct ggaggatgtg   3480
agccaggctg caaggcacat aaaactcggc ccctctgaag tctggaggac tgagcgaatg   3540
tcatatgaag gacccactgc agaagtggtg gagatggatg tgagtaacgt agaggcgatc   3600
cgcagccgga cacaggaagc gggagctctc ggtgtgtctg accgtggttc ctggagagac   3660
gcggacagta ggaatgacca ggcagttggt gtgagcttta aggcctctgc tggggaagga   3720
gaccaggccc acagagaaca gggcaaggag caggccatgt ttgataagaa ggtgcagctc   3780
cagagaatgg tagaccaaag gtcggtgatt tcagatgaaa agaaagttgc cctcctctat   3840
ctagacaatg aggaggagga gaatgatggg cattggtttt aataagcaga aacattttgt   3900
tttaatggca gcctgttggc gacgtgccaa catccaaagg ccttaactta ttttaagagg   3960
ccgagggagt ctatgaaaat ctccccttttt ttactttttt aaagagtact cccggcatgg   4020
tcaatttcct ttatagttaa tccgtaaagg tttccagtta attcatgcct taaaaggcac   4080
tgcaatttta tttttgagtt gggactttta caaaacactt ttttccctgg agtcttctct   4140
ccacttctgg agatgaattt ctatgttttg cacctggtca cagacatggc ttgcatctgt   4200
ttgaaactac aattaattat agatgtcaaa acattaacca gattaaagta atatatttaa   4260
gagtaaattt tgcttgcatg tgctaatatg aaataacaga ctaacatttt agggaaaaa   4320 taaatacaat ttagactcta aaaagtcttt tcaaaagaa atgggaaata gcagactgt   4380 ttatgttaaa aaaattcttg ctaaatgatt tcatctttag gaaaaaatta cttgccatat   4440
agagctaaat tcatcttaag acttgaatga attgctttct atgtacagaa ctttaaacaa   4500
tatagtattt atggcgagga cagctgtagt ctgttgtgat atttcacatt ctatttgcac   4560
aggttccctg gcactggtag ggtagatgat tattgggaat cgcttacagt accatttcat   4620
tttttggcac taggtcatta agtagcacac agtctgaatg ccctttttctg gagtggccag   4680 ttcctatcag actgtgcaga cttgcgcttc tctgcacctt atcccttagc acccaaacat   4740
ttaatttcac tggtgggagg tagaccttga agacaatgaa gagaatgccg atactcagac   4800
tgcagctgga ccggcaagct ggctgtgtac aggaaaattg gaagcacaca gtggactgtg   4860
cctcttaaag atgcctttcc caaccctcca ttcatgggat gcaggtcttt ctgagctcaa   4920
gggtgaaaga tgaatacaat aacaaccatg aacccacctc acggaagctt tttttgcact   4980
ttgaacagaa gtcattgcag ttggggtgtt ttgtccaggg aaacagttta ttaaatagaa   5040
ggatgttttg gggaaggaac tggatatctc tcctgcagcc cagcaccgag atacccagga   5100
cgggcctggg gggcgagaaa ggcccccatg ctcatgggcc gcggagtgtg gacctgtaga   5160
taggcaccac cgagtttaag atactgggat gagcatgctt cattggattc attttatttt   5220
acacgtcagt attgttttaa agtttctgtc tgtaaagtgt agcatcatat ataaaaagag   5280
tttcgctagc agcgcatttt ttttagttca ggctagcttc tttcacataa tgctgtctca   5340
gctgtatttc cagtaacaca gcatcatcac actgactgtg gcgcactggg gaataacagt   5400
ctgagctagc accaccctca gccaggctac aacgacagca ctggagggtc ttccctctca   5460
gattcacctg gaggccctca gaccccaggt gtgcacgtct ccccaggtcc tgggagtggc   5520
taccgcaggt agtttctgga gagcacgttt tcttcattga taagtggagg agaaatgcag   5580
cacagctttc aagatactat tttaaaaaca ccatgaatca gataggggaaa gaaagttgat   5640
```

```
tggaatggca agtttaaacc tttgttgtcc atctgccaaa tgaactagtg attgtcagac      5700
tggtatggag gtgactgctt tgtaaggttt tgtcgtttct aatacagaca gagatgtgct      5760
gattttgttt tagctgtaac aggtaatggt ttttggatag atgattgact ggtgagaatt      5820
tggtcaaggt gacagcctcc tgtctgatga caggacagac tggtggtgag gagtctaagt      5880
gggctcagtt tgatgtcagt gtctgggctc atgacttgta aatggaagct gatgtgaaca      5940
ggtaattaat attatgaccc acttctattt actttgggaa atatcttgga tcttaattat      6000
catctgcaag tttcaagaag tattctgcca aaagtattta caagtatgga ctcatgagct      6060
attgttggtt gctaaatgtg aatcacgcgg gagtgagtgt gcccttcaca ctgtgacatt      6120
gtgacattgt gacaagctcc atgtccttta aaatcagtca ctctgcacac aagagaaatc      6180
aacttcgtgg ttggatgggg ccggaacaca accagtcttt tgtatttat tgttactgag       6240 acaaaacagt actcactgag tgttttcag tttcctactg gtggttttga tattgtttgt       6300
ttaagatgta tatttagaat gacatcatct aagaagctga ttttgctaaa ctcctgttcc      6360
ctacaatggg aaatgtcaca agaatgtgca aaaataaaaa tctgagg                    6407

<210> SEQ ID NO 28
<211> LENGTH: 1295
<212> TYPE: DNA
<213> ORGANISM: Homo sapiens

<400> SEQUENCE: 28
cacgtcagcc ggggctagaa aaggcggcgg ggctgggccc agcgaggtga cagcctcgct        60
tggacgcaga gcccggcccg acgccgccat gagcgccgcg ctcttcagcc tggacggccc       120
ggcgcgcggc gcgcccctgg ctgcggagcc tgcgccttc tacgaaccgg gccgggcggg       180
caagccgggc cgcggggccg agccaggggc cctaggcgag ccaggcgccg ccgccccgc       240 catgtacgac gacgagagcg ccatcgactt cagcgcctac atcgactcca tggccgccgt       300
gcccaccctg gagctgtgcc acgacgagct cttcgccgac ctcttcaaca gcaatcacaa       360
ggcgggcggc gcggggcccc tggagcttct tcccggcggc cccgcgcgcc ccttgggccc       420
gggccctgcc gctccccgcc tgctcaagcg cgagcccgac tggggcgacg gcgacgcgcc       480
cggctcgctg ttgcccgcgc aggtggccgc gtgcgcacag accgtggtga gcttggcggc       540
cgcagggcag cccaccccgc ccacgtcgcc ggagccgccg cgcagcagcc ccaggcagac       600
ccccgcgccc ggccccgccc gggagaagag cgccggcaag aggggccggg accgcggcag       660
ccccgagtac cggcagcggc gcgagcgcaa caacatcgcc gtgcgcaaga gccgcgacaa       720
ggccaagcgg cgcaaccagg agatgcagca gaagttggtg gagctgtcgg ctgagaacga       780
gaagctgcac cagcgcgtgg agcagctcac gcgggacctg gccggcctcc ggcagttctt       840
caagcagctg cccagcccgc ccttcctgcc ggccgccggg acagcagact gccgtaacg       900 cgcggccggg gcgggagaga ctcagcaacg acccataccct cagacccgac ggcccggagc       960
ggagcgcgcc ctgccctggc gcagccagag ccgccgggtg cccgctgcag tttcttggga      1020
cataggagcg caaagaagct acagcctgga cttaccacca ctaaactgcg agagaagcta      1080
aacgtgttta ttttcccta aattattttt gtaatggtag cttttctac atcttactcc       1140 tgttgatgca gctaaggtac atttgtaaaa agaaaaaaaa ccagactttt cagacaaacc      1200
ctttgtattg tagataagag gaaaagactg agcatgctca ctttttata ttaattttta      1260 cagtatttgt aagaataaag cagcatttga aatcg                                 1295
```

<210> SEQ ID NO 29
<211> LENGTH: 1526
<212> TYPE: DNA
<213> ORGANISM: Homo sapiens

<400> SEQUENCE: 29

```
ggccactgct caccatgcac ataacccagc tcaaccggga gtgcctgctg cacctcttct      60
ccttcctaga caaggacagc aggaagagcc ttgccaggac ctgctcccag ctccacgacg     120
tgtttgagga ccccgcactc tggtccctgc tgcacttccg ttccctcact gaactccaga     180
aggacaactt cctcctgggc ccggcactcc gcagcctctc catctgctgg cactccagcc     240
gcgtgcaggt gtgcagcatt gaggactggc tcaagagtgc cttccagaga agcatctgca     300
gccggcacga gagcctggtc aatgatttcc tcctccgggt gtgcgacagg ctttctgctg     360
tgcgctcccc acggaggcgg gaggcgcctg caccgtcctc ggggactccg atcgccgttg     420
gaccgaaatc acctcggtgg ggaggacctg accactcgga gttcgccgac ttgcgctcgg     480
gggtgacggg ggccagggct gccgcgcgca ggggtctggg gagcctccgg gcggagcgac     540
ccagcgagac cccgccggct cccggagtgt cctggggacc gccacctcca ggagccccgg     600
tggtgatctc ggtgaagcag gaggagggga gcaggggcg cacgggcaga aggagccacc     660
gagccgctcc tccttgcggt tttgcccgca cgcgcgtctg cccgcccacc tttcctgggg     720
cggatgcgtt cccgcagtga ccgcactcgc gattgtagaa aattcgctcc caattgttga     780
atgcttacat aaactgcata gttacccata ttttctactg ttctcataag ggaaaaagaa     840
atgatttgga agaaaaaaaa agcctcaaac taaacaaaaa caaaccagc agccctggct     900
aagcttttga taatggaacc attataagct gacaagctag attttcacc tgttggattt     960
gctggacatg agcacaagcc taggcttcca atttgaattt cagggctgta gtcactgatg    1020
tgtcacattt agtgaaggct ctcggcccc cggcagccgc ctggtcctgg gtcactgggg    1080
agaattctgg gtgggtggaa gaggcgagga gcactgtgat gggcgctgtt cacactccgg    1140
ctccacccag cgccagctgc gacaaagccc tttacccctc ccaggccagg tgtttcttct    1200
gtgtgaaaga ggagcttgat ccctactcac aggttcctta attcattgct caaagaggga    1260
aacagcaagg aaaaagacaa attctgttct catgaagctt accttctagt gggggaagag    1320
acaacaggta actggtatat aagagggtag aagggccagg tgcggtggct caatgcctgt    1380
aatcccagca ctttaggagg ccaagatggg cgattcacga ggtcaggaga tcgagaccat    1440
cctggctaac aaggtgaaac ccccgtctgt actaaaaaaa aaaaaaaaa aaaaaaaaa    1500
aaaaaaaaa aaaaaaaaa aaaaaa                                           1526
```

<210> SEQ ID NO 30
<211> LENGTH: 1353
<212> TYPE: DNA
<213> ORGANISM: Homo sapiens

<400> SEQUENCE: 30

```
atgcgggaga tcgtgcacat ccaggccggc cagtgcggca accagatcgg ggccaagttc      60
tgggaagtca tcagtgatga gcatggcatc gaccccagcg gcaactacgt gggcgactcg     120
gacttgcagc tggagcggat cagcgtctac tacaacgagg cctcttctca caagtacgtg     180
cctcgagcca ttctggtgga cctggaaccc ggaaccatgg acagtgtccg ctcagggggcc     240
tttggacatc tcttcaggcc tgacaatttc atctttggtc agagtggggc cggcaacaac     300
tgggccaagg tcactacac ggaggggcg gagctggtgg attcggtcct ggatgtggtg     360
cggaaggagt gtgaaaactg cgactgcctg caggggcttcc agctgaccca ctcgctgggg     420
```

```
ggcggcacgg gctccggcat gggcacgttg ctcatcagca aggtgcgtga ggagtatccc    480
gaccgcatca tgaacacctt cagcgtcgtg ccctcaccca aggtgtcaga cacggtggtg    540
gagccctaca acgccacgct gtccatccac cagctggtgg agaacacgga tgagacctac    600
tgcatcgaca acgaggcgct ctacgacatc tgcttccgca ccctcaagct ggccacgccc    660
acctacgggg acctcaacca cctggtatcg gccaccatga gcggagtcac cacctccttg    720
cgcttcccgg gccagctcaa cgctgacctg cgcaagctgg ccgtcaacat ggtgcccttc    780
ccgcgcctgc acttcttcat gcccggcttc gccccccctca gcccggggg cagccagcag    840 taccgggccc tgaccgtgcc cgagctcacc cagcagatgt tcgatgccaa gaacatgatg    900
gccgcctgcg acccgcgcca cggccgctac ctgacggtgg ccaccgtgtt ccggggccgc    960
atgtccatga aggaggtgga cgagcagatg ctggccatcc agagcaagaa cagcagctac   1020
ttcgtggagt ggatccccaa caacgtgaag gtggccgtgt gtgacatccc gccccgcggc   1080
ctcaagatgt cctccacctt catcgggaac agcacggcca tccaggagct gttcaagcgc   1140
atctccgagc agttcacggc catgttccgg cgcaaggcct tcctgcactg gtacacgggc   1200
gagggcatgg acgagatgga gttcaccgag gccgagagca catgaacga cctggtgtcc   1260 gagtaccagc agtaccagga cgccacggcc gaggaagagg gcgagatgta cgaagacgac   1320
gaggaggagt cggaggccca gggccccaag tga                                1353

<210> SEQ ID NO 31
<211> LENGTH: 2853
<212> TYPE: DNA
<213> ORGANISM: Homo sapiens

<400> SEQUENCE: 31
gctctgctcc aggcatctgc cacaatgtgg gtgcttacac ctgctgcttt gctgggaag     60 ctcttgagtg tgttcaggca acctctgagc tctctgtgga ggagcctggt cccgctgttc    120
tgctggctga gggcaacctt ctggctgcta gctaccaaga ggagaaagca gcagctggtc    180
ctgagagggc cagatgagac caaagaggag gaagaggacc ctcctctgcc caccaccccca   240 accagcgtca actatcactt cactcgccag tgcaactaca aatgcggctt ctgtttccac    300
acagccaaaa catcctttgt gctgccccct gaggaagcaa agagaggatt gcttttgctt    360
aaggaagctg gtatggagaa gatcaacttt tcaggtggag agccatttct tcaagaccgg    420
ggagaatacc tgggcaagtt ggtgaggttc tgcaaagtag agttgcggct gcccagcgtg    480
agcatcgtga gcaatggaag cctgatccgg gagaggtggt tccagaatta tggtgagtat    540
ttggacattc tcgctatctc ctgtgacagc tttgacgagg aagtcaatgt ccttattggc    600
cgtggccaag gaaagaagaa ccatgtggaa aaccttcaaa agctgaggag gtggtgtagg    660
gattatagag tcgctttcaa gataaattct gtcattaatc gtttcaacgt ggaagaggac    720
atgacggaac agatcaaagc actaaaccct gtccgctgga agtgttccag tgcctcctta    780
attgagggtg agaattgtgg agaagatgct ctaagagaag cagaaagatt tgttattggt    840
gatgaagaat ttgaaagatt cttggagcgc acaaagaag tgtcctgctt ggtgcctgaa    900
tctaaccaga agatgaaaga ctcctacctt attctggatg aatatatgcg ctttctgaac    960
tgtagaaagg gacggaagga cccttccaag tccatcctgg atgttggtgt agaagaagct   1020
ataaaattca gtggatttga tgaaaagatg tttctgaagc gaggaggaaa atacatatgg   1080
agtaaggctg atctgaagct ggattggtag agcggaaagt ggaacgagac ttcaacacac   1140
cagtgggaaa actcctagag taactgccat tgtctgcaat actatcccgt tggtatttcc   1200
```

```
cagtggctga aaacctgatt ttctgctgca cgtggcatct gattacctgt ggtcactgaa    1260
cacacgaata acttggatag caaatcctga gacaatggaa aaccattaac tttacttcat    1320
tggcttataa ccttgttgtt attgaaacag cacttctgtt tttgagtttg ttttagctaa    1380
aaagaaggaa tacacacagg aataatgacc ccaaaaatgc ttagataagg cccctataca    1440
caggacctga catttagctc aatgatgcgt ttgtaagaaa taagctctag tgatatctgt    1500
gggggcaaaa tttaatttgg atttgatttt ttaaaacaat gtttactgcg atttctatat    1560
ttccattttg aaactatttc ttgttccagg tttgttcatt tgacagagtc agtatttttt    1620
gccaaatatc cagataacca gttttcacat ctgagacatt acaaagtatc tgcctcaatt    1680
atttctgctg gttataatgc ttttttttt ttgcctttat gccattgcag tcttgtactt    1740
tttactgtga tgtacagaaa tagtcaacag atgtttccaa gaacatatga tatgataatc    1800
ctaccaattt tcaagaagtc tctagaaaga gataacacat ggaagacgg cgtggtgcag    1860 cccagcccac ggtgcctgtt ccatgaatgc tggctaccta tgtgtgtggt acctgttgtg    1920 tcccttctc ttcaaagatc cctgagcaaa acaaagatac gctttccatt tgatgatgga    1980
gttgacatgg aggcagtgct tgcattgctt tgttcgccta tcatctggcc acatgaggct    2040
gtcaagcaaa agaataggag tgtagttgag tagctggttg gccctacatt tctgagaagt    2100
gacgttacac tgggttggca taagatatcc taaaatcacg ctggaacctt gggcaaggaa    2160
gaatgtgagc aagagtagag agagtgcctg gatttcatgt cagtgaagcc atgtcaccat    2220
atcatatttt tgaatgaact ctgagtcagt tgaaataggg taccatctag gtcagtttaa    2280
gaagagtcag ctcagagaaa gcaagcataa gggaaaatgt cacgtaaact agatcaggga    2340
acaaaatcct ctccttgtgg aaatatccca tgcagtttgt tgatacaact tagtatctta    2400
ttgcctaaaa aaaaatttct tatcattgtt tcaaaaaagc aaaatcatgg aaaattttg    2460 ttgtccaggc aaataaaagg tcattttaat ttaaaaaaaa aaaaaaaaa aaaaaaaaa    2520 aaaaggccaa ggaaaaaaaa tattcctact taaattttaa gtctataatt caatttaaat    2580
atgtgtgtgt ctcatccagg ataggatagg ttgtcttcta ttttccattt tacctattta    2640
ctttttttgt aagaaaagag aagaatgaat tctaaagatg ttccccatgg gttttgattg    2700
tgtctaagct atgatgacct tcatataatc agcataaaca taaaacaaat ttttacttta    2760
acatgagtgc actttactaa tcctcatggc acagtggctc acgcctgtaa tcccagcact    2820
tggggaggac aatgtggggt ggatcacgag gtc                                 2853
```

<210> SEQ ID NO 32  
<211> LENGTH: 6853  
<212> TYPE: DNA  
<213> ORGANISM: Homo sapiens

<400> SEQUENCE: 32

```
atacatagac ttccgttaaa accagaatga ggaaaatact tttctctagc atcgtaggag      60
gaagaaaaca aacacatcag atattttcag cactaaaaga gatggttttc cccacatata     120
tgtaaaagaa atttgcaaga ctactggatt ttgatctcat ggttgcagtg ggtgaatagg     180
tggccttttg tgatctccta catcaccctg gaagtgagac ttcttcggtt tcttctagag     240
tcagtttggt atcagaatgg caaagcaact taaccttcca gaaaatacag atgattggac     300
aaaagaggat gtaaatcagt ggttagaaag tcataagatt gaccaaaaac acagggaaat     360
tttgactgaa caagacgtga atggagcagt cttgaagtgg ttaaaaaaag aacatcttgt     420
tgatatgggc atcacacatg gaccagctat tcaaatagaa gaactattca aagaattgcg     480
```

```
gaaaacagcc attgaagatt cgattcagac atctaagatg ggaaagccca gtaaaaatgc    540
tcctaaagac caaactgtgt ctcaaaagga acgtagagaa acttcaaagc aaaaacaaaa    600
gggtaaagag aacccagata tggctaatcc gtctgcaatg agtacaactg ctaaaggttc    660
taagtcacta aaagttgagc tcatagaaga taaaatagat tatacaaagg aaaggcaacc    720
atccatagac ctgacatgtg tatcatatcc atttgatgaa ttcagtaatc catatcgtta    780
caagttggat tttagtctac agcctgaaac aggaccaggc aatctcattg atccgataca    840
tgaattcaaa gccttcacaa atacagcaac agccacagaa gaggatgtca agatgaaatt    900
tagcaatgag gttttccgat ttgcttcagc ttgtatgaat tcacgtacca atggcactat    960
tcattttgga gtcaaagaca aaccccatgg gaaaattgtt ggcatcaaag tcaccaatga   1020
taccaaggaa gccctcatta accatttcaa tctgatgata aacaagtatt ttgaagacca   1080
tcaagtccaa caagcaaaga agtgcattcg agagccaaga tttgtggaag ttttactgcc   1140
aaatagtact ctatctgaca gatttgttat tgaagtggac attattccac agttctctga   1200
atgccaatat gattatttcc agattaaaat gcaaaattac aacaacaaaa tatgggaaca   1260
aagtaaaaaa ttctcactat ttgtgcgaga tgggaccagc tctaaggaca ttacgaaaaa   1320
taaagttgat ttcagagcat taaaagcaga ttttaaaaca ctggcagagt ccagaaaagc   1380
agcagaagaa aaattcagag caaaaacaaa taaaaaagaa agagagggac caaagttggt   1440
taaattattg acaggaaatc aagatttgtt agataattca tactatgaac agtacattct   1500
tgtaacaaat aaatgccacc cagatcaaac aaaaacactta gatttcctga aggaaattaa   1560 atggttttgct gtattggagt ttgatcctga gtctaacatc aatggagtgg tcaaagctta   1620
caaagaaagc cgagtagcaa accttcactt tccaagtgta tatgtagaac agaaaaccac   1680
accaaatgag acgatttcta ctctaaatct ttaccatcaa cccagctgga ttttctgcaa   1740
tggcaggtta gaccttgaca gtgaaaaata taaacccttt gatccaagtt cctggcaaag   1800
agaaagagct tctgatgtca ggaaactgat ttcatttctt acacatgaag acataatgcc   1860
aagagggaag ttttttggtgg tatttctatt actgtcctct gtggatgacc aagagatcc   1920 cctcattgag actttctgtg ctttctacca ggatctcaaa ggaatggaaa atatactgtg   1980
tatttgtgtg cacccacaca tatttcaggg atggaaagat ctacttgaag caagattaat   2040
aaaacaccaa gatgaaattt caagccaatg tatttctgct ttaagccttg aagagatcaa   2100
tggcactatt cttaaactaa aatctgtgac tcaatcttca aaaaggcttt tgccatctat   2160
tggtttatcg actgtccttc tgaaaaagga agaagatatc atgactgctc tggaaattat   2220
ctgtgaaaat gaatgtgagg gtacactgtt agagaaggac aaaaataaat tccttgaatt   2280
caaggcatca aagaggaag acttctatcg aggtggcaaa gtgtcatggt ggaacttcta   2340
cttctcttct gaaagttatt cttcacctttt tgtcaaaagg ataaatatg aaagacttga   2400 agcaatgatt caaaactgtg cagattcttc taaaccaaca agtaccaaaa ttattcatct   2460
gtatcatcat ccaggctgtg ggggaactac cttggctatg cacattctct gggaactaag   2520
gaagaaattc agatgtgctg tgctgaaaaa caagacagtg gattttctg aaattggaga   2580 acaggtaacc agtttaatca cctatggggc aatgaaccgt caggaatacg tacctgtact   2640
actccttgtt gatgattttg aagaacaaga taatgtctat cttctgcagt actctattca   2700
aacagctata gctaaaaagt acattcgata tgaaaaacct ctggtgatta tcctaaattg   2760
tatgagatca caaaatcctg aaaaaagtgc aaggatccca gacagtattg ccgtaataca   2820
gcaactctct cccaaagaac agagagcttt tgagcttaaa ttgaaagaaa tcaaagaaca   2880
```

```
gcataaaaac tttgaggatt tttattcctt tatgatcatg aaaaccaatt ttaataaaga    2940
atacatagaa aatgtggtcc ggaatatcct gaaagggcag aatattttca ccaaggaagc    3000
aaagctcttt tcttttctgg ctcttcttaa ttcatatgtg cctgatacca ccatttcact    3060
atcacagtgt gaaaaattct taggaattgg aaacaagaag gctttctggg ggacagaaaa    3120
atttgaagac aagatgggca cctactctac aattctgata aaaacagagg tcatcgaatg    3180
tgggaactac tgtggagtac gcatcattca ctctttgatt gcagagttct cactggaaga    3240
attgaagaaa agctatcacc tgaataaaag tcaaattatg ttggatatgc taactgagaa    3300
tttgttcttc gatactggta tgggaaaaag taaattttg caagatatgc acacactcct    3360
actcacaaga caccgcgatg aacatgaagg tgaaacagga aattggtttt ccccatttat    3420
tgaagcatta cataaagatg aaggaaatga agcagttgaa gctgtattgc ttgaaagtat    3480
ccatcggttc aacccaaatg cattcatttg ccaagcgttg gcaagacatt tctacattaa    3540
aaagaaggac tttggcaatg ctctaaactg gcaaaacaa gcaaaatca tagaacctga    3600 caattcttat atctcagata cactgggtca gtctacaaa agtaaaataa gatggtggat    3660
agaggaaaac ggaggaaacg ggaacatttc agttgatgat ctaattgctc ttttggattt    3720
agcagaacat gcctcaagtg cattcaaaga atctcaacag caaagtgaag atagagagta    3780
tgaagtgaag gaaagattgt atccgaagtc aaaaaggcgg tatgatactt acaatatagc    3840
tggttatcaa ggagagatag aagttgggct ttacacaatc caaattctcc agctcattcc    3900 ttttttttgat aataaaaatg agctatctaa aagatatatg gtcaattttg tatcaggaag    3960
tagtgatatt ccaggggatc aaacaatga atataaatta gccctcaaaa actatattcc    4020
ttatttaact aaattgaaat tttctttgaa aaagtccttt gatttttttg atgaatactt    4080
tgtcctgcta aaacccagga acaatattaa gcaaaatgaa gaggccaaaa ctcggagaaa    4140
ggtggctgga tattttaaga aatatgtaga tatattttgt ctcttagaag aatcacaaaa    4200
caacacaggt cttggatcaa agttcagtga gccacttcaa gtagagagat gcaggagaaa    4260
cctagtagct ttaaaagcag acaagttttc tgggctcttg gaatatctta tcaaaagtca    4320
agaggatgct ataagcacta tgaaatgtat agtgaacgaa tatacttttc tcttagaaca    4380
atgcactgtc aaaatccagt caaaagaaaa gctaaatttc atcttggcca acattattct    4440
ctcctgtatc caacctacct ccagattagt aaagccagtt gaaaaactaa aagatcagct    4500
tcgagaagtc ttgcaaccaa taggactgac ttatcagttt tcagaaccgt attttctagc    4560
ttccctctta ttctggccag aaaatcaaca actagatcaa cattctgaac aaatgaaaga    4620
gtatgctcaa gcactaaaaa attctttcaa ggggcaatat aaacatatgc atcgtacaaa    4680
gcaaccaatt gcatatttct ttcttggaaa aggtaaaaga ctggaaagac ttgttcacaa    4740
aggaaaaatt gaccagtgct ttaagaagac accagatatt aattccttgt ggcagagtgg    4800
agatgtgtgg aaggaggaaa aagtccaaga acttttgctt cgtttacaag gtcgagctga    4860
aaacaattgt ttatatatag aatatggaat caatgaaaaa atcacaatac ccatcactcc    4920
cgctttttta ggtcaactta gaagtggcag aagcatagag aaggtgtctt tttacctggg    4980
attttccatt ggaggcccac ttgcttatga cattgaaatt gtttaagagc ctgatattct    5040
tcctccaaga atttgatctc agtacccatt taatttttt ggactcaaga tctatgcttt    5100
aaaccggcaa ggttatagat acagcctcta gctcttcaga tctgtacatg cagtatttaa    5160
tttcctctta aacatgttat gagttctaca aagacaatag tgaaaagga aggagtgaga    5220 tatatgaaaa gtagcaaata tgttccttgg tttggttaac atcattgatg acaaaataat    5280
```

```
aaggagctat gactggagtc aggagaagtt agtgtaataa gctggctaca cagaacccca      5340
ctacttacca ggcatggatt gaagaagatt gtctactcaa atggcattta gacattagaa      5400
tgtctgggaa atatttctc aaagacagca aaaacctctc aaactgagga gcaacattta       5460
ttcttactaa gcagatcatc aatgtatcat gtgcttggca ctcaaggatc ttccaaaaca      5520
gaggaccaac cagtcttctg aaggtcatgc ccacagaagt catcagacct taccaaagta      5580
ggttggagaa ttagattgcc ttttcatgca gtgagattca gttaagcaaa atgaaatt       5640 gtctctatag ctaattagct tatcaactcc cctccaaaca aacaattaaa aaaaaaacat      5700
acagacactc aaattccaca agctaatgaa caaaagggac tcttgtgaga agactaatga     5760
gtccctcatc cagaagatgc caatgtactg gcagattaac atacaaccta tgttttgaac     5820
aaaaacaacc agcgatacgt aatcaaaatg taattttccc ctaataaaat tatgatatg      5880 ggcagtcatc aatggctgcc aaaaccatta agtggaaagc tgattaaaaa acaaaaattt     5940
ctaatggatt tatcaaactg tcccaaatcc tgataaatat taacatcaca gaggaagacc     6000
agacattatg ggcctggaag tactatagga gtgcacacat cacccgtgac atggtcttgc     6060
caaataatta aacctgaatt tgatcaggtc tctggatctt atttgcaatt caaagaaat     6120 tttaaaaaaa tcctactaac accaccacaa atatgcaatc agcaatatcc agaaggga     6180 aattcacagg acaaaaacct ggttttcttt tttggtttct tcaaccaaaa aagaaagaaa    6240
ttgcaaagga ccaaaaaaat gttggggaat ctatacatta aagggactt aacaactaaa    6300 gggcaacata tagactttag atcctaattt gagcaaaatc taaaatcaat tattaggcaa    6360
tcagaaaaat ttgaacacag actagatatt tgaggatat aaggtactat attattgaag    6420
attccatggt tatgttttt aaagagttca tgccttttag agatacatac taagtatt     6480 gtaaataaat gacatgatct agaatcagta attttgtgtt tggggtgtgg gggtggtgaa    6540
agggaagtag aaccgaaaca agattagtcc tgagttaaca atggctgcaa gctggataca    6600
tggaattcag cacacttttc tccctcttac tgattatgct tttgaaattt tctcttgtaa    6660
aacatttaga aaacaaaaac aaaaaaaatg tgatttgttt ctgtcttcaa aatctcatta    6720 gaatttttc actggaggaa gattttccct tgcttctgca taaaatttta actccataac    6780
ttataagctc actctttatt gttactttct aattgacaaa taaaaattgt atattaaaaa    6840
aaaaaaaaaa aaa                                                        6853

<210> SEQ ID NO 33
<211> LENGTH: 672
<212> TYPE: DNA
<213> ORGANISM: Homo sapiens

<400> SEQUENCE: 33
aacacatcca agcttaagac ggtgaggtca gcttcacatt ctcaggaact ctccttcttt       60
gggtctggct gaagttgagg atctcttact ctctaggcca cggaattaac ccgagcaggc      120
atggaggcct ctgctctcac ctcatcagca gtgaccagtg tggccaaagt ggtcagggtg      180
gcctctggct ctgccgtagt tttgcccctg gccaggattg ctacagttgt gattggagga      240
gttgtggcca tggcggctgt gcccatggtg ctcagtgcca tgggcttcac tgcggcggga      300
atcgcctcgt cctccatagc agccaagatg atgtccgcgg cggccattgc caatgggggt      360
ggagttgcct cgggcagcct tgtggctact ctgcagtcac tgggagcaac tggactctcc      420
ggattgacca agttcatcct gggctccatt gggtctgcca ttgcggctgt cattgcgagg      480
ttctactagc tccctgcccc tcgccctgca gagaagagaa ccatgccagg ggagaaggca      540
```

```
cccagccatc ctgacccagc gaggagccaa ctatcccaaa tatacctggg gtgaaatata    600
ccaaattctg catctccaga ggaaaataag aaataaagat gaattgttgc aactcttaaa    660
aaaaaaaaaa aa                                                        672
```

<210> SEQ ID NO 34
<211> LENGTH: 469
<212> TYPE: PRT
<213> ORGANISM: Homo sapiens

<400> SEQUENCE: 34

```
Met Ser Gln Ala Tyr Ser Ser Gln Arg Val Ser Tyr Arg Arg
  1               5                  10                  15

Thr Phe Gly Gly Ala Pro Val Phe Pro Leu Gly Ser Pro Leu Ser Ser
                 20                  25                  30

Pro Val Phe Pro Arg Ala Pro Phe Gly Ser Lys Gly Ser Ser Ser
                 35                  40                  45

Val Thr Ser Arg Val Tyr Gln Val Ser Arg Thr Ser Gly Gly Ala Gly
         50                  55                  60

Gly Leu Gly Ser Leu Arg Ala Ser Arg Leu Gly Thr Thr Arg Thr Pro
 65                  70                  75                  80

Ser Ser Tyr Gly Ala Gly Glu Leu Leu Asp Phe Ser Leu Ala Asp Ala
                 85                  90                  95

Val Asn Gln Glu Phe Leu Thr Thr Arg Thr Asn Glu Lys Val Glu Leu
                100                 105                 110

Gln Glu Leu Asn Asp Arg Ser Pro Ile Tyr Met Glu Lys Val Arg Phe
                115                 120                 125

Leu Glu Gln Gln Asn Ala Leu Ala Ala Glu Val Asn Arg Leu Lys Gly
            130                 135                 140

Arg Glu Pro Thr Arg Val Ala Glu Leu Tyr Glu Glu Leu Arg Glu
145                 150                 155                 160

Leu Arg Arg Gln Val Glu Val Leu Thr Asn Gln Arg Ala Arg Val Asp
                165                 170                 175

Val Glu Arg Asp Asn Leu Leu Asp Asp Leu Gln Arg Leu Lys Ala Lys
                180                 185                 190

Leu Gln Glu Glu Ile Gln Leu Lys Glu Glu Ala Glu Asn Asn Leu Ala
            195                 200                 205

Ala Phe Arg Ala Asp Val Asp Ala Ala Thr Leu Ala Arg Ile Asp Leu
        210                 215                 220

Glu Arg Arg Ile Glu Ser Leu Asn Glu Glu Ile Ala Phe Leu Lys Lys
225                 230                 235                 240

Val His Glu Glu Glu Ile Arg Glu Leu Gln Ala Gln Leu Gln Glu Gln
                245                 250                 255

Gln Val Gln Val Glu Met Asp Met Ser Lys Pro Asp Leu Thr Ala Ala
                260                 265                 270

Leu Arg Asp Ile Arg Ala Gln Tyr Glu Thr Ile Ala Ala Lys Asn Ile
            275                 280                 285

Ser Glu Ala Glu Glu Trp Tyr Lys Ser Lys Val Ser Asp Leu Thr Gln
        290                 295                 300

Ala Ala Asn Lys Asn Asn Asp Ala Leu Arg Gln Ala Lys Gln Glu Met
305                 310                 315                 320

Met Glu Tyr Arg His Gln Ile Gln Ser Tyr Thr Cys Glu Ile Asp Ala
                325                 330                 335

Leu Lys Gly Thr Asn Asp Ser Leu Met Arg Gln Met Arg Glu Leu Glu
                340                 345                 350
```

```
Asp Arg Phe Ala Ser Glu Ala Ser Gly Tyr Gln Asp Asn Ile Ala Arg
            355                 360                 365

Leu Glu Glu Glu Ile Arg His Leu Lys Asp Glu Met Ala Arg His Leu
        370                 375                 380

Arg Glu Tyr Gln Asp Leu Leu Asn Val Lys Met Ala Leu Asp Val Glu
385                 390                 395                 400

Ile Ala Thr Tyr Arg Lys Leu Leu Glu Gly Glu Glu Ser Arg Ile Asn
                405                 410                 415

Leu Pro Ile Gln Thr Tyr Ser Ala Leu Asn Phe Arg Glu Thr Ser Pro
            420                 425                 430

Glu Gln Arg Gly Ser Glu Val His Thr Lys Lys Thr Val Met Ile Lys
        435                 440                 445

Thr Ile Glu Thr Arg Asp Gly Glu Val Val Ser Glu Ala Thr Gln Gln
    450                 455                 460

Gln His Glu Val Leu
465

<210> SEQ ID NO 35
<211> LENGTH: 62
<212> TYPE: PRT
<213> ORGANISM: Homo sapiens

<400> SEQUENCE: 35

Met Ser Glu Arg Gln Gly Ala Gly Ala Thr Asn Gly Lys Asp Lys Thr
1               5                   10                  15

Ser Gly Glu Asn Asp Gly Gln Lys Lys Val Gln Glu Glu Phe Asp Ile
            20                  25                  30

Asp Met Asp Ala Pro Glu Thr Glu Arg Ala Ala Val Ala Ile Gln Ser
        35                  40                  45

Gln Phe Arg Lys Phe Gln Lys Lys Lys Ala Gly Ser Gln Ser
    50                  55                  60

<210> SEQ ID NO 36
<211> LENGTH: 328
<212> TYPE: PRT
<213> ORGANISM: Homo sapiens

<400> SEQUENCE: 36

Met Leu Pro Arg Val Gly Cys Pro Ala Leu Pro Leu Pro Pro Pro Pro
1               5                   10                  15

Leu Leu Pro Leu Leu Pro Leu Leu Leu Leu Leu Gly Ala Ser Gly Gly
            20                  25                  30

Gly Gly Gly Gly Ala Arg Ala Glu Val Leu Phe Arg Cys Pro Pro Cys
        35                  40                  45

Thr Pro Glu Arg Leu Ala Ala Cys Gly Pro Pro Pro Val Ala Pro Pro
    50                  55                  60

Ala Ala Val Ala Ala Val Ala Gly Gly Ala Arg Met Pro Cys Ala Glu
65                  70                  75                  80

Leu Val Arg Glu Pro Gly Cys Gly Cys Cys Ser Val Cys Ala Arg Leu
            85                  90                  95

Glu Gly Glu Ala Cys Gly Val Tyr Thr Pro Arg Cys Gly Gln Gly Leu
        100                 105                 110

Arg Cys Tyr Pro His Pro Gly Ser Glu Leu Pro Leu Gln Ala Leu Val
    115                 120                 125

Met Gly Glu Gly Thr Cys Glu Lys Arg Arg Asp Ala Glu Tyr Gly Ala
130                 135                 140
```

```
Ser Pro Glu Gln Val Ala Asp Asn Gly Asp Asp His Ser Glu Gly Gly
145                 150                 155                 160

Leu Val Glu Asn His Val Asp Ser Thr Met Asn Met Leu Gly Gly Gly
                165                 170                 175

Gly Ser Ala Gly Arg Lys Pro Leu Lys Ser Gly Met Lys Glu Leu Ala
            180                 185                 190

Val Phe Arg Glu Lys Val Thr Glu Gln His Arg Gln Met Gly Lys Gly
        195                 200                 205

Gly Lys His His Leu Gly Leu Glu Pro Lys Lys Leu Arg Pro Pro
    210                 215                 220

Pro Ala Arg Thr Pro Cys Gln Gln Glu Leu Asp Gln Val Leu Glu Arg
225                 230                 235                 240

Ile Ser Thr Met Arg Leu Pro Asp Glu Arg Gly Pro Leu Glu His Leu
                245                 250                 255

Tyr Ser Leu His Ile Pro Asn Cys Asp Lys His Gly Leu Tyr Asn Leu
                260                 265                 270

Lys Gln Cys Lys Met Ser Leu Asn Gly Gln Arg Gly Glu Cys Trp Cys
            275                 280                 285

Val Asn Pro Asn Thr Gly Lys Leu Ile Gln Gly Ala Pro Thr Ile Arg
        290                 295                 300

Gly Asp Pro Glu Cys His Leu Phe Tyr Asn Glu Gln Gln Glu Ala Cys
305                 310                 315                 320

Gly Val His Thr Gln Arg Met Gln
                325

<210> SEQ ID NO 37
<211> LENGTH: 967
<212> TYPE: PRT
<213> ORGANISM: Homo sapiens

<400> SEQUENCE: 37

Met Gln Arg Ala Val Pro Glu Gly Phe Gly Arg Lys Leu Gly Ser
 1               5                  10                  15

Asp Met Gly Asn Ala Glu Arg Ala Pro Gly Ser Arg Ser Phe Gly Pro
                20                  25                  30

Val Pro Thr Leu Leu Leu Ala Ala Ala Leu Leu Ala Val Ser Asp
                35                  40                  45

Ala Leu Gly Arg Pro Ser Glu Glu Asp Glu Glu Leu Val Val Pro Glu
    50                  55                  60

Leu Glu Arg Ala Pro Gly His Gly Thr Thr Arg Leu Arg Leu His Ala
65                  70                  75                  80

Phe Asp Gln Gln Leu Asp Leu Glu Leu Arg Pro Asp Ser Ser Phe Leu
                85                  90                  95

Ala Pro Gly Phe Thr Leu Gln Asn Val Gly Arg Lys Ser Gly Ser Glu
                100                 105                 110

Thr Pro Leu Pro Glu Thr Asp Leu Ala His Cys Phe Tyr Ser Gly Thr
            115                 120                 125

Val Asn Gly Asp Pro Ser Ser Ala Ala Ala Leu Ser Leu Cys Glu Gly
        130                 135                 140

Val Arg Gly Ala Phe Tyr Leu Leu Gly Glu Ala Tyr Phe Ile Gln Pro
145                 150                 155                 160

Leu Pro Ala Ala Ser Glu Arg Leu Ala Thr Ala Ala Pro Gly Glu Lys
                165                 170                 175

Pro Pro Ala Pro Leu Gln Phe His Leu Leu Arg Arg Asn Arg Gln Gly
                180                 185                 190
```

-continued

Asp Val Gly Gly Thr Cys Gly Val Asp Asp Glu Pro Arg Pro Thr
        195                 200                 205

Gly Lys Ala Glu Thr Glu Asp Glu Gly Thr Glu Gly Glu Asp
    210                 215                 220

Glu Gly Ala Gln Trp Ser Pro Gln Asp Pro Ala Leu Gln Gly Val Gly
225                 230                 235                 240

Gln Pro Thr Gly Thr Gly Ser Ile Arg Lys Lys Arg Phe Val Ser Ser
                245                 250                 255

His Arg Tyr Val Glu Thr Met Leu Val Ala Asp Gln Ser Met Ala Glu
                260                 265                 270

Phe His Gly Ser Gly Leu Lys His Tyr Leu Leu Thr Leu Phe Ser Val
            275                 280                 285

Ala Ala Arg Leu Tyr Lys His Pro Ser Ile Arg Asn Ser Val Ser Leu
        290                 295                 300

Val Val Val Lys Ile Leu Val Ile His Asp Glu Gln Lys Gly Pro Glu
305                 310                 315                 320

Val Thr Ser Asn Ala Ala Leu Thr Leu Arg Asn Phe Cys Asn Trp Gln
                325                 330                 335

Lys Gln His Asn Pro Pro Ser Asp Arg Asp Ala Glu His Tyr Asp Thr
            340                 345                 350

Ala Ile Leu Phe Thr Arg Gln Asp Leu Cys Gly Ser Gln Thr Cys Asp
        355                 360                 365

Thr Leu Gly Met Ala Asp Val Gly Thr Val Cys Asp Pro Ser Arg Ser
370                 375                 380

Cys Ser Val Ile Glu Asp Asp Gly Leu Gln Ala Ala Phe Thr Thr Ala
385                 390                 395                 400

His Glu Leu Gly His Val Phe Asn Met Pro His Asp Asp Ala Lys Gln
                405                 410                 415

Cys Ala Ser Leu Asn Gly Val Asn Gln Asp Ser His Met Met Ala Ser
            420                 425                 430

Met Leu Ser Asn Leu Asp His Ser Gln Pro Trp Ser Pro Cys Ser Ala
        435                 440                 445

Tyr Met Ile Thr Ser Phe Leu Asp Asn Gly His Gly Glu Cys Leu Met
    450                 455                 460

Asp Lys Pro Gln Asn Pro Ile Gln Leu Pro Gly Asp Leu Pro Gly Thr
465                 470                 475                 480

Ser Tyr Asp Ala Asn Arg Gln Cys Gln Phe Thr Phe Gly Glu Asp Ser
                485                 490                 495

Lys His Cys Pro Asp Ala Ala Ser Thr Cys Ser Thr Leu Trp Cys Thr
            500                 505                 510

Gly Thr Ser Gly Gly Val Leu Val Cys Gln Thr Lys His Phe Pro Trp
        515                 520                 525

Ala Asp Gly Thr Ser Cys Gly Glu Gly Lys Trp Cys Ile Asn Gly Lys
    530                 535                 540

Cys Val Asn Lys Thr Asp Arg Lys His Phe Asp Thr Pro Phe His Gly
545                 550                 555                 560

Ser Trp Gly Met Trp Gly Pro Trp Gly Asp Cys Ser Arg Thr Cys Gly
                565                 570                 575

Gly Gly Val Gln Tyr Thr Met Arg Glu Cys Asp Asn Pro Val Pro Lys
            580                 585                 590

Asn Gly Gly Lys Tyr Cys Glu Gly Lys Arg Val Arg Tyr Arg Ser Cys
        595                 600                 605

Asn Leu Glu Asp Cys Pro Asp Asn Asn Gly Lys Thr Phe Arg Glu Glu
    610                 615                 620

-continued

```
Gln Cys Glu Ala His Asn Glu Phe Ser Lys Ala Ser Phe Gly Ser Gly
625                 630                 635                 640

Pro Ala Val Glu Trp Ile Pro Lys Tyr Ala Gly Val Ser Pro Lys Asp
            645                 650                 655

Arg Cys Lys Leu Ile Cys Gln Ala Lys Gly Ile Gly Tyr Phe Phe Val
                660                 665                 670

Leu Gln Pro Lys Val Val Asp Gly Thr Pro Cys Ser Pro Asp Ser Thr
        675                 680                 685

Ser Val Cys Val Gln Gly Gln Cys Val Lys Ala Gly Cys Asp Arg Ile
    690                 695                 700

Ile Asp Ser Lys Lys Lys Phe Asp Lys Cys Gly Val Cys Gly Gly Asn
705                 710                 715                 720

Gly Ser Thr Cys Lys Lys Ile Ser Gly Ser Val Thr Ser Ala Lys Pro
                725                 730                 735

Gly Tyr His Asp Ile Ile Thr Ile Pro Thr Gly Ala Thr Asn Ile Glu
            740                 745                 750

Val Lys Gln Arg Asn Gln Arg Gly Ser Arg Asn Asn Gly Ser Phe Leu
        755                 760                 765

Ala Ile Lys Ala Ala Asp Gly Thr Tyr Ile Leu Asn Gly Asp Tyr Thr
    770                 775                 780

Leu Ser Thr Leu Glu Gln Asp Ile Met Tyr Lys Gly Val Val Leu Arg
785                 790                 795                 800

Tyr Ser Gly Ser Ser Ala Ala Leu Glu Arg Ile Arg Ser Phe Ser Pro
                805                 810                 815

Leu Lys Glu Pro Leu Thr Ile Gln Val Leu Thr Val Gly Asn Ala Leu
            820                 825                 830

Arg Pro Lys Ile Lys Tyr Thr Tyr Phe Val Lys Lys Lys Glu Ser
        835                 840                 845

Phe Asn Ala Ile Pro Thr Phe Ser Ala Trp Val Ile Glu Glu Trp Gly
    850                 855                 860

Glu Cys Ser Lys Ser Cys Glu Leu Gly Trp Gln Arg Arg Leu Val Glu
865                 870                 875                 880

Cys Arg Asp Ile Asn Gly Gln Pro Ala Ser Glu Cys Ala Lys Glu Val
                885                 890                 895

Lys Pro Ala Ser Thr Arg Pro Cys Ala Asp His Pro Cys Pro Gln Trp
            900                 905                 910

Gln Leu Gly Glu Trp Ser Ser Cys Ser Lys Thr Cys Gly Lys Gly Tyr
        915                 920                 925

Lys Lys Arg Ser Leu Lys Cys Leu Ser His Asp Gly Gly Val Leu Ser
    930                 935                 940

His Glu Ser Cys Asp Pro Leu Lys Lys Pro Lys His Phe Ile Asp Phe
945                 950                 955                 960

Cys Thr Met Ala Glu Cys Ser
                965

<210> SEQ ID NO 38
<211> LENGTH: 620
<212> TYPE: PRT
<213> ORGANISM: Homo sapiens

<400> SEQUENCE: 38

Met Ser Tyr Tyr Gln Arg Pro Phe Ser Pro Ser Ala Tyr Ser Leu Pro
1               5                   10                  15

Ala Ser Leu Asn Ser Ser Ile Val Met Gln His Gly Thr Ser Leu Asp
            20                  25                  30
```

```
Ser Thr Asp Thr Tyr Pro Gln His Ala Gln Ser Leu Asp Gly Thr Thr
         35                  40                  45

Ser Ser Ser Ile Pro Leu Tyr Arg Ser Ser Glu Glu Glu Lys Arg Val
 50                  55                  60

Thr Val Ile Lys Ala Pro His Tyr Pro Gly Ile Gly Pro Val Asp Glu
 65                  70                  75                  80

Ser Gly Ile Pro Thr Ala Ile Arg Thr Thr Val Asp Arg Pro Lys Asp
                     85                  90                  95

Trp Tyr Lys Thr Met Phe Lys Gln Ile His Met Val His Lys Pro Asp
                 100                 105                 110

Asp Asp Thr Asp Met Tyr Asn Thr Pro Tyr Thr Tyr Asn Ala Gly Leu
             115                 120                 125

Tyr Asn Pro Pro Tyr Ser Ala Gln Ser His Pro Ala Ala Lys Thr Gln
         130                 135                 140

Thr Tyr Arg Pro Leu Ser Lys Ser His Ser Asp Asn Ser Pro Asn Ala
145                 150                 155                 160

Phe Lys Asp Ala Ser Ser Pro Val Pro Pro His Val Pro Pro Pro
                 165                 170                 175

Val Pro Pro Leu Arg Pro Arg Asp Ser Ser Thr Glu Lys His Asp
                 180                 185                 190

Trp Asp Pro Pro Asp Arg Lys Val Asp Thr Arg Lys Phe Arg Ser Glu
                 195                 200                 205

Pro Arg Ser Ile Phe Glu Tyr Glu Pro Gly Lys Ser Ser Ile Leu Gln
         210                 215                 220

His Glu Arg Pro Thr Asp Arg Ile Asn Pro Asp Asp Ile Asp Leu Glu
225                 230                 235                 240

Asn Glu Pro Trp Tyr Lys Phe Phe Ser Glu Leu Glu Phe Gly Arg Pro
                 245                 250                 255

Pro Pro Lys Lys Pro Leu Asp Tyr Val Gln Asp His Ser Ser Gly Val
                 260                 265                 270

Phe Asn Glu Ala Ser Leu Tyr Gln Ser Ser Ile Asp Arg Ser Leu Glu
         275                 280                 285

Arg Pro Met Ser Ser Ala Ser Met Ala Ser Asp Phe Arg Lys Arg Arg
         290                 295                 300

Lys Ser Glu Pro Ala Val Gly Pro Pro Arg Gly Leu Gly Asp Gln Ser
305                 310                 315                 320

Ala Ser Arg Thr Ser Pro Gly Arg Val Asp Leu Pro Gly Ser Ser Thr
                 325                 330                 335

Thr Leu Thr Lys Ser Phe Thr Ser Ser Ser Pro Ser Ser Pro Ser Arg
                 340                 345                 350

Ala Lys Asp Arg Glu Ser Pro Arg Ser Tyr Ser Ser Thr Leu Thr Asp
                 355                 360                 365

Met Gly Arg Ser Ala Pro Arg Glu Arg Arg Gly Thr Pro Glu Lys Glu
         370                 375                 380

Lys Leu Pro Ala Lys Ala Val Tyr Asp Phe Lys Ala Gln Thr Ser Lys
385                 390                 395                 400

Glu Leu Ser Phe Lys Lys Gly Asp Thr Val Tyr Ile Leu Arg Lys Ile
                 405                 410                 415

Asp Gln Asn Trp Tyr Glu Gly Glu His His Gly Arg Val Gly Ile Phe
         420                 425                 430

Pro Ile Ser Tyr Val Glu Lys Leu Thr Pro Pro Glu Lys Ala Gln Pro
         435                 440                 445

Ala Arg Pro Pro Pro Pro Ala Gln Pro Gly Glu Ile Gly Glu Ala Ile
```

```
                        450                 455                 460

Ala Lys Tyr Asn Phe Asn Ala Asp Thr Asn Val Glu Leu Ser Leu Arg
465                 470                 475                 480

Lys Gly Asp Arg Val Ile Leu Leu Lys Arg Val Asp Gln Asn Trp Tyr
                485                 490                 495

Glu Gly Lys Ile Pro Gly Thr Asn Arg Gln Gly Ile Phe Pro Val Ser
            500                 505                 510

Tyr Val Glu Val Val Lys Lys Asn Thr Lys Gly Ala Glu Asp Tyr Pro
        515                 520                 525

Asp Pro Pro Ile Pro His Ser Tyr Ser Ser Asp Arg Ile His Ser Leu
530                 535                 540

Ser Ser Asn Lys Pro Gln Arg Pro Val Phe Thr His Glu Asn Ile Gln
545                 550                 555                 560

Gly Gly Gly Glu Pro Phe Gln Ala Leu Tyr Asn Tyr Thr Pro Arg Asn
                565                 570                 575

Glu Asp Glu Leu Glu Leu Arg Glu Ser Asp Val Ile Asp Val Met Glu
            580                 585                 590

Lys Cys Asp Asp Gly Trp Phe Val Gly Thr Ser Arg Arg Thr Lys Phe
        595                 600                 605

Phe Gly Thr Phe Pro Gly Asn Tyr Val Lys Arg Leu
610                 615                 620

<210> SEQ ID NO 39
<211> LENGTH: 179
<212> TYPE: PRT
<213> ORGANISM: Homo sapiens

<400> SEQUENCE: 39

Met Ala Lys Thr Ala Met Ala Tyr Lys Glu Lys Met Lys Glu Leu Ser
1               5                   10                  15

Met Leu Ser Leu Ile Cys Ser Cys Phe Tyr Pro Glu Pro Arg Asn Ile
            20                  25                  30

Asn Ile Tyr Thr Tyr Asp Asp Met Glu Val Lys Gln Ile Asn Lys Arg
        35                  40                  45

Ala Ser Gly Gln Ala Phe Glu Leu Ile Leu Lys Pro Pro Ser Pro Ile
50                  55                  60

Ser Glu Ala Pro Arg Thr Leu Ala Ser Pro Lys Lys Lys Asp Leu Ser
65                  70                  75                  80

Leu Glu Glu Ile Gln Lys Lys Leu Glu Ala Ala Glu Glu Arg Arg Lys
                85                  90                  95

Ser Gln Glu Ala Gln Val Leu Lys Gln Leu Ala Glu Lys Arg Glu His
            100                 105                 110

Glu Arg Glu Val Leu Gln Lys Ala Leu Glu Glu Asn Asn Asn Phe Ser
        115                 120                 125

Lys Met Ala Glu Glu Lys Leu Ile Leu Lys Met Glu Gln Ile Lys Glu
130                 135                 140

Asn Arg Glu Ala Asn Leu Ala Ala Ile Ile Glu Arg Leu Gln Glu Lys
145                 150                 155                 160

Glu Arg His Ala Ala Glu Val Arg Arg Asn Lys Glu Leu Gln Val Glu
                165                 170                 175

Leu Ser Gly

<210> SEQ ID NO 40
<211> LENGTH: 715
<212> TYPE: PRT
<213> ORGANISM: Homo sapiens
```

<400> SEQUENCE: 40

```
Met Ser Lys Ala His Lys Pro Trp Pro Tyr Arg Arg Arg Ser Gln Phe
 1               5                  10                  15

Ser Ser Arg Lys Tyr Leu Lys Lys Glu Met Asn Ser Phe Gln Gln Gln
            20                  25                  30

Pro Pro Pro Phe Gly Thr Val Pro Gln Met Met Phe Pro Pro Asn
        35                  40                  45

Trp Gln Gly Ala Glu Lys Asp Ala Ala Phe Leu Ala Lys Asp Phe Asn
    50                  55                  60

Phe Leu Thr Leu Asn Asn Gln Pro Pro Gly Asn Arg Ser Gln Pro
65                  70                  75                  80

Arg Ala Met Gly Pro Glu Asn Asn Leu Tyr Ser Gln Tyr Glu Gln Lys
                85                  90                  95

Val Arg Pro Cys Ile Asp Leu Ile Asp Ser Leu Arg Ala Leu Gly Val
            100                 105                 110

Glu Gln Asp Leu Ala Leu Pro Ala Ile Ala Val Ile Gly Asp Gln Ser
            115                 120                 125

Ser Gly Lys Ser Ser Val Leu Glu Ala Leu Ser Gly Val Ala Leu Pro
        130                 135                 140

Arg Gly Ser Gly Ile Val Thr Arg Cys Pro Leu Val Leu Lys Leu Lys
145                 150                 155                 160

Lys Gln Pro Cys Glu Ala Trp Ala Gly Arg Ile Ser Tyr Arg Asn Thr
                165                 170                 175

Glu Leu Glu Leu Gln Asp Pro Gly Gln Val Lys Glu Ile His Lys
            180                 185                 190

Ala Gln Asn Val Met Ala Gly Asn Gly Arg Gly Ile Ser His Glu Leu
        195                 200                 205

Ile Ser Leu Glu Ile Thr Ser Pro Glu Val Pro Asp Leu Thr Ile Ile
        210                 215                 220

Asp Leu Pro Gly Ile Thr Arg Val Ala Val Asp Asn Gln Pro Arg Asp
225                 230                 235                 240

Ile Gly Leu Gln Ile Lys Ala Leu Ile Lys Lys Tyr Ile Gln Arg Gln
                245                 250                 255

Gln Thr Ile Asn Leu Val Val Val Pro Cys Asn Val Asp Ile Ala Thr
            260                 265                 270

Thr Glu Ala Leu Ser Met Ala His Glu Val Asp Pro Glu Gly Asp Arg
        275                 280                 285

Thr Ile Gly Ile Leu Thr Lys Pro Asp Leu Met Asp Arg Gly Thr Glu
        290                 295                 300

Lys Ser Val Met Asn Val Val Arg Asn Leu Thr Tyr Pro Leu Lys Lys
305                 310                 315                 320

Gly Tyr Met Ile Val Lys Cys Arg Gly Gln Gln Glu Ile Thr Asn Arg
                325                 330                 335

Leu Ser Leu Ala Glu Ala Thr Lys Lys Glu Ile Thr Phe Phe Gln Thr
            340                 345                 350

His Pro Tyr Phe Arg Val Leu Leu Glu Glu Gly Ser Ala Thr Val Pro
        355                 360                 365

Arg Leu Ala Glu Arg Leu Thr Thr Glu Leu Ile Met His Ile Gln Lys
370                 375                 380

Ser Leu Pro Leu Leu Glu Gly Gln Ile Arg Glu Ser His Gln Lys Ala
385                 390                 395                 400

Thr Glu Glu Leu Arg Arg Cys Gly Ala Asp Ile Pro Ser Gln Glu Ala
                405                 410                 415
```

```
Asp Lys Met Phe Phe Leu Ile Glu Lys Ile Lys Met Phe Asn Gln Asp
            420                 425                 430
Ile Glu Lys Leu Val Glu Gly Glu Glu Val Val Arg Glu Asn Glu Thr
            435                 440                 445
Arg Leu Tyr Asn Lys Ile Arg Glu Asp Phe Lys Asn Trp Val Gly Ile
            450                 455                 460
Leu Ala Thr Asn Thr Gln Lys Val Lys Asn Ile Ile His Glu Glu Val
465                 470                 475                 480
Glu Lys Tyr Glu Lys Gln Tyr Arg Gly Lys Glu Leu Leu Gly Phe Val
            485                 490                 495
Asn Tyr Lys Thr Phe Glu Ile Ile Val His Gln Tyr Ile Gln Gln Leu
            500                 505                 510
Val Glu Pro Ala Leu Ser Met Leu Gln Lys Ala Met Glu Ile Ile Gln
            515                 520                 525
Gln Ala Phe Ile Asn Val Ala Lys Lys His Phe Gly Glu Phe Phe Asn
            530                 535                 540
Leu Asn Gln Thr Val Gln Ser Thr Ile Glu Asp Ile Lys Val Lys His
545                 550                 555                 560
Thr Ala Lys Ala Glu Asn Met Ile Gln Leu Gln Phe Arg Met Glu Gln
            565                 570                 575
Met Val Phe Cys Gln Asp Gln Ile Tyr Ser Val Val Leu Lys Lys Val
            580                 585                 590
Arg Glu Glu Ile Phe Asn Pro Leu Gly Thr Pro Ser Gln Asn Met Lys
            595                 600                 605
Leu Asn Ser His Phe Pro Ser Asn Glu Ser Ser Val Ser Ser Phe Thr
            610                 615                 620
Glu Ile Gly Ile His Leu Asn Ala Tyr Phe Leu Glu Thr Ser Lys Arg
625                 630                 635                 640
Leu Ala Asn Gln Ile Pro Phe Ile Ile Gln Tyr Phe Met Leu Arg Glu
            645                 650                 655
Asn Gly Asp Ser Leu Gln Lys Ala Met Met Gln Ile Leu Gln Glu Lys
            660                 665                 670
Asn Arg Tyr Ser Trp Leu Leu Gln Glu Gln Ser Glu Thr Ala Thr Lys
            675                 680                 685
Arg Arg Ile Leu Lys Glu Arg Ile Tyr Arg Leu Thr Gln Ala Arg His
            690                 695                 700
Ala Leu Cys Gln Phe Ser Ser Lys Glu Ile His
705                 710                 715

<210> SEQ ID NO 41
<211> LENGTH: 503
<212> TYPE: PRT
<213> ORGANISM: Homo sapiens

<400> SEQUENCE: 41

Met Ala Leu Ala Pro Glu Arg Ala Ala Pro Arg Val Leu Phe Gly Glu
1               5                   10                  15
Trp Leu Leu Gly Glu Ile Ser Ser Gly Cys Tyr Glu Gly Leu Gln Trp
            20                  25                  30
Leu Asp Glu Ala Arg Thr Cys Phe Arg Val Pro Trp Lys His Phe Ala
            35                  40                  45
Arg Lys Asp Leu Ser Glu Ala Asp Ala Arg Ile Phe Lys Ala Trp Ala
            50                  55                  60
Val Ala Arg Gly Arg Trp Pro Pro Ser Ser Arg Gly Gly Gly Pro Pro
65              70                  75                  80
```

```
Pro Glu Ala Glu Thr Ala Glu Arg Ala Gly Trp Lys Thr Asn Phe Arg
                85                  90                  95
Cys Ala Leu Arg Ser Thr Arg Arg Phe Val Met Leu Arg Asp Asn Ser
                100                 105                 110
Gly Asp Pro Ala Asp Pro His Lys Val Tyr Ala Leu Ser Arg Glu Leu
                115                 120                 125
Cys Trp Arg Glu Gly Pro Gly Thr Asp Gln Thr Glu Ala Glu Ala Pro
            130                 135                 140
Ala Ala Val Pro Pro Pro Gln Gly Gly Pro Pro Gly Pro Phe Leu Ala
145                 150                 155                 160
His Thr His Ala Gly Leu Gln Ala Pro Gly Pro Leu Pro Ala Pro Ala
                165                 170                 175
Gly Asp Lys Gly Asp Leu Leu Leu Gln Ala Val Gln Gln Ser Cys Leu
                180                 185                 190
Ala Asp His Leu Leu Thr Ala Ser Trp Gly Ala Asp Pro Val Pro Thr
            195                 200                 205
Lys Ala Pro Gly Glu Gly Gln Glu Gly Leu Pro Leu Thr Gly Ala Cys
210                 215                 220
Ala Gly Gly Pro Gly Leu Pro Ala Gly Glu Leu Tyr Gly Trp Ala Val
225                 230                 235                 240
Glu Thr Thr Pro Ser Pro Gly Pro Gln Pro Ala Ala Leu Thr Thr Gly
                245                 250                 255
Glu Ala Ala Ala Pro Glu Ser Pro His Gln Ala Glu Pro Tyr Leu Ser
                260                 265                 270
Pro Ser Pro Ser Ala Cys Thr Ala Val Gln Glu Pro Ser Pro Gly Ala
            275                 280                 285
Leu Asp Val Thr Ile Met Tyr Lys Gly Arg Thr Val Leu Gln Lys Val
            290                 295                 300
Val Gly His Pro Ser Cys Thr Phe Leu Tyr Gly Pro Pro Asp Pro Ala
305                 310                 315                 320
Val Arg Ala Thr Asp Pro Gln Gln Val Ala Phe Pro Ser Pro Ala Glu
                325                 330                 335
Leu Pro Asp Gln Lys Gln Leu Arg Tyr Thr Glu Glu Leu Leu Arg His
                340                 345                 350
Val Ala Pro Gly Leu His Leu Glu Leu Arg Gly Pro Gln Leu Trp Ala
            355                 360                 365
Arg Arg Met Gly Lys Cys Lys Val Tyr Trp Glu Val Gly Gly Pro Pro
        370                 375                 380
Gly Ser Ala Ser Pro Ser Thr Pro Ala Cys Leu Leu Pro Arg Asn Cys
385                 390                 395                 400
Asp Thr Pro Ile Phe Asp Phe Arg Val Phe Phe Gln Glu Leu Val Glu
                405                 410                 415
Phe Arg Ala Arg Gln Arg Arg Gly Ser Pro Arg Tyr Thr Ile Tyr Leu
            420                 425                 430
Gly Phe Gly Gln Asp Leu Ser Ala Gly Arg Pro Lys Glu Lys Ser Leu
            435                 440                 445
Val Leu Val Lys Leu Glu Pro Trp Leu Cys Arg Val His Leu Glu Gly
            450                 455                 460
Thr Gln Arg Glu Gly Val Ser Ser Leu Asp Ser Ser Leu Ser Leu
465                 470                 475                 480
Cys Leu Ser Ser Ala Asn Ser Leu Tyr Asp Asp Ile Glu Cys Phe Leu
                485                 490                 495
Met Glu Leu Glu Gln Pro Ala
```

<210> SEQ ID NO 42
<211> LENGTH: 591
<212> TYPE: PRT
<213> ORGANISM: Homo sapiens

<400> SEQUENCE: 42

```
Met Ala Pro Glu Ile Asn Leu Pro Gly Pro Met Ser Leu Ile Asp Asn
 1               5                  10                  15
Thr Lys Gly Gln Leu Val Val Asn Pro Glu Ala Leu Lys Ile Leu Ser
                20                  25                  30
Ala Ile Thr Gln Pro Val Val Val Ala Ile Val Gly Leu Tyr Arg
             35                  40                  45
Thr Gly Lys Ser Tyr Leu Met Asn Lys Leu Ala Gly Lys Lys Asn Gly
     50                  55                  60
Phe Ser Leu Gly Ser Thr Val Lys Ser His Thr Lys Gly Ile Trp Met
65                  70                  75                  80
Trp Cys Val Pro His Pro Lys Lys Pro Glu His Thr Leu Val Leu Leu
                 85                  90                  95
Asp Thr Glu Gly Leu Gly Asp Ile Glu Lys Gly Asp Asn Glu Asn Asp
            100                 105                 110
Ser Trp Ile Phe Ala Leu Ala Ile Leu Leu Ser Ser Thr Phe Val Tyr
        115                 120                 125
Asn Ser Met Gly Thr Ile Asn Gln Gln Ala Met Asp Gln Leu His Tyr
    130                 135                 140
Val Thr Glu Leu Thr Asp Arg Ile Lys Ala Asn Ser Ser Pro Gly Asn
145                 150                 155                 160
Asn Ser Val Asp Asp Ser Ala Asp Phe Val Ser Phe Phe Pro Ala Phe
                165                 170                 175
Val Trp Thr Leu Arg Asp Phe Thr Leu Glu Leu Glu Val Asp Gly Glu
            180                 185                 190
Pro Ile Thr Ala Asp Asp Tyr Leu Glu Leu Ser Leu Lys Leu Arg Lys
        195                 200                 205
Gly Thr Asp Lys Lys Ser Lys Ser Phe Asn Asp Pro Arg Leu Cys Ile
    210                 215                 220
Arg Lys Phe Phe Pro Lys Arg Lys Cys Phe Val Phe Asp Trp Pro Ala
225                 230                 235                 240
Pro Lys Lys Tyr Leu Ala His Leu Glu Gln Leu Lys Glu Glu Glu Leu
                245                 250                 255
Asn Pro Asp Phe Ile Glu Gln Val Ala Glu Phe Cys Ser Tyr Ile Leu
            260                 265                 270
Ser His Ser Asn Val Lys Thr Leu Ser Gly Ile Pro Val Asn Gly
        275                 280                 285
Pro Arg Leu Glu Ser Leu Val Leu Thr Tyr Val Asn Ala Ile Ser Ser
    290                 295                 300
Gly Asp Leu Pro Cys Met Glu Asn Ala Val Leu Ala Leu Ala Gln Ile
305                 310                 315                 320
Glu Asn Ser Ala Ala Val Glu Lys Ala Ile Ala His Tyr Glu Gln Gln
                325                 330                 335
Met Gly Gln Lys Val Gln Leu Pro Thr Glu Thr Leu Gln Glu Leu Leu
            340                 345                 350
Asp Leu His Arg Asp Ser Glu Arg Glu Ala Ile Glu Val Phe Met Lys
        355                 360                 365
Asn Ser Phe Lys Asp Val Asp Gln Met Phe Gln Arg Lys Leu Gly Ala
```

```
                    370                 375                 380
Gln Leu Glu Ala Arg Arg Asp Asp Phe Cys Lys Gln Asn Ser Lys Ala
385                 390                 395                 400

Ser Ser Asp Cys Cys Met Ala Leu Leu Gln Asp Ile Phe Gly Pro Leu
                405                 410                 415

Glu Glu Asp Val Lys Gln Gly Thr Phe Ser Lys Pro Gly Gly Tyr Arg
            420                 425                 430

Leu Phe Thr Gln Lys Leu Gln Glu Leu Lys Asn Lys Tyr Tyr Gln Val
        435                 440                 445

Pro Arg Lys Gly Ile Gln Ala Lys Glu Val Leu Lys Lys Tyr Leu Glu
    450                 455                 460

Ser Lys Glu Asp Val Ala Asp Ala Leu Leu Gln Thr Asp Gln Ser Leu
465                 470                 475                 480

Ser Glu Lys Glu Lys Ala Ile Glu Val Glu Arg Ile Lys Ala Glu Ser
                485                 490                 495

Ala Glu Ala Ala Lys Lys Met Leu Glu Glu Ile Gln Lys Lys Asn Glu
            500                 505                 510

Glu Met Met Glu Gln Lys Glu Lys Ser Tyr Gln Glu His Val Lys Gln
        515                 520                 525

Leu Thr Glu Lys Met Glu Arg Asp Arg Ala Gln Leu Met Ala Glu Gln
    530                 535                 540

Glu Lys Thr Leu Ala Leu Lys Leu Gln Glu Gln Glu Arg Leu Leu Lys
545                 550                 555                 560

Glu Gly Phe Glu Asn Glu Ser Lys Arg Leu Gln Lys Asp Ile Trp Asp
                565                 570                 575

Ile Gln Met Arg Ser Lys Ser Leu Glu Pro Ile Cys Asn Ile Leu
            580                 585                 590

<210> SEQ ID NO 43
<211> LENGTH: 658
<212> TYPE: PRT
<213> ORGANISM: Homo sapiens

<400> SEQUENCE: 43

Met Glu Lys Ala Ser Gly Arg Gln Ser Ile Ala Leu Ser Thr Val Glu
1               5                   10                  15

Thr Gly Thr Val Asn Pro Gly Leu Glu Leu Met Glu Lys Glu Val Glu
            20                  25                  30

Pro Glu Gly Ser Lys Arg Thr Asp Ala Gln Gly His Ser Leu Gly Asp
        35                  40                  45

Gly Leu Gly Pro Ser Thr Tyr Gln Arg Arg Ser Arg Trp Pro Phe Ser
    50                  55                  60

Lys Ala Arg Ser Phe Cys Lys Thr His Ala Arg Leu Phe Lys Lys Ile
65                  70                  75                  80

Leu Leu Gly Leu Leu Cys Leu Ala Tyr Ala Ala Tyr Leu Leu Ala Ala
                85                  90                  95

Cys Ile Leu Asn Phe Gln Arg Ala Leu Ala Leu Phe Val Ile Thr Cys
            100                 105                 110

Leu Val Ile Phe Val Leu Val His Ser Phe Leu Lys Lys Leu Leu Gly
        115                 120                 125

Lys Lys Leu Thr Arg Cys Leu Lys Pro Phe Glu Asn Ser Arg Leu Arg
    130                 135                 140

Leu Trp Thr Lys Trp Val Phe Ala Gly Val Ser Leu Val Gly Leu Ile
145                 150                 155                 160

Leu Trp Leu Ala Leu Asp Thr Ala Gln Arg Pro Glu Gln Leu Ile Pro
```

```
                165                 170                 175
Phe Ala Gly Ile Cys Met Phe Ile Leu Ile Leu Phe Ala Cys Ser Lys
            180                 185                 190

His His Ser Ala Val Ser Trp Arg Thr Val Phe Ser Gly Leu Gly Leu
        195                 200                 205

Gln Phe Val Phe Gly Ile Leu Val Ile Arg Thr Asp Leu Gly Tyr Thr
    210                 215                 220

Val Phe Gln Trp Leu Gly Glu Gln Val Gln Ile Phe Leu Asn Tyr Thr
225                 230                 235                 240

Val Ala Gly Ser Ser Phe Val Phe Gly Asp Thr Leu Val Lys Asp Val
            245                 250                 255

Phe Ala Phe Gln Ala Leu Pro Ile Ile Ile Phe Phe Gly Cys Val Val
        260                 265                 270

Ser Ile Leu Tyr Tyr Leu Gly Leu Val Gln Trp Val Val Gln Lys Val
    275                 280                 285

Ala Trp Phe Leu Gln Ile Thr Met Gly Thr Thr Ala Thr Glu Thr Leu
290                 295                 300

Ala Val Ala Gly Asn Ile Phe Val Gly Met Thr Glu Ala Pro Leu Leu
305                 310                 315                 320

Ile Arg Pro Tyr Leu Gly Asp Met Thr Leu Ser Glu Ile His Ala Val
            325                 330                 335

Met Thr Gly Gly Phe Ala Thr Ile Ser Gly Thr Val Leu Gly Ala Phe
            340                 345                 350

Ile Ala Phe Gly Val Asp Ala Ser Ser Leu Ile Ser Ala Ser Val Met
        355                 360                 365

Ala Ala Pro Cys Ala Leu Ala Ser Ser Lys Leu Ala Tyr Pro Glu Val
    370                 375                 380

Glu Ser Lys Phe Lys Ser Glu Glu Gly Val Lys Leu Pro Arg Gly
385                 390                 395                 400

Lys Glu Arg Asn Val Leu Glu Ala Ala Ser Asn Gly Ala Val Asp Ala
            405                 410                 415

Ile Gly Leu Ala Thr Asn Val Ala Ala Asn Leu Ile Ala Phe Leu Ala
            420                 425                 430

Val Leu Ala Phe Ile Asn Ala Ala Leu Ser Trp Leu Gly Glu Leu Val
        435                 440                 445

Asp Ile Gln Gly Leu Thr Phe Gln Val Ile Cys Ser Tyr Leu Leu Arg
    450                 455                 460

Pro Met Val Phe Met Met Gly Val Glu Trp Thr Asp Cys Pro Met Val
465                 470                 475                 480

Ala Glu Met Val Gly Ile Lys Phe Phe Ile Asn Glu Phe Val Ala Tyr
            485                 490                 495

Gln Gln Leu Ser Gln Tyr Lys Asn Lys Arg Leu Ser Gly Met Glu Glu
        500                 505                 510

Trp Ile Glu Gly Glu Lys Gln Trp Ile Ser Val Arg Ala Glu Ile Ile
    515                 520                 525

Thr Thr Phe Ser Leu Cys Gly Phe Ala Asn Leu Ser Ser Ile Gly Ile
530                 535                 540

Thr Leu Gly Gly Leu Thr Ser Ile Val Pro His Arg Lys Ser Asp Leu
545                 550                 555                 560

Ser Lys Val Val Val Arg Ala Leu Phe Thr Gly Ala Cys Val Ser Leu
            565                 570                 575

Ile Ser Ala Cys Met Ala Gly Ile Leu Tyr Val Pro Arg Gly Ala Glu
            580                 585                 590
```

-continued

Ala Asp Cys Val Ser Phe Pro Asn Thr Ser Phe Thr Asn Arg Thr Tyr
            595                 600                 605

Glu Thr Tyr Met Cys Cys Arg Gly Leu Phe Gln Ser Thr Ser Leu Asn
    610                 615                 620

Gly Thr Asn Pro Pro Ser Phe Ser Gly Pro Trp Glu Asp Lys Glu Phe
625                 630                 635                 640

Ser Ala Met Ala Leu Thr Asn Cys Cys Gly Phe Tyr Asn Asn Thr Val
                645                 650                 655

Cys Ala

<210> SEQ ID NO 44
<211> LENGTH: 247
<212> TYPE: PRT
<213> ORGANISM: Homo sapiens

<400> SEQUENCE: 44

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Arg Gly Arg
                245

<210> SEQ ID NO 45
<211> LENGTH: 1112
<212> TYPE: PRT
<213> ORGANISM: Homo sapiens

<400> SEQUENCE: 45

Met Arg Arg Asp Glu Arg Asp Ala Lys Ala Met Arg Ser Leu Gln Pro
1               5                   10                  15

Pro Asp Gly Ala Gly Ser Pro Pro Glu Ser Leu Arg Asn Gly Tyr Val
            20                  25                  30

Lys Ser Cys Val Ser Pro Leu Arg Gln Asp Pro Pro Arg Gly Phe Phe
            35                  40                  45

Phe His Leu Cys Arg Phe Cys Asn Val Glu Leu Arg Pro Pro Pro Ala
    50                  55                  60

Ser Pro Gln Gln Pro Arg Arg Cys Ser Pro Phe Cys Arg Ala Arg Leu
65                  70                  75                  80

Ser Leu Gly Ala Leu Ala Ala Phe Val Leu Ala Leu Leu Gly Ala
                85                  90                  95

Glu Pro Glu Ser Trp Ala Ala Gly Ala Ala Trp Leu Arg Thr Leu Leu
            100                 105                 110

Ser Val Cys Ser His Ser Leu Ser Pro Leu Phe Ser Ile Ala Cys Ala
            115                 120                 125

Phe Phe Phe Leu Thr Cys Phe Leu Thr Arg Thr Lys Arg Gly Pro Gly
    130                 135                 140

Pro Gly Arg Ser Cys Gly Ser Trp Trp Leu Leu Ala Leu Pro Ala Cys
145                 150                 155                 160

Cys Tyr Leu Gly Asp Phe Leu Val Trp Gln Trp Ser Trp Pro Trp
                165                 170                 175

Gly Asp Gly Asp Ala Gly Ser Ala Ala Pro His Thr Pro Glu Ala
            180                 185                 190

Ala Ala Gly Arg Leu Leu Leu Val Leu Ser Cys Val Gly Leu Leu Leu
        195                 200                 205

Thr Leu Ala His Pro Leu Arg Leu Arg His Cys Val Leu Val Leu Leu
210                 215                 220

Leu Ala Ser Phe Val Trp Trp Val Ser Phe Thr Ser Leu Gly Ser Leu
225                 230                 235                 240

Pro Ser Ala Leu Arg Pro Leu Leu Ser Gly Leu Val Gly Gly Ala Gly
                245                 250                 255

Cys Leu Leu Ala Leu Gly Leu Asp His Phe Phe Gln Ile Arg Glu Ala
            260                 265                 270

Pro Leu His Pro Arg Leu Ser Ser Ala Ala Glu Glu Lys Val Pro Val
        275                 280                 285

Ile Arg Pro Arg Arg Arg Ser Ser Cys Val Ser Leu Gly Glu Thr Ala
    290                 295                 300

Ala Ser Tyr Tyr Gly Ser Cys Lys Ile Phe Arg Arg Pro Ser Leu Pro
305                 310                 315                 320

Cys Ile Ser Arg Glu Gln Met Ile Leu Trp Asp Trp Asp Leu Lys Gln
                325                 330                 335

Trp Tyr Lys Pro His Tyr Gln Asn Ser Gly Gly Gly Asn Gly Val Asp
            340                 345                 350

Leu Ser Val Leu Asn Glu Ala Arg Asn Met Val Ser Asp Leu Leu Thr
        355                 360                 365

Asp Pro Ser Leu Pro Pro Gln Val Ile Ser Ser Leu Arg Ser Ile Ser
    370                 375                 380

Ser Leu Met Gly Ala Phe Ser Gly Ser Cys Arg Pro Lys Ile Asn Pro
385                 390                 395                 400

Leu Thr Pro Phe Pro Gly Phe Tyr Pro Cys Ser Glu Ile Glu Asp Pro
                405                 410                 415

Ala Glu Lys Gly Asp Arg Lys Leu Asn Lys Gly Leu Asn Arg Asn Ser
            420                 425                 430

Leu Pro Thr Pro Gln Leu Arg Arg Ser Ser Gly Thr Ser Gly Leu Leu

-continued

```
                435                 440                 445
Pro Val Glu Gln Ser Ser Arg Trp Asp Arg Asn Asn Gly Lys Arg Pro
450                 455                 460
His Gln Glu Phe Gly Ile Ser Ser Gln Gly Cys Tyr Leu Asn Gly Pro
465                 470                 475                 480
Phe Asn Ser Asn Leu Leu Thr Ile Pro Lys Gln Arg Ser Ser Ser Val
                485                 490                 495
Ser Leu Thr His His Val Gly Leu Arg Arg Ala Gly Val Leu Ser Ser
                500                 505                 510
Leu Ser Pro Val Asn Ser Ser Asn His Gly Pro Val Ser Thr Gly Ser
            515                 520                 525
Leu Thr Asn Arg Ser Pro Ile Glu Phe Pro Asp Thr Ala Asp Phe Leu
            530                 535                 540
Asn Lys Pro Ser Val Ile Leu Gln Arg Ser Leu Gly Asn Ala Pro Asn
545                 550                 555                 560
Thr Pro Asp Phe Tyr Gln Gln Leu Arg Asn Ser Asp Ser Asn Leu Cys
                565                 570                 575
Asn Ser Cys Gly His Gln Met Leu Lys Tyr Val Ser Thr Ser Glu Ser
                580                 585                 590
Asp Gly Thr Asp Cys Cys Ser Gly Lys Ser Gly Glu Glu Asn Ile
                595                 600                 605
Phe Ser Lys Glu Ser Phe Lys Leu Met Glu Thr Gln Gln Glu Glu Glu
            610                 615                 620
Thr Glu Lys Lys Asp Ser Arg Lys Leu Phe Gln Glu Gly Asp Lys Trp
625                 630                 635                 640
Leu Thr Glu Glu Ala Gln Ser Glu Gln Gln Thr Asn Ile Glu Gln Glu
                645                 650                 655
Val Ser Leu Asp Leu Ile Leu Val Glu Glu Tyr Asp Ser Leu Ile Glu
                660                 665                 670
Lys Met Ser Asn Trp Asn Phe Pro Ile Phe Glu Leu Val Glu Lys Met
            675                 680                 685
Gly Glu Lys Ser Gly Arg Ile Leu Ser Gln Val Met Tyr Thr Leu Phe
            690                 695                 700
Gln Asp Thr Gly Leu Leu Glu Ile Phe Lys Ile Pro Thr Gln Gln Phe
705                 710                 715                 720
Met Asn Tyr Phe Arg Ala Leu Glu Asn Gly Tyr Arg Asp Ile Pro Tyr
                725                 730                 735
His Asn Arg Ile His Ala Thr Asp Val Leu His Ala Val Trp Tyr Leu
                740                 745                 750
Thr Thr Arg Pro Val Pro Gly Leu Gln Gln Ile His Asn Gly Cys Gly
            755                 760                 765
Thr Gly Asn Glu Thr Asp Ser Asp Gly Arg Ile Asn His Gly Arg Ile
            770                 775                 780
Ala Tyr Ile Ser Ser Lys Ser Cys Ser Asn Pro Asp Glu Ser Tyr Gly
785                 790                 795                 800
Cys Leu Ser Ser Asn Ile Pro Ala Leu Glu Leu Met Ala Leu Tyr Val
                805                 810                 815
Ala Ala Ala Met His Asp Tyr Asp His Pro Gly Arg Thr Asn Ala Phe
                820                 825                 830
Leu Val Ala Thr Asn Ala Pro Gln Ala Val Leu Tyr Asn Asp Arg Ser
            835                 840                 845
Val Leu Glu Asn His His Ala Ser Ala Trp Asn Leu Tyr Leu Ser
            850                 855                 860
```

Arg Pro Glu Tyr Asn Phe Leu Leu His Leu Asp His Val Glu Phe Lys
865                 870                 875                 880

Arg Phe Arg Phe Leu Val Ile Glu Ala Ile Leu Ala Thr Asp Leu Lys
            885                 890                 895

Lys His Phe Asp Phe Leu Ala Glu Phe Asn Ala Lys Ala Asn Asp Val
        900                 905                 910

Asn Ser Asn Gly Ile Glu Trp Ser Asn Glu Asn Asp Arg Leu Leu Val
    915                 920                 925

Cys Gln Val Cys Ile Lys Leu Ala Asp Ile Asn Gly Pro Ala Lys Val
930                 935                 940

Arg Asp Leu His Leu Lys Trp Thr Glu Gly Ile Val Asn Glu Phe Tyr
945                 950                 955                 960

Glu Gln Gly Asp Glu Glu Ala Asn Leu Gly Leu Pro Ile Ser Pro Phe
                965                 970                 975

Met Asp Arg Ser Ser Pro Gln Leu Ala Lys Leu Gln Glu Ser Phe Ile
            980                 985                 990

Thr His Ile Val Gly Pro Leu Cys Asn Ser Tyr Asp Ala Ala Gly Leu
        995                 1000                1005

Leu Pro Gly Gln Trp Leu Glu Ala Glu Asp Asn Asp Thr Glu Ser
    1010                1015                1020

Gly Asp Asp Glu Asp Gly Glu Glu Leu Asp Thr Glu Asp Glu Met
1025                1030                1035                1040

Glu Asn Asn Leu Asn Pro Lys Pro Pro Arg Arg Lys Ser Arg Arg Arg
                1045                1050                1055

Ile Phe Cys Gln Leu Met His His Leu Thr Glu Asn His Lys Ile Trp
    1060                1065                1070

Lys Glu Ile Val Glu Glu Glu Lys Cys Lys Ala Asp Gly Asn Lys
    1075                1080                1085

Leu Gln Val Glu Asn Ser Ser Leu Pro Gln Ala Asp Glu Ile Gln Val
    1090                1095                1100

Ile Glu Glu Ala Asp Glu Glu Glu
1105                1110

<210> SEQ ID NO 46
<211> LENGTH: 538
<212> TYPE: PRT
<213> ORGANISM: Homo sapiens

<400> SEQUENCE: 46

Met Phe Phe Leu Tyr Thr Asp Phe Phe Leu Ser Leu Val Ala Val Pro
 1               5                  10                  15

Ala Ala Ala Pro Val Cys Gln Pro Lys Ser Ala Thr Asn Gly Gln Pro
            20                  25                  30

Pro Ala Pro Ala Pro Thr Pro Thr Pro Arg Leu Ser Ile Ser Ser Arg
        35                  40                  45

Ala Thr Val Val Ala Arg Met Glu Gly Thr Ser Gln Gly Gly Leu Gln
    50                  55                  60

Thr Val Met Lys Trp Lys Thr Val Val Ala Ile Phe Val Val Val Val
65                  70                  75                  80

Val Tyr Leu Val Thr Gly Gly Leu Val Phe Arg Ala Leu Glu Gln Pro
                85                  90                  95

Phe Glu Ser Ser Gln Lys Asn Thr Ile Ala Leu Glu Lys Ala Glu Phe
            100                 105                 110

Leu Arg Asp His Val Cys Val Ser Pro Gln Glu Leu Glu Thr Leu Ile
        115                 120                 125

```
Gln His Ala Leu Asp Ala Asp Asn Ala Gly Val Ser Pro Ile Gly Asn
    130                 135                 140

Ser Ser Asn Asn Ser Ser His Trp Asp Leu Gly Ser Ala Phe Phe Phe
145                 150                 155                 160

Ala Gly Thr Val Ile Thr Thr Ile Gly Tyr Gly Asn Ile Ala Pro Ser
                165                 170                 175

Thr Glu Gly Gly Lys Ile Phe Cys Ile Leu Tyr Ala Ile Phe Gly Ile
            180                 185                 190

Pro Leu Phe Gly Phe Leu Leu Ala Gly Ile Gly Asp Gln Leu Gly Thr
        195                 200                 205

Ile Phe Gly Lys Ser Ile Ala Arg Val Glu Lys Val Phe Arg Lys Lys
    210                 215                 220

Gln Val Ser Gln Thr Lys Ile Arg Val Ile Ser Thr Ile Leu Phe Ile
225                 230                 235                 240

Leu Ala Gly Cys Ile Val Phe Val Thr Ile Pro Ala Val Ile Phe Lys
                245                 250                 255

Tyr Ile Glu Gly Trp Thr Ala Leu Glu Ser Ile Tyr Phe Val Val Val
            260                 265                 270

Thr Leu Thr Thr Val Gly Phe Gly Asp Phe Val Ala Gly Gly Asn Ala
        275                 280                 285

Gly Ile Asn Tyr Arg Glu Trp Tyr Lys Pro Leu Val Trp Phe Trp Ile
    290                 295                 300

Leu Val Gly Leu Ala Tyr Phe Ala Ala Val Leu Ser Met Ile Gly Asp
305                 310                 315                 320

Trp Leu Arg Val Leu Ser Lys Lys Thr Lys Glu Glu Val Gly Glu Ile
                325                 330                 335

Lys Ala His Ala Ala Glu Trp Lys Ala Asn Val Thr Ala Glu Phe Arg
            340                 345                 350

Glu Thr Arg Arg Arg Leu Ser Val Glu Ile His Asp Lys Leu Gln Arg
        355                 360                 365

Ala Ala Thr Ile Arg Ser Met Glu Arg Arg Leu Gly Leu Asp Gln
    370                 375                 380

Arg Ala His Ser Leu Asp Met Leu Ser Pro Glu Lys Arg Ser Val Phe
385                 390                 395                 400

Ala Ala Leu Asp Thr Gly Arg Phe Lys Ala Ser Ser Gln Glu Ser Ile
                405                 410                 415

Asn Asn Arg Pro Asn Asn Leu Arg Leu Lys Gly Pro Glu Gln Leu Asn
            420                 425                 430

Lys His Gly Gln Gly Ala Ser Glu Asp Asn Ile Ile Asn Lys Phe Gly
        435                 440                 445

Ser Thr Ser Arg Leu Thr Lys Arg Lys Asn Lys Asp Leu Lys Lys Thr
450                 455                 460

Leu Pro Glu Asp Val Gln Lys Ile Tyr Lys Thr Phe Arg Asn Tyr Ser
465                 470                 475                 480

Leu Asp Glu Glu Lys Lys Glu Glu Thr Glu Lys Met Cys Asn Ser
                485                 490                 495

Asp Asn Ser Ser Thr Ala Met Leu Thr Asp Cys Ile Gln Gln His Ala
            500                 505                 510

Glu Leu Glu Asn Gly Met Ile Pro Thr Asp Thr Lys Asp Arg Glu Pro
        515                 520                 525

Glu Asn Asn Ser Leu Leu Glu Asp Arg Asn
    530                 535

<210> SEQ ID NO 47
```

```
<211> LENGTH: 796
<212> TYPE: PRT
<213> ORGANISM: Homo sapiens

<400> SEQUENCE: 47

Met Leu Arg Gly Gly Arg Arg Gly Gln Leu Gly Trp His Ser Trp Ala
 1               5                  10                  15

Ala Gly Pro Gly Ser Leu Leu Ala Trp Leu Ile Leu Ala Ser Ala Gly
             20                  25                  30

Ala Ala Pro Cys Pro Asp Ala Cys Cys Pro His Gly Ser Ser Gly Leu
         35                  40                  45

Arg Cys Thr Arg Asp Gly Ala Leu Asp Ser Leu His His Leu Pro Gly
 50                  55                  60

Ala Glu Asn Leu Thr Glu Leu Tyr Ile Glu Asn Gln Gln His Leu Gln
65                  70                  75                  80

His Leu Glu Leu Arg Asp Leu Arg Gly Leu Gly Glu Leu Arg Asn Leu
                 85                  90                  95

Thr Ile Val Lys Ser Gly Leu Arg Phe Val Ala Pro Asp Ala Phe His
            100                 105                 110

Phe Thr Pro Arg Leu Ser Arg Leu Asn Leu Ser Phe Asn Ala Leu Glu
        115                 120                 125

Ser Leu Ser Trp Lys Thr Val Gln Gly Leu Ser Leu Gln Glu Leu Val
130                 135                 140

Leu Ser Gly Asn Pro Leu His Cys Ser Cys Ala Leu Arg Trp Leu Gln
145                 150                 155                 160

Arg Trp Glu Glu Glu Gly Leu Gly Gly Val Pro Glu Gln Lys Leu Gln
                165                 170                 175

Cys His Gly Gln Gly Pro Leu Ala His Met Pro Asn Ala Ser Cys Gly
            180                 185                 190

Val Pro Thr Leu Lys Val Gln Val Pro Asn Ala Ser Val Asp Val Gly
        195                 200                 205

Asp Asp Val Leu Leu Arg Cys Gln Val Glu Gly Arg Gly Leu Glu Gln
210                 215                 220

Ala Gly Trp Ile Leu Thr Glu Leu Glu Gln Ser Ala Thr Val Met Lys
225                 230                 235                 240

Ser Gly Gly Leu Pro Ser Leu Gly Leu Thr Leu Ala Asn Val Thr Ser
                245                 250                 255

Asp Leu Asn Arg Lys Asn Val Thr Cys Trp Ala Glu Asn Asp Val Gly
            260                 265                 270

Arg Ala Glu Val Ser Val Gln Val Asn Val Ser Phe Pro Ala Ser Val
        275                 280                 285

Gln Leu His Thr Ala Val Glu Met His His Trp Cys Ile Pro Phe Ser
290                 295                 300

Val Asp Gly Gln Pro Ala Pro Ser Leu Arg Trp Leu Phe Asn Gly Ser
305                 310                 315                 320

Val Leu Asn Glu Thr Ser Phe Ile Phe Thr Glu Phe Leu Glu Pro Ala
                325                 330                 335

Ala Asn Glu Thr Val Arg His Gly Cys Leu Arg Leu Asn Gln Pro Thr
            340                 345                 350

His Val Asn Asn Gly Asn Tyr Thr Leu Leu Ala Ala Asn Pro Phe Gly
        355                 360                 365

Gln Ala Ser Ala Ser Ile Met Ala Ala Phe Met Asp Asn Pro Phe Glu
370                 375                 380

Phe Asn Pro Glu Asp Pro Ile Pro Val Ser Phe Ser Pro Val Asp Thr
385                 390                 395                 400
```

Asn Ser Thr Ser Gly Asp Pro Val Glu Lys Lys Asp Glu Thr Pro Phe
            405                 410                 415

Gly Val Ser Val Ala Val Gly Leu Ala Val Phe Ala Cys Leu Phe Leu
        420                 425                 430

Ser Thr Leu Leu Leu Val Leu Asn Lys Cys Gly Arg Arg Asn Lys Phe
        435                 440                 445

Gly Ile Asn Arg Pro Ala Val Leu Ala Pro Glu Asp Gly Leu Ala Met
    450                 455                 460

Ser Leu His Phe Met Thr Leu Gly Gly Ser Ser Leu Ser Pro Thr Glu
465                 470                 475                 480

Gly Lys Gly Ser Gly Leu Gln Gly His Ile Ile Glu Asn Pro Gln Tyr
                485                 490                 495

Phe Ser Asp Ala Cys Val His His Ile Lys Arg Arg Asp Ile Val Leu
                500                 505                 510

Lys Trp Glu Leu Gly Glu Gly Ala Phe Gly Lys Val Phe Leu Ala Glu
        515                 520                 525

Cys His Asn Leu Leu Pro Glu Gln Asp Lys Met Leu Val Ala Val Lys
    530                 535                 540

Ala Leu Lys Glu Ala Ser Glu Ser Ala Arg Gln Asp Phe Gln Arg Glu
545                 550                 555                 560

Ala Glu Leu Leu Thr Met Leu Gln His Gln His Ile Val Arg Phe Phe
                565                 570                 575

Gly Val Cys Thr Glu Gly Arg Pro Leu Leu Met Val Phe Glu Tyr Met
                580                 585                 590

Arg His Gly Asp Leu Asn Arg Phe Leu Arg Ser His Gly Pro Asp Ala
        595                 600                 605

Lys Leu Leu Ala Gly Gly Glu Asp Val Ala Pro Gly Pro Leu Gly Leu
    610                 615                 620

Gly Gln Leu Leu Ala Val Ala Ser Gln Val Ala Ala Gly Met Val Tyr
625                 630                 635                 640

Leu Ala Gly Leu His Phe Val His Arg Asp Leu Ala Thr Arg Asn Cys
                645                 650                 655

Leu Val Gly Gln Gly Leu Val Val Lys Ile Gly Asp Phe Gly Met Ser
                660                 665                 670

Arg Asp Ile Tyr Ser Thr Asp Tyr Tyr Arg Val Gly Gly Arg Thr Met
        675                 680                 685

Leu Pro Ile Arg Trp Met Pro Pro Glu Ser Ile Leu Tyr Arg Lys Phe
    690                 695                 700

Thr Thr Glu Ser Asp Val Trp Ser Phe Gly Val Val Leu Trp Glu Ile
705                 710                 715                 720

Phe Thr Tyr Gly Lys Gln Pro Trp Tyr Gln Leu Ser Asn Thr Glu Ala
                725                 730                 735

Ile Asp Cys Ile Thr Gln Gly Arg Glu Leu Glu Arg Pro Arg Ala Cys
        740                 745                 750

Pro Pro Glu Val Tyr Ala Ile Met Arg Gly Cys Trp Gln Arg Glu Pro
    755                 760                 765

Gln Gln Arg His Ser Ile Lys Asp Val His Ala Arg Leu Gln Ala Leu
    770                 775                 780

Ala Gln Ala Pro Pro Val Tyr Leu Asp Val Leu Gly
785                 790                 795

<210> SEQ ID NO 48
<211> LENGTH: 569
<212> TYPE: PRT

<213> ORGANISM: Homo sapiens

<400> SEQUENCE: 48

```
Met Lys Val Leu Leu Arg Leu Ile Cys Phe Ile Ala Leu Leu Ile Ser
  1               5                  10                  15
Ser Leu Glu Ala Asp Lys Cys Lys Glu Arg Glu Lys Ile Ile Leu
             20                  25                  30
Val Ser Ser Ala Asn Glu Ile Asp Val Arg Pro Cys Pro Leu Asn Pro
             35                  40                  45
Asn Glu His Lys Gly Thr Ile Thr Trp Tyr Lys Asp Asp Ser Lys Thr
         50                  55                  60
Pro Val Ser Thr Glu Gln Ala Ser Arg Ile His Gln His Lys Glu Lys
 65                  70                  75                  80
Leu Trp Phe Val Pro Ala Lys Val Glu Asp Ser Gly His Tyr Tyr Cys
                 85                  90                  95
Val Val Arg Asn Ser Ser Tyr Cys Leu Arg Ile Lys Ile Ser Ala Lys
                100                 105                 110
Phe Val Glu Asn Glu Pro Asn Leu Cys Tyr Asn Ala Gln Ala Ile Phe
            115                 120                 125
Lys Gln Lys Leu Pro Val Ala Gly Asp Gly Gly Leu Val Cys Pro Tyr
    130                 135                 140
Met Glu Phe Phe Lys Asn Glu Asn Asn Glu Leu Pro Lys Leu Gln Trp
145                 150                 155                 160
Tyr Lys Asp Cys Lys Pro Leu Leu Leu Asp Asn Ile His Phe Ser Gly
                165                 170                 175
Val Lys Asp Arg Leu Ile Val Met Asn Val Ala Glu Lys His Arg Gly
                180                 185                 190
Asn Tyr Thr Cys His Ala Ser Tyr Thr Tyr Leu Gly Lys Gln Tyr Pro
            195                 200                 205
Ile Thr Arg Val Ile Glu Phe Ile Thr Leu Glu Glu Asn Lys Pro Thr
    210                 215                 220
Arg Pro Val Ile Val Ser Pro Ala Asn Glu Thr Met Glu Val Asp Leu
225                 230                 235                 240
Gly Ser Gln Ile Gln Leu Ile Cys Asn Val Thr Gly Gln Leu Ser Asp
                245                 250                 255
Ile Ala Tyr Trp Lys Trp Asn Gly Ser Val Ile Asp Glu Asp Asp Pro
            260                 265                 270
Val Leu Gly Glu Asp Tyr Tyr Ser Val Glu Asn Pro Ala Asn Lys Arg
    275                 280                 285
Arg Ser Thr Leu Ile Thr Val Leu Asn Ile Ser Glu Ile Glu Ser Arg
290                 295                 300
Phe Tyr Lys His Pro Phe Thr Cys Phe Ala Lys Asn Thr His Gly Ile
305                 310                 315                 320
Asp Ala Ala Tyr Ile Gln Leu Ile Tyr Pro Val Thr Asn Phe Gln Lys
                325                 330                 335
His Met Ile Gly Ile Cys Val Thr Leu Thr Val Ile Ile Val Cys Ser
            340                 345                 350
Val Phe Ile Tyr Lys Ile Phe Lys Ile Asp Ile Val Leu Trp Tyr Arg
    355                 360                 365
Asp Ser Cys Tyr Asp Phe Leu Pro Ile Lys Ala Ser Asp Gly Lys Thr
    370                 375                 380
Tyr Asp Ala Tyr Ile Leu Tyr Pro Lys Thr Val Gly Glu Gly Ser Thr
385                 390                 395                 400
Ser Asp Cys Asp Ile Phe Val Phe Lys Val Leu Pro Glu Val Leu Glu
```

```
                405                 410                 415
Lys Gln Cys Gly Tyr Lys Leu Phe Ile Tyr Gly Arg Asp Asp Tyr Val
            420                 425                 430

Gly Glu Asp Ile Val Glu Val Ile Asn Glu Asn Val Lys Lys Ser Arg
            435                 440                 445

Arg Leu Ile Ile Ile Leu Val Arg Glu Thr Ser Gly Phe Ser Trp Leu
            450                 455                 460

Gly Gly Ser Ser Glu Gln Ile Ala Met Tyr Asn Ala Leu Val Gln
465                 470                 475                 480

Asp Gly Ile Lys Val Val Leu Glu Leu Glu Lys Ile Gln Asp Tyr
                485                 490                 495

Glu Lys Met Pro Glu Ser Ile Lys Phe Ile Lys Gln Lys His Gly Ala
            500                 505                 510

Ile Arg Trp Ser Gly Asp Phe Thr Gln Gly Pro Gln Ser Ala Lys Thr
            515                 520                 525

Arg Phe Trp Lys Asn Val Arg Tyr His Met Pro Val Gln Arg Arg Ser
            530                 535                 540

Pro Ser Ser Lys His Gln Leu Leu Ser Pro Ala Thr Lys Glu Lys Leu
545                 550                 555                 560

Gln Arg Glu Ala His Val Pro Leu Gly
                565

<210> SEQ ID NO 49
<211> LENGTH: 725
<212> TYPE: PRT
<213> ORGANISM: Homo sapiens

<400> SEQUENCE: 49

Met Ala Asp Glu Asp Leu Ile Phe Arg Leu Glu Gly Val Asp Gly Gly
 1               5                  10                  15

Gln Ser Pro Arg Ala Gly His Asp Gly Asp Ser Asp Gly Asp Ser Asp
            20                  25                  30

Asp Glu Glu Gly Tyr Phe Ile Cys Pro Ile Thr Asp Asp Pro Ser Ser
        35                  40                  45

Asn Gln Asn Val Asn Ser Lys Val Asn Lys Tyr Tyr Ser Asn Leu Thr
    50                  55                  60

Lys Ser Glu Arg Tyr Ser Ser Gly Ser Pro Ala Asn Ser Phe His
65                  70                  75                  80

Phe Lys Glu Ala Trp Lys His Ala Ile Gln Lys Ala Lys His Met Pro
                85                  90                  95

Asp Pro Trp Ala Glu Phe His Leu Glu Asp Ile Ala Thr Glu Arg Ala
            100                 105                 110

Thr Arg His Arg Tyr Asn Ala Val Thr Gly Glu Trp Leu Asp Asp Glu
            115                 120                 125

Val Leu Ile Lys Met Ala Ser Gln Pro Phe Gly Arg Gly Ala Met Arg
130                 135                 140

Glu Cys Phe Arg Thr Lys Lys Leu Ser Asn Phe Leu His Ala Gln Gln
145                 150                 155                 160

Trp Lys Gly Ala Ser Asn Tyr Val Ala Lys Arg Tyr Ile Glu Pro Val
                165                 170                 175

Asp Arg Asp Val Tyr Phe Glu Asp Val Arg Leu Gln Met Glu Ala Lys
            180                 185                 190

Leu Trp Gly Glu Glu Tyr Asn Arg His Lys Pro Pro Lys Gln Val Asp
        195                 200                 205

Ile Met Gln Met Cys Ile Ile Glu Leu Lys Asp Arg Pro Gly Lys Pro
```

```
                210                 215                 220
Leu Phe His Leu Glu His Tyr Ile Glu Gly Lys Tyr Ile Lys Tyr Asn
225                 230                 235                 240

Ser Asn Ser Gly Phe Val Arg Asp Asn Ile Arg Leu Thr Pro Gln
                245                 250                 255

Ala Phe Ser His Phe Thr Phe Glu Arg Ser Gly His Gln Leu Ile Val
                260                 265                 270

Val Asp Ile Gln Gly Val Gly Asp Leu Tyr Thr Asp Pro Gln Ile His
                275                 280                 285

Thr Glu Thr Gly Thr Asp Phe Gly Asp Gly Asn Leu Gly Val Arg Gly
                290                 295                 300

Met Ala Leu Phe Phe Tyr Ser His Ala Cys Asn Arg Ile Cys Glu Ser
305                 310                 315                 320

Met Gly Leu Ala Pro Phe Asp Leu Ser Pro Arg Glu Arg Asp Ala Val
                325                 330                 335

Asn Gln Asn Thr Lys Leu Leu Gln Ser Ala Lys Thr Ile Leu Arg Gly
                340                 345                 350

Thr Glu Glu Lys Cys Gly Ser Pro Arg Val Arg Thr Leu Ser Gly Ser
                355                 360                 365

Arg Pro Pro Leu Leu Arg Pro Leu Ser Glu Asn Ser Gly Asp Glu Asn
370                 375                 380

Met Ser Asp Val Thr Phe Asp Ser Leu Pro Ser Pro Ser Ser Ala
385                 390                 395                 400

Thr Pro His Ser Gln Lys Leu Asp His Leu His Trp Pro Val Phe Ser
                405                 410                 415

Asp Leu Asp Asn Met Ala Ser Arg Asp His Asp His Leu Asp Asn His
                420                 425                 430

Arg Glu Ser Glu Asn Ser Gly Asp Ser Gly Tyr Pro Ser Glu Lys Arg
                435                 440                 445

Gly Glu Leu Asp Asp Pro Glu Pro Arg Glu His Gly His Ser Tyr Ser
450                 455                 460

Asn Arg Lys Tyr Glu Ser Asp Glu Asp Ser Leu Gly Ser Ser Gly Arg
465                 470                 475                 480

Val Cys Val Glu Lys Trp Asn Leu Leu Asn Ser Ser Arg Leu His Leu
                485                 490                 495

Pro Arg Ala Ser Ala Val Ala Leu Glu Val Gln Arg Leu Asn Ala Leu
                500                 505                 510

Asp Leu Glu Lys Lys Ile Gly Lys Ser Ile Leu Gly Lys Val His Leu
                515                 520                 525

Ala Met Val Arg Tyr His Glu Gly Gly Arg Phe Cys Glu Lys Gly Glu
530                 535                 540

Glu Trp Asp Gln Glu Ser Ala Val Phe His Leu Glu His Ala Ala Asn
545                 550                 555                 560

Leu Gly Glu Leu Glu Ala Ile Val Gly Leu Gly Leu Met Tyr Ser Gln
                565                 570                 575

Leu Pro His His Ile Leu Ala Asp Val Ser Leu Lys Glu Thr Glu Glu
                580                 585                 590

Asn Lys Thr Lys Gly Phe Asp Tyr Leu Leu Lys Ala Ala Glu Ala Gly
                595                 600                 605

Asp Arg Gln Ser Met Ile Leu Val Ala Arg Ala Phe Asp Ser Gly Gln
                610                 615                 620

Asn Leu Ser Pro Asp Arg Cys Gln Asp Trp Leu Glu Ala Leu His Trp
625                 630                 635                 640
```

-continued

Tyr Asn Thr Ala Leu Glu Met Thr Asp Cys Asp Gly Gly Glu Tyr
            645                 650                 655

Asp Gly Met Gln Asp Glu Pro Arg Tyr Met Met Leu Ala Arg Glu Ala
        660                 665                 670

Glu Met Leu Phe Thr Gly Gly Tyr Gly Leu Glu Lys Asp Pro Gln Arg
    675                 680                 685

Ser Gly Asp Leu Tyr Thr Gln Ala Ala Glu Ala Ala Met Glu Ala Met
690                 695                 700

Lys Gly Arg Leu Ala Asn Gln Tyr Tyr Gln Lys Ala Glu Glu Ala Trp
705                 710                 715                 720

Ala Gln Met Glu Glu
            725

<210> SEQ ID NO 50
<211> LENGTH: 376
<212> TYPE: PRT
<213> ORGANISM: Homo sapiens

<400> SEQUENCE: 50

Met Cys Glu Glu Glu Thr Thr Ala Leu Val Cys Asp Asn Gly Ser Gly
1               5                   10                  15

Leu Cys Lys Ala Gly Phe Ala Gly Asp Asp Ala Pro Arg Ala Val Phe
            20                  25                  30

Pro Ser Ile Val Gly Arg Pro Arg His Gln Gly Val Met Val Gly Met
        35                  40                  45

Gly Gln Lys Asp Ser Tyr Val Gly Asp Glu Ala Gln Ser Lys Arg Gly
    50                  55                  60

Ile Leu Thr Leu Lys Tyr Pro Ile Glu His Gly Ile Ile Thr Asn Trp
65                  70                  75                  80

Asp Asp Met Glu Lys Ile Trp His His Ser Phe Tyr Asn Glu Leu Arg
                85                  90                  95

Val Ala Pro Glu Glu His Pro Thr Leu Leu Thr Glu Ala Pro Leu Asn
            100                 105                 110

Pro Lys Ala Asn Arg Glu Lys Met Thr Gln Ile Met Phe Glu Thr Phe
        115                 120                 125

Asn Val Pro Ala Met Tyr Val Ala Ile Gln Ala Val Leu Ser Leu Tyr
    130                 135                 140

Ala Ser Gly Arg Thr Thr Gly Ile Val Leu Asp Ser Gly Asp Gly Val
145                 150                 155                 160

Thr His Asn Val Pro Ile Tyr Glu Gly Tyr Ala Leu Pro His Ala Ile
                165                 170                 175

Met Arg Leu Asp Leu Ala Gly Arg Asp Leu Thr Asp Tyr Leu Met Lys
            180                 185                 190

Ile Leu Thr Glu Arg Gly Tyr Ser Phe Val Thr Thr Ala Glu Arg Glu
        195                 200                 205

Ile Val Arg Asp Ile Lys Glu Lys Leu Cys Tyr Val Ala Leu Asp Phe
    210                 215                 220

Glu Asn Glu Met Ala Thr Ala Ala Ser Ser Ser Ser Leu Glu Lys Ser
225                 230                 235                 240

Tyr Glu Leu Pro Asp Gly Gln Val Ile Thr Ile Gly Asn Glu Arg Phe
                245                 250                 255

Arg Cys Pro Glu Thr Leu Phe Gln Pro Ser Phe Ile Gly Met Glu Ser
            260                 265                 270

Ala Gly Ile His Glu Thr Thr Tyr Asn Ser Ile Met Lys Cys Asp Ile
        275                 280                 285

-continued

Asp Ile Arg Lys Asp Leu Tyr Ala Asn Asn Val Leu Ser Gly Gly Thr
290                 295                 300

Thr Met Tyr Pro Gly Ile Ala Asp Arg Met Gln Lys Glu Ile Thr Ala
305                 310                 315                 320

Leu Ala Pro Ser Thr Met Lys Ile Lys Ile Ile Ala Pro Pro Glu Arg
            325                 330                 335

Lys Tyr Ser Val Trp Ile Gly Gly Ser Ile Leu Ala Ser Leu Ser Thr
            340                 345                 350

Phe Gln Gln Met Trp Ile Ser Lys Pro Glu Tyr Asp Glu Ala Gly Pro
            355                 360                 365

Ser Ile Val His Arg Lys Cys Phe
370                 375

<210> SEQ ID NO 51
<211> LENGTH: 1972
<212> TYPE: PRT
<213> ORGANISM: Homo sapiens

<400> SEQUENCE: 51

Met Ala Gln Lys Gly Gln Leu Ser Asp Asp Glu Lys Phe Leu Phe Val
1               5                   10                  15

Asp Lys Asn Phe Ile Asn Ser Pro Val Ala Gln Ala Asp Trp Ala Ala
                20                  25                  30

Lys Arg Leu Val Trp Val Pro Ser Glu Lys Gln Gly Phe Glu Ala Ala
            35                  40                  45

Ser Ile Lys Glu Glu Lys Gly Asp Glu Val Val Val Glu Leu Val Glu
            50                  55                  60

Asn Gly Lys Lys Val Thr Val Gly Lys Asp Asp Ile Gln Lys Met Asn
65                  70                  75                  80

Pro Pro Lys Phe Ser Lys Val Glu Asp Met Ala Glu Leu Thr Cys Leu
                85                  90                  95

Asn Glu Ala Ser Val Leu His Asn Leu Arg Glu Arg Tyr Phe Ser Gly
            100                 105                 110

Leu Ile Tyr Thr Tyr Ser Gly Leu Phe Cys Val Val Val Asn Pro Tyr
            115                 120                 125

Lys His Leu Pro Ile Tyr Ser Glu Lys Ile Val Asp Met Tyr Lys Gly
            130                 135                 140

Lys Lys Arg His Glu Met Pro Pro His Ile Tyr Ala Ile Ala Asp Thr
145                 150                 155                 160

Ala Tyr Arg Ser Met Leu Gln Asp Arg Glu Asp Gln Ser Ile Leu Cys
                165                 170                 175

Thr Gly Glu Ser Gly Ala Gly Lys Thr Glu Asn Thr Lys Lys Val Ile
            180                 185                 190

Gln Tyr Leu Ala Val Val Ala Ser Ser His Lys Gly Lys Lys Asp Thr
            195                 200                 205

Ser Ile Thr Gly Glu Leu Glu Lys Gln Leu Leu Gln Ala Asn Pro Ile
            210                 215                 220

Leu Glu Ala Phe Gly Asn Ala Lys Thr Val Lys Asn Asp Asn Ser Ser
225                 230                 235                 240

Arg Phe Gly Lys Phe Ile Arg Ile Asn Phe Asp Val Thr Gly Tyr Ile
                245                 250                 255

Val Gly Ala Asn Ile Glu Thr Tyr Leu Leu Glu Lys Ser Arg Ala Ile
            260                 265                 270

Arg Gln Ala Arg Asp Glu Arg Thr Phe His Ile Phe Tyr Tyr Met Ile
            275                 280                 285

-continued

```
Ala Gly Ala Lys Glu Lys Met Arg Ser Asp Leu Leu Leu Glu Gly Phe
    290             295                 300

Asn Asn Tyr Thr Phe Leu Ser Asn Gly Phe Val Pro Ile Pro Ala Ala
305             310                 315                 320

Gln Asp Asp Glu Met Phe Gln Glu Thr Val Glu Ala Met Ala Ile Met
                325                 330                 335

Gly Phe Ser Glu Glu Gln Leu Ser Ile Leu Lys Val Val Ser Ser
                340                 345                 350

Val Leu Gln Leu Gly Asn Ile Val Phe Lys Lys Glu Arg Asn Thr Asp
        355                 360                 365

Gln Ala Ser Met Pro Asp Asn Thr Ala Ala Gln Lys Val Cys His Leu
    370                 375                 380

Met Gly Ile Asn Val Thr Asp Phe Thr Arg Ser Ile Leu Thr Pro Arg
385                 390                 395                 400

Ile Lys Val Gly Arg Asp Val Val Gln Lys Ala Gln Thr Lys Glu Gln
                405                 410                 415

Ala Asp Phe Ala Val Glu Ala Leu Ala Lys Ala Thr Tyr Glu Arg Leu
                420                 425                 430

Phe Arg Trp Ile Leu Thr Arg Val Asn Lys Ala Leu Asp Lys Thr His
        435                 440                 445

Arg Gln Gly Ala Ser Phe Leu Gly Ile Leu Asp Ile Ala Gly Phe Glu
    450                 455                 460

Ile Phe Glu Val Asn Ser Phe Glu Gln Leu Cys Ile Asn Tyr Thr Asn
465                 470                 475                 480

Glu Lys Leu Gln Gln Leu Phe Asn His Thr Met Phe Ile Leu Glu Gln
                485                 490                 495

Glu Glu Tyr Gln Arg Glu Gly Ile Glu Trp Asn Phe Ile Asp Phe Gly
                500                 505                 510

Leu Asp Leu Gln Pro Cys Ile Glu Leu Ile Glu Arg Pro Asn Asn Pro
        515                 520                 525

Pro Gly Val Leu Ala Leu Leu Asp Glu Glu Cys Trp Phe Pro Lys Ala
    530                 535                 540

Thr Asp Lys Ser Phe Val Glu Lys Leu Cys Thr Glu Gln Gly Ser His
545                 550                 555                 560

Pro Lys Phe Gln Lys Pro Lys Gln Leu Lys Asp Lys Thr Glu Phe Ser
                565                 570                 575

Ile Ile His Tyr Ala Gly Lys Val Asp Tyr Asn Ala Ser Ala Trp Leu
                580                 585                 590

Thr Lys Asn Met Asp Pro Leu Asn Asp Asn Val Thr Ser Leu Leu Asn
        595                 600                 605

Ala Ser Ser Asp Lys Phe Val Ala Asp Leu Trp Lys Asp Val Asp Arg
    610                 615                 620

Ile Val Gly Leu Asp Gln Met Ala Lys Met Thr Glu Ser Ser Leu Pro
625                 630                 635                 640

Ser Ala Ser Lys Thr Lys Lys Gly Met Phe Arg Thr Val Gly Gln Leu
                645                 650                 655

Tyr Lys Glu Gln Leu Gly Lys Leu Met Thr Thr Leu Arg Asn Thr Thr
                660                 665                 670

Pro Asn Phe Val Arg Cys Ile Ile Pro Asn His Glu Lys Arg Ser Gly
        675                 680                 685

Lys Leu Asp Ala Phe Leu Val Leu Glu Gln Leu Arg Cys Asn Gly Val
    690                 695                 700

Leu Glu Gly Ile Arg Ile Cys Arg Gln Gly Phe Pro Asn Arg Ile Val
705                 710                 715                 720
```

```
Phe Gln Glu Phe Arg Gln Arg Tyr Glu Ile Leu Ala Ala Asn Ala Ile
                725                 730                 735
Pro Lys Gly Phe Met Asp Gly Lys Gln Ala Cys Ile Leu Met Ile Lys
                740                 745                 750
Ala Leu Glu Leu Asp Pro Asn Leu Tyr Arg Ile Gly Gln Ser Lys Ile
                755                 760                 765
Phe Phe Arg Thr Gly Val Leu Ala His Leu Glu Glu Arg Asp Leu
770                 775                 780
Lys Ile Thr Asp Val Ile Met Ala Phe Gln Ala Met Cys Arg Gly Tyr
785                 790                 795                 800
Leu Ala Arg Lys Ala Phe Ala Lys Arg Gln Gln Gln Leu Thr Ala Met
                805                 810                 815
Lys Val Ile Gln Arg Asn Cys Ala Ala Tyr Leu Lys Leu Arg Asn Trp
                820                 825                 830
Gln Trp Trp Arg Leu Phe Thr Lys Val Lys Pro Leu Leu Gln Val Thr
                835                 840                 845
Arg Gln Glu Glu Glu Met Gln Ala Lys Glu Asp Glu Leu Gln Lys Thr
                850                 855                 860
Lys Glu Arg Gln Gln Lys Ala Glu Asn Glu Leu Lys Glu Leu Glu Gln
865                 870                 875                 880
Lys His Ser Gln Leu Thr Glu Glu Lys Asn Leu Leu Gln Glu Gln Leu
                885                 890                 895
Gln Ala Glu Thr Glu Leu Tyr Ala Glu Ala Glu Glu Met Arg Val Arg
                900                 905                 910
Leu Ala Ala Lys Lys Gln Glu Leu Glu Glu Ile Leu His Glu Met Glu
                915                 920                 925
Ala Arg Leu Glu Glu Glu Asp Arg Gly Gln Gln Leu Gln Ala Glu
                930                 935                 940
Arg Lys Lys Met Ala Gln Gln Met Leu Asp Leu Glu Glu Gln Leu Glu
945                 950                 955                 960
Glu Glu Glu Ala Ala Arg Gln Lys Leu Gln Leu Glu Lys Val Thr Ala
                965                 970                 975
Glu Ala Lys Ile Lys Lys Leu Glu Asp Glu Ile Leu Val Met Asp Asp
                980                 985                 990
Gln Asn Asn Lys Leu Ser Lys Glu Arg Lys Leu Leu Glu Glu Arg Ile
                995                 1000                1005
Ser Asp Leu Thr Thr Asn Leu Ala Glu Glu Glu Lys Ala Lys Asn
                1010                1015                1020
Leu Thr Lys Leu Lys Asn Lys His Glu Ser Met Ile Ser Glu Leu Glu
1025                1030                1035                1040
Val Arg Leu Lys Lys Glu Glu Lys Ser Arg Gln Glu Leu Glu Lys Leu
                1045                1050                1055
Lys Arg Lys Leu Glu Gly Asp Ala Ser Asp Phe His Glu Gln Ile Ala
                1060                1065                1070
Asp Leu Gln Ala Gln Ile Ala Glu Leu Lys Met Gln Leu Ala Lys Lys
                1075                1080                1085
Glu Glu Glu Leu Gln Ala Ala Leu Ala Arg Leu Asp Asp Glu Ile Ala
                1090                1095                1100
Gln Lys Asn Asn Ala Leu Lys Lys Ile Arg Glu Leu Glu Gly His Ile
1105                1110                1115                1120
Ser Asp Leu Gln Glu Asp Leu Asp Ser Glu Arg Ala Ala Arg Asn Lys
                1125                1130                1135
Ala Glu Lys Gln Lys Arg Asp Leu Gly Glu Glu Leu Glu Ala Leu Lys
```

-continued

```
                1140                1145                1150
Thr Glu Leu Glu Asp Thr Leu Asp Ser Thr Ala Thr Gln Gln Glu Leu
            1155                1160                1165
Arg Ala Lys Arg Glu Gln Glu Val Thr Val Leu Lys Lys Ala Leu Asp
        1170                1175                1180
Glu Glu Thr Arg Ser His Glu Ala Gln Val Gln Glu Met Arg Gln Lys
1185                1190                1195                1200
His Ala Gln Ala Val Glu Glu Leu Thr Glu Gln Leu Glu Gln Phe Lys
                1205                1210                1215
Arg Ala Lys Ala Asn Leu Asp Lys Asn Lys Gln Thr Leu Glu Lys Glu
            1220                1225                1230
Asn Ala Asp Leu Ala Gly Glu Leu Arg Val Leu Gly Gln Ala Lys Gln
        1235                1240                1245
Glu Val Glu His Lys Lys Lys Lys Leu Glu Ala Gln Val Gln Glu Leu
    1250                1255                1260
Gln Ser Lys Cys Ser Asp Gly Glu Arg Ala Arg Ala Glu Leu Asn Asp
1265                1270                1275                1280
Lys Val His Lys Leu Gln Asn Glu Val Glu Ser Val Thr Gly Met Leu
                1285                1290                1295
Asn Glu Ala Glu Gly Lys Ala Ile Lys Leu Ala Lys Asp Val Ala Ser
            1300                1305                1310
Leu Ser Ser Gln Leu Gln Asp Thr Gln Glu Leu Leu Gln Glu Glu Thr
        1315                1320                1325
Arg Gln Lys Leu Asn Val Ser Thr Lys Leu Arg Gln Leu Glu Glu Glu
    1330                1335                1340
Arg Asn Ser Leu Gln Asp Gln Leu Asp Glu Glu Met Glu Ala Lys Gln
1345                1350                1355                1360
Asn Leu Glu Arg His Ile Ser Thr Leu Asn Ile Gln Leu Ser Asp Ser
                1365                1370                1375
Lys Lys Lys Leu Gln Asp Phe Ala Ser Thr Val Glu Ala Leu Glu Glu
            1380                1385                1390
Gly Lys Lys Arg Phe Gln Lys Glu Ile Glu Asn Leu Thr Gln Gln Tyr
        1395                1400                1405
Glu Glu Lys Ala Ala Ala Tyr Asp Lys Leu Glu Lys Thr Lys Asn Arg
    1410                1415                1420
Leu Gln Gln Glu Leu Asp Asp Leu Val Val Asp Leu Asp Asn Gln Arg
1425                1430                1435                1440
Gln Leu Val Ser Asn Leu Glu Lys Lys Gln Arg Lys Phe Asp Gln Leu
            1445                1450                1455
Leu Ala Glu Glu Lys Asn Ile Ser Ser Lys Tyr Ala Asp Glu Arg Asp
        1460                1465                1470
Arg Ala Glu Ala Glu Ala Arg Glu Lys Glu Thr Lys Ala Leu Ser Leu
    1475                1480                1485
Ala Arg Ala Leu Glu Glu Ala Leu Glu Ala Lys Glu Glu Leu Glu Arg
        1490                1495                1500
Thr Asn Lys Met Leu Lys Ala Glu Met Glu Asp Leu Val Ser Ser Lys
1505                1510                1515                1520
Asp Asp Val Gly Lys Asn Val His Glu Leu Glu Lys Ser Lys Arg Ala
                1525                1530                1535
Leu Glu Thr Gln Met Glu Glu Met Lys Thr Gln Leu Glu Glu Leu Glu
            1540                1545                1550
Asp Glu Leu Gln Ala Thr Glu Asp Ala Lys Leu Arg Leu Glu Val Asn
        1555                1560                1565
```

Met Gln Ala Leu Lys Gly Gln Phe Glu Arg Asp Leu Gln Ala Arg Asp
            1570                1575                1580

Glu Gln Asn Glu Glu Lys Arg Arg Gln Leu Gln Arg Gln Leu His Glu
1585                1590                1595                1600

Tyr Glu Thr Glu Leu Glu Asp Glu Arg Lys Gln Arg Ala Leu Ala Ala
                1605                1610                1615

Ala Ala Lys Lys Lys Leu Glu Gly Asp Leu Lys Asp Leu Glu Leu Gln
            1620                1625                1630

Ala Asp Ser Ala Ile Lys Gly Arg Glu Glu Ala Ile Lys Gln Leu Arg
        1635                1640                1645

Lys Leu Gln Ala Gln Met Lys Asp Phe Gln Arg Glu Leu Glu Asp Ala
    1650                1655                1660

Arg Ala Ser Arg Asp Glu Ile Phe Ala Thr Ala Lys Glu Asn Glu Lys
1665                1670                1675                1680

Lys Ala Lys Ser Leu Glu Ala Asp Leu Met Gln Leu Gln Glu Asp Leu
                1685                1690                1695

Ala Ala Ala Glu Arg Ala Arg Lys Gln Ala Asp Leu Glu Lys Glu Glu
            1700                1705                1710

Leu Ala Glu Glu Leu Ala Ser Ser Leu Ser Gly Arg Asn Ala Leu Gln
        1715                1720                1725

Asp Glu Lys Arg Arg Leu Glu Ala Arg Ile Ala Gln Leu Glu Glu Glu
    1730                1735                1740

Leu Glu Glu Glu Gln Gly Asn Met Glu Ala Met Ser Asp Arg Val Arg
1745                1750                1755                1760

Lys Ala Thr Gln Gln Ala Glu Gln Leu Ser Asn Glu Leu Ala Thr Glu
                1765                1770                1775

Arg Ser Thr Ala Gln Lys Asn Glu Ser Ala Arg Gln Gln Leu Glu Arg
            1780                1785                1790

Gln Asn Lys Glu Leu Arg Ser Lys Leu His Glu Met Glu Gly Ala Val
        1795                1800                1805

Lys Ser Lys Phe Lys Ser Thr Ile Ala Ala Leu Glu Ala Lys Ile Ala
    1810                1815                1820

Gln Leu Glu Glu Gln Val Glu Gln Glu Ala Arg Glu Lys Gln Ala Ala
1825                1830                1835                1840

Thr Lys Ser Leu Lys Gln Lys Asp Lys Lys Leu Lys Glu Ile Leu Leu
                1845                1850                1855

Gln Val Glu Asp Glu Arg Lys Met Ala Glu Gln Tyr Lys Glu Gln Ala
            1860                1865                1870

Glu Lys Gly Asn Ala Arg Val Lys Gln Leu Lys Arg Gln Leu Glu Glu
        1875                1880                1885

Ala Glu Glu Glu Ser Gln Arg Ile Asn Ala Asn Arg Arg Lys Leu Gln
    1890                1895                1900

Arg Glu Leu Asp Glu Ala Thr Glu Ser Asn Glu Ala Met Gly Arg Glu
1905                1910                1915                1920

Val Asn Ala Leu Lys Ser Lys Leu Arg Arg Gly Asn Glu Thr Ser Phe
                1925                1930                1935

Val Pro Ser Arg Arg Ser Gly Gly Arg Arg Val Ile Glu Asn Ala Asp
            1940                1945                1950

Gly Ser Glu Glu Glu Thr Asp Thr Arg Asp Ala Asp Phe Asn Gly Thr
        1955                1960                1965

Lys Ala Ser Glu
    1970

<210> SEQ ID NO 52

```
<211> LENGTH: 171
<212> TYPE: PRT
<213> ORGANISM: Homo sapiens

<400> SEQUENCE: 52

Met Ser Ser Lys Arg Thr Lys Thr Lys Lys Arg Pro Gln Arg
 1               5                  10                  15

Ala Thr Ser Asn Val Phe Ala Met Phe Asp Gln Ser Gln Ile Gln Glu
                20                  25                  30

Phe Lys Glu Ala Phe Asn Met Ile Asp Gln Asn Arg Asp Gly Phe Ile
            35                  40                  45

Asp Lys Glu Asp Leu His Asp Met Leu Ala Ser Leu Gly Lys Asn Pro
50                  55                  60

Thr Asp Glu Tyr Leu Asp Ala Met Met Asn Glu Ala Pro Gly Pro Ile
65                  70                  75                  80

Asn Phe Thr Met Phe Leu Thr Met Phe Gly Glu Lys Leu Asn Gly Thr
                85                  90                  95

Asp Pro Glu Asp Val Ile Arg Asn Ala Phe Ala Cys Phe Asp Glu Glu
            100                 105                 110

Ala Thr Gly Thr Ile Gln Glu Asp Tyr Leu Arg Glu Leu Leu Thr Thr
        115                 120                 125

Met Gly Asp Arg Phe Thr Asp Glu Glu Val Asp Glu Leu Tyr Arg Glu
130                 135                 140

Ala Pro Ile Asp Lys Lys Gly Asn Phe Asn Tyr Ile Glu Phe Thr Arg
145                 150                 155                 160

Ile Leu Lys His Gly Ala Lys Asp Lys Asp
                165                 170

<210> SEQ ID NO 53
<211> LENGTH: 172
<212> TYPE: PRT
<213> ORGANISM: Homo sapiens

<400> SEQUENCE: 53

Met Ser Ser Lys Lys Ala Lys Thr Lys Thr Lys Lys Arg Pro Gln
 1               5                  10                  15

Arg Ala Thr Ser Asn Val Phe Ala Met Phe Asp Gln Ser Gln Ile Gln
                20                  25                  30

Glu Phe Lys Glu Ala Phe Asn Met Ile Asp Gln Asn Arg Asp Gly Phe
            35                  40                  45

Ile Asp Lys Glu Asp Leu His Asp Met Leu Ala Ser Leu Gly Lys Asn
        50                  55                  60

Pro Thr Asp Ala Tyr Leu Asp Ala Met Met Asn Glu Ala Pro Gly Pro
65                  70                  75                  80

Ile Asn Phe Thr Met Phe Leu Thr Met Phe Gly Glu Lys Leu Asn Gly
                85                  90                  95

Thr Asp Pro Glu Asp Val Ile Arg Asn Ala Phe Ala Cys Phe Asp Glu
            100                 105                 110

Glu Ala Thr Gly Thr Ile Gln Glu Asp Tyr Leu Arg Glu Leu Leu Thr
        115                 120                 125

Thr Met Gly Asp Arg Phe Thr Asp Glu Glu Val Asp Glu Leu Tyr Arg
130                 135                 140

Glu Ala Pro Ile Asp Lys Lys Gly Asn Phe Asn Tyr Ile Glu Phe Thr
145                 150                 155                 160

Arg Ile Leu Lys His Gly Ala Lys Asp Lys Asp
                165                 170
```

<210> SEQ ID NO 54
<211> LENGTH: 232
<212> TYPE: PRT
<213> ORGANISM: Homo sapiens

<400> SEQUENCE: 54

Met Lys Glu Arg Arg Ala Pro Gln Pro Val Ala Arg Cys Lys Leu
1               5                   10                  15

Val Leu Val Gly Asp Val Gln Cys Gly Lys Thr Ala Met Leu Gln Val
            20                  25                  30

Leu Ala Lys Asp Cys Tyr Pro Glu Thr Tyr Val Pro Thr Val Phe Glu
        35                  40                  45

Asn Tyr Thr Ala Cys Leu Glu Thr Glu Glu Gln Arg Val Glu Leu Ser
    50                  55                  60

Leu Trp Asp Thr Ser Gly Ser Pro Tyr Tyr Asp Asn Val Arg Pro Leu
65                  70                  75                  80

Cys Tyr Ser Asp Ser Asp Ala Val Leu Leu Cys Phe Asp Ile Ser Arg
                85                  90                  95

Pro Glu Thr Val Asp Ser Ala Leu Lys Lys Trp Arg Thr Glu Ile Leu
            100                 105                 110

Asp Tyr Cys Pro Ser Thr Arg Val Leu Leu Ile Gly Cys Lys Thr Asp
        115                 120                 125

Leu Arg Thr Asp Leu Ser Thr Leu Met Glu Leu Ser His Gln Lys Gln
    130                 135                 140

Ala Pro Ile Ser Tyr Glu Gln Gly Cys Ala Ile Ala Lys Gln Leu Gly
145                 150                 155                 160

Ala Glu Ile Tyr Leu Glu Gly Ser Ala Phe Thr Ser Glu Lys Ser Ile
                165                 170                 175

His Ser Ile Phe Arg Thr Ala Ser Met Leu Cys Leu Asn Lys Pro Ser
            180                 185                 190

Pro Leu Pro Gln Lys Ser Pro Val Arg Ser Leu Ser Lys Arg Leu Leu
        195                 200                 205

His Leu Pro Ser Arg Ser Glu Leu Ile Ser Ser Thr Phe Lys Lys Glu
    210                 215                 220

Lys Ala Lys Ser Cys Ser Ile Met
225                 230

<210> SEQ ID NO 55
<211> LENGTH: 205
<212> TYPE: PRT
<213> ORGANISM: Homo sapiens

<400> SEQUENCE: 55

Met Thr Glu Arg Arg Val Pro Phe Ser Leu Leu Arg Gly Pro Ser Trp
1               5                   10                  15

Asp Pro Phe Arg Asp Trp Tyr Pro His Ser Arg Leu Phe Asp Gln Ala
            20                  25                  30

Phe Gly Leu Pro Arg Leu Pro Glu Glu Trp Ser Gln Trp Leu Gly Gly
        35                  40                  45

Ser Ser Trp Pro Gly Tyr Val Arg Pro Leu Pro Pro Ala Ala Ile Glu
    50                  55                  60

Ser Pro Ala Val Ala Ala Pro Ala Tyr Ser Arg Ala Leu Ser Arg Gln
65                  70                  75                  80

Leu Ser Ser Gly Val Ser Glu Ile Arg His Thr Ala Asp Arg Trp Arg
                85                  90                  95

Val Ser Leu Asp Val Asn His Phe Ala Pro Asp Glu Leu Thr Val Lys

```
                    100                 105                 110
Thr Lys Asp Gly Val Val Glu Ile Thr Gly Lys His Glu Arg Gln
                115                 120                 125
Asp Glu His Gly Tyr Ile Ser Arg Cys Phe Thr Arg Lys Tyr Thr Leu
130                 135                 140
Pro Pro Gly Val Asp Pro Thr Gln Val Ser Ser Ser Leu Ser Pro Glu
145                 150                 155                 160
Gly Thr Leu Thr Val Glu Ala Pro Met Pro Lys Leu Ala Thr Gln Ser
                165                 170                 175
Asn Glu Ile Thr Ile Pro Val Thr Phe Glu Ser Arg Ala Gln Leu Gly
                180                 185                 190
Gly Pro Glu Ala Ala Lys Ser Asp Glu Thr Ala Ala Lys
                195                 200                 205

<210> SEQ ID NO 56
<211> LENGTH: 784
<212> TYPE: PRT
<213> ORGANISM: Homo sapiens

<400> SEQUENCE: 56

Met Glu Gly Asp Gly Gly Thr Pro Trp Ala Leu Ala Leu Leu Arg Thr
1               5                   10                  15
Phe Asp Ala Gly Glu Phe Thr Gly Trp Glu Lys Val Gly Ser Gly Gly
                20                  25                  30
Phe Gly Gln Val Tyr Lys Val Arg His Val His Trp Lys Thr Trp Leu
            35                  40                  45
Ala Ile Lys Cys Ser Pro Ser Leu His Val Asp Asp Arg Glu Arg Met
50                  55                  60
Glu Leu Leu Glu Glu Ala Lys Lys Met Glu Met Ala Lys Phe Arg Tyr
65                  70                  75                  80
Ile Leu Pro Val Tyr Gly Ile Cys Arg Glu Pro Val Gly Leu Val Met
                85                  90                  95
Glu Tyr Met Glu Thr Gly Ser Leu Glu Lys Leu Leu Ala Ser Glu Pro
                100                 105                 110
Leu Pro Trp Asp Leu Arg Phe Arg Ile Ile His Glu Thr Ala Val Gly
                115                 120                 125
Met Asn Phe Leu His Cys Met Ala Pro Pro Leu Leu His Leu Asp Leu
130                 135                 140
Lys Pro Ala Asn Ile Leu Leu Asp Ala His Tyr His Val Lys Ile Ser
145                 150                 155                 160
Asp Phe Gly Leu Ala Lys Cys Asn Gly Leu Ser His Ser His Asp Leu
                165                 170                 175
Ser Met Asp Gly Leu Phe Gly Thr Ile Ala Tyr Leu Pro Pro Glu Arg
                180                 185                 190
Ile Arg Glu Lys Ser Arg Leu Phe Asp Thr Lys His Asp Val Tyr Ser
                195                 200                 205
Phe Ala Ile Val Ile Trp Gly Val Leu Thr Gln Lys Lys Pro Phe Ala
            210                 215                 220
Asp Glu Lys Asn Ile Leu His Ile Met Val Lys Val Lys Gly His
225                 230                 235                 240
Arg Pro Glu Leu Pro Pro Val Cys Arg Ala Arg Pro Arg Ala Cys Ser
                245                 250                 255
His Leu Ile Arg Leu Met Gln Arg Cys Trp Gln Gly Asp Pro Arg Val
                260                 265                 270
Arg Pro Thr Phe Gln Glu Ile Thr Ser Glu Thr Glu Asp Leu Cys Glu
```

```
                275                 280                 285
Lys Pro Asp Asp Glu Val Lys Glu Thr Ala His Asp Leu Asp Val Lys
    290                 295                 300

Ser Pro Pro Glu Pro Arg Ser Glu Val Val Pro Ala Arg Leu Lys Arg
305                 310                 315                 320

Ala Ser Ala Pro Thr Phe Asp Asn Asp Tyr Ser Leu Ser Glu Leu Leu
                325                 330                 335

Ser Gln Leu Asp Ser Gly Val Ser Gln Ala Val Glu Gly Pro Glu Glu
            340                 345                 350

Leu Ser Arg Ser Ser Ser Glu Ser Lys Leu Pro Ser Ser Gly Ser Gly
        355                 360                 365

Lys Arg Leu Ser Gly Val Ser Ser Val Asp Ser Ala Phe Ser Ser Arg
    370                 375                 380

Gly Ser Leu Ser Leu Ser Phe Glu Arg Glu Pro Ser Thr Ser Asp Leu
385                 390                 395                 400

Gly Thr Thr Asp Val Gln Lys Lys Lys Leu Val Asp Ala Ile Val Ser
                405                 410                 415

Gly Asp Thr Ser Lys Leu Met Lys Ile Leu Gln Pro Gln Asp Val Asp
            420                 425                 430

Leu Ala Leu Asp Ser Gly Ala Ser Leu Leu His Leu Ala Val Glu Ala
        435                 440                 445

Gly Gln Glu Glu Cys Ala Lys Trp Leu Leu Leu Asn Ala Asn Pro
    450                 455                 460

Asn Leu Ser Asn Arg Arg Gly Ser Thr Pro Leu His Met Ala Val Glu
465                 470                 475                 480

Arg Arg Val Arg Gly Val Val Glu Leu Leu Leu Ala Arg Lys Ile Ser
                485                 490                 495

Val Asn Ala Lys Asp Glu Asp Gln Trp Thr Ala Leu His Phe Ala Ala
            500                 505                 510

Gln Asn Gly Asp Glu Ser Ser Thr Arg Leu Leu Leu Glu Lys Asn Ala
        515                 520                 525

Ser Val Asn Glu Val Asp Phe Glu Gly Arg Thr Pro Met His Val Ala
    530                 535                 540

Cys Gln His Gly Gln Glu Asn Ile Val Arg Ile Leu Leu Arg Arg Gly
545                 550                 555                 560

Val Asp Val Ser Leu Gln Gly Lys Asp Ala Trp Leu Pro Leu His Tyr
                565                 570                 575

Ala Ala Trp Gln Gly His Leu Pro Ile Val Lys Leu Leu Ala Lys Gln
            580                 585                 590

Pro Gly Val Ser Val Asn Ala Gln Thr Leu Asp Gly Arg Thr Pro Leu
        595                 600                 605

His Leu Ala Ala Gln Arg Gly His Tyr Arg Val Ala Arg Ile Leu Ile
    610                 615                 620

Asp Leu Cys Ser Asp Val Asn Val Cys Ser Leu Leu Ala Gln Thr Pro
625                 630                 635                 640

Leu His Val Ala Ala Glu Thr Gly His Thr Ser Thr Ala Arg Leu Leu
                645                 650                 655

Leu His Arg Gly Ala Gly Lys Glu Ala Met Thr Ser Asp Gly Tyr Thr
            660                 665                 670

Ala Leu His Leu Ala Ala Arg Asn Gly His Leu Ala Thr Val Lys Leu
        675                 680                 685

Leu Val Glu Glu Lys Ala Asp Val Leu Ala Arg Gly Pro Leu Asn Gln
    690                 695                 700
```

```
Thr Ala Leu His Leu Ala Ala His Gly His Ser Glu Val Val Glu
705                 710                 715                 720

Glu Leu Val Ser Ala Asp Val Ile Asp Leu Phe Asp Glu Gln Gly Leu
            725                 730                 735

Ser Ala Leu His Leu Ala Ala Gln Gly Arg His Ala Gln Thr Val Glu
        740                 745                 750

Thr Leu Leu Arg His Gly Ala His Ile Asn Leu Gln Ser Leu Lys Phe
    755                 760                 765

Gln Gly Gly His Gly Pro Ala Ala Thr Leu Leu Arg Arg Ser Lys Thr
        770                 775                 780
```

<210> SEQ ID NO 57
<211> LENGTH: 202
<212> TYPE: PRT
<213> ORGANISM: Homo sapiens

<400> SEQUENCE: 57

```
Met Ser Ala Ser Thr Ser Ser His Arg Pro Ile Lys Gly Ile Leu Lys
1               5                   10                  15

Asn Lys Ser Ser Ser Gly Ser Ser Val Ala Thr Ser Gly Gln Gln Ser
            20                  25                  30

Gly Gly Thr Ile Gln Asp Val Lys Arg Lys Ser Gln Lys Trp Asp
        35                  40                  45

Glu Ser Ser Ile Leu Ala Ala His Arg Ala Thr Tyr Arg Asp Tyr Asp
50                  55                  60

Leu Met Lys Ala Asn Glu Pro Gly Thr Ser Tyr Met Ser Val Gln Asp
65                  70                  75                  80

Asn Gly Glu Asp Ser Val Arg Asp Val Glu Gly Glu Asp Ser Val Arg
            85                  90                  95

Gly Val Glu Gly Lys Glu Ala Thr Asp Ala Ser Asp His Ser Cys Glu
        100                 105                 110

Val Asp Glu Gln Glu Ser Ser Glu Ala Tyr Met Arg Lys Ile Leu Leu
    115                 120                 125

His Lys Gln Glu Lys Lys Arg Gln Phe Glu Met Arg Arg Arg Leu His
130                 135                 140

Tyr Asn Glu Glu Leu Asn Ile Lys Leu Ala Arg Gln Leu Met Trp Lys
145                 150                 155                 160

Glu Leu Gln Ser Glu Asp Asn Glu Asn Glu Thr Pro Gln Gly Thr
            165                 170                 175

Asn Glu Glu Lys Thr Ala Ala Glu Glu Ser Glu Glu Ala Pro Leu Thr
        180                 185                 190

Gly Gly Leu Gln Thr Gln Ser Cys Asp Pro
    195                 200
```

<210> SEQ ID NO 58
<211> LENGTH: 201
<212> TYPE: PRT
<213> ORGANISM: Homo sapiens

<400> SEQUENCE: 58

```
Met Ala Asn Lys Gly Pro Ser Tyr Gly Met Ser Arg Glu Val Gln Ser
1               5                   10                  15

Lys Ile Glu Lys Lys Tyr Asp Glu Glu Leu Glu Arg Leu Val Glu
            20                  25                  30

Trp Ile Ile Val Gln Cys Gly Pro Asp Val Gly Arg Pro Asp Arg Gly
        35                  40                  45

Arg Leu Gly Phe Gln Val Trp Leu Lys Asn Gly Val Ile Leu Ser Lys
```

```
              50                  55                  60
Leu Val Asn Ser Leu Tyr Pro Asp Gly Ser Lys Pro Val Lys Val Pro
65                  70                  75                  80

Glu Asn Pro Pro Ser Met Val Phe Lys Gln Met Glu Gln Val Ala Gln
                85                  90                  95

Phe Leu Lys Ala Ala Glu Asp Tyr Gly Val Ile Lys Thr Asp Met Phe
            100                 105                 110

Gln Thr Val Asp Leu Phe Glu Gly Lys Asp Met Ala Ala Val Gln Arg
        115                 120                 125

Thr Leu Met Ala Leu Gly Ser Leu Ala Val Thr Lys Asn Asp Gly His
    130                 135                 140

Tyr Arg Gly Asp Pro Asn Trp Phe Met Lys Lys Ala Gln Glu His Lys
145                 150                 155                 160

Arg Glu Phe Thr Glu Ser Gln Leu Gln Glu Gly Lys His Val Ile Gly
                165                 170                 175

Leu Gln Met Gly Ser Asn Arg Gly Ala Ser Gln Ala Gly Met Thr Gly
            180                 185                 190

Tyr Gly Arg Pro Arg Gln Ile Ile Ser
        195                 200

<210> SEQ ID NO 59
<211> LENGTH: 798
<212> TYPE: PRT
<213> ORGANISM: Homo sapiens

<400> SEQUENCE: 59

Met Asn Leu Gln Pro Ile Phe Trp Ile Gly Leu Ile Ser Ser Val Cys
1               5                   10                  15

Cys Val Phe Ala Gln Thr Asp Glu Asn Arg Cys Leu Lys Ala Asn Ala
                20                  25                  30

Lys Ser Cys Gly Glu Cys Ile Gln Ala Gly Pro Asn Cys Gly Trp Cys
            35                  40                  45

Thr Asn Ser Thr Phe Leu Gln Glu Gly Met Pro Thr Ser Ala Arg Cys
        50                  55                  60

Asp Asp Leu Glu Ala Leu Lys Lys Lys Gly Cys Pro Pro Asp Asp Ile
65                  70                  75                  80

Glu Asn Pro Arg Gly Ser Lys Asp Ile Lys Lys Asn Lys Asn Val Thr
                85                  90                  95

Asn Arg Ser Lys Gly Thr Ala Glu Lys Leu Lys Pro Glu Asp Ile Thr
            100                 105                 110

Gln Ile Gln Pro Gln Gln Leu Val Leu Arg Leu Arg Ser Gly Glu Pro
        115                 120                 125

Gln Thr Phe Thr Leu Lys Phe Lys Arg Ala Glu Asp Tyr Pro Ile Asp
    130                 135                 140

Leu Tyr Tyr Leu Met Asp Leu Ser Tyr Ser Met Lys Asp Asp Leu Glu
145                 150                 155                 160

Asn Val Lys Ser Leu Gly Thr Asp Leu Met Asn Glu Met Arg Arg Ile
                165                 170                 175

Thr Ser Asp Phe Arg Ile Gly Phe Gly Ser Phe Val Glu Lys Thr Val
            180                 185                 190

Met Pro Tyr Ile Ser Thr Thr Pro Ala Lys Leu Arg Asn Pro Cys Thr
        195                 200                 205

Ser Glu Gln Asn Cys Thr Ser Pro Phe Ser Tyr Lys Asn Val Leu Ser
    210                 215                 220

Leu Thr Asn Lys Gly Glu Val Phe Asn Glu Leu Val Gly Lys Gln Arg
```

```
                    225                 230                 235                 240
Ile Ser Gly Asn Leu Asp Ser Pro Glu Gly Gly Phe Asp Ala Ile Met
                245                 250                 255
Gln Val Ala Val Cys Gly Ser Leu Ile Gly Trp Arg Asn Val Thr Arg
                260                 265                 270
Leu Leu Val Phe Ser Thr Asp Ala Gly Phe His Phe Ala Gly Asp Gly
                275                 280                 285
Lys Leu Gly Gly Ile Val Leu Pro Asn Asp Gly Gln Cys His Leu Glu
            290                 295                 300
Asn Asn Met Tyr Thr Met Ser His Tyr Asp Tyr Pro Ser Ile Ala
305                 310                 315                 320
His Leu Val Gln Lys Leu Ser Glu Asn Ile Gln Thr Ile Phe Ala
                325                 330                 335
Val Thr Glu Glu Phe Gln Pro Val Tyr Lys Glu Leu Lys Asn Leu Ile
                340                 345                 350
Pro Lys Ser Ala Val Gly Thr Leu Ser Ala Asn Ser Ser Asn Val Ile
            355                 360                 365
Gln Leu Ile Ile Asp Ala Tyr Asn Ser Leu Ser Ser Glu Val Ile Leu
        370                 375                 380
Glu Asn Gly Lys Leu Ser Glu Gly Val Thr Ile Ser Tyr Lys Ser Tyr
385                 390                 395                 400
Cys Lys Asn Gly Val Asn Gly Thr Gly Glu Asn Gly Arg Lys Cys Ser
                405                 410                 415
Asn Ile Ser Ile Gly Asp Glu Val Gln Phe Glu Ile Ser Ile Thr Ser
                420                 425                 430
Asn Lys Cys Pro Lys Lys Asp Ser Asp Ser Phe Lys Ile Arg Pro Leu
                435                 440                 445
Gly Phe Thr Glu Glu Val Glu Val Ile Leu Gln Tyr Ile Cys Glu Cys
            450                 455                 460
Glu Cys Gln Ser Glu Gly Ile Pro Glu Ser Pro Lys Cys His Glu Gly
465                 470                 475                 480
Asn Gly Thr Phe Glu Cys Gly Ala Cys Arg Cys Asn Glu Gly Arg Val
                485                 490                 495
Gly Arg His Cys Glu Cys Ser Thr Asp Glu Val Asn Ser Glu Asp Met
            500                 505                 510
Asp Ala Tyr Cys Arg Lys Glu Asn Ser Ser Glu Ile Cys Ser Asn Asn
            515                 520                 525
Gly Glu Cys Val Cys Gly Gln Cys Val Cys Arg Lys Arg Asp Asn Thr
            530                 535                 540
Asn Glu Ile Tyr Ser Gly Lys Phe Cys Glu Cys Asp Asn Phe Asn Cys
545                 550                 555                 560
Asp Arg Ser Asn Gly Leu Ile Cys Gly Gly Asn Gly Val Cys Lys Cys
                565                 570                 575
Arg Val Cys Glu Cys Asn Pro Asn Tyr Thr Gly Ser Ala Cys Asp Cys
            580                 585                 590
Ser Leu Asp Thr Ser Thr Cys Glu Ala Ser Asn Gly Gln Ile Cys Asn
        595                 600                 605
Gly Arg Gly Ile Cys Glu Cys Gly Val Cys Lys Cys Thr Asp Pro Lys
    610                 615                 620
Phe Gln Gly Gln Thr Cys Glu Met Cys Gln Thr Cys Leu Gly Val Cys
625                 630                 635                 640
Ala Glu His Lys Glu Cys Val Gln Cys Arg Ala Phe Asn Lys Gly Glu
                645                 650                 655
```

```
Lys Lys Asp Thr Cys Thr Gln Glu Cys Ser Tyr Phe Asn Ile Thr Lys
            660                 665                 670

Val Glu Ser Arg Asp Lys Leu Pro Gln Pro Val Gln Pro Asp Pro Val
        675                 680                 685

Ser His Cys Lys Glu Lys Asp Val Asp Asp Cys Trp Phe Tyr Phe Thr
    690                 695                 700

Tyr Ser Val Asn Gly Asn Asn Glu Val Met Val His Val Val Glu Asn
705                 710                 715                 720

Pro Glu Cys Pro Thr Gly Pro Asp Ile Ile Pro Ile Val Ala Gly Val
                725                 730                 735

Val Ala Gly Ile Val Leu Ile Gly Leu Ala Leu Leu Leu Ile Trp Lys
            740                 745                 750

Leu Leu Met Ile Ile His Asp Arg Arg Glu Phe Ala Lys Phe Glu Lys
        755                 760                 765

Glu Lys Met Asn Ala Lys Trp Asp Thr Gly Glu Asn Pro Ile Tyr Lys
    770                 775                 780

Ser Ala Val Thr Thr Val Val Asn Pro Lys Tyr Glu Gly Lys
785                 790                 795
```

`<210> SEQ ID NO 60`
`<211> LENGTH: 1253`
`<212> TYPE: PRT`
`<213> ORGANISM: Homo sapiens`

`<400> SEQUENCE: 60`

```
Met Leu Ser Leu Arg Leu Gln Thr Gly Pro Glu Lys Ala Glu Leu Gln
  1               5                  10                  15

Glu Leu Asn Ala Arg Leu Tyr Asp Tyr Val Cys Arg Val Arg Glu Leu
                 20                  25                  30

Glu Arg Glu Asn Leu Leu Leu Glu Glu Leu Arg Gly Arg Arg Gly
             35                  40                  45

Arg Glu Gly Leu Trp Ala Glu Gly Gln Ala Arg Cys Ala Glu Glu Ala
         50                  55                  60

Arg Ser Leu Arg Gln Gln Leu Asp Glu Leu Ser Trp Ala Thr Ala Leu
 65                  70                  75                  80

Ala Glu Gly Glu Arg Asp Ala Leu Arg Arg Glu Leu Arg Glu Leu Gln
                 85                  90                  95

Arg Leu Asp Ala Glu Arg Ala Ala Arg Gly Arg Leu Asp Ala Glu
             100                 105                 110

Leu Gly Ala Gln Gln Arg Glu Leu Gln Glu Ala Leu Gly Ala Arg Ala
         115                 120                 125

Ala Leu Glu Ala Leu Leu Gly Arg Leu Gln Ala Glu Arg Arg Gly Leu
130                 135                 140

Asp Ala Ala His Glu Arg Asp Val Arg Glu Leu Arg Ala Arg Ala Ala
145                 150                 155                 160

Ser Leu Thr Met His Phe Arg Ala Arg Ala Thr Gly Pro Ala Ala Pro
                 165                 170                 175

Pro Pro Arg Leu Arg Glu Val His Asp Ser Tyr Ala Leu Leu Val Ala
             180                 185                 190

Glu Ser Trp Arg Glu Thr Val Gln Leu Tyr Glu Asp Glu Val Arg Glu
         195                 200                 205

Leu Glu Glu Ala Leu Arg Arg Gly Gln Glu Ser Arg Leu Gln Ala Glu
     210                 215                 220

Glu Glu Thr Arg Leu Cys Ala Gln Glu Ala Glu Ala Leu Arg Arg Glu
225                 230                 235                 240
```

```
Ala Leu Gly Leu Glu Gln Leu Arg Ala Arg Leu Glu Asp Ala Leu Leu
            245                 250                 255

Arg Met Arg Glu Glu Tyr Gly Ile Gln Ala Glu Arg Gln Arg Val
        260                 265                 270

Ile Asp Cys Leu Glu Asp Glu Lys Ala Thr Leu Thr Leu Ala Met Ala
            275                 280                 285

Asp Trp Leu Arg Asp Tyr Gln Asp Leu Leu Gln Val Lys Thr Gly Leu
        290                 295                 300

Ser Leu Glu Val Ala Thr Tyr Arg Ala Leu Leu Glu Gly Glu Ser Asn
305                 310                 315                 320

Pro Glu Ile Val Ile Trp Ala Glu His Val Glu Asn Met Pro Ser Glu
                325                 330                 335

Phe Arg Asn Lys Ser Tyr His Tyr Thr Asp Ser Leu Leu Gln Arg Glu
            340                 345                 350

Asn Glu Arg Asn Leu Phe Ser Arg Gln Lys Ala Pro Leu Ala Ser Phe
                355                 360                 365

Asn His Ser Ser Ala Leu Tyr Ser Asn Leu Ser Gly His Arg Gly Ser
            370                 375                 380

Gln Thr Gly Thr Ser Ile Gly Gly Asp Ala Arg Arg Gly Phe Leu Gly
385                 390                 395                 400

Ser Gly Tyr Ser Ser Ala Thr Thr Gln Gln Glu Asn Ser Tyr Gly
                405                 410                 415

Lys Ala Val Ser Ser Gln Thr Asn Val Arg Thr Phe Ser Pro Thr Tyr
            420                 425                 430

Gly Leu Leu Arg Asn Thr Glu Ala Gln Val Lys Thr Phe Pro Asp Arg
                435                 440                 445

Pro Lys Ala Gly Asp Thr Arg Glu Val Pro Val Tyr Ile Gly Glu Asp
450                 455                 460

Ser Thr Ile Ala Arg Glu Ser Tyr Arg Asp Arg Asp Lys Val Ala
465                 470                 475                 480

Ala Gly Ala Ser Glu Ser Thr Arg Ser Asn Glu Arg Thr Val Ile Leu
                485                 490                 495

Gly Lys Lys Thr Glu Val Lys Ala Thr Arg Glu Gln Glu Arg Asn Arg
                500                 505                 510

Pro Glu Thr Ile Arg Thr Lys Pro Glu Glu Lys Met Phe Asp Ser Lys
            515                 520                 525

Glu Lys Ala Ser Glu Glu Arg Asn Leu Arg Trp Glu Glu Leu Thr Lys
            530                 535                 540

Leu Asp Lys Glu Ala Arg Gln Arg Glu Ser Gln Gln Met Lys Glu Lys
545                 550                 555                 560

Ala Lys Glu Lys Asp Ser Leu Lys Glu Lys Ser Val Arg Glu Arg Glu
                565                 570                 575

Val Pro Ile Ser Leu Glu Val Ser Gln Asp Arg Arg Ala Glu Val Ser
            580                 585                 590

Pro Lys Gly Leu Gln Thr Pro Val Lys Asp Ala Gly Gly Thr Gly
            595                 600                 605

Arg Glu Ala Glu Ala Arg Glu Leu Arg Phe Arg Leu Gly Thr Ser Asp
        610                 615                 620

Ala Thr Gly Ser Leu Gln Gly Asp Ser Met Thr Glu Thr Val Ala Glu
625                 630                 635                 640

Asn Ile Val Thr Ser Ile Leu Lys Gln Phe Thr Gln Ser Pro Glu Thr
                645                 650                 655

Glu Ala Ser Ala Asp Ser Phe Pro Asp Thr Lys Val Thr Tyr Val Asp
            660                 665                 670
```

```
Arg Lys Glu Leu Pro Gly Glu Arg Lys Thr Lys Thr Glu Ile Leu Val
            675                 680                 685

Glu Ser Lys Leu Thr Glu Asp Val Asp Val Ser Asp Glu Ala Gly Leu
        690                 695                 700

Asp Tyr Leu Leu Ser Lys Asp Ile Lys Glu Val Gly Leu Lys Gly Lys
705                 710                 715                 720

Ser Ala Glu Gln Met Ile Gly Asp Ile Ile Asn Leu Gly Leu Lys Gly
                725                 730                 735

Arg Glu Gly Arg Ala Lys Val Val Asn Val Glu Ile Val Glu Glu Pro
            740                 745                 750

Val Ser Tyr Val Ser Gly Glu Lys Pro Glu Glu Phe Ser Val Pro Phe
        755                 760                 765

Lys Val Glu Glu Val Glu Asp Val Ser Pro Gly Pro Trp Gly Leu Val
770                 775                 780

Lys Glu Glu Glu Gly Tyr Gly Glu Ser Asp Val Thr Phe Ser Val Asn
785                 790                 795                 800

Gln His Arg Arg Thr Lys Gln Pro Gln Glu Asn Thr Thr His Val Glu
                805                 810                 815

Glu Val Thr Glu Ala Gly Asp Ser Gly Glu Gln Ser Tyr Phe Val
            820                 825                 830

Ser Thr Pro Asp Glu His Pro Gly Gly His Asp Arg Asp Asp Gly Ser
        835                 840                 845

Val Tyr Gly Gln Ile His Ile Glu Glu Ser Thr Ile Arg Tyr Ser
850                 855                 860

Trp Gln Asp Glu Ile Val Gln Gly Thr Arg Arg Thr Gln Lys Asp
865                 870                 875                 880

Gly Ala Gly Glu Lys Val Val Lys Pro Leu Asp Val Pro Ala Pro
                885                 890                 895

Ser Leu Glu Gly Asp Leu Gly Ser Thr His Trp Lys Glu Gln Ala Arg
            900                 905                 910

Ser Gly Glu Phe His Ala Glu Pro Thr Val Ile Glu Lys Glu Ile Lys
        915                 920                 925

Ile Pro His Glu Phe His Thr Ser Met Lys Gly Ile Ser Ser Lys Glu
930                 935                 940

Pro Arg Gln Gln Leu Val Glu Val Ile Gly Gln Leu Glu Glu Thr Leu
945                 950                 955                 960

Pro Glu Arg Met Arg Glu Glu Leu Ser Ala Leu Thr Arg Glu Gly Gln
                965                 970                 975

Gly Gly Pro Gly Ser Val Ser Val Asp Val Lys Lys Val Gln Gly Ala
            980                 985                 990

Gly Gly Ser Ser Val Thr Leu Val Ala Glu Val Asn Val Ser Gln Thr
        995                 1000                1005

Val Asp Ala Asp Arg Leu Asp Leu Glu Glu Val Ser Lys Asp Glu Ala
1010                1015                1020

Ser Glu Met Glu Lys Ala Val Glu Ser Val Arg Glu Ser Leu Ser
1025                1030                1035                1040

Arg Gln Arg Ser Pro Ala Pro Gly Ser Pro Asp Glu Glu Gly Ala
                1045                1050                1055

Glu Ala Pro Ala Ala Gly Ile Arg Phe Arg Arg Trp Ala Thr Arg Glu
            1060                1065                1070

Leu Tyr Ile Pro Ser Gly Glu Ser Glu Val Ala Gly Ala Ser His
        1075                1080                1085

Ser Ser Gly Gln Arg Thr Pro Gln Gly Pro Val Ser Ala Thr Val Glu
```

-continued

```
              1090               1095               1100

Val Ser Ser Pro Thr Gly Phe Ala Gln Ser Gln Val Leu Glu Asp Val
1105               1110               1115               1120

Ser Gln Ala Ala Arg His Ile Lys Leu Gly Pro Ser Glu Val Trp Arg
              1125               1130               1135

Thr Glu Arg Met Ser Tyr Glu Gly Pro Thr Ala Glu Val Val Glu Met
              1140               1145               1150

Asp Val Ser Asn Val Glu Ala Ile Arg Ser Arg Thr Gln Glu Ala Gly
              1155               1160               1165

Ala Leu Gly Val Ser Asp Arg Gly Ser Trp Arg Asp Ala Asp Ser Arg
              1170               1175               1180

Asn Asp Gln Ala Val Gly Val Ser Phe Lys Ala Ser Ala Gly Glu Gly
1185               1190               1195               1200

Asp Gln Ala His Arg Glu Gln Gly Lys Glu Gln Ala Met Phe Asp Lys
              1205               1210               1215

Lys Val Gln Leu Gln Arg Met Val Asp Gln Arg Ser Val Ile Ser Asp
              1220               1225               1230

Glu Lys Lys Val Ala Leu Leu Tyr Leu Asp Asn Glu Glu Glu Glu Asn
              1235               1240               1245

Asp Gly His Trp Phe
    1250

<210> SEQ ID NO 61
<211> LENGTH: 269
<212> TYPE: PRT
<213> ORGANISM: Homo sapiens

<400> SEQUENCE: 61

Met Ser Ala Ala Leu Phe Ser Leu Asp Gly Pro Ala Arg Gly Ala Pro
1               5                   10                  15

Trp Pro Ala Glu Pro Ala Pro Phe Tyr Glu Pro Gly Arg Ala Gly Lys
                20                  25                  30

Pro Gly Arg Gly Ala Glu Pro Gly Ala Leu Gly Glu Pro Gly Ala Ala
            35                  40                  45

Ala Pro Ala Met Tyr Asp Asp Glu Ser Ala Ile Asp Phe Ser Ala Tyr
        50                  55                  60

Ile Asp Ser Met Ala Ala Val Pro Thr Leu Glu Leu Cys His Asp Glu
65                  70                  75                  80

Leu Phe Ala Asp Leu Phe Asn Ser Asn His Lys Ala Gly Gly Ala Gly
                85                  90                  95

Pro Leu Glu Leu Leu Pro Gly Gly Pro Ala Arg Pro Leu Gly Pro Gly
                100                 105                 110

Pro Ala Ala Pro Arg Leu Leu Lys Arg Glu Pro Asp Trp Gly Asp Gly
            115                 120                 125

Asp Ala Pro Gly Ser Leu Leu Pro Ala Gln Val Ala Ala Cys Ala Gln
        130                 135                 140

Thr Val Val Ser Leu Ala Ala Ala Gly Gln Pro Thr Pro Pro Thr Ser
145                 150                 155                 160

Pro Glu Pro Pro Arg Ser Ser Pro Arg Gln Thr Pro Ala Pro Gly Pro
                165                 170                 175

Ala Arg Glu Lys Ser Ala Gly Lys Arg Gly Pro Asp Arg Gly Ser Pro
                180                 185                 190

Glu Tyr Arg Gln Arg Arg Glu Arg Asn Asn Ile Ala Val Arg Lys Ser
            195                 200                 205

Arg Asp Lys Ala Lys Arg Arg Asn Gln Glu Met Gln Gln Lys Leu Val
```

```
                210                 215                 220
Glu Leu Ser Ala Glu Asn Glu Lys Leu His Gln Arg Val Gln Leu
225                 230                 235                 240

Thr Arg Asp Leu Ala Gly Leu Arg Gln Phe Phe Lys Gln Leu Pro Ser
                245                 250                 255

Pro Pro Phe Leu Pro Ala Ala Gly Thr Ala Asp Cys Arg
            260                 265

<210> SEQ ID NO 62
<211> LENGTH: 241
<212> TYPE: PRT
<213> ORGANISM: Homo sapiens

<400> SEQUENCE: 62

Met His Ile Thr Gln Leu Asn Arg Glu Cys Leu Leu His Leu Phe Ser
1               5                   10                  15

Phe Leu Asp Lys Asp Ser Arg Lys Ser Leu Ala Arg Thr Cys Ser Gln
            20                  25                  30

Leu His Asp Val Phe Glu Asp Pro Ala Leu Trp Ser Leu Leu His Phe
        35                  40                  45

Arg Ser Leu Thr Glu Leu Gln Lys Asp Asn Phe Leu Leu Gly Pro Ala
50                  55                  60

Leu Arg Ser Leu Ser Ile Cys Trp His Ser Ser Arg Val Gln Val Cys
65                  70                  75                  80

Ser Ile Glu Asp Trp Leu Lys Ser Ala Phe Gln Arg Ser Ile Cys Ser
                85                  90                  95

Arg His Glu Ser Leu Val Asn Asp Phe Leu Leu Arg Val Cys Asp Arg
            100                 105                 110

Leu Ser Ala Val Arg Ser Pro Arg Arg Arg Glu Ala Pro Ala Pro Ser
        115                 120                 125

Ser Gly Thr Pro Ile Ala Val Gly Pro Lys Ser Pro Arg Trp Gly Gly
    130                 135                 140

Pro Asp His Ser Glu Phe Ala Asp Leu Arg Ser Gly Val Thr Gly Ala
145                 150                 155                 160

Arg Ala Ala Ala Arg Arg Gly Leu Gly Ser Leu Arg Ala Glu Arg Pro
                165                 170                 175

Ser Glu Thr Pro Pro Ala Pro Gly Val Ser Trp Gly Pro Pro Pro Pro
            180                 185                 190

Gly Ala Pro Val Val Ile Ser Val Lys Gln Glu Glu Gly Lys Gln Gly
        195                 200                 205

Arg Thr Gly Arg Arg Ser His Arg Ala Ala Pro Pro Cys Gly Phe Ala
    210                 215                 220

Arg Thr Arg Val Cys Pro Pro Thr Phe Pro Gly Ala Asp Ala Phe Pro
225                 230                 235                 240

Gln

<210> SEQ ID NO 63
<211> LENGTH: 450
<212> TYPE: PRT
<213> ORGANISM: Homo sapiens

<400> SEQUENCE: 63

Met Arg Glu Ile Val His Ile Gln Ala Gly Gln Cys Gly Asn Gln Ile
1               5                   10                  15

Gly Ala Lys Phe Trp Glu Val Ile Ser Asp Glu His Gly Ile Asp Pro
            20                  25                  30
```

```
Ser Gly Asn Tyr Val Gly Asp Ser Asp Leu Gln Leu Glu Arg Ile Ser
     35                  40                  45

Val Tyr Tyr Asn Glu Ala Ser Ser His Lys Tyr Val Pro Arg Ala Ile
 50                  55                  60

Leu Val Asp Leu Glu Pro Gly Thr Met Asp Ser Val Arg Ser Gly Ala
 65                  70                  75                  80

Phe Gly His Leu Phe Arg Pro Asp Asn Phe Ile Phe Gly Gln Ser Gly
                 85                  90                  95

Ala Gly Asn Asn Trp Ala Lys Gly His Tyr Thr Glu Gly Ala Glu Leu
                100                 105                 110

Val Asp Ser Val Leu Asp Val Val Arg Lys Glu Cys Glu Asn Cys Asp
            115                 120                 125

Cys Leu Gln Gly Phe Gln Leu Thr His Ser Leu Gly Gly Gly Thr Gly
130                 135                 140

Ser Gly Met Gly Thr Leu Leu Ile Ser Lys Val Arg Glu Glu Tyr Pro
145                 150                 155                 160

Asp Arg Ile Met Asn Thr Phe Ser Val Val Pro Ser Pro Lys Val Ser
                165                 170                 175

Asp Thr Val Val Glu Pro Tyr Asn Ala Thr Leu Ser Ile His Gln Leu
            180                 185                 190

Val Glu Asn Thr Asp Glu Thr Tyr Cys Ile Asp Asn Glu Ala Leu Tyr
        195                 200                 205

Asp Ile Cys Phe Arg Thr Leu Lys Leu Ala Thr Pro Thr Tyr Gly Asp
210                 215                 220

Leu Asn His Leu Val Ser Ala Thr Met Ser Gly Val Thr Thr Ser Leu
225                 230                 235                 240

Arg Phe Pro Gly Gln Leu Asn Ala Asp Leu Arg Lys Leu Ala Val Asn
                245                 250                 255

Met Val Pro Phe Pro Arg Leu His Phe Phe Met Pro Gly Phe Ala Pro
            260                 265                 270

Leu Thr Ala Arg Gly Ser Gln Gln Tyr Arg Ala Leu Thr Val Pro Glu
        275                 280                 285

Leu Thr Gln Gln Met Phe Asp Ala Lys Asn Met Met Ala Ala Cys Asp
290                 295                 300

Pro Arg His Gly Arg Tyr Leu Thr Val Ala Thr Val Phe Arg Gly Arg
305                 310                 315                 320

Met Ser Met Lys Glu Val Asp Glu Gln Met Leu Ala Ile Gln Ser Lys
                325                 330                 335

Asn Ser Ser Tyr Phe Val Glu Trp Ile Pro Asn Asn Val Lys Val Ala
            340                 345                 350

Val Cys Asp Ile Pro Pro Arg Gly Leu Lys Met Ser Ser Thr Phe Ile
        355                 360                 365

Gly Asn Ser Thr Ala Ile Gln Glu Leu Phe Lys Arg Ile Ser Glu Gln
370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ala Glu Glu
            420                 425                 430

Glu Gly Glu Met Tyr Glu Asp Asp Glu Glu Ser Glu Ala Gln Gly
        435                 440                 445

Pro Lys
450
```

<210> SEQ ID NO 64
<211> LENGTH: 361
<212> TYPE: PRT
<213> ORGANISM: Homo sapiens

<400> SEQUENCE: 64

```
Met Trp Val Leu Thr Pro Ala Ala Phe Ala Gly Lys Leu Leu Ser Val
  1               5                  10                  15
Phe Arg Gln Pro Leu Ser Ser Leu Trp Arg Ser Leu Val Pro Leu Phe
                 20                  25                  30
Cys Trp Leu Arg Ala Thr Phe Trp Leu Leu Ala Thr Lys Arg Arg Lys
             35                  40                  45
Gln Gln Leu Val Leu Arg Gly Pro Asp Glu Thr Lys Glu Glu Glu Glu
         50                  55                  60
Asp Pro Pro Leu Pro Thr Thr Pro Thr Ser Val Asn Tyr His Phe Thr
 65                  70                  75                  80
Arg Gln Cys Asn Tyr Lys Cys Gly Phe Cys Phe His Thr Ala Lys Thr
                 85                  90                  95
Ser Phe Val Leu Pro Leu Glu Glu Ala Lys Arg Gly Leu Leu Leu Leu
            100                 105                 110
Lys Glu Ala Gly Met Glu Lys Ile Asn Phe Ser Gly Gly Glu Pro Phe
        115                 120                 125
Leu Gln Asp Arg Gly Glu Tyr Leu Gly Lys Leu Val Arg Phe Cys Lys
    130                 135                 140
Val Glu Leu Arg Leu Pro Ser Val Ser Ile Val Ser Asn Gly Ser Leu
145                 150                 155                 160
Ile Arg Glu Arg Trp Phe Gln Asn Tyr Gly Glu Tyr Leu Asp Ile Leu
                165                 170                 175
Ala Ile Ser Cys Asp Ser Phe Asp Glu Glu Val Asn Val Leu Ile Gly
            180                 185                 190
Arg Gly Gln Gly Lys Lys Asn His Val Glu Asn Leu Gln Lys Leu Arg
        195                 200                 205
Arg Trp Cys Arg Asp Tyr Arg Val Ala Phe Lys Ile Asn Ser Val Ile
    210                 215                 220
Asn Arg Phe Asn Val Glu Glu Asp Met Thr Glu Gln Ile Lys Ala Leu
225                 230                 235                 240
Asn Pro Val Arg Trp Lys Val Phe Gln Cys Leu Leu Ile Glu Gly Glu
                245                 250                 255
Asn Cys Gly Glu Asp Ala Leu Arg Glu Ala Glu Arg Phe Val Ile Gly
            260                 265                 270
Asp Glu Glu Phe Glu Arg Phe Leu Glu Arg His Lys Glu Val Ser Cys
        275                 280                 285
Leu Val Pro Glu Ser Asn Gln Lys Met Lys Asp Ser Tyr Leu Ile Leu
    290                 295                 300
Asp Glu Tyr Met Arg Phe Leu Asn Cys Arg Lys Gly Arg Lys Asp Pro
305                 310                 315                 320
Ser Lys Ser Ile Leu Asp Val Gly Val Glu Ala Ile Lys Phe Ser
                325                 330                 335
Gly Phe Asp Glu Lys Met Phe Leu Lys Arg Gly Gly Lys Tyr Ile Trp
            340                 345                 350
Ser Lys Ala Asp Leu Lys Leu Asp Trp
        355                 360
```

<210> SEQ ID NO 65

<211> LENGTH: 1589
<212> TYPE: PRT
<213> ORGANISM: Homo sapiens

<400> SEQUENCE: 65

```
Met Ala Lys Gln Leu Asn Leu Pro Glu Asn Thr Asp Asp Trp Thr Lys
1               5                   10                  15

Glu Asp Val Asn Gln Trp Leu Glu Ser His Lys Ile Asp Gln Lys His
            20                  25                  30

Arg Glu Ile Leu Thr Glu Gln Asp Val Asn Gly Ala Val Leu Lys Trp
        35                  40                  45

Leu Lys Lys Glu His Leu Val Asp Met Gly Ile Thr His Gly Pro Ala
50                  55                  60

Ile Gln Ile Glu Glu Leu Phe Lys Glu Leu Arg Lys Thr Ala Ile Glu
65                  70                  75                  80

Asp Ser Ile Gln Thr Ser Lys Met Gly Lys Pro Ser Lys Asn Ala Pro
                85                  90                  95

Lys Asp Gln Thr Val Ser Gln Lys Glu Arg Arg Glu Thr Ser Lys Gln
            100                 105                 110

Lys Gln Lys Gly Lys Glu Asn Pro Asp Met Ala Asn Pro Ser Ala Met
        115                 120                 125

Ser Thr Thr Ala Lys Gly Ser Lys Ser Leu Lys Val Glu Leu Ile Glu
130                 135                 140

Asp Lys Ile Asp Tyr Thr Lys Glu Arg Gln Pro Ser Ile Asp Leu Thr
145                 150                 155                 160

Cys Val Ser Tyr Pro Phe Asp Glu Phe Ser Asn Pro Tyr Arg Tyr Lys
                165                 170                 175

Leu Asp Phe Ser Leu Gln Pro Glu Thr Gly Pro Gly Asn Leu Ile Asp
            180                 185                 190

Pro Ile His Glu Phe Lys Ala Phe Thr Asn Thr Ala Thr Ala Thr Glu
        195                 200                 205

Glu Asp Val Lys Met Lys Phe Ser Asn Glu Val Phe Arg Phe Ala Ser
210                 215                 220

Ala Cys Met Asn Ser Arg Thr Asn Gly Thr Ile His Phe Gly Val Lys
225                 230                 235                 240

Asp Lys Pro His Gly Lys Ile Val Gly Ile Lys Val Thr Asn Asp Thr
                245                 250                 255

Lys Glu Ala Leu Ile Asn His Phe Asn Leu Met Ile Asn Lys Tyr Phe
            260                 265                 270

Glu Asp His Gln Val Gln Ala Lys Lys Cys Ile Arg Glu Pro Arg
        275                 280                 285

Phe Val Glu Val Leu Leu Pro Asn Ser Thr Leu Ser Asp Arg Phe Val
290                 295                 300

Ile Glu Val Asp Ile Ile Pro Gln Phe Ser Glu Cys Gln Tyr Asp Tyr
305                 310                 315                 320

Phe Gln Ile Lys Met Gln Asn Tyr Asn Asn Lys Ile Trp Glu Gln Ser
                325                 330                 335

Lys Lys Phe Ser Leu Phe Val Arg Asp Gly Thr Ser Ser Lys Asp Ile
            340                 345                 350

Thr Lys Asn Lys Val Asp Phe Arg Ala Phe Lys Ala Asp Phe Lys Thr
        355                 360                 365

Leu Ala Glu Ser Arg Lys Ala Ala Glu Glu Lys Phe Arg Ala Lys Thr
370                 375                 380

Asn Lys Lys Glu Arg Glu Gly Pro Lys Leu Val Lys Leu Leu Thr Gly
385                 390                 395                 400
```

Asn Gln Asp Leu Leu Asp Asn Ser Tyr Tyr Glu Gln Tyr Ile Leu Val
            405                 410                 415

Thr Asn Lys Cys His Pro Asp Gln Thr Lys His Leu Asp Phe Leu Lys
            420                 425                 430

Glu Ile Lys Trp Phe Ala Val Leu Glu Phe Asp Pro Glu Ser Asn Ile
            435                 440                 445

Asn Gly Val Val Lys Ala Tyr Lys Glu Ser Arg Val Ala Asn Leu His
450                 455                 460

Phe Pro Ser Val Tyr Val Glu Gln Lys Thr Thr Pro Asn Glu Thr Ile
465                 470                 475                 480

Ser Thr Leu Asn Leu Tyr His Gln Pro Ser Trp Ile Phe Cys Asn Gly
            485                 490                 495

Arg Leu Asp Leu Asp Ser Glu Lys Tyr Lys Pro Phe Asp Pro Ser Ser
            500                 505                 510

Trp Gln Arg Glu Arg Ala Ser Asp Val Arg Lys Leu Ile Ser Phe Leu
            515                 520                 525

Thr His Glu Asp Ile Met Pro Arg Gly Lys Phe Leu Val Val Phe Leu
            530                 535                 540

Leu Leu Ser Ser Val Asp Asp Pro Arg Asp Pro Leu Ile Glu Thr Phe
545                 550                 555                 560

Cys Ala Phe Tyr Gln Asp Leu Lys Gly Met Glu Asn Ile Leu Cys Ile
                    565                 570                 575

Cys Val His Pro His Ile Phe Gln Gly Trp Lys Asp Leu Leu Glu Ala
            580                 585                 590

Arg Leu Ile Lys His Gln Asp Glu Ile Ser Ser Gln Cys Ile Ser Ala
            595                 600                 605

Leu Ser Leu Glu Glu Ile Asn Gly Thr Ile Leu Lys Leu Lys Ser Val
            610                 615                 620

Thr Gln Ser Ser Lys Arg Leu Leu Pro Ser Ile Gly Leu Ser Thr Val
625                 630                 635                 640

Leu Leu Lys Lys Glu Glu Asp Ile Met Thr Ala Leu Glu Ile Ile Cys
                    645                 650                 655

Glu Asn Glu Cys Glu Gly Thr Leu Leu Glu Lys Asp Lys Asn Lys Phe
            660                 665                 670

Leu Glu Phe Lys Ala Ser Lys Glu Glu Asp Phe Tyr Arg Gly Gly Lys
            675                 680                 685

Val Ser Trp Trp Asn Phe Tyr Phe Ser Ser Glu Ser Tyr Ser Ser Pro
690                 695                 700

Phe Val Lys Arg Asp Lys Tyr Glu Arg Leu Glu Ala Met Ile Gln Asn
705                 710                 715                 720

Cys Ala Asp Ser Ser Lys Pro Thr Ser Thr Lys Ile Ile His Leu Tyr
                    725                 730                 735

His His Pro Gly Cys Gly Gly Thr Thr Leu Ala Met His Ile Leu Trp
            740                 745                 750

Glu Leu Arg Lys Lys Phe Arg Cys Ala Val Leu Lys Asn Lys Thr Val
            755                 760                 765

Asp Phe Ser Glu Ile Gly Glu Gln Val Thr Ser Leu Ile Thr Tyr Gly
            770                 775                 780

Ala Met Asn Arg Gln Glu Tyr Val Pro Val Leu Leu Leu Val Asp Asp
785                 790                 795                 800

Phe Glu Glu Gln Asp Asn Val Tyr Leu Leu Gln Tyr Ser Ile Gln Thr
                    805                 810                 815

Ala Ile Ala Lys Lys Tyr Ile Arg Tyr Glu Lys Pro Leu Val Ile Ile

```
                   820                 825                 830
Leu Asn Cys Met Arg Ser Gln Asn Pro Glu Lys Ser Ala Arg Ile Pro
        835                 840                 845
Asp Ser Ile Ala Val Ile Gln Gln Leu Ser Pro Lys Glu Gln Arg Ala
        850                 855                 860
Phe Glu Leu Lys Leu Lys Glu Ile Lys Glu Gln His Lys Asn Phe Glu
865                 870                 875                 880
Asp Phe Tyr Ser Phe Met Ile Met Lys Thr Asn Phe Asn Lys Glu Tyr
                885                 890                 895
Ile Glu Asn Val Val Arg Asn Ile Leu Lys Gly Gln Asn Ile Phe Thr
                900                 905                 910
Lys Glu Ala Lys Leu Phe Ser Phe Leu Ala Leu Leu Asn Ser Tyr Val
                915                 920                 925
Pro Asp Thr Thr Ile Ser Leu Ser Gln Cys Glu Lys Phe Leu Gly Ile
                930                 935                 940
Gly Asn Lys Lys Ala Phe Trp Gly Thr Glu Lys Phe Glu Asp Lys Met
945                 950                 955                 960
Gly Thr Tyr Ser Thr Ile Leu Ile Lys Thr Glu Val Ile Glu Cys Gly
                965                 970                 975
Asn Tyr Cys Gly Val Arg Ile Ile His Ser Leu Ile Ala Glu Phe Ser
                980                 985                 990
Leu Glu Glu Leu Lys Lys Ser Tyr His Leu Asn Lys Ser Gln Ile Met
                995                1000                1005
Leu Asp Met Leu Thr Glu Asn Leu Phe Phe Asp Thr Gly Met Gly Lys
        1010                1015                1020
Ser Lys Phe Leu Gln Asp Met His Thr Leu Leu Leu Thr Arg His Arg
1025                1030                1035                1040
Asp Glu His Glu Gly Glu Thr Gly Asn Trp Phe Ser Pro Phe Ile Glu
                1045                1050                1055
Ala Leu His Lys Asp Glu Gly Asn Glu Ala Val Glu Ala Val Leu Leu
        1060                1065                1070
Glu Ser Ile His Arg Phe Asn Pro Asn Ala Phe Ile Cys Gln Ala Leu
        1075                1080                1085
Ala Arg His Phe Tyr Ile Lys Lys Lys Asp Phe Gly Asn Ala Leu Asn
        1090                1095                1100
Trp Ala Lys Gln Ala Lys Ile Ile Glu Pro Asp Asn Ser Tyr Ile Ser
1105                1110                1115                1120
Asp Thr Leu Gly Gln Val Tyr Lys Ser Lys Ile Arg Trp Trp Ile Glu
                1125                1130                1135
Glu Asn Gly Gly Asn Gly Asn Ile Ser Val Asp Asp Leu Ile Ala Leu
        1140                1145                1150
Leu Asp Leu Ala Glu His Ala Ser Ser Ala Phe Lys Glu Ser Gln Gln
        1155                1160                1165
Gln Ser Glu Asp Arg Glu Tyr Glu Val Lys Glu Arg Leu Tyr Pro Lys
        1170                1175                1180
Ser Lys Arg Arg Tyr Asp Thr Tyr Asn Ile Ala Gly Tyr Gln Gly Glu
1185                1190                1195                1200
Ile Glu Val Gly Leu Tyr Thr Ile Gln Ile Leu Gln Leu Ile Pro Phe
                1205                1210                1215
Phe Asp Asn Lys Asn Glu Leu Ser Lys Arg Tyr Met Val Asn Phe Val
                1220                1225                1230
Ser Gly Ser Ser Asp Ile Pro Gly Asp Pro Asn Asn Glu Tyr Lys Leu
                1235                1240                1245
```

```
Ala Leu Lys Asn Tyr Ile Pro Tyr Leu Thr Lys Leu Lys Phe Ser Leu
    1250                1255                1260

Lys Lys Ser Phe Asp Phe Asp Glu Tyr Phe Val Leu Leu Lys Pro
1265                1270                1275                1280

Arg Asn Asn Ile Lys Gln Asn Glu Glu Ala Lys Thr Arg Arg Lys Val
                1285                1290                1295

Ala Gly Tyr Phe Lys Lys Tyr Val Asp Ile Phe Cys Leu Leu Glu Glu
            1300                1305                1310

Ser Gln Asn Asn Thr Gly Leu Gly Ser Lys Phe Ser Glu Pro Leu Gln
            1315                1320                1325

Val Glu Arg Cys Arg Arg Asn Leu Val Ala Leu Lys Ala Asp Lys Phe
        1330                1335                1340

Ser Gly Leu Leu Glu Tyr Leu Ile Lys Ser Gln Glu Asp Ala Ile Ser
1345                1350                1355                1360

Thr Met Lys Cys Ile Val Asn Glu Tyr Thr Phe Leu Leu Glu Gln Cys
                1365                1370                1375

Thr Val Lys Ile Gln Ser Lys Glu Lys Leu Asn Phe Ile Leu Ala Asn
                1380                1385                1390

Ile Ile Leu Ser Cys Ile Gln Pro Thr Ser Arg Leu Val Lys Pro Val
            1395                1400                1405

Glu Lys Leu Lys Asp Gln Leu Arg Glu Val Leu Gln Pro Ile Gly Leu
        1410                1415                1420

Thr Tyr Gln Phe Ser Glu Pro Tyr Phe Leu Ala Ser Leu Leu Phe Trp
1425                1430                1435                1440

Pro Glu Asn Gln Gln Leu Asp Gln His Ser Glu Gln Met Lys Glu Tyr
                1445                1450                1455

Ala Gln Ala Leu Lys Asn Ser Phe Lys Gly Gln Tyr Lys His Met His
                1460                1465                1470

Arg Thr Lys Gln Pro Ile Ala Tyr Phe Phe Leu Gly Lys Gly Lys Arg
            1475                1480                1485

Leu Glu Arg Leu Val His Lys Gly Lys Ile Asp Gln Cys Phe Lys Lys
        1490                1495                1500

Thr Pro Asp Ile Asn Ser Leu Trp Gln Ser Gly Asp Val Trp Lys Glu
1505                1510                1515                1520

Glu Lys Val Gln Glu Leu Leu Leu Arg Leu Gln Gly Arg Ala Glu Asn
                1525                1530                1535

Asn Cys Leu Tyr Ile Glu Tyr Gly Ile Asn Glu Lys Ile Thr Ile Pro
                1540                1545                1550

Ile Thr Pro Ala Phe Leu Gly Gln Leu Arg Ser Gly Arg Ser Ile Glu
            1555                1560                1565

Lys Val Ser Phe Tyr Leu Gly Phe Ser Ile Gly Gly Pro Leu Ala Tyr
            1570                1575                1580

Asp Ile Glu Ile Val
1585

<210> SEQ ID NO 66
<211> LENGTH: 122
<212> TYPE: PRT
<213> ORGANISM: Homo sapiens

<400> SEQUENCE: 66

Met Glu Ala Ser Ala Leu Thr Ser Ser Ala Val Thr Ser Val Ala Lys
1               5                   10                  15

Val Val Arg Val Ala Ser Gly Ser Ala Val Val Leu Pro Leu Ala Arg
            20                  25                  30
```

```
-continued

Ile Ala Thr Val Val Ile Gly Gly Val Val Ala Met Ala Ala Val Pro
        35              40              45

Met Val Leu Ser Ala Met Gly Phe Thr Ala Ala Gly Ile Ala Ser Ser
    50              55              60

Ser Ile Ala Ala Lys Met Met Ser Ala Ala Ile Ala Asn Gly Gly
65              70              75              80

Gly Val Ala Ser Gly Ser Leu Val Ala Thr Leu Gln Ser Leu Gly Ala
            85              90              95

Thr Gly Leu Ser Gly Leu Thr Lys Phe Ile Leu Gly Ser Ile Gly Ser
            100             105             110

Ala Ile Ala Ala Val Ile Ala Arg Phe Tyr
            115             120
```

METHOD OF TREATING IRRITABLE BOWEL SYNDROME

This application claims priority from U.S. Provisional Application Ser. No. 60/496,716 filed Aug. 21, 2003, The entirety of that provisional application is incorporated herein by reference.

TECHNICAL FIELD

The present invention relates generally to the diagnosis and treatment of disorders associated with chromic visceral hypersensitivity (CVH), and in particular irritable bowel syndrome (IBS). The invention also relates to genes associated with CVH, polynucleotides transcribed from these genes and polypeptides encoded by these genes. Such polynucleotides and polypeptides can be used for the diagnosis and treatment of CVH.

BACKGROUND OF THE INVENTION

Irritable Bowel Syndrome (IBS) is a functional bowel disorder of unknown etiology. A functional disorder refers to a disorder or disease where the primary abnormality is an altered physiological function, rather than an identifiable structural or biochemical cause. IBS is characterized by a group of symptoms including intermittent abdominal pain and discomfort and alterations in bowel habits, such as loose or more frequent bowel movements, diarrhea, and/or constipation that occur in the absence of detectable ongoing organic disease.

IBS affects approximately 10-20% of the general population. It is the most common disease diagnosed by gastroenterologists and one of the most common disorders seen by primary care physicians. EBS is understood as a multi-faceted disorder. In people with IBS, symptoms result from what appears to be a disturbance in the interaction between the gut or intestines, the brain, and the autonomic nervous system that alters regulation of bowel motility (motor function) or sensory function.

Human studies demonstrate that IBS is associated with a state of chronic visceral hypersensitivity (CVH) suggesting that processing of visceral sensory information is altered. However, little is known about how the afferent nervous system is changed in this syndrome. A hallmark of IBS is increased visceral hypersensitivity, but the molecular changes underlying the development and maintenance of chronic visceral hypersensitivity in IBS are not known. Current medical treatments for IBS primarily target peripheral symptoms rather than the underlying causes, and therapeutic gains from drug treatments are usually modest and the placebo responses are high (Mertz et al., Gastroenterology, 109: 40-52, 1995). Defining the underlying neurological and molecular defects is therefore important to the design of more successful therapeutic strategies. Moreover, there is a need in the art for improved methods for screening, diagnosing, and treating IBS and other CVH-related disorders.

N,N'-bis[3,5-diacetylphenl] decanediamidetetrakis[amidinohydrazone] tetrahvdrochloride (CNI-1493) is a MAPK and TNF inhibitor with anti-inflammatory and possible analgesic actions. CNI-1493 inhibits signal transduction pathways by preventing phosphorylation of p38 MAP kinase and JNK, and inhibits production of the proinflammatory cytokines such as TNF-alpha, IL-1, IL-6, MIP-1 alpha and MIP-beta. In animal models, CNI-1493 has shown protective activity against a wide variety of conditions, ranging from stroke to inflammatory bowel disease. However, CNI-1493 has never been tested for its anti-nociceptive activity in the absence of inflammation. Recently, an animal model of chronic visceral hypersensitivity was created using mechanical and chemical irritation of the colon of neonatal rats (Al-Chaer et al., Gastroenterology, 119: 1276-1285, 2000). The animal model provides an ideal platform for studying IBS, validating the neurogenic components of functional abdominal pain, and testing agents that may reduce visceral hypersensitivity.

SUMMARY OF THE INVENTION

One aspect of the present invention relates to the treatment for disorders associated with CVH using guanylhydrazone. In one embodiment, the present invention provides a treatment for IBS using CNI1493.

Another aspect of the present invention relates to CVH-related genes (CVHGs) and the gene products, which include the polynucleotides transcribed from the CVHGs (CHVPNs) and the polypeptides encoded by the CVHGs (CHVPPs).

In one embodiment, the present invention provides methods for diagnosing and monitoring CVH and CVH-related disorders by comparing the expression levels of one or more CVHGs at the nucleotide or protein level in biological samples from a subject to control samples.

In another embodiment, the present invention provides pharmaceutical compositions for the treatment of CVH and CVH-related disorders. The pharmaceutical compositions comprise a pharmaceutically acceptable carrier and at least one of the following: (1) a CVHG product; (2) an agent that modulates an activity of a CVHG product; and (3) an agent that modulates the expression of a CVHG.

In another embodiment, the present invention provides methods for treating CVH and CVH-related disorders in a patient with the pharmaceutical compositions described above. The patient may be afflicted with CVH, in which case the methods provide treatment for the disease. The patient may also be considered at risk for CVH, in which case the methods provide prevention for disease development.

In another embodiment, the present invention provides methods for screening anti-CVH agents based on the agents' interaction with CVHPPs, or the agents' effect on the activity or expression of CVHPPs.

In another embodiment, the present invention provides biochips for diagnosing CVH and CHH-related disorders, and for screening agents that inhibit CVH. The biochips comprise at least one of the following (1) a CVHPP or its variant, (2) a portion of a CVHPP or its variant (3) a CVHPN or its variant, and (4) a portion of a CVHPN or its variant.

In another embodiment, the present invention provides a kit for diagnosing CVH and CVH-related disorders. The kit comprises at least one of the following (1) polynucleotide probe that specifically hybridizes to a CVHPN, and (2) an antibody capable of specific binding to a CVHPP.

DETAILED DESCRIPTION OF THE INVENTION

Figure 1:
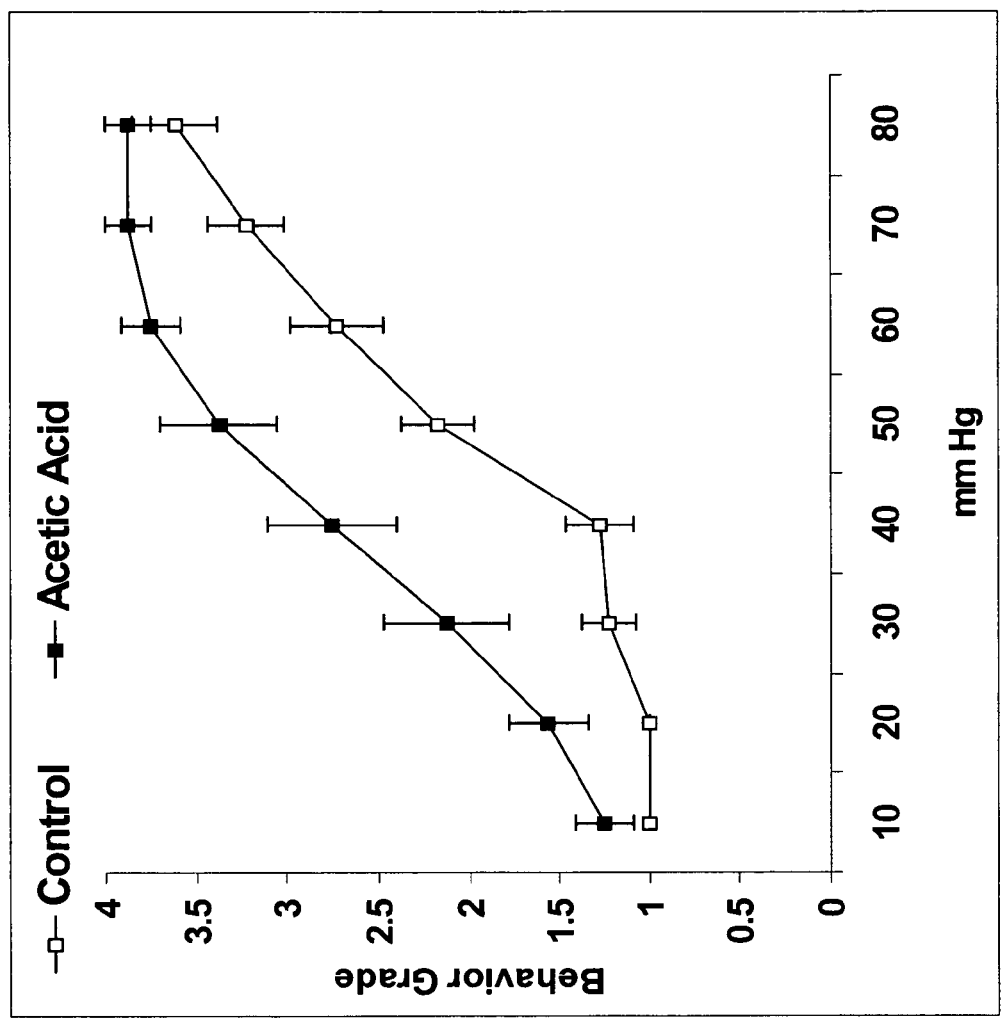
FIG. 1. Increased sensitivity to CRD in adult rats treated with acetic acid on P 10 (n=8). Data was analyzed by two-way repeated measures ANOVA with distention pressure as the repeated factor and P10 treatment as a between group factor. There was a significant effect of P10 treatment (F 1, 12.98) $p<0.003$, of distention pressure (F 7, 89.9) $p<0.001$, and there was a significant interaction between distention pressure and P10 treatment (F 7, 4.04) $p<0.001$, Means were compared with a Tukey test. Significant differences between acetic acid treated and controls were found at distention pressures of 30 (p=0.004), 40 (p<0.001), 50 (p<0.001), 60 (p=0.001) and 70 (p=0.035) mm Hg.

The preferred embodiments of the invention are described below. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase.

It is further intended that the inventions not be limited only to the specific structure, material or acts that are described in the preferred embodiments, but in addition, include any and all structures, materials or acts that perform the claimed function, along with any and all known or later-developed equivalent structures, materials or acts for performing the claimed function.

Further examples exist throughout the disclosure, and it is not applicant's intention to exclude from the scope of his invention the use of structures, materials, methods, or acts that are not expressly identified in the specification, but nonetheless are capable of performing a claimed function.

The present invention is generally directed to compositions and methods for the diagnosis, treatment, and prevention of CVH and CVH-related disorders; and to the identification of novel therapeutic agents for CVH and CVH-related disorders. The present invention is based on the finding that guanylhydrazone is capable of ameliorating CVH in a rat model of EBS and the discovery of transcribed polynucleotides that are differentially expressed in the colon tissue of rats with chemically induced CVH relative to control animals.

Definitions and Terms

To facilitate an understanding of the present invention, a number of terms and phrases are defined below:

As used herein, the terms "a differentially expressed gene" refer to a gene that meets all of the following criteria during an Affymetrix microarray analysis: (1) the average expression of the gene shows a fold change of two or greater compared with controls and (2) significant changes in gene expression were detected by analyzing signal intensity values by two-way ANOVA with 99% confidence. The differentially expressed genes identified in the colon tissue samples of CVH and CNI1493-treated rats are designated as CVH-related genes (CVHGs). CVHGs generally refer to the genes listed in Tables 3-8.

As used herein, the terms "CVH-related polynucleotide (CVHPN)" and "CVHG polynucleotide" are used interchangeably. The terms include a transcribed polynucleotide (e.g., DNA, cDNA or mRNA) that comprises one of the CVHG sequences or a portion thereof.

As used herein, the terms "CVH-related polypeptide (CVHPP)" and "CVHG protein" are used interchangeably. The terms include polypeptides encoded by an CVHG, an CVHPN, or a portion of an CVHG or CVHPN.

As used herein, a "CVHG product" includes a nucleic acid sequence and an amino acid sequence (e.g., a polynucleotide or polypeptide) generated when an CVHG is transcribed and/or translated. Specifically, CVHG products include CVHPNs and CVHPPs.

As used herein, a "variant of a polynucleotide" includes a polynucleotide that differs from the original polynucleotide by one or more substitutions, additions, deletions and/or insertions such that the activity of the encoded polypeptide is not substantially changed (e.g., the activity may be diminished or enhanced, by less than 50%, and preferably less than 20%) relative to the polypeptide encoded by the original polynucleotide.

A variant of a polynucleotide also includes polynucleotides that are capable of hybridizing under reduced stringency conditions, more preferably stringent conditions, and most preferably highly stringent conditions to the original polynucleotide (or a complementary sequence). Examples of conditions of different stringency are listed in Table 2.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention.

As used herein, a "variant of a polypeptide" is a polypeptide that differs from a native polypeptide in one or more substitutions, deletions, additions and/or insertions, such that the bioactivity or immunogenicity of the native polypeptide is not substantially diminished. In other words, the bioactivity of a variant polypeptide or the ability of a variant polypeptide to react with antigen-specific antisera may be enhanced or diminished by less than 50%, and preferably less than 20%, relative to the native polypeptide. Variant polypeptides include those in which one or more portions, such as an N-terminal leader sequence or transmembrane domain, have been removed. Other preferred variants include variants in which a small portion (e.g., 1-30 amino acids, preferably 5-15 amino acids) has been removed from the N- and/or C-terminal of the mature protein.

Modifications and changes can be made in the structure of a polypeptide of the present invention and still obtain a molecule having biological activity and/or immunogenic properties. Because it is the interactive capacity and nature of a polypeptide that defines that polypeptide's biological activity, certain amino acid sequence substitutions can be made in a polypeptide sequence (or, of course, its underlying DNA coding sequence) and nevertheless obtain a polypeptide with like properties.

In making such changes, the hydropathic index of amino acids can be considered. The importance of the hydropathic amino acid index in conferring interactive biologic function on a polypeptide is generally understood in the art. It is believed that the relative hydropathic character of the amino acid residue determines the secondary and tertiary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those that are within ±1 are particularly preferred, and those within ±0.5 are even more particularly preferred.

Substitution of like amino acids can also be made on the basis of hydrophilicity, particularly where the biological functional equivalent polypeptide or polypeptide fragment, is intended for use in immunological embodiments. U.S. Pat. No. 4,554,101, incorporated hereinafter by reference, states that the greatest local average hydrophilicity of a polypeptide, as governed by the hydrophilicity of its adjacent amino acids, correlates with its immunogenicity and antigenicity, i.e. with a biological property of the polypeptide.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2) glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those that are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine (See Table 1, below). The present invention thus contemplates functional or biological equivalents of an CVHPP as set forth above.

TABLE 1

Amino Acid Substitutions

| Original Residue | Exemplary Residue Substitution |
|---|---|
| Ala | Gly; Ser |
| Arg | Lys |
| Asn | Gln; His |
| Asp | Glu |
| Cys | Ser |
| Gln | Asn |
| Glu | Asp |
| Gly | Ala |
| His | Asn; Gln |
| Ile | Leu; Val |
| Leu | Ile; Val |
| Lys | Arg |
| Met | Leu; Tyr |
| Ser | Thr |
| Thr | Ser |
| Trp | Tyr |
| Tyr | Trp; Phe |
| Val | Ile; Leu |

A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure, tertiary structure, and hydropathic nature of the polypeptide.

Polypeptide variants preferably exhibit at least about 70%, more preferably at least about 90% and most preferably at least about 95% sequence homology to the original polypeptide.

A polypeptide variant also includes a polypeptide that is modified from the original polypeptide by either natural processes, such as post-translational processing, or by chemical modification techniques which are well known in the art. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from post-translation natural processes or may be made by synthetic methods. Modifications include acetylation, acylation, ADP-ribosylation, amidation, covalent attachment of flavin, covalent attachment of a fluorophore or a chromophore, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination.

As used herein, a "biologically active portion" of a CVHPP includes a fragment of a CVHPP comprising amino acid sequences sufficiently homologous to or derived from the amino acid sequence of the CVHPP, which includes fewer amino acids than the full length CVHPP, and exhibits at least one activity of the CVHPP. Typically, a biologically active portion of a CVHPP comprises a domain or motif with at least one activity of the CVHPP. A biologically active portion of a CVHPP can be a polypeptide which is, for example, 10, 25, 50, 100, 200 or more amino acids in length. Biologically active portions of a CVHPP can be used as targets for developing agents which modulate a CVHPP-mediated activity.

As used herein, an "immunogenic portion," an "antigen," an "immunogen," or an "epitope" of a CVHPP includes a fragment of a CVHPP comprising an amino acid sequence sufficiently homologous to, or derived from, the amino acid sequence of the CVHPP, which includes fewer amino acids than the full length CVHPP and can be used to induce an anti-CVHPP humoral and/or cellular immune response.

As used herein, the term "modulation" includes, in its various grammatical forms (e.g., "modulated", "modulation", "modulating", etc.), up-regulation, induction, stimulation, potentiation, and/or relief of inhibition, as well as inhibition and/or down-regulation or suppression.

As used herein, the term "control sequences" or "regulatory sequences" refers to DNA sequences necessary for the expression of an operably linked coding sequence in a particular host organism. The term "control/regulatory sequence" is intended to include promoters, enhancers and other expression control elements (e.g., polyadenylation signals). Control/regulatory sequences include those which direct constitutive expression of a nucleotide sequence in many types of host cells and those which direct expression of the nucleotide sequence only in certain host cells (e.g., tissue-specific regulatory sequences).

A nucleic acid sequence is "operably linked" to another nucleic acid sequence when the former is placed into a functional relationship with the latter. For example, a DNA for a presequence or secretory leader peptide is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, synthetic oligonucleotide adaptors or linkers are used in accordance with conventional practice.

As used herein, the "stringency" of a hybridization reaction refers to the difficulty with which any two nucleic acid molecules will hybridize to one another. The present invention also includes polynucleotides capable of hybridizing under reduced stringency conditions, more preferably stringent conditions, and most preferably highly stringent conditions, to polynucleotides described herein. Examples of stringency conditions are shown in Table 2 below: highly stringent conditions are those that are at least as stringent as, for example, conditions A-F; stringent conditions are at least as stringent as, for example, conditions G-L; and reduced stringency conditions are at least as stringent as, for example, conditions M-R.

TABLE 2

Stringency Condition

| Stringency Condition | Polynucleotide Hybrid | Hybrid Length (bp)[1] | Hybridization Temperature and Buffer[H] | Wash Temp. and Buffer[H] |
|---|---|---|---|---|
| A | DNA:DNA | >50 | 65° C.; 1xSSC -or- 42° C.; 1xSSC, 50% formamide | 65° C.; 0.3xSSC |
| B | DNA:DNA | <50 | $T_B^*$; 1xSSC | $T_B^*$; 1xSSC |
| C | DNA:RNA | >50 | 67° C.; 1xSSC -or- 45° C.; 1xSSC, 50% formamide | 67° C.; 0.3xSSC |
| D | DNA:RNA | <50 | $T_D^*$; 1xSSC | $T_D^*$; 1xSSC |
| E | RNA:RNA | >50 | 70° C.; 1xSSC -or- 50° C.; 1xSSC, 50% formamide | 70° C.; 0.3xSSC |
| F | RNA:RNA | <50 | $T_F^*$; 1xSSC | $T_F^*$; 1xSSC |
| G | DNA:DNA | >50 | 65° C.; 4xSSC -or- 42° C.; 4xSSC, 50% formamide | 65° C.; 1xSSC |
| H | DNA:DNA | <50 | $T_H^*$; 4xSSC | $T_H^*$; 4xSSC |
| I | DNA:RNA | >50 | 67° C.; 4xSSC -or- 45° C.; 4xSSC, 50% formamide | 67° C.; 1xSSC |
| J | DNA:RNA | <50 | $T_J^*$; 4xSSC | $T_J^*$; 4xSSC |
| K | RNA:RNA | >50 | 70° C.; 4xSSC -or- 50° C.; 4xSSC, 50% formamide | 67° C.; 1xSSC |
| L | RNA:RNA | <50 | $T_L^*$; 2xSSC | $T_L^*$; 2xSSC |
| M | DNA:DNA | >50 | 50° C.; 4xSSC -or- 40° C.; 6xSSC, 50% formamide | 50° C.; 2xSSC |
| N | DNA:DNA | <50 | $T_N^*$; 6xSSC | $T_N^*$; 6xSSC |
| O | DNA:RNA | >50 | 55° C.; 4xSSC -or- 42° C.; 6xSSC, 50% formamide | 55° C.; 2xSSC |
| P | DNA:RNA | <50 | $T_P^*$; 6xSSC | $T_P^*$; 6xSSC |
| Q | RNA:RNA | >50 | 60° C.; 4xSSC -or- 45° C.; 6xSSC, 50% formamide | 60° C.; 2xSSC |
| R | RNA:RNA | <50 | $T_R^*$; 4xSSC | $T_R^*$; 4xSSC |

[1]The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.
[H]SSPE (1xSSPE is 0.15M NaCl, 10 mM NaH$_2$PO$_4$, and 1.25 mM EDTA, pH 7.4) can be substituted for SSC (1xSSC is 0.15M NaCl and 15 mM sodium citrate) in the hybridization and wash buffers; washes are performed for 15 minutes after hybridization is complete.
$T_B^*$-$T_R^*$: The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$(° C.) = 2(# of A + T bases) + 4(# of G + C bases). For hybrids between 18 and 49 base pairs in length, $T_m$(° C.) = 81.5 + 16.6($\log_{10}$Na$^+$) + 0.41(% G+C) − (600/N), where N is the number of bases in the hybrid, and Na$^+$ is the concentration of sodium ions in the hybridization buffer (Na$^+$ for 1xSSC = 0.165M).

As used herein, the terms "immunospecific binding" and "specifically bind to" refer to antibodies that bind to an antigen with a binding affinity or 105 Moles taken either from pre-CVH or from a subject who has not suffered CVH, or from a cell, tissue or sample that is not affected by CVH. Control samples of the present invention are taken from normal samples.

As used herein, the term "expression pattern" includes expression of a group of genes at RNA or protein level, the quantity or activity of each member of which is correlated with the incidence or risk of incidence of CVH and CVH associated diseases. An expression pattern comprises expression level of 2 or more CVHGs. An expression pattern may also comprise expression level of 2-5, 5-15, 15-35, 35-50, or more than 50 CVHGs.

As used herein, the terms "treating," "treatment," and "therapy" refer to curative therapy, prophylactic therapy, and preventative therapy.

Various aspects of the invention are described in further detail in the following subsections. The subsections below describe in more detail the present invention. The use of subsections is not meant to limit the invention; subsections may apply to any aspect of the invention.

One aspect of the present invention relates to a method for treating CVH and CVH-related disorders with compositions comprising a guanylhydrazone compound. In one embodiment, the CVH-related disorder is IBS and the guanylhydrazone compound is CNI1493.

Another aspect of the present invention relates to CVH-related genes. Briefly, new born rats were sensitized by infusion of acetic acid into the colon at P10. Control rats received saline. At eight weeks, the animals were divided into four groups: control+vehicle; control+CNI1493; sensitized+vehicle; and sensitized+CNI1493, Colon samples were obtained after CNI1493 treatment (5 mg/kg for four days, the vehicle group received vehicle only). Gene expression patterns in the colon tissue samples and S1 dorsal root ganglia (S1 DRG) were analyzed using Affymetrix rat genome 230A chips (Affymetrix, Santa Clara, Calif.). Single array analysis for each chip was performed by Affymetrix Microarray Suite (MAS) software to produce a detection call, present, absent or marginal and a signal intensity value for each gene that is a relative measure of abundance of the transcript. For comparison of signal intensity values between chips, all chips will be scaled to an average intensity of 500, Genes called "Absent" across all chips and genes without a Fold-change$\geq$2.0 in at least one of the pairwise comparisons of chips from different treatment groups are excluded. The probe sets with absolute call "Absent" across all chips and Fold-change<2.0 in all of the possible pairwise comparisons, are filtered out. ANOVA was then performed on the filtered data set. Significant changes in gene expression were detected by analyzing signal intensity values by two-way ANOVA with 99% confidence limits. The differentially regulated genes were subjected to cluster analysis to identify genes associated with sensitization and treatment.

Tables 3 and 4 provides a list of the genes that are differentially expressed in the colon and S1 DRG, respectively, of the sensitized animals, i.e., animals suffering from CVH. Tables 5 and 6 provide a list of the genes that are differentially expressed in the colon and S1 DRG, respectively, in CNI493-treated animals. Since CNI1493 treatment ameliorates CVH in the sensitized animals, genes differentially regulated by CNI1493 may also be related to the etiology of Accordingly, genes listed in Tables 3-6 are designated as CVH-related (CVHGs).

TABLE 3

Genes differentially expressed in sensitized colon

| No. | Acce. No. | Symbol | CTRL-VHL | CTRL-CNI | IBS-VHL | IBS-CNI |
|---|---|---|---|---|---|---|
| 73 | NM_021769 | Sult-n | 1.00 | 0.85 | 2.98 | 1.85 |
| 57 | NM_022531 | Des | 1.00 | 1.03 | 2.55 | 1.31 |
| 14 | BF389682 | zzN/A | 1.00 | 1.53 | 2.49 | 2.04 |
| 16 | BF419200 | Cebpd | 1.00 | 1.03 | 2.44 | 2.28 |
| 26 | BI296437 | zzN/A | 1.00 | 1.14 | 2.43 | 1.21 |

TABLE 3-continued

Genes differentially expressed in sensitized colon

| No. | Acce. No. | Symbol | CTRL-VHL | CTRL-CNI | IBS-VHL | IBS-CNI |
|---|---|---|---|---|---|---|
| 25 | NM_013002 | Pcp4 | 1.00 | 0.88 | 2.29 | 1.14 |
| 55 | NM_013122 | Igfbp2 | 1.00 | 0.75 | 2.19 | 0.94 |
| 74 | NM_024400 | Adamts1 | 1.00 | 0.90 | 2.11 | 1.14 |
| 65 | AI229029 | Tubb3 | 1.00 | 0.93 | 2.05 | 1.53 |
| 43 | BI282702 | Acta2 | 1.00 | 0.95 | 2.03 | 0.99 |
| 44 | BF399310 | zzN/A | 1.00 | 0.64 | 2.01 | 0.78 |
| 64 | NM_031970 | Hspb1 | 1.00 | 1.14 | 1.90 | 1.40 |
| 12 | ILGFBP4 | BC019836 | 1.00 | 1.41 | 1.88 | 2.00 |
| 58 | BF290193 | zzN/A | 1.00 | 0.65 | 1.84 | 0.90 |
| 36 | AA012755 |  | 1.00 | 0.72 | 1.83 | 0.79 |
| 45 | AI103600 | zzN/A | 1.00 | 0.57 | 1.81 | 0.58 |
| 63 | AA851939 | Fxyd6 | 1.00 | 0.95 | 1.81 | 1.26 |
| 56 | AA799832 | zzN/A | 1.00 | 0.78 | 1.80 | 0.95 |
| 50 | NM_019904 | Lgals1 | 1.00 | 0.74 | 1.79 | 0.96 |
| 37 | NM_017148 | Csrp1 | 1.00 | 0.63 | 1.72 | 0.71 |
| 35 | BI283060 | zzN/A | 1.00 | 0.63 | 1.71 | 0.69 |
| 39 | AA800892 | zzN/A | 1.00 | 0.57 | 1.71 | 0.68 |
| 29 | BG373779 | LOC308709 | 1.00 | 0.48 | 1.68 | 0.59 |
| 2 | BI285494 | Ifitm31 | 1.00 | 3.86 | 1.66 | 4.90 |
| 47 | NM_053770 | Argbp2 | 1.00 | 0.79 | 1.66 | 0.77 |
| 34 | NM_012893 | Actg2 | 1.00 | 0.48 | 1.66 | 0.56 |
| 46 | NM_130403 | Ppp1r14a | 1.00 | 0.91 | 1.65 | 0.99 |
| 15 | BG663107 | zzN/A | 1.00 | 1.06 | 1.65 | 1.23 |
| 30 | D29960 | Loc192245 | 1.00 | 0.51 | 1.64 | 0.54 |
| 48 | BM386598 | zzN/A | 1.00 | 0.90 | 1.60 | 0.95 |
| 71 | AA818342 | zzN/A | 1.00 | 0.88 | 1.58 | 1.25 |
| 5 | AW523747 | Amigo2 | 1.00 | 0.88 | 1.57 | 2.10 |
| 40 | AA817802 | zzN/A | 1.00 | 0.55 | 1.57 | 0.69 |
| 75 | BE112887 | zzN/A | 1.00 | 1.06 | 1.55 | 1.05 |
| 33 | M23764 | Tpm1 | 1.00 | 0.60 | 1.54 | 0.68 |
| 59 | AW522471 | Exo70 | 1.00 | 0.65 | 1.54 | 1.00 |
| 8 | EST |  | 1.00 | 0.93 | 1.52 | 2.14 |
| 31 | AI044427 | zzN/A | 1.00 | 0.59 | 1.52 | 0.69 |
| 41 | BI279044 | zzN/A | 1.00 | 0.49 | 1.51 | 0.52 |
| 9 | EST |  | 1.00 | 1.48 | 1.51 | 2.10 |
| 28 | BI291848 | zzN/A | 1.00 | 0.62 | 1.51 | 0.81 |
| 24 | AI411809 | zzN/A | 1.00 | 0.89 | 1.51 | 1.06 |
| 67 | NM_053440 | Stmn2 | 1.00 | 0.79 | 1.49 | 1.06 |
| 54 | BI285456 | zzN/A | 1.00 | 0.83 | 1.49 | 1.06 |
| 32 | NM_031549 | Tagln | 1.00 | 0.54 | 1.47 | 0.64 |
| 38 | AI177055 | zzN/A | 1.00 | 0.79 | 1.47 | 0.82 |
| 52 | BI279661 | Wfdc1 | 1.00 | 0.66 | 1.46 | 0.94 |
| 20 | AI229240 | zzN/A | 1.00 | 0.68 | 1.46 | 1.69 |
| 1 | BI285346 | Ppp4r1 | 1.00 | 1.34 | 1.46 | 1.51 |
| 53 | NM_134449 | Prkcdbp | 1.00 | 0.87 | 1.45 | 1.01 |
| 49 | BF555956 | zzN/A | 1.00 | 0.85 | 1.45 | 0.91 |
| 42 | X16262 | Myh11 | 1.00 | 0.54 | 1.44 | 0.60 |
| 51 | BG666999 | Slc25a4 | 1.00 | 0.79 | 1.44 | 0.94 |
| 70 | AI177366 | Itgb1 | 1.00 | 1.00 | 1.42 | 1.24 |
| 61 | AA686007 | Parva | 1.00 | 0.80 | 1.41 | 0.99 |
| 68 | BM389644 | zzN/A | 1.00 | 0.88 | 1.41 | 1.07 |
| 18 | BG378721 | zzN/A | 1.00 | 0.95 | 1.40 | 1.21 |
| 60 | AA893484 | Fn1 | 1.00 | 0.51 | 1.40 | 0.88 |
| 27 | NM_019304 | Dgkb | 1.00 | 0.67 | 1.31 | 0.86 |
| 7 | EST |  | 1.00 | 1.09 | 1.31 | 1.51 |
| 19 | NM_017131 | Casq2 | 1.00 | 0.71 | 1.30 | 1.19 |
| 6 | U06434 | Scya4 | 1.00 | 1.18 | 1.30 | 1.76 |
| 10 | AB043636 | Kcnj8 | 1.00 | 1.22 | 1.29 | 1.65 |
| 11 | EST |  | 1.00 | 0.82 | 1.29 | 1.55 |
| 66 | AF081582 | Evt1 | 1.00 | 0.85 | 1.29 | 1.03 |
| 3 | NM_024145 | Fgr | 1.00 | 1.03 | 1.26 | 1.70 |
| 72 | BI296312 | zzN/A | 1.00 | 0.80 | 1.26 | 1.04 |
| 13 | AA859496 | Gch | 1.00 | 0.93 | 1.24 | 1.34 |
| 22 | BF394235 | zzN/A | 1.00 | 0.55 | 1.23 | 0.99 |
| 69 | BF551377 | zzN/A | 1.00 | 0.81 | 1.21 | 0.99 |
| 62 | AI179984 | Dmrs91 | 1.00 | 0.49 | 1.21 | 0.70 |
| 21 | NM_133605 | Camk2g | 1.00 | 0.77 | 1.18 | 1.01 |
| 17 | U27518 | LOC286989 | 1.00 | 0.50 | 1.11 | 1.19 |
| 4 | NM_022688 | Porf1 | 1.00 | 0.80 | 1.08 | 1.42 |
| 23 | AW254190 |  | 1.00 | 0.66 | 1.05 | 1.03 |
| 87 | BM386844 | zzN/A | 1.00 | 1.40 | 1.00 | 0.84 |
| 94 | BF390024 | Ncor1 | 1.00 | 1.34 | 0.93 | 0.89 |
| 92 | BE098713 | zzN/A | 1.00 | 1.11 | 0.87 | 0.82 |
| 86 | BF404414 | zzN/A | 1.00 | 1.19 | 0.85 | 0.80 |
| 82 | AA945828 | zzN/A | 1.00 | 1.54 | 0.84 | 1.07 |

TABLE 3-continued

Genes differentially expressed in sensitized colon

| No. | Acce. No. | Symbol | CTRL-VHL | CTRL-CNI | IBS-VHL | IBS-CNI |
|---|---|---|---|---|---|---|
| 88 | AA849756 | zzN/A | 1.00 | 0.86 | 0.84 | 0.66 |
| 83 | BM392373 | Ceacam1 | 1.00 | 1.38 | 0.82 | 0.87 |
| 78 | BM385170 | zzN/A | 1.00 | 1.30 | 0.81 | 1.11 |
| 77 | BF411331 | zzN/A | 1.00 | 1.22 | 0.80 | 1.04 |
| 104 | AI177513 | zzN/A | 1.00 | 0.90 | 0.80 | 0.70 |
| 107 | AA964600 | zzN/A | 1.00 | 0.83 | 0.79 | 0.68 |
| 85 | BI295141 | zzN/A | 1.00 | 1.07 | 0.78 | 0.82 |
| 108 | AI227627 | Cd9 | 1.00 | 0.74 | 0.77 | 0.61 |
| 90 | NM_031762 | Cdkn1b | 1.00 | 1.02 | 0.74 | 0.45 |
| 89 | AI180286 | zzN/A | 1.00 | 0.90 | 0.74 | 0.70 |
| 91 | AI105205 | Ctl1 | 1.00 | 0.93 | 0.73 | 0.57 |
| 103 | BG380281 | zzN/A | 1.00 | 0.72 | 0.72 | 0.64 |
| 101 | BI301490 | zzN/A | 1.00 | 0.68 | 0.69 | 0.66 |
| 113 | BM384203 | zzN/A | 1.00 | 0.90 | 0.69 | 0.66 |
| 114 | BG373555 | zzN/A | 1.00 | 0.98 | 0.68 | 0.74 |
| 105 | BI288816 | zzN/A | 1.00 | 0.65 | 0.68 | 0.48 |
| 109 | AA894262 | zzN/A | 1.00 | 1.07 | 0.68 | 0.59 |
| 106 | AI228548 | zzN/A | 1.00 | 0.62 | 0.67 | 0.30 |
| 76 | AW433971 | Mvk | 1.00 | 1.12 | 0.67 | 0.98 |
| 80 | AA800750 | zzN/A | 1.00 | 1.13 | 0.65 | 0.92 |
| 84 | AI171229 | zzN/A | 1.00 | 1.23 | 0.65 | 0.78 |
| 112 | AI407835 | Add3 | 1.00 | 0.74 | 0.65 | 0.65 |
| 97 | NM_023989 | LOC78973 | 1.00 | 0.84 | 0.65 | 0.70 |
| 81 | AA893602 | zzN/A | 1.00 | 1.13 | 0.65 | 0.93 |
| 98 | AA943165 | zzN/A | 1.00 | 0.71 | 0.64 | 0.52 |
| 93 | NM_031347 | Ppargc1 | 1.00 | 1.17 | 0.62 | 0.52 |
| 79 | BE102350 | zzN/A | 1.00 | 1.64 | 0.61 | 1.18 |
| 110 | AI408598 | zzN/A | 1.00 | 0.85 | 0.61 | 0.53 |
| 111 | AI175820 | zzN/A | 1.00 | 0.64 | 0.61 | 0.57 |
| 99 | AI179665 |  | 1.00 | 0.77 | 0.59 | 0.64 |
| 100 | BI296591 | zzN/A | 1.00 | 0.53 | 0.54 | 0.55 |
| 102 | AF189724 | Cxcl12 | 1.00 | 0.73 | 0.50 | 0.61 |
| 96 | BF417032 | zzN/A | 1.00 | 0.87 | 0.49 | 0.57 |
| 95 | M58040 | Tfrc | 1.00 | 0.63 | 0.45 | 0.42 |

TABLE 4

Genes differentially expressed in sensitized S1 DRG

| No. | Identifier | Acce. No. | CTRL-VHL | CTRL-CNI | IBS-VHL | IBS-CNI |
|---|---|---|---|---|---|---|
| 11 | 1376554_at | BE121079 | 1 | 1.74 | 2.23 | 2.01 |
| 23 | 1369233_at | AF196965 | 1 | 1.45 | 2.09 | 1.71 |
| 4 | 1374620_at | BM392373 | 1 | 1.43 | 1.87 | 2.41 |
| 6 | 1390403_at | BE108405 | 1 | 1.39 | 1.83 | 1.86 |
| 8 | 1379272_at | AA963084 | 1 | 1.08 | 1.83 | 1.70 |
| 24 | 1369157_at | NM_017229 | 1 | 1.05 | 1.78 | 1.09 |

TABLE 4-continued

Genes differentially expressed in sensitized S1 DRG

| No. | Identifier | Acce. No. | CTRL-VHL | CTRL-CNI | IBS-VHL | IBS-CNI |
|---|---|---|---|---|---|---|
| 19 | 1382915_at | AI237079 | 1 | 1.26 | 1.76 | 1.38 |
| 25 | 1374802_at | AI010721 | 1 | 0.90 | 1.72 | 0.96 |
| 5 | 1389222_at | BI282847 | 1 | 1.30 | 1.69 | 1.66 |
| 22 | 1368379_at | NM_054001 | 1 | 1.31 | 1.68 | 1.66 |
| 7 | 1368678_at | X67108 | 1 | 1.38 | 1.66 | 1.72 |
| 10 | 1386218_at | AI639301 | 1 | 1.35 | 1.65 | 1.58 |
| 26 | 1370301_at | U65656 | 1 | 1.17 | 1.64 | 1.02 |
| 17 | 1389099_at | AI600184 | 1 | 1.50 | 1.64 | 1.50 |
| 18 | 1383159_at | AW434445 | 1 | 1.40 | 1.64 | 1.58 |
| 13 | 1384217_at | BI276341 | 1 | 1.24 | 1.59 | 1.67 |
| 21 | 1389713_at | AI602851 | 1 | 1.17 | 1.58 | 1.45 |
| 12 | 1372620_at | AI008642 | 1 | 1.32 | 1.57 | 1.94 |
| 78 | 1385386_at | BI302745 | 1 | 0.79 | 0.09 | 0.31 |
| 28 | 1387658_at | U93849 | 1 | 1.60 | 0.43 | 0.82 |
| 47 | 1368703_at | NM_053326 | 1 | 0.65 | 0.44 | 0.70 |
| 62 | 1377061_at | AI500913 | 1 | 0.49 | 0.44 | 0.36 |
| 50 | 1375606_at | AI235906 | 1 | 0.75 | 0.46 | 0.43 |
| 49 | 1369255_at | NM_013123 | 1 | 0.80 | 0.46 | 0.58 |
| 40 | 1386999_at | BG380730 | 1 | 0.78 | 0.47 | 0.68 |
| 42 | 1388589_at | BG381046 | 1 | 0.74 | 0.47 | 0.61 |
| 41 | 1370666_at | AF201839 | 1 | 0.66 | 0.49 | 0.44 |
| 52 | 1389864_at | BF405086 | 1 | 0.69 | 0.50 | 0.58 |
| 72 | 1374283_at | BF419505 | 1 | 0.82 | 0.51 | 0.59 |
| 34 | 1375469_at | BE111847 | 1 | 0.67 | 0.52 | 0.67 |
| 38 | 1374002_at | AI045904 | 1 | 0.71 | 0.55 | 0.79 |
| 65 | 1394114_at | AA799434 | 1 | 0.67 | 0.56 | 0.63 |
| 67 | 1388101_at | AF389425 | 1 | 0.73 | 0.56 | 0.71 |
| 57 | 1368279_at | NM_053718 | 1 | 0.78 | 0.56 | 0.39 |
| 45 | 1376350_at | BF396151 | 1 | 0.90 | 0.57 | 0.75 |
| 74 | 1376122_at | BF401577 | 1 | 0.77 | 0.57 | 0.44 |
| 36 | 1369036_at | NM_019309 | 1 | 0.72 | 0.58 | 0.65 |
| 66 | 1367814_at | M14137 | 1 | 0.67 | 0.59 | 0.67 |
| 71 | 1372177_at | AI180033 | 1 | 0.63 | 0.60 | 0.61 |
| 70 | 1373981_at | BI299720 | 1 | 0.62 | 0.60 | 0.55 |
| 35 | 1383468_at | BM958512 | 1 | 0.66 | 0.62 | 0.67 |
| 46 | 1376931_at | BG380736 | 1 | 0.73 | 0.62 | 0.75 |
| 75 | 1371281_at | M37568 | 1 | 0.97 | 0.63 | 0.39 |
| 44 | 1387818_at | NM_053736 | 1 | 0.87 | 0.63 | 0.75 |
| 51 | 1369048_at | NM_017289 | 1 | 0.71 | 0.64 | 0.56 |
| 37 | 1374084_at | BE119993 | 1 | 0.68 | 0.64 | 0.59 |
| 30 | 1387327_at | NM_133318 | 1 | 1.25 | 0.65 | 0.66 |
| 39 | 1373031_at | BI275757 | 1 | 0.83 | 0.65 | 0.77 |
| 32 | 1375448_at | BM391628 | 1 | 0.90 | 0.65 | 0.74 |
| 88 | 1369884_at | NM_022182 | 1 | 0.90 | 0.66 | 0.54 |
| 59 | 1375294_at | BF415950 | 1 | 0.75 | 0.66 | 0.42 |
| 90 | 1387404_at | NM_078620 | 1 | 1.02 | 0.66 | 0.50 |
| 69 | 1386907_at | NM_012949 | 1 | 0.75 | 0.67 | 0.67 |
| 63 | 1392500_at | AA957990 | 1 | 0.59 | 0.67 | 0.58 |
| 68 | 1369000_at | NM_021589 | 1 | 0.75 | 0.67 | 0.67 |

TABLE 5

Genes differentially expressed in CNI1493-treated colon

| No. | Identifier | Acce. No. | Description |
|---|---|---|---|
| 1 | 1370531_at | U69550 | phospholipase D gene 1 |
| 2 | 1369708_at | NM_031017 | cAMP response element binding protein 1 |
| 3 | 1368889_at | NM_023101 | SNARE Vtila-beta protein |
| 4 | 1387046_at | NM_053792 | selective LIM binding factor |
| 5 | 1371192_at | BF566236 | neurofibromatosis 2 |
| 6 | 1369195_at | NM_013068 | Fatty acid binding protein 2 |
| 7 | 1398540_at | BM386789 | *Rattus norvegicus* transcribed sequences |
| 8 | 1375464_at | BI290815 | *Rattus norvegicus* transcribed sequences |
| 9 | 1387119_at | AW433971 | mevalonate kinase |
| 10 | 1374034_at | BG379410 | *Rattus norvegicus* transcribed sequence with strong similarity to protein sp: P49589 (*H. sapiens*) SYC_HUMAN CYSTEINYL-TRNA SYNTHETASE (CYSTEINE--TRNA LIGASE) (CYSRS) |
| 11 | 1392633_at | AI045724 | *Rattus norvegicus* transcribed sequences |
| 12 | 1371027_at | BF556820 | Cas-Br-M (murine) ectropic retroviral transforming sequence b |

TABLE 5-continued

Genes differentially expressed in CNI1493-treated colon

| No. | Identifier | Acce. No. | Description |
|---|---|---|---|
| 13 | 1376708_at | BM385170 | *Rattus norvegicus* transcribed sequences |
| 14 | 1387220_at | NM_019323 | mast cell protease 9 |
| 15 | 1377034_at | BF411331 | "*Rattus norvegicus* transcribed sequence with moderate similarity to protein ref: NP_109591.1 (*H. sapiens*) serine (or cysteine) proteinase inhibitor, clade B (ovalbumin), member 1; protease inhibitor 2 (anti-elastase), monocyte/neutrophil; protease inhibitor |
| 16 | 1374324_at | AA945828 | *Rattus norvegicus* transcribed sequences |
| 17 | 1370510_a_at | AB012600 | aryl hydrocarbon receptor nuclear translocator-like |
| 18 | 1387130_at | NM_133315 | "solute carrier family 39 (iron-regulated transporter), member 1" |
| 19 | 1390562_s_at | BE102350 | *Rattus norvegicus* transcribed sequences |
| 20 | 1390960_at | AA893602 | *Rattus norvegicus* transcribed sequences |
| 21 | 1371925_at | AA893621 | *Rattus norvegicus* clone C201 intestinal epithelium proliferating cell-associated mRNA sequence |
| 22 | 1370693_a_at | M18630 | cyclic nucleotide phosphodiesterase 1 |
| 23 | 1377036_at | BE102350 | *Rattus norvegicus* transcribed sequences |
| 24 | 1392794_at | AA893579 | *Rattus norvegicus* transcribed sequences |
| 25 | 1388694_at | AI233121 | MHC class I RT1.O type 149 processed pseudogene |
| 26 | 1388754_at | AI176839 | *Rattus norvegicus* transcribed sequences |
| 27 | 1368233_at | NM_031042 | "general transcription factor IIF, polypeptide 2 (30 kD subunit)" |
| 28 | 1368679_a_at | L14782 | lyn protein non-receptor kinase |
| 29 | 1372177_at | AI180033 | *Rattus norvegicus* transcribed sequence with moderate similarity to protein ref: NP_004522.1 (*H. sapiens*) molybdenum cofactor synthesis 2 [*Homo sapiens*] |
| 30 | 1372868_at | BF284295 | *Rattus norvegicus* transcribed sequence with weak similarity to protein sp: O14657 (*H. sapiens*) TO1B_HUMAN Torsin B precursor |
| 31 | 1380472_at | AI639486 | *Rattus norvegicus* transcribed sequence with weak similarity to protein ref: NP_003860.1 (*H. sapiens*) carboxylesterase 2; intestinal carboxylesterase; liver carboxylesterase-2 [*Homo sapiens*] |
| 32 | 1387994_at | U89280 | oxidative 17 beta hydroxysteroid dehydrogenase type 6 |
| 33 | 1390531_at | BE098021 | *Rattus norvegicus* transcribed sequences |
| 34 | 1388055_at | U39207 | cytochrome P450 4F5 |
| 35 | 1368379_at | NM_054001 | "CD36 antigen (collagen type I receptor, thrombospondin receptor)-like 2" |
| 36 | 1368101_at | NM_012518 | calmodulin 3 |
| 37 | 1389302_at | BI289482 | *Rattus norvegicus* transcribed sequence with weak similarity to protein pir: S30833 (*S. cerevisiae*) S30833 hypothetical protein YEL044w —yeast (*Saccharomyces cerevisiae*) |
| 38 | 1389378_at | AI599324 | *Rattus norvegicus* transcribed sequence with weak similarity to protein pir: A42973 (*H. sapiens*) A42973 serum protein MSE55 - human |
| 39 | 1387444_at | NM_133592 | brain-enriched membrane-associated protein tyrosine BEM-2 |
| 40 | 1374284_at | AI227769 | *Rattus norvegicus* transcribed sequences |
| 41 | 1371239_s_at | AF053361 | "tropomyosin 3, gamma" |
| 42 | 1387596_at | NM_053897 | "Proteinase-activated receptor-2, G protein-coupled receptor 11" |
| 43 | 1389873_at | BI282953 | apoptosis-associated speck-like protein containing a CARD |
| 44 | 1369773_at | NM_017105 | Bone morphogenetic protein 3 |
| 45 | 1374119_at | BI279615 | "*Rattus norvegicus* transcribed sequence with strong similarity to protein ref: NP_004424.1 (*H. sapiens*) E74-like factor 3 (ets domain transcription factor, epithelial-specific); E74-like factor 3 (ets domain transcription factor); ets domain transcription |
| 46 | 1368128_at | NM_031598 | "phospholipase A2, group IIA (platelets, synovial fluid)" |
| 47 | 1368270_at | NM_012907 | Apolipoprotein B editing protein |
| 48 | 1367960_at | NM_019186 | ADP-ribosylation-like 4 |
| 49 | 1367942_at | NM_019144 | acid phosphatase 5 |
| 50 | 1392694_at | AW526101 | *Rattus norvegicus* transcribed sequences |
| 51 | 1374452_at | BF399743 | phosphodiesterase 9A |
| 52 | 1368727_at | NM_053929 | "solute carrier family 7 (cationic amino acid transporter, y+ system), member 9" |
| 53 | 1376625_at | BI296015 | *Rattus norvegicus* transcribed sequences |
| 54 | 1367768_at | NM_031655 | latexin |
| 55 | 1369193_at | AF474979 | cyclin dependent kinase inhibitor 2B |
| 56 | 1382714_at | AA875186 | *Rattus norvegicus* transcribed sequences |
| 57 | 1376359_at | BG375355 | "*Rattus norvegicus* transcribed sequence with weak similarity to protein ref: NP_113645.1 (*H. sapiens*) membrane-spanning 4-domains, subfamily A, member 8B [*Homo sapiens*]" |

TABLE 5-continued

Genes differentially expressed in CNI1493-treated colon

| No. | Identifier | Acce. No. | Description |
|---|---|---|---|
| 58 | 1372064_at | BI296385 | *Rattus norvegicus* CDK104 mRNA |
| 59 | 1388396_at | BI275932 | *Rattus norvegicus* transcribed sequence with strong similarity to protein sp: O00506 (*H. sapiens*) ST25_HUMAN Serine/threonine protein kinase 25 (Sterile 20/oxidant stress-response kinase 1) (Ste20/oxidant stress response kinase-1) (SOK-1) (Ste20-like kinase) |
| 60 | 1384191_at | BF387765 | *Rattus norvegicus* transcribed sequences |
| 61 | 1372255_at | BF283284 | *Rattus norvegicus* transcribed sequence with strong similarity to protein sp: P54136 (*H. sapiens*) SYR_HUMAN ARGINYL-TRNA SYNTHETASE (ARGININE--TRNA LIGASE) (ARGRS) |
| 62 | 1369262_at | NM_022277 | caspase-8 |
| 63 | 1376117_at | BI289103 | *Rattus norvegicus* transcribed sequence with moderate similarity to protein ref: NP_079533.1 (*H. sapiens*) NG22 protein; choline transporter-like protein 4 [*Homo sapiens*] |
| 64 | 1380262_at | AA893436 | *Rattus norvegicus* transcribed sequences |
| 65 | 1370113_at | NM_023987 | inhibitor of apoptosis protein 1 |
| 66 | 1368437_at | NM_019174 | carbonic anhydrase 4 |
| 67 | 1390455_at | AI013474 | *Rattus norvegicus* transcribed sequence with strong similarity to protein sp: P08910 (*H. sapiens*) HPS1 HUMAN Protein PHPS1-2 |
| 68 | 1378658_at | BI292185 | *Rattus norvegicus* transcribed sequence with weak similarity to protein ref: NP_036260.1 (*H. sapiens*) calcium activated chloride channel 4 [*Homo sapiens*] |
| 69 | 1376976_at | AI009823 | *Rattus norvegicus* transcribed sequence with weak similarity to protein ref: NP_002995.1 (*H. sapiens*) secreted and transmembrane 1 precursor; K12 protein precursor; type 1a transmembrane protein [*Homo sapiens*] |
| 70 | 1370706_a_at | U39943 | cytochrome P450 monooxygenase |
| 71 | 1372997_at | AI105243 | *Rattus norvegicus* transcribed sequences |
| 72 | 1369183_at | NM_019231 | mitogen activated protein kinase 13 |
| 73 | 1386917_at | NM_012744 | Pyruvate carboxylase |
| 74 | 1390678_at | AA955527 | *Rattus norvegicus* transcribed sequences |
| 75 | 1398847_at | BG376935 | diphosphoinositol polyphosphate phosphohydolase type II |
| 76 | 1368073_at | NM_012591 | Interferon regulatory factor 1 |
| 77 | 1371394_x_at | BG664827 | "*Rattus norvegicus* endogenous retrovirus mRNA, partial sequence" |
| 78 | 1370422_at | AF036537 | homocysteine respondent protein HCYP2 |
| 79 | 1375230_at | AA800192 | "*Rattus norvegicus* endogenous retrovirus mRNA, partial sequence" |
| 80 | 1368007_at | NM_022849 | deleted in malignant brain tumors 1 |
| 81 | 1372671_at | BI284293 | *Rattus norvegicus* transcribed sequence with strong similarity to protein ref: NP_060809.1 (*H. sapiens*) hypothetical protein FLJ11149 [*Homo sapiens*] |
| 82 | 1368219_at | NM_017137 | chloride channel 2 |
| 83 | 1367760_at | D13341 | mitogen activated protein kinase kinase 1 |
| 84 | 1388006_at | U89744 | putative cell surface antigen |
| 85 | 1367925_at | NM_022715 | major vault protein |
| 86 | 1390128_at | BF557618 | *Rattus norvegicus* transcribed sequence with strong similarity to protein ref: NP 065145.1 (*H. sapiens*) CHMP1.5 protein [*Homo sapiens*] |
| 87 | 1388745_at | AI228417 | "*Rattus norvegicus* transcribed sequence with strong similarity to protein pdb: 1BGM (*E. coli*) O Chain O, Beta-Galactosidase (Chains I-P)" |
| 88 | 1369940_at | NM_031811 | transaldolase 1 |
| 89 | 1370400_at | L23128 | "*Rattus norvegicus* MHC class I mRNA, complete cds" |
| 90 | 1371970_at | AA799328 | *Rattus norvegicus* transcribed sequences |
| 91 | 1386933_at | NM_134418 | secretory (zymogen) granule membrane glycoprotein GP2 |
| 92 | 1369100_at | NM_134375 | angiotensin/vasopressin receptor |
| 93 | 1372619_at | AI172185 | "*Rattus norvegicus* Aa2-277 mRNA, complete cds" |
| 94 | 1380129_at | AA818937 | *Rattus norvegicus* transcribed sequence with weak similarity to protein sp: P10266 (*H. sapiens*) POL1_HUMAN Endogenous retrovirus HERV-K10 putative pol polyprotein [Includes: Reverse transcriptase; Endonuclease] |
| 95 | 1371078_at | AI500830 | RT1 class Ib gene |
| 96 | 1367586_at | NM_017025 | lactate dehydrogenase A |
| 97 | 1374033_at | BG373505 | *Rattus norvegicus* transcribed sequence with moderate similarity to protein pir: I38135 (*H. sapiens*) I38135 multicatalytic endopeptidase complex (EC 3.4.99.46) beta chain MECL-1-human |

TABLE 5-continued

Genes differentially expressed in CNI1493-treated colon

| No. | Identifier | Acce. No. | Description |
|---|---|---|---|
| 98 | 1373913_at | BF282271 | *Rattus norvegicus* transcribed sequence with strong similarity to protein pir: T50626 (*H. sapiens*) T50626 hypothetical protein DKFZp762K1914.1 - human (fragment) |
| 99 | 1372665_at | AI230228 | "*Rattus norvegicus* phosphoserine aminotransferase mRNA, complete cds" |
| 100 | 1376056_at | BF291214 | *Rattus norvegicus* transcribed sequence with moderate similarity to protein ref: NP_116178.1 (*H. sapiens*) hypothetical protein FLJ14464 [*Homo sapiens*] |
| 101 | 1368066_at | NM_053812 | BCL2-antagonist/killer 1 |
| 102 | 1374838_at | BI293504 | *Rattus norvegicus* transcribed sequence with weak similarity to protein sp: Q13342 (*H. sapiens*) LY10_HUMAN LYSP100 protein (Lymphoid-restricted homolog of Sp100) (Nuclear autoantigen Sp-140) (Speckled 140 kDa) (Nuclear body protein Sp140) |
| 103 | 1372816_at | BE107319 | *Rattus norvegicus* transcribed sequences |
| 104 | 1388236_x_at | M24026 | RT1 class Ib gene |
| 105 | 1371210_s_at | AJ276126 | RT1 class Ib gene |
| 106 | 1390325_at | BI289418 | *Rattus norvegicus* transcribed sequence with weak similarity to protein ref: NP_083693.1 (*M. musculus*) RIKEN cDNA 9030605E16 [*Mus musculus*] |
| 107 | 1369279_at | NM_130819 | retinol dehydrogenase homolog |
| 108 | 1390021_at | BM391206 | histone 2b |
| 109 | 1368317_at | NM_019157 | aquaporin 7 |
| 110 | 1387100_at | NM_031703 | aquaporin 3 |
| 111 | 1368975_at | NM_013127 | CD38 antigen |
| 112 | 1386908_at | NM_022278 | glutaredoxin 1 (thioltransferase) |
| 113 | 1369427_at | NM_022617 | macrophage expressed gene 1 |
| 114 | 1369110_x_at | NM_012645 | RT1 class Ib gene |
| 115 | 1369957_at | NM_019341 | regulator of G-protein signaling 5 |
| 116 | 1398985_at | AI716480 | *Rattus norvegicus* transcribed sequence with moderate similarity to protein ref: NP_004277.1 (*H. sapiens*) GTP binding protein 1 [*Homo sapiens*] |
| 117 | 1368413_at | NM_022935 | Amiloride binding protein 1 |
| 118 | 1370960_at | BE104060 | insulin-like growth factor-binding protein 5 |
| 119 | 1368505_at | NM_017214 | regulator of G-protein signaling 4 |
| 120 | 1373386_at | AI179953 | *Rattus norvegicus* transcribed sequences |
| 121 | 1387348_at | BE113270 | insulin-like growth factor-binding protein 5 |
| 122 | 1370638_at | AF069525 | ankyrin 3 (G) |
| 123 | 1377112_at | AA859352 | *Rattus norvegicus* transcribed sequence with moderate similarity to protein ref: NP_001776.1 (*H. sapiens*) cytidine deaminase [*Homo sapiens*] |
| 124 | 1389611_at | AA849857 | Very low density lipoprotein receptor |
| 125 | 1369098_at | NM_013155 | Very low density lipoprotein receptor |
| 126 | 1368294_at | NM_053907 | deoxyribonuclease I-like 3 |
| 127 | 1368342_at | NM_031544 | Adenosine monophosphate deaminase 3 |
| 128 | 1368965_at | NM_030834 | monocarboxylate transporter |
| 129 | 1392819_at | AW921478 | "*Rattus norvegicus* transcribed sequence with weak similarity to protein ref: NP_071744.1 (*H. sapiens*) CD20-like precursor; membrane-spanning 4-domains, subfamily A, member 6 [*Homo sapiens*]" |
| 130 | 1367774_at | NM_031509 | "glutathione S-transferase, alpha 1" |
| 131 | 1387687_at | NM_133542 | "immunoglobulin superfamily, member 6" |
| 132 | 1369173_at | NM_032060 | complement component 3a receptor 1 |
| 133 | 1372013_at | BG380285 | *Rattus norvegicus* transcribed sequence with weak similarity to protein ref: NP_006426.1 (*H. sapiens*) interferon induced transmembrane protein 2 (1-8D); interferon-inducible [*Homo sapiens*] |
| 134 | 1373025_at | AI411618 | *Rattus norvegicus* transcribed sequence with moderate similarity to protein pir: C1HUQC (*H. sapiens*) C1HUQC complement subcomponent C1q chain C precursor - human |
| 135 | 1376652_at | BF418957 | *Rattus norvegicus* transcribed sequence with moderate similarity to protein pir: C1HUQA (*H. sapiens*) C1HUQA complement subcomponent C1q chain A precursor - human |
| 136 | 1368420_at | NM_012532 | ceruloplasmin |
| 137 | 1373932_at | BE098739 | *Rattus norvegicus* transcribed sequences |
| 138 | 1387893_at | D88250 | "complement component 1, s subcomponent" |
| 139 | 1388557_at | BF284922 | *Rattus norvegicus* transcribed sequences |
| 140 | 1374730_at | AI102519 | *Rattus norvegicus* transcribed sequence with weak similarity to protein ref: NP_003323.1 (*H. sapiens*) TYRO protein tyrosine kinase binding protein; polycystic lipomembranous osteodysplasia with sclerosing leukoencephalopathy [*Homo sapiens*] |

TABLE 5-continued

Genes differentially expressed in CNI1493-treated colon

| No. | Identifier | Acce. No. | Description |
|---|---|---|---|
| 141 | 1368000_at | NM_016994 | Complement component 3 |
| 142 | 1368558_s_at | NM_017196 | allograft inflammatory factor 1 |
| 143 | 1373523_at | AI011757 | *Rattus norvegicus* transcribed sequence with weak similarity to protein sp: P08637 (*H. sapiens*) FC3A_HUMAN Low affinity immunoglobulin gamma FC region receptor III-A precursor (IGG FC receptor III-2) (FC-gamma RIII-alpha) (FC-gamma RIIIA) (FCRIIIA) (FC-gamm |
| 144 | 1387011_at | NM_130741 | lipocalin 2 |
| 145 | 1370885_at | AA849399 | cathepsin Y |
| 146 | 1389470_at | AI639117 | Complement component 2 |
| 147 | 1368430_at | AF154349 | "protease, cysteine, 1 (legumain)" |
| 148 | 1375010_at | AI177761 | *Rattus norvegicus* transcribed sequence with weak similarity to protein ref: NP_001242.1 (*H. sapiens*) CD68 antigen; Macrophage antigen CD68 (microsialin) [*Homo sapiens*] |
| 149 | 1389006_at | AI170394 | *Rattus norvegicus* transcribed sequences |
| 150 | 1373575_at | BE111722 | *Rattus norvegicus* transcribed sequence with moderate similarity to protein pir: A35241 (*H. sapiens*) A35241 IgE Fc receptor gamma chain precursor - human |
| 151 | 1390510_at | BI294706 | "*Rattus norvegicus* transcribed sequence with weak similarity to protein ref: NP_071744.1 (*H. sapiens*) CD20-like precursor; membrane-spanning 4-domains, subfamily A, member 6 [*Homo sapiens*]" |
| 152 | 1376390_at | BF395317 | "*Rattus norvegicus* transcribed sequence with weak similarity to protein ref: NP_071744.1 (*H. sapiens*) CD20-like precursor; membrane-spanning 4-domains, subfamily A, member 6 [*Homo sapiens*]" |
| 153 | 1368187_at | NM_133298 | glycoprotein (transmembrane) nmb |
| 154 | 1389553_at | BF393825 | "*Rattus norvegicus* transcribed sequence with weak similarity to protein ref: NP_057268.1 (*H. sapiens*) C-type (calcium dependent, carbohydrate-recognition domain) lectin, superfamily member 6; dendritic cell immunoreceptor; C-type lectin [*Homo sapiens*]" |
| 155 | 1367568_a_at | NM_012862 | matrix Gla protein |
| 156 | 1370628_at | M34097 | granzyme B |
| 157 | 1379604_at | BF284937 | "*Rattus norvegicus* transcribed sequence with weak similarity to protein ref: NP_085146.1 (*H. sapiens*) apolipoprotein L, 4 [*Homo sapiens*]" |
| 158 | 1368464_at | NM_022393 | macrophage galactose N-acetyl-galactosamine specific lectin |
| 159 | 1379766_at | AI500952 | *Rattus norvegicus* transcribed sequences |
| 160 | 1370516_at | AB026665 | peptide/histidine transporter PHT2 |
| 161 | 1373071_at | AI103101 | *Rattus norvegicus* transcribed sequence with strong similarity to protein pir: T00702 (*H. sapiens*) T00702 hypothetical protein F25965 1 - human (fragment) |
| 162 | 1393224_at | AW529774 | *Rattus norvegicus* transcribed sequences |
| 163 | 1390312_at | BG670441 | *Rattus norvegicus* transcribed sequence with weak similarity to protein ref: NP_060124.1 (*H. sapiens*) hypothetical protein FLJ20073 [*Homo sapiens*] |
| 164 | 1377412_at | AI146237 | *Rattus norvegicus* transcribed sequences |
| 165 | 1399125_at | BI275516 | *Rattus norvegicus* transcribed sequence with weak similarity to protein sp: P49441 (*H. sapiens*) INPP_HUMAN Inositol polyphosphate 1-phosphatase (IPPase) (IPP) |
| 166 | 1386986_at | NM_053340 | opioid growth factor receptor |
| 167 | 1374731_at | BI275929 | "*Rattus norvegicus* transcribed sequence with moderate similarity to protein pdb: 1LBG (*E. coli*) B Chain B, Lactose Operon Repressor Bound To 21-Base Pair Symmetric Operator Dna, Alpha Carbons Only" |
| 168 | 1388880_at | BI278962 | Lysosomal associated membrane protein 1 (120 kDa) |
| 169 | 1376075_at | BM385544 | *Rattus norvegicus* transcribed sequences |
| 170 | 1369559_a_at | NM_019195 | integrin-associated protein |
| 171 | 1376972_at | AI407028 | "solute carrier family 39 (iron-regulated transporter), member 1" |
| 172 | 1388776_at | AI169176 | *Rattus norvegicus* transcribed sequence with weak similarity to protein ref: NP_057563.1 (*H. sapiens*) hypothetical protein LOC51246 [*Homo sapiens*] |
| 173 | 1376029_at | BI295991 | *Rattus norvegicus* transcribed sequences |
| 174 | 1388164_at | AF029241 | "Rat MHC class I RT1.C/E mRNA, 3' end" |
| 175 | 1389734_x_at | BI282965 | RT1 class Ib gene |
| 176 | 1370429_at | L40362 | RT1 class Ib gene |
| 177 | 1388900_at | BG381414 | *Rattus norvegicus* transcribed sequences |
| 178 | 1375955_at | BI289415 | *Rattus norvegicus* transcribed sequences |
| 179 | 1389011_at | BG374333 | *Rattus norvegicus* transcribed sequences |
| 180 | 1389387_at | BF561377 | hydroxyindole-O-methyltransferase |

TABLE 5-continued

Genes differentially expressed in CNI1493-treated colon

| No. | Identifier | Acce. No. | Description |
|---|---|---|---|
| 181 | 1387206_at | NM_031740 | "UDP-Gal: betaGlcNAc beta 1,4-galactosyltransferase, polypeptide 6" |
| 182 | 1388071_x_at | M24024 | RT1 class Ib gene |
| 183 | 1398925_at | BI274664 | *Rattus norvegicus* transcribed sequence with weak similarity to protein ref: NP_060818.1 (*H. sapiens*) hypothetical protein FLJ11171 [*Homo sapiens*] |
| 184 | 1368224_at | NM_031531 | Serine protease inhibitor |
| 185 | 1374718_at | AA945915 | *Rattus norvegicus* transcribed sequences |
| 186 | 1394340_at | BF523172 | *Rattus norvegicus* transcribed sequence with weak similarity to protein sp: P49441 (*H. sapiens*) INPP_HUMAN Inositol polyphosphate 1-phosphatase (IPPase) (IPP) |
| 187 | 1376022_at | BI292196 | *Rattus norvegicus* transcribed sequences |
| 188 | 1368732_at | NM_032056 | "transporter 2, ATP-binding cassette, sub-family B (MDR/TAP)" |
| 189 | 1367710_at | NM_017257 | "protease (prosome, macropain) 28 subunit, beta" |
| 190 | 1367786_at | NM_080767 | "proteasome (prosome, macropain) subunit, beta type, 8 (low molecular mass polypeptide 7)" |
| 191 | 1389170_at | BF283754 | *Rattus norvegicus* transcribed sequences |
| 192 | 1375853_at | BF284358 | *Rattus norvegicus* transcribed sequences |
| 193 | 1373757_at | AW529298 | *Rattus norvegicus* transcribed sequence with moderate similarity to protein ref: NP_006691.1 (*H. sapiens*) FLN29 gene product [*Homo sapiens*] |
| 194 | 1388149_at | X57523 | "transporter 1, ATP-binding cassette, sub-family B (MDR/TAP)" |
| 195 | 1372604_at | BI289459 | "*Rattus norvegicus* transcribed sequence with weak similarity to protein ref: NP_055164.1 (*H. sapiens*) apolipoprotein L, 3; TNF-inducible protein CG12-1 [*Homo sapiens*]" |
| 196 | 1387027_a_at | U72741 | "Lectin, galactose binding, soluble 9 (Galectin-9)" |
| 197 | 1372034_at | BF284106 | *Rattus norvegicus* transcribed sequences |
| 198 | 1370186_at | AI599350 | "proteosome (prosome, macropain) subunit, beta type 9 (large multifunctional protease 2)" |
| 199 | 1388212_a_at | AJ243974 | "Rat MHC class I RT1.C/E mRNA, 3' end" |
| 200 | 1388213_a_at | AJ243973 | "Rat MHC class I RT1.C/E mRNA, 3' end" |
| 201 | 1371123_x_at | AJ243973 | "Rat MHC class I RT1.C/E mRNA, 3' end" |
| 202 | 1371152_a_at | Z18877 | 25 oligoadenylate synthetase |
| 203 | 1372930_at | AI411381 | "*Rattus norvegicus* cDNA, clone: aC10, differentially expressed in pylorus" |
| 204 | 1388791_at | BI275911 | *Rattus norvegicus* transcribed sequence with moderate similarity to protein pir: T14738 (*H. sapiens*) T14738 hypothetical protein DKFZp564A2416.1 - human (fragment) |
| 205 | 1369716_s_at | NM_012976 | "Lectin, galactose binding, soluble 5 (Galectin-5)" |
| 206 | 1376496_at | AI717736 | "*Rattus norvegicus* transcribed sequence with weak similarity to protein ref: NP_112092.1 (*H. sapiens*) apolipoprotein L, 2 [*Homo sapiens*]" |
| 207 | 1374337_at | AI408954 | "*Rattus norvegicus* transcribed sequence with moderate similarity to protein pdb: 1LBG (*E. coli*) B Chain B, Lactose Operon Repressor Bound To 21-Base Pair Symmetric Operator Dna, Alpha Carbons Only" |
| 208 | 1387242_at | NM_019335 | "Protein kinase, interferon-inducible double stranded RNA dependent" |
| 209 | 1376144_at | AA819679 | *Rattus norvegicus* transcribed sequence with weak similarity to protein ref: NP_113646.1 (*H. sapiens*) B aggressive lymphoma gene [*Homo sapiens*] |
| 210 | 1368835_at | AW434718 | signal transducer and activator of transcription 1 |
| 211 | 1387946_at | AF065438 | peptidylprolyl isomerase C-associated protein |
| 212 | 1383564_at | BF411036 | *Rattus norvegicus* transcribed sequence with moderate similarity to protein ref: NP_004022.1 (*H. sapiens*) interferon regulatory factor 7 isoform d [*Homo sapiens*] |
| 213 | 1389034_at | BI295179 | *Rattus norvegicus* transcribed sequence with weak similarity to protein sp: Q9UMW8 (*H. sapiens*) UBPI_HUMAN Ubiquitin carboxyl-terminal hydrolase 18 (Ubiquitin thiolesterase 18) (Ubiquitin-specific processing protease 18) (Deubiquitinating enzyme 18) (Ubiqui |
| 214 | 1388347_at | AI233210 | *Rattus norvegicus* transcribed sequence with weak similarity to protein sp: Q16553 (*H. sapiens*) LY6E_HUMAN Lymphocyte antigen Ly-6E precursor (Retinoic acid-induced gene E protein) (RIG-E) (Thymic shared antigen-1) (TSA-1) (Stem cell antigen 2) (SCA-2) |
| 215 | 1376845_at | AA819034 | *Rattus norvegicus* transcribed sequence with moderate similarity to protein ref: NP_114425.1 (*H. sapiens*) TLH29 protein precursor [*Homo sapiens*] |

TABLE 5-continued

Genes differentially expressed in CNI1493-treated colon

| No. | Identifier | Acce. No. | Description |
|---|---|---|---|
| 216 | 1376693_at | AA998964 | *Rattus norvegicus* transcribed sequence with moderate similarity to protein ref: NP_060124.1 (*H. sapiens*) hypothetical protein FLJ20073 [*Homo sapiens*] |
| 217 | 1387770_at | NM_130743 | "interferon, alpha-inducible protein 27-like" |
| 218 | 1376920_at | BF408536 | *Rattus norvegicus* transcribed sequence with weak similarity to protein ref: NP_060124.1 (*H. sapiens*) hypothetical protein FLJ20073 [*Homo sapiens*] |
| 219 | 1387354_at | NM_032612 | signal transducer and activator of transcription 1 |
| 220 | 1373037_at | BI279216 | *Rattus norvegicus* transcribed sequence with moderate similarity to protein ref: NP_004214.1 (*H. sapiens*) ubiquitin-conjugating enzyme E2L 6 [*Homo sapiens*] |
| 221 | 1387995_a_at | BI285494 | interferon induced transmembrane protein 3-like |
| 222 | 1377497_at | BF419319 | "*Rattus norvegicus* transcribed sequence with moderate similarity to protein pir: I60307 (*E. coli*) I60307 beta-galactosidase, alpha peptide - *Escherichia coli*" |
| 223 | 1368227_at | NM_031664 | "solute carrier family 28, member 2" |
| 224 | 1390507_at | BI296097 | *Rattus norvegicus* transcribed sequence with moderate similarity to protein ref: NP_002192.2 (*H. sapiens*) interferon stimulated gene (20 kD) [*Homo sapiens*] |
| 225 | 1371440_at | AW916647 | Prostaglandin F receptor |
| 226 | 1369590_a_at | NM_024134 | DNA-damage inducible transcript 3 |
| 227 | 1369202_at | NM_017028 | myxovirus (influenza virus) resistance 2 |
| 228 | 1374627_at | BF283727 | *Rattus norvegicus* transcribed sequences |
| 229 | 1374551_at | BM388891 | *Rattus norvegicus* transcribed sequence with weak similarity to protein pir: JC5262 (*H. sapiens*) JC5262 leucine zipper protein IFP35 - human |
| 230 | 1387134_at | NM_053687 | schlafen 4 |
| 231 | 1373514_at | AA899109 | *Rattus norvegicus* transcribed sequences |
| 232 | 1372585_at | BM388445 | *Rattus norvegicus* transcribed sequences |
| 233 | 1369031_at | NM_053374 | interferon gamma inducing factor binding protein |
| 234 | 1371070_at | AJ302054 | tumor stroma and activated macrophage protein DLM-1 |
| 235 | 1367595_s_at | NM_012512 | Beta-2-microglobulin |
| 236 | 1367663_at | NM_017264 | "protease (prosome, macropain) 28 subunit, alpha" |
| 237 | 1390042_at | AI071166 | *Rattus norvegicus* transcribed sequences |
| 238 | 1369186_at | D85899 | caspase 1 |
| 239 | 1389571_at | BG666368 | *Rattus norvegicus* transcribed sequence with moderate similarity to protein sp: P52630 (*H. sapiens*) STA2_HUMAN Signal transducer and activator of transcription 2 (p113) |
| 240 | 1370913_at | AI409634 | Best5 protein |
| 241 | 1387969_at | U22520 | chemokine (C-X-C motif) ligand 10 |
| 242 | 1376908_at | AW531805 | *Rattus norvegicus* transcribed sequence with weak similarity to protein sp: O14879 (*H. sapiens*) IFT4_HUMAN Interferon-induced protein with tetratricopeptide repeats 4 (IFIT-4) (Interferon-induced 60 kDa protein) (IFI-60K) (ISG-60) (CIG49) (Retinoic acid-ind |
| 243 | 1369973_at | NM_017154 | xanthine dehydrogenase |
| 244 | 1368332_at | NM_133624 | "guanylate binding protein 2, interferon-inducible" |
| 245 | 1372254_at | AW915763 | *Rattus norvegicus* transcribed sequence with moderate similarity to protein sp: P05155 (*H. sapiens*) IC1_HUMAN Plasma protease C1 inhibitor precursor (C1 Inh) (C1Inh) |
| 246 | 1373197_at | AI578263 | *Rattus norvegicus* transcribed sequences |
| 247 | 1370892_at | BI285347 | complement component 4a |
| 248 | 1372757_at | BM386875 | signal transducer and activator of transcription 1 |
| 249 | 1376151_a_at | AI407953 | *Rattus norvegicus* transcribed sequences |
| 250 | 1387283_at | NM_134350 | myxovirus (influenza virus) resistance 2 |
| 251 | 1371015_at | X52711 | myxovirus (influenza virus) resistance |
| 252 | 1373992_at | AI408440 | "*Rattus norvegicus* cDNA, clone: aD9, differentially expressed in pylorus" |
| 253 | 1390738_at | BM385476 | *Rattus norvegicus* mRNA for DAMP-1 protein |
| 254 | 1388056_at | AF068268 | 2'5' oligoadenylate synthetase-2 |
| 255 | 1389365_at | AI228291 | *Rattus norvegicus* transcribed sequences |
| 256 | 1369726_at | NM_033098 | TAP binding protein |
| 257 | 1370172_at | AA892254 | superoxide dismutase 2 |
| 258 | 1386893_at | NM_017113 | granulin |
| 259 | 1375796_at | BI300770 | "*Rattus norvegicus* Ac2-233 mRNA, complete cds" |
| 260 | 1389014_at | BI297612 | pre-B-cell colony-enhancing factor |
| 261 | 1371209_at | AJ243338 | RT1 class Ib gene |
| 262 | 1388255_x_at | AJ243338 | RT1 class Ib gene |
| 263 | 1373406_at | BM384991 | *Rattus norvegicus* transcribed sequences |
| 264 | 1375006_at | BE121050 | *Rattus norvegicus* transcribed sequences |
| 265 | 1387897_at | L16532 | cyclic nucleotide phosphodiesterase 1 |
| 266 | 1369456_at | NM_017250 | 5-hydroxytryptamine (serotonin) receptor 2B |

TABLE 5-continued

Genes differentially expressed in CNI1493-treated colon

| No. | Identifier | Acce. No. | Description |
|---|---|---|---|
| 267 | 1374141_at | BG372419 | *Rattus norvegicus* transcribed sequence with strong similarity to protein ref: NP_071387.1 (*H. sapiens*) chromosome 20 open reading frame 67 [*Homo sapiens*] |
| 268 | 1374678_at | BE109578 | *Rattus norvegicus* transcribed sequences |
| 269 | 1372968_at | BM385950 | *Rattus norvegicus* transcribed sequence with weak similarity to protein pir: S37032 (*R. norvegicus*) S37032 gene LL5 protein - rat |
| 270 | 1371832_at | AW526333 | *Rattus norvegicus* transcribed sequences |
| 271 | 1390117_at | BG372455 | *Rattus norvegicus* transcribed sequences |
| 272 | 1369381_a_at | D50306 | "solute carrier family 15 (oligopeptide transporter), member 1" |
| 273 | 1388103_at | AF361355 | voltage-dependent calcium channel gamma subunit-like protein |
| 274 | 1386943_at | NM_022533 | plasmolipin |
| 275 | 1373060_at | AI406281 | *Rattus norvegicus* transcribed sequence with strong similarity to protein pir: T12468 (*H. sapiens*) T12468 hypothetical protein DKFZp564O123.1 - human |
| 276 | 1375911_at | AI171772 | "*Rattus norvegicus* hypothetical protein LK44 mRNA, complete cds" |
| 277 | 1370071_at | NM_130399 | Adenosine deaminase |
| 278 | 1368762_at | NM_053299 | ubiquitin D |
| 279 | 1369712_at | NM_031735 | serine/threonine kinase 3 |
| 280 | 1368419_at | AF202115 | ceruloplasmin |
| 281 | 1369029_at | NM_057194 | phospholipid scramblase 1 |
| 282 | 1369888_at | NM_012707 | glucagon |
| 283 | 1398879_at | BE329031 | arrestin-E |
| 284 | 1369942_at | NM_031675 | actinin alpha 4 |
| 285 | 1370807_at | AF411216 | vacuole Membrane Protein 1 |
| 286 | 1377124_at | AA964824 | *Rattus norvegicus* transcribed sequence with weak similarity to protein pir: S48059 (*H. sapiens*) S48059 metal-regulatory transcription factor - human |
| 287 | 1390221_at | BM385216 | *Rattus norvegicus* transcribed sequences |
| 288 | 1390604_s_at | BM387863 | *Rattus norvegicus* transcribed sequence with weak similarity to protein ref: NP_055103.1 (*H. sapiens*) integrin beta 3 binding protein (beta3-endonexin); beta 3 endonexin [*Homo sapiens*] |
| 289 | 1398916_at | AI104388 | heat shock 27 kDa protein 1 |
| 290 | 1374600_at | BM986536 | germinal histone H4 gene |
| 291 | 1370307_at | M64780 | Agrin |
| 292 | 1371888_at | AA892843 | *Rattus norvegicus* transcribed sequence with moderate similarity to protein ref: NP_078816.1 (*H. sapiens*) hypothetical protein FLJ20917 [*Homo sapiens*] |
| 293 | 1373603_at | BG673166 | *Rattus norvegicus* transcribed sequence with moderate similarity to protein pir: T45061 (*H. sapiens*) T45061 hypothetical protein c316G12.2 [imported] - human |
| 294 | 1388408_at | AA800199 | *Rattus norvegicus* transcribed sequence with weak similarity to protein pir: T34520 (*H. sapiens*) T34520 hypothetical protein DKFZp564J157.1 - human (fragment) |
| 295 | 1368471_at | NM_013118 | guanylate cyclase activator 2A |
| 296 | 1374401_at | AI549249 | *Rattus norvegicus* transcribed sequence with strong similarity to protein sp: O60749 (*H. sapiens*) SNX2_HUMAN Sorting nexin 2 |
| 297 | 1371267_at | M64795 | zzN/A |
| 298 | 1370832_at | U06434 | small inducible cytokine A4 |
| 299 | 1383241_at | BI292425 | *Rattus norvegicus* transcribed sequence with moderate similarity to protein sp: P00736 (*H. sapiens*) C1R_HUMAN Complement C1r component precursor |
| 300 | 1387922_at | AF109674 | late gestation lung protein 1 |
| 301 | 1376447_at | AI706850 | *Rattus norvegicus* transcribed sequence with weak similarity to protein sp: P10163 (*H. sapiens*) PRB4_HUMAN Salivary proline-rich protein PO precursor (Allele S) |
| 302 | 1367740_at | M14400 | "creatine kinase, brain" |
| 303 | 1387036_at | NM_024360 | hairy and enhancer of split 1 (*Drosophila*) |
| 304 | 1370360_at | AF146738 | testis specific protein |
| 305 | 1389111_at | BF396316 | *Rattus norvegicus* transcribed sequences |
| 306 | 1374454_at | BM388557 | *Rattus norvegicus* transcribed sequences |
| 307 | 1367764_at | NM_012923 | Cyclin G1 |
| 308 | 1368038_at | AF260258 | synaptojanin 2 binding protein |
| 309 | 1372635_at | BF282163 | *Rattus norvegicus* transcribed sequences |
| 310 | 1373571_at | AI170276 | *Rattus norvegicus* transcribed sequences |
| 311 | 1375872_at | AI144944 | *Rattus norvegicus* transcribed sequences |
| 312 | 1383767_at | AW524430 | *Rattus norvegicus* transcribed sequences |

TABLE 5-continued

Genes differentially expressed in CNI1493-treated colon

| No. | Identifier | Acce. No. | Description |
|---|---|---|---|
| 313 | 1376325_at | BM388975 | *Rattus norvegicus* transcribed sequence with strong similarity to protein pir: S52863 (*H. sapiens*) S52863 DNA-binding protein R kappa B - human |
| 314 | 1388485_at | BG380414 | *Rattus norvegicus* transcribed sequences |
| 315 | 1368782_at | NM_019348 | somatostatin receptor 2 |
| 316 | 1375867_at | AW524493 | *Rattus norvegicus* transcribed sequences |
| 317 | 1375138_at | AA893169 | Tissue inhibitor of metalloproteinase 3 |
| 318 | 1390112_at | BF284634 | "*Rattus norvegicus* transcribed sequence with strong similarity to protein ref: NP_004096.2 (*H. sapiens*) EGF-containing fibulin-like extracellular matrix protein 1 precursor, isoform a precursor; fibrillin-like [*Homo sapiens*]" |
| 319 | 1372935_at | AI598550 | *Rattus norvegicus* transcribed sequences |
| 320 | 1368322_at | NM_012880 | superoxide dismutase 3 |
| 321 | 1372104_at | BF289002 | *Rattus norvegicus* transcribed sequence with weak similarity to protein ref: NP_003106.1 (*H. sapiens*) UDP-N-acteylglucosamine pyrophosphorylase 1; AgX; sperm associated antigen 2; UDP-N-acteylglucosamine pyrophosphorylase 1; Sperm associated antigen 2 [Hom |
| 322 | 1367687_a_at | M25719 | Peptidylglycine alpha-amidating monooxygenase |
| 323 | 1372455_at | AI410264 | *Rattus norvegicus* transcribed sequence with strong similarity to protein sp: O95859 (*H. sapiens*) TNE2_HUMAN Tetraspan NET-2 |
| 324 | 1372940_at | BM389329 | *Rattus norvegicus* transcribed sequences |
| 325 | 1367631_at | NM_022266 | connective tissue growth factor |
| 326 | 1376344_at | AI010267 | *Rattus norvegicus* transcribed sequences |
| 327 | 1370408_at | AF313411 | putative small membrane protein NID67 |
| 328 | 1390283_at | BI274636 | *Rattus norvegicus* transcribed sequences |
| 329 | 1372327_at | BF552877 | *Rattus norvegicus* transcribed sequence with strong similarity to protein ref: NP_057216.1 (*H. sapiens*) myelin gene expression factor 2 [*Homo sapiens*] |
| 330 | 1376175_at | BF283433 | *Rattus norvegicus* transcribed sequences |
| 331 | 1373966_at | BF406242 | *Rattus norvegicus* transcribed sequence with moderate similarity to protein pir: T43490 (*H. sapiens*) T43490 hypothetical protein DKFZp434A139.1 - human (fragments) |
| 332 | 1376749_at | AA945955 | *Rattus norvegicus* transcribed sequence with moderate similarity to protein pir: B35272 (*H. sapiens*) B35272 osteoinductive factor - human |
| 333 | 1367604_at | NM_022501 | cysteine-rich protein 2 |
| 334 | 1398345_at | BM389225 | angiopoietin-like 2 |
| 335 | 1389836_a_at | AI599265 | Tissue inhibitor of metalloproteinase 3 |
| 336 | 1389256_at | BG381256 | *Rattus norvegicus* transcribed sequences |
| 337 | 1371500_at | BG375362 | *Rattus norvegicus* transcribed sequence with moderate similarity to protein ref: NP_003564.1 (*H. sapiens*) latent transforming growth factor beta binding protein 4 [*Homo sapiens*] |
| 338 | 1371629_at | AI105444 | "*Rattus norvegicus* transcribed sequence with moderate similarity to protein pir: I60307 (*E. coli*) I60307 beta-galactosidase, alpha peptide - *Escherichia coli*" |
| 339 | 1387707_at | NM_017102 | "solute carrier family 2, member 2" |
| 340 | 1387505_at | NM_013145 | "Guanine nucleotide binding protein, alpha inhibiting 1" |
| 341 | 1388890_at | BM390316 | *Rattus norvegicus* transcribed sequences |
| 342 | 1373506_at | AA944568 | *Rattus norvegicus* transcribed sequences |
| 343 | 1369415_at | NM_053328 | "basic helix-loop-helix domain containing, class B2" |
| 344 | 1372264_at | BI277460 | "*Rattus norvegicus* transcribed sequence with strong similarity to protein sp: P35558 (*H. sapiens*) PPCC_HUMAN Phosphoenolpyruvate carboxykinase, cytosolic [GTP] (Phosphoenolpyruvate carboxylase) (PEPCK-C)" |
| 345 | 1374105_at | H31665 | *Rattus norvegicus* transcribed sequences |
| 346 | 1387156_at | NM_024391 | 17-beta hydroxysteroid dehydrogenase type 2 |
| 347 | 1376569_at | BM385790 | *Rattus norvegicus* transcribed sequence with strong similarity to protein sp: Q9Y5W3 (*H. sapiens*) KLF2_HUMAN Kruppel-like factor 2 (Lung kruppel-like factor) |
| 348 | 1387028_a_at | M86708 | "Inhibitor of DNA binding 1, helix-loop-helix protein (splice variation)" |
| 349 | 1376661_at | AI556122 | *Rattus norvegicus* transcribed sequences |
| 350 | 1377287_at | AA957673 | *Rattus norvegicus* transcribed sequences |
| 351 | 1375910_at | AA874943 | *Rattus norvegicus* transcribed sequence with moderate similarity to protein pir: T46465 (*H. sapiens*) T46465 hypothetical protein DKFZp434A0530.1 - human |
| 352 | 1388447_at | AA800701 | *Rattus norvegicus* transcribed sequences |
| 353 | 1370912_at | BI278231 | *R. norvegicus* hsp70.2 mRNA for heat shock protein 70 |
| 354 | 1368883_at | NM_030868 | NOV protein |

TABLE 5-continued

Genes differentially expressed in CNI1493-treated colon

| No. | Identifier | Acce. No. | Description |
|---|---|---|---|
| 355 | 1388945_at | BM385779 | "*Rattus norvegicus* transcribed sequence with moderate similarity to protein pir: I60307 (*E. coli*) I60307 beta-galactosidase, alpha peptide - *Escherichia coli*" |
| 356 | 1389514_at | AI711152 | *Rattus norvegicus* transcribed sequences |
| 357 | 1377086_at | AI233530 | *Rattus norvegicus* transcribed sequences |
| 358 | 1373947_at | BI278545 | *Rattus norvegicus* transcribed sequence with strong similarity to protein pir: A47220 (*H. sapiens*) A47220 dermatopontin precursor - human |
| 359 | 1374171_at | AI170507 | "ATP-binding cassette, sub-family C (CFTR/MRP), member 9" |
| 360 | 1372490_at | BF283759 | *Rattus norvegicus* transcribed sequences |
| 361 | 1390257_at | BG376956 | *Rattus norvegicus* transcribed sequences |
| 362 | 1369651_at | NM_012673 | Thymus cell surface antigen |
| 363 | 1388866_at | AA799392 | "*Rattus norvegicus* transcribed sequence with moderate similarity to protein pdb: 1LBG (*E. coli*) B Chain B, Lactose Operon Repressor Bound To 21-Base Pair Symmetric Operator Dna, Alpha Carbons Only" |
| 364 | 1368303_at | NM_031678 | period homolog 2 |
| 365 | 1370399_at | M29853 | "cytochrome P450, subfamily 4B, polypeptide 1" |
| 366 | 1385606_at | BF559626 | *Rattus norvegicus* transcribed sequences |
| 367 | 1376170_at | BI290821 | *Rattus norvegicus* transcribed sequence with moderate similarity to protein pir: S46657 (*H. sapiens*) S46657 collagen alpha 1(XIV) chain - human (fragments) |
| 368 | 1376832_at | AA800763 | *Rattus norvegicus* transcribed sequences |
| 369 | 1376049_at | AA925805 | *Rattus norvegicus* transcribed sequences |
| 370 | 1398365_at | AI171466 | *Rattus norvegicus* transcribed sequence with strong similarity to protein ref: NP_057048.1 (*H. sapiens*) CGI-38 protein [*Homo sapiens*] |
| 371 | 1372847_at | AW524458 | *Rattus norvegicus* transcribed sequence with strong similarity to protein ref: NP_064571.1 (*H. sapiens*) DC11 protein [*Homo sapiens*] |
| 372 | 1372872_at | BI291271 | *Rattus norvegicus* transcribed sequences |
| 373 | 1376177_at | AI179609 | *Rattus norvegicus* transcribed sequences |
| 374 | 1387039_at | NM_030828 | glypican 1 |
| 375 | 1372208_at | AA942959 | "protein phosphatase 1, regulatory (inhibitor) subunit 1B" |
| 376 | 1376933_at | AI170377 | *Rattus norvegicus* transcribed sequences |
| 377 | 1388034_at | AB070355 | kinesin family member 1B |
| 378 | 1371794_at | BM391449 | *Rattus norvegicus* transcribed sequence with moderate similarity to protein pir: T14273 (*M. musculus*) T14273 zinc finger protein 106 - mouse |
| 379 | 1393464_at | BM383378 | *Rattus norvegicus* transcribed sequences |
| 380 | 1389007_at | AI231799 | *Rattus norvegicus* transcribed sequences |
| 381 | 1371508_at | AI412098 | "protein tyrosine phosphatase type IVA, member 2" |
| 382 | 1374694_at | BF284602 | *Rattus norvegicus* transcribed sequences |
| 383 | 1374558_at | AI010316 | *Rattus norvegicus* transcribed sequences |
| 384 | 1399028_at | AI171954 | *Rattus norvegicus* transcribed sequences |
| 385 | 1368550_at | NM_022858 | HNF-3/forkhead homolog-1 |
| 386 | 1370211_at | BE106940 | neurogranin |
| 387 | 1387090_a_at | NM_024135 | LIM motif-containing protein kinase 2 |
| 388 | 1370072_at | NM_012608 | membrane metallo endopeptidase |
| 389 | 1371703_at | AI407114 | Complement component 3 |
| 390 | 1390319_at | BG378301 | *Rattus norvegicus* transcribed sequence |
| 391 | 1387008_at | NM_022948 | tricarboxylate carrier-like protein |
| 392 | 1389561_at | BE110624 | *Rattus norvegicus* transcribed sequence with strong similarity to protein ref: NP_079740.1 (*M. musculus*) RIKEN cDNA 1810021J13 [*Mus musculus*] |
| 393 | 1376023_at | BM386555 | *Rattus norvegicus* transcribed sequences |
| 394 | 1386979_at | NM_133395 | developmentally regulated protein TPO1 |
| 395 | 1368163_at | J02997 | Dipeptidyl peptidase 4 |
| 396 | 1374935_at | AI412099 | "*Rattus norvegicus* transcribed sequence with moderate similarity to protein pir: I60307 (*E. coli*) I60307 beta-galactosidase, alpha peptide - *Escherichia coli*" |
| 397 | 1387084_at | NM_012789 | Dipeptidyl peptidase 4 |
| 398 | 1369770_at | NM_012719 | somatostatin receptor 1 |
| 399 | 1389601_at | BI293610 | "*Rattus norvegicus* transcribed sequence with moderate similarity to protein pir: I60307 (*E. coli*) I60307 beta-galactosidase, alpha peptide - *Escherichia coli*" |
| 400 | 1368295_at | NM_080786 | "solute carrier family 21 (organic anion transporter), member 9" |
| 401 | 1376242_at | BF402365 | *Rattus norvegicus* transcribed sequences |
| 402 | 1387059_at | NM_019362 | "serine threonine kinase 39 (STE20/SPS1 homolog, yeast)" |
| 403 | 1389310_at | BF400694 | *Rattus norvegicus* transcribed sequences |
| 404 | 1387169_at | NM_053400 | "transducin-like enhancer of split 3, homolog of *Drosophila*" |

TABLE 5-continued

Genes differentially expressed in CNI1493-treated colon

| No. | Identifier | Acce. No. | Description |
|---|---|---|---|
| 405 | 1387023_at | NM_031154 | "glutathione S-transferase, mu type 3 (Yb3)" |
| 406 | 1398430_at | AW524711 | *Rattus norvegicus* transcribed sequences |
| 407 | 1369249_at | NM_053714 | progressive ankylosis |
| 408 | 1387913_at | U48220 | cytochrome P450 2D18 |
| 409 | 1370320_at | AY083160 | MAWD binding protein |
| 410 | 1376047_at | BI285321 | *Rattus norvegicus* transcribed sequences |
| 411 | 1387315_at | NM_012878 | "surfactant, pulmonary-associated protein D" |
| 412 | 1387239_a_at | AB008803 | "peptidyl arginine deiminase, type 4" |
| 413 | 1371477_at | BG380735 | *Rattus norvegicus* transcribed sequences |
| 414 | 1386974_at | NM_134397 | LL5 protein |
| 415 | 1370930_at | BF417285 | kinesin 1C |
| 416 | 1371689_at | BE107334 | eukaryotic translation elongation factor 1 alpha 1 |
| 417 | 1389040_at | AI170825 | *Rattus norvegicus* transcribed sequences |
| 418 | 1390710_x_at | AA850618 | *Rattus norvegicus* transcribed sequence with strong similarity to protein ref: NP_003096.1 (*H. sapiens*) sortilin-related receptor containing LDLR class A repeats preproprotein; sorting protein-related receptor containing LDLR class A repeats; low-density li |
| 419 | 1367700_at | NM_080698 | fibromodulin |
| 420 | 1388317_at | BE110655 | *Rattus norvegicus* transcribed sequences |
| 421 | 1387184_at | NM_024355 | axin 2 |
| 422 | 1390399_at | BE102391 | *Rattus norvegicus* transcribed sequences |
| 423 | 1375590_at | AA894335 | *Rattus norvegicus* transcribed sequence with moderate similarity to protein pir: T00368 (*H. sapiens*) T00368 hypothetical protein KIAA0663 - human |
| 424 | 1387901_at | L19180 | "protein tyrosine phosphatase, receptor type, D" |
| 425 | 1388768_at | BI285601 | *Rattus norvegicus* transcribed sequences |
| 426 | 1373434_at | AA944179 | *Rattus norvegicus* transcribed sequences |
| 427 | 1376784_at | BI274481 | *Rattus norvegicus* transcribed sequences |
| 428 | 1390311_at | AW528602 | *Rattus norvegicus* transcribed sequences |
| 429 | 1389150_at | AW524559 | *Rattus norvegicus* transcribed sequence with moderate similarity to protein ref: NP_076933.1 (*H. sapiens*) hypothetical protein MGC3265 [*Homo sapiens*] |
| 430 | 1372728_at | BE103745 | *Rattus norvegicus* transcribed sequence with moderate similarity to protein sp: Q99523 (*H. sapiens*) SORT_HUMAN Sortilin precursor (Glycoprotein 95) (Gp95) (Neurotensin receptor 3) (NT3) (100 kDa NT receptor) |
| 431 | 1377325_a_at | AW531278 | *Rattus norvegicus* transcribed sequences |
| 432 | 1389288_at | BI279838 | "*Rattus norvegicus* transcribed sequence with moderate similarity to protein ref: NP_002479.1 (*H. sapiens*) NADH dehydrogenase (ubiquinone) 1 alpha subcomplex, 2 (8 kD, B8) [*Homo sapiens*]" |
| 433 | 1375951_at | AA818521 | thrombomodulin |
| 434 | 1367880_at | NM_012974 | Laminin chain beta 2 |
| 435 | 1399109_at | BI281673 | *Rattus norvegicus* transcribed sequences |
| 436 | 1369926_at | NM_022525 | glutathione peroxidase 3 |
| 437 | 1388145_at | BM390128 | Tenascin X |
| 438 | 1398973_at | BI296499 | *Rattus norvegicus* transcribed sequence with strong similarity to protein sp: Q9HD45 (*H. sapiens*) T9S3_HUMAN Transmembrane 9 superfamily protein member 3 precursor (SM-11044 binding protein) (EP70-P-iso) |
| 439 | 1398990_at | BI281754 | *Rattus norvegicus* transcribed sequences |
| 440 | 1371245_a_at | BI287300 | hemoglobin beta chain complex |
| 441 | 1392890_at | BG663460 | *Rattus norvegicus* transcribed sequences |
| 442 | 1371102_x_at | X05080 | hemoglobin beta chain complex |
| 443 | 1370240_x_at | AI179404 | "hemoglobin, alpha 1" |
| 444 | 1367553_x_at | NM_033234 | hemoglobin beta chain complex |
| 445 | 1370239_at | AI179404 | "hemoglobin, alpha 1" |
| 446 | 1388608_x_at | AI577319 | "hemoglobin, alpha 1" |
| 447 | 1388848_at | AA891760 | *Rattus norvegicus* transcribed sequence with moderate similarity to protein ref: NP_071934.1 (*H. sapiens*) hypothetical protein FLJ22056 [*Homo sapiens*] |
| 448 | 1389186_at | AA944175 | "*Rattus norvegicus* transcribed sequence with moderate similarity to protein pir: I60307 (*E. coli*) I60307 beta-galactosidase, alpha peptide - *Escherichia coli*" |
| 449 | 1371972_at | BM388888 | *Rattus norvegicus* transcribed sequence with moderate similarity to protein pir: T00371 (*H. sapiens*) T00371 hypothetical protein KIAA0668 - human (fragment) |
| 450 | 1372640_at | BI277758 | *Rattus norvegicus* transcribed sequence with moderate similarity to protein ref: NP_076223.1 (*M. musculus*) RIKEN cDNA 1200009H11 [*Mus musculus*] |
| 451 | 1373162_at | AI600085 | "*Rattus norvegicus* NYGGF3 mRNA, partial cds" |
| 452 | 1387310_at | NM_134462 | putative secretory pathway Ca-ATPase SPCA2 |
| 453 | 1388698_at | AI407838 | extracellular matrix protein 1 |

TABLE 5-continued

Genes differentially expressed in CNI1493-treated colon

| No. | Identifier | Acce. No. | Description |
|---|---|---|---|
| 454 | 1376105_at | AI599143 | *Rattus norvegicus* transcribed sequence with moderate similarity to protein pir: S46657 (*H. sapiens*) S46657 collagen alpha 1(XIV) chain - human (fragments) |
| 455 | 1373674_at | BI283094 | *Rattus norvegicus* transcribed sequence with moderate similarity to protein sp: Q13361 (*H. sapiens*) MGP2_HUMAN Microfibril-associated glycoprotein 2 precursor (MAGP-2) (MP25) |
| 456 | 1373952_at | AI409841 | *Rattus norvegicus* transcribed sequences |
| 457 | 1387625_at | NM_013104 | zzN/A |
| 458 | 1374674_at | AW528792 | *Rattus norvegicus* transcribed sequences |
| 459 | 1375844_at | AI406370 | *Rattus norvegicus* transcribed sequence with strong similarity to protein ref: NP_067013.1 (*H. sapiens*) polypyrimidine tract binding protein 2; neural polypyrimidine tract binding protein; PTB-like protein [*Homo sapiens*] |
| 460 | 1368407_at | NM_022605 | heparanase |
| 461 | 1377076_at | AI716131 | *Rattus norvegicus* transcribed sequences |
| 462 | 1375412_at | AI101331 | *Rattus norvegicus* transcribed sequences |
| 463 | 1376398_at | BF417784 | *Rattus norvegicus* transcribed sequences |
| 464 | 1399054_at | BG375798 | *Rattus norvegicus* transcribed sequences |
| 465 | 1374126_at | BG374261 | *Rattus norvegicus* transcribed sequences |
| 466 | 1368099_at | NM_053722 | CLIP-associating protein 2 |
| 467 | 1387182_at | NM_057201 | G protein-coupled receptor 37 (endothelin receptor type B-like) |
| 468 | 1372814_at | BF283084 | *Rattus norvegicus* transcribed sequences |
| 469 | 1376115_at | AA964244 | *Rattus norvegicus* transcribed sequences |
| 470 | 1369373_at | NM_053429 | fibroblast growth factor receptor 3 |
| 471 | 1376781_at | BI286116 | *Rattus norvegicus* transcribed sequences |
| 472 | 1369638_at | NM_012947 | Eukaryotic elongation factor 2 kinase |
| 473 | 1389003_at | BI282008 | *Rattus norvegicus* transcribed sequences |
| 474 | 1376089_at | BI294974 | Low density lipoprotein receptor |
| 475 | 1367932_at | NM_017268 | 3-hydroxy-3-methylglutaryl-Coenzyme A synthase 1 |
| 476 | 1387809_at | NM_053703 | mitogen-activated protein kinase kinase 6 |
| 477 | 1375549_at | AI407719 | *Rattus norvegicus* transcribed sequences |
| 478 | 1370209_at | BE101336 | Kruppel-like factor 9 |
| 479 | 1389311_at | AW915161 | *Rattus norvegicus* transcribed sequences |
| 480 | 1390164_at | BE099850 | *Rattus norvegicus* transcribed sequences |
| 481 | 1376989_at | BE099568 | *Rattus norvegicus* transcribed sequences |
| 482 | 1368656_at | NM_053856 | secretogranin III |
| 483 | 1373415_at | AI407050 | *Rattus norvegicus* transcribed sequences |
| 484 | 1374819_at | AI599945 | *Rattus norvegicus* transcribed sequences |
| 485 | 1367594_at | NM_017087 | biglycan |
| 486 | 1372624_at | BF551377 | *Rattus norvegicus* transcribed sequences |
| 487 | 1376425_at | BF420705 | "transforming growth factor, beta 2" |
| 488 | 1389138_at | AA945574 | *Rattus norvegicus* transcribed sequences |
| 489 | 1367940_at | NM_053352 | chemokine orphan receptor 1 |
| 490 | 1371747_at | AI406304 | *Rattus norvegicus* transcribed sequence with moderate similarity to protein ref: NP_077275.1 (*H. sapiens*) chromosome 20 open reading frame 149 [*Homo sapiens*] |
| 491 | 1372978_at | BI291218 | *Rattus norvegicus* transcribed sequences |
| 492 | 1387812_at | NM_012999 | Subtilisin - like endoprotease |
| 493 | 1389794_at | AI044984 | *Rattus norvegicus* transcribed sequences |
| 494 | 1388384_at | AI407618 | *Rattus norvegicus* transcribed sequences |
| 495 | 1374557_at | BF394235 | *Rattus norvegicus* transcribed sequence with strong similarity to protein ref: NP_079187.1 (*H. sapiens*) hypothetical protein FLJ23091 [*Homo sapiens*] |
| 496 | 1370579_at | U53513 | "glycine-, glutamate-, thienylcyclohexylpiperidine-binding protein" |
| 497 | 1367918_at | NM_031066 | protein kinase C-binding protein Zeta 1 |
| 498 | 1368930_at | NM_023021 | intermediate conductance calcium-activated potassium channel |
| 499 | 1387654_at | NM_023092 | unconventional myosin Myr2 I heavy chain |
| 500 | 1367759_at | NM_012578 | Histone H1-0 |
| 501 | 1386957_at | NM_053622 | nuclear pore membrane glycoprotein 121 kD |
| 502 | 1388709_at | BF284695 | *Rattus norvegicus* transcribed sequence with weak similarity to protein pir: A35804 (*H. sapiens*) A35804 nucleolin - human |
| 503 | 1384371_at | AW921429 | zzN/A |
| 504 | 1371940_at | AW920000 | *Rattus norvegicus* transcribed sequence with strong similarity to protein sp: Q9UPN3 (*H. sapiens*) ACF7_HUMAN Actin cross-linking family protein 7 (Macrophin) (Trabeculin-alpha) (620 kDa actin-binding protein) (ABP620) |
| 505 | 1370131_at | NM_031556 | caveolin |
| 506 | 1372825_at | BI290551 | *Rattus norvegicus* transcribed sequences |
| 507 | 1367989_at | NM_012751 | "solute carrier family 2, member 4" |

TABLE 5-continued

Genes differentially expressed in CNI1493-treated colon

| No. | Identifier | Acce. No. | Description |
|---|---|---|---|
| 508 | 1376724_at | AI170671 | *Rattus norvegicus* transcribed sequences |
| 509 | 1372967_at | BI280323 | *Rattus norvegicus* transcribed sequences |
| 510 | 1370291_at | AF002281 | actinin alpha 2 associated LIM protein |
| 511 | 1377281_at | BM388545 | *Rattus norvegicus* transcribed sequence with moderate similarity to protein ref: NP_065099.1 (*H. sapiens*) retinitis pigmentosa GTPase regulator interacting protein 1; RPGR-interacting protein [*Homo sapiens*] |
| 512 | 1367930_at | NM_017195 | growth associated protein 43 |
| 513 | 1367628_at | NM_019904 | "lectin, galactose binding, soluble 1" |
| 514 | 1388112_at | BG666999 | solute carrier family 25 (mitochondrial adenine nucleotide translocator) member 4 |
| 515 | 1387873_at | BI279661 | wap four-disulfide core domain 1 |
| 516 | 1389194_at | AI406491 | *Rattus norvegicus* transcribed sequences |
| 517 | 1388928_at | BF399310 | *Rattus norvegicus* transcribed sequence with strong similarity to protein ref: NP_068733.1 (*H. sapiens*) cofilin 2 (muscle) [*Homo sapiens*] |
| 518 | 1370857_at | BI282702 | smooth muscle alpha-actin |
| 519 | 1387018_at | NM_053770 | Arg/Abl-interacting protein ArgBP2 |
| 520 | 1398327_at | BM386598 | *Rattus norvegicus* transcribed sequence with strong similarity to protein pir: S69890 (*H. sapiens*) S69890 mitogen inducible gene mig-2 - human |
| 521 | 1389189_at | BF555956 | *Rattus norvegicus* transcribed sequence with weak similarity to protein sp: Q9Z1P2 (*R. norvegicus*) AAC1_RAT Alpha-actinin 1 (Alpha-actinin cytoskeletal isoform) (Non-muscle alpha-actinin 1) (F-actin cross linking protein) |
| 522 | 1371361_at | BI278826 | tensin |
| 523 | 1375349_at | BI295776 | *Rattus norvegicus* transcribed sequence with strong similarity to protein pir: T17257 (*H. sapiens*) T17257 hypothetical protein DKFZp586P1422.1 - human |
| 524 | 1376572_a_at | AI045848 | "*Rattus norvegicus* transcribed sequence with moderate similarity to protein ref: NP_068506.1 (*H. sapiens*) supervillin, isoform 2; membrane-associated F-actin binding protein p205; archvillin [*Homo sapiens*]" |
| 525 | 1367813_at | NM_130403 | "protein phosphatase 1, regulatory (inhibitor) subunit 14a" |
| 526 | 1367648_at | NM_013122 | Insulin-like growth factor binding protein 2 |
| 527 | 1374969_at | AA799832 | *Rattus norvegicus* transcribed sequences |
| 528 | 1371954_at | BF290193 | *Rattus norvegicus* transcribed sequences |
| 529 | 1370347_at | AF095585 | enigma (LIM domain protein) |
| 530 | 1388483_at | BI296011 | *Rattus norvegicus* transcribed sequence with strong similarity to protein ref: NP_068733.1 (*H. sapiens*) cofilin 2 (muscle) [*Homo sapiens*] |
| 531 | 1375890_at | BI296994 | *Rattus norvegicus* transcribed sequences |
| 532 | 1368724_a_at | NM_019131 | "tropomyosin 1, alpha" |
| 533 | 1370288_a_at | AF372216 | "tropomyosin 1, alpha" |
| 534 | 1367785_at | NM_031747 | Calponin 1 |
| 535 | 1388422_at | BI275904 | *Rattus norvegicus* transcribed sequence with moderate similarity to protein pir: JC2324 (*H. sapiens*) JC2324 LIM protein - human |
| 536 | 1368988_at | AW520914 | calsequestrin 2 |
| 537 | 1370585_a_at | X04440 | "protein kinase C, beta 1" |
| 538 | 1389187_at | BI286421 | *Rattus norvegicus* transcribed sequence with weak similarity to protein ref: NP_115950.1 (*H. sapiens*) EVG1 protein [*Homo sapiens*] |
| 539 | 1389050_at | AI170797 | *Rattus norvegicus* transcribed sequences |
| 540 | 1372658_at | BG373779 | desmuslin |
| 541 | 1387898_at | D29960 | heat shock 20-kDa protein |
| 542 | 1373915_at | AI044427 | "*Rattus norvegicus* transcribed sequence with moderate similarity to protein pir: B49364 (*H. sapiens*) B49364 protein kinase (EC 2.7.1.37), myotonic dystrophy-associated - human" |
| 543 | 1367570_at | NM_031549 | Transgelin (Smooth muscle 22 protein) |
| 544 | 1370287_a_at | M23764 | "tropomyosin 1, alpha" |
| 545 | 1386869_at | NM_012893 | "actin, gamma 2" |
| 546 | 1388842_at | BG380385 | *Rattus norvegicus* transcribed sequences |
| 547 | 1371382_at | BI283060 | "*Rattus norvegicus* transcribed sequence with strong similarity to protein pir: A37098 (*H. sapiens*) A37098 gelation factor ABP-280, long form - human" |
| 548 | 1372219_at | AA012755 | "*Rattus norvegicus* transcribed sequence with strong similarity to protein sp: P06468 (*H. sapiens*) TPM2_HUMAN Tropomyosin beta chain, fibroblast and epithelial muscle-type (Tropomyosin 2, fibroblast and epithelial muscle-type) (TM36) (TME1) (TM1)" |
| 549 | 1370057_at | NM_017148 | cysteine rich protein 1 |

TABLE 5-continued

Genes differentially expressed in CNI1493-treated colon

| No. | Identifier | Acce. No. | Description |
|---|---|---|---|
| 550 | 1371541_at | AI177055 | *Rattus norvegicus* transcribed sequence with moderate similarity to protein ref: NP_444278.1 (*H. sapiens*) mitochondrial ribosomal protein L53 [*Homo sapiens*] |
| 551 | 1388496_at | AI103600 | "*Rattus norvegicus* transcribed sequence with strong similarity to protein ref: NP_001449.1 (*H. sapiens*) gamma filamin; filamin C, gamma (actin-binding protein-280); filamin 2; actin-binding protein 280 [*Homo sapiens*]" |
| 552 | 1370896_a_at | X16262 | myosin heavy chain 11 |
| 553 | 1372015_at | AI008689 | *Rattus norvegicus* transcribed sequence with weak similarity to protein sp: O75410 (*H. sapiens*) TAC1_HUMAN Transforming acidic coiled-coil-containing protein 1 |
| 554 | 1372296_at | AA800892 | *Rattus norvegicus* transcribed sequence with weak similarity to protein sp: P55822 (*H. sapiens*) SH3B_HUMAN SH3 domain-binding glutamic acid-rich protein (SH3BGR protein) (21-glutamic acid-rich protein) (21-GARP) |
| 555 | 1388451_at | AA817802 | *Rattus norvegicus* transcribed sequences |
| 556 | 1388298_at | BI279044 | "*Rattus norvegicus* transcribed sequence with strong similarity to protein pir: A32031 (*H. sapiens*) A32031 myosin regulatory light chain, smooth muscle - human" |
| 557 | 1371677_at | BE113200 | *Rattus norvegicus* transcribed sequences |
| 558 | 1367691_at | NM_134449 | PKC-delta binding protein |
| 559 | 1372159_at | BI285456 | *Rattus norvegicus* transcribed sequence with strong similarity to protein ref: NP_067541.1 (*M. musculus*) junctophilin 2 [*Mus musculus*] |
| 560 | 1371331_at | BG665037 | *Rattus norvegicus* transcribed sequences |
| 561 | 1370234_at | AA893484 | Fibronectin 1 |
| 562 | 1372111_at | BI285449 | caveolin |
| 563 | 1399065_at | BM389543 | *Rattus norvegicus* transcribed sequences |
| 564 | 1371855_at | BM390254 | *Rattus norvegicus* transcribed sequences |
| 565 | 1389394_at | AI411809 | *Rattus norvegicus* transcribed sequences |
| 566 | 1368145_at | NM_013002 | Neuron specific protein PEP-19 (Purkinje cell protein 4) |
| 567 | 1371566_at | BI296437 | *Rattus norvegicus* transcribed sequence with weak similarity to protein ref: NP_116264.1 (*H. sapiens*) hypothetical protein MGC15482 [*Homo sapiens*] |
| 568 | 1368105_at | AI228231 | Tspan-2 protein |
| 569 | 1372625_at | AA851663 | *Rattus norvegicus* transcribed sequences |
| 570 | 1372537_at | BI289642 | *Rattus norvegicus* transcribed sequence with strong similarity to protein sp: O00423 (*H. sapiens*) EML1_HUMAN Echinoderm microtubule-associated protein-like 1 (EMAP-1) (HuEMAP-1) |
| 571 | 1390430_at | BF284190 | "nuclear receptor subfamily 1, group D, member 2" |
| 572 | 1371969_at | BI291848 | *Rattus norvegicus* transcribed sequences |
| 573 | 1386860_at | NM_012811 | milk fat globule-EGF factor 8 protein |
| 574 | 1371588_at | AA686007 | "parvin, alpha" |
| 575 | 1387224_at | NM_019304 | "diacylglycerol kinase, beta" |
| 576 | 1374237_at | BI286025 | "*Rattus norvegicus* transcribed sequence with strong similarity to protein sp: P29536 (*H. sapiens*) LMD1_HUMAN Leiomodin 1 (Leiomodin, muscle form) (64 kDa autoantigen D1) (64 kDa autoantigen 1D) (64 kDa autoantigen 1D3) (Thyroid-associated ophthalmopathy aut |
| 577 | 1373911_at | BM389026 | *Rattus norvegicus* transcribed sequence with moderate similarity to protein pir: S36110 (*H. sapiens*) S36110 osteoblast-specific factor 2 - human |
| 578 | 1371732_at | BI285485 | *Rattus norvegicus* transcribed sequences |
| 579 | 1371700_at | AI177059 | *Rattus norvegicus* transcribed sequence with strong similarity to protein sp: P55083 (*H. sapiens*) MFA4 HUMAN Microfibril-associated glycoprotein 4 |
| 580 | 1376099_at | AW254017 | "collagen, type V, alpha 1" |
| 581 | 1388935_at | AI231814 | *Rattus norvegicus* transcribed sequences |
| 582 | 1379936_at | AA875132 | *Rattus norvegicus* transcribed sequences |
| 583 | 1372342_at | AI176583 | *Rattus norvegicus* transcribed sequences |
| 584 | 1398370_at | AW522471 | rexo70 |
| 585 | 1369652_at | AI145313 | Thymus cell surface antigen |
| 586 | 1376640_at | BF285466 | *Rattus norvegicus* transcribed sequences |
| 587 | 1369955_at | NM_134452 | "collagen, type V, alpha 1" |
| 588 | 1373858_at | BE109064 | "*Rattus norvegicus* transcribed sequence with moderate similarity to protein pdb: 1LBG (*E. coli*) B Chain B, Lactose Operon Repressor Bound To 21-Base Pair Symmetric Operator Dna, Alpha Carbons Only" |
| 589 | 1387854_at | BI282748 | "procollagen, type I, alpha 2" |
| 590 | 1386862_at | NM_013132 | annexin 5 |
| 591 | 1388116_at | BI285575 | "collagen, type 1, alpha 1" |

TABLE 5-continued

Genes differentially expressed in CNI1493-treated colon

| No. | Identifier | Acce. No. | Description |
|---|---|---|---|
| 592 | 1370959_at | BI275716 | "collagen, type III, alpha 1" |
| 593 | 1370155_at | BM388837 | "procollagen, type I, alpha 2" |
| 594 | 1388569_at | AI179984 | alpha-2 antiplasmin |
| 595 | 1373032_at | AW251450 | fracture callus protein MUSTANG |
| 596 | 1376265_at | AI411542 | *Rattus norvegicus* transcribed sequences |
| 597 | 1389367_at | AI409747 | *Rattus norvegicus* transcribed sequence with strong similarity to protein ref: NP_055390.1 (*H. sapiens*) schwannomin interacting protein 1 [*Homo sapiens*] |
| 598 | 1373957_at | BF281544 | Reelin |
| 599 | 1370927_at | BE108345 | "procollagen, type XII, alpha 1" |
| 600 | 1372305_at | AA893634 | *Rattus norvegicus* transcribed sequence with moderate similarity to protein ref: NP_057513.1 (*H. sapiens*) COPZ2 for nonclathrin coat protein zeta-COP [*Homo sapiens*] |
| 601 | 1383822_at | AI029990 | "*Rattus norvegicus* transcribed sequence with weak similarity to protein ref: NP_001705.1 (*H. sapiens*) Bicaudal D homolog 1 (*Drosophila*); Bicaudal-D, *Drosophila*, homolog of, 1; Bicaudal D (*Drosophila*) homolog 1 [*Homo sapiens*]" |
| 602 | 1374774_at | BF552241 | *Rattus norvegicus* transcribed sequences |
| 603 | 1388312_at | BI274487 | tissue inhibitor of metalloproteinase 2 |
| 604 | 1376662_at | BF390141 | *Rattus norvegicus* transcribed sequences |
| 605 | 1374971_at | AA818954 | *Rattus norvegicus* transcribed sequences |
| 606 | 1389066_at | BI274408 | *Rattus norvegicus* transcribed sequences |
| 607 | 1373102_at | BI282750 | *Rattus norvegicus* transcribed sequences |
| 608 | 1388738_at | AI411227 | *Rattus norvegicus* transcribed sequences |
| 609 | 1368842_at | BG377130 | *Rattus norvegicus* transcribed sequences |
| 610 | 1390444_at | AI044433 | *Rattus norvegicus* transcribed sequences |
| 611 | 1377087_at | AA963029 | *Rattus norvegicus* transcribed sequences |
| 612 | 1387042_at | NM_012828 | "calcium channel, voltage-dependent, beta 3 subunit" |
| 613 | 1369974_at | NM_012663 | vesicle-associated membrane protein 2 |
| 614 | 1374870_at | BF286402 | *Rattus norvegicus* transcribed sequences |
| 615 | 1374087_at | AI411088 | *Rattus norvegicus* transcribed sequences |
| 616 | 1374117_at | BI279562 | brain-specific angiogenesis inhibitor 1-associated protein 2 |
| 617 | 1390016_at | BF415854 | *Rattus norvegicus* transcribed sequences |
| 618 | 1390341_at | BF396709 | *Rattus norvegicus* transcribed sequences |
| 619 | 1374709_at | AI406795 | *Rattus norvegicus* transcribed sequences |
| 620 | 1374726_at | AI411941 | *Rattus norvegicus* transcribed sequences |
| 621 | 1389511_s_at | BF403383 | synaptogyrin 1 |
| 622 | 1390489_at | BE108860 | *Rattus norvegicus* transcribed sequences |
| 623 | 1388598_at | BI281230 | *Rattus norvegicus* transcribed sequences |
| 624 | 1370375_at | J05499 | liver mitochondrial glutaminase |
| 625 | 1388821_at | AI010430 | *Rattus norvegicus* transcribed sequences |
| 626 | 1368276_at | NM_012664 | Synaptophysin |
| 627 | 1375862_at | BM384701 | *Rattus norvegicus* transcribed sequence with weak similarity to protein sp: P07202 (*H. sapiens*) PERT_HUMAN Thyroid peroxidase precursor (TPO) |
| 628 | 1377136_at | AW254190 | *Rattus norvegicus* transcribed sequences |
| 629 | 1392887_at | AI575082 | *Rattus norvegicus* transcribed sequences |
| 630 | 1389157_at | BI275583 | *Rattus norvegicus* transcribed sequences |
| 631 | 1377013_at | AI639108 | *Rattus norvegicus* transcribed sequences |
| 632 | 1371389_at | AI170668 | *Rattus norvegicus* transcribed sequences |
| 633 | 1370969_at | BE107303 | *Rattus norvegicus* transcribed sequence with moderate similarity to protein sp: P03845 (*E. coli*) YPA1_ECOLI HYPOTHETICAL PROTEIN 1 |
| 634 | 1373438_at | BE329352 | *Rattus norvegicus* transcribed sequence with weak similarity to protein pir: RGECDW (*E. coli*) RGECDW transcription activator of D-serine dehydratase - *Escherichia coli* |
| 635 | 1388456_at | AI228548 | "*Rattus norvegicus* transcribed sequence with strong similarity to protein sp: P23297 (*H. sapiens*) S10A_HUMAN S-100 protein, alpha chain (S100 calcium-binding protein A1)" |
| 636 | 1373427_at | BI288816 | *Rattus norvegicus* transcribed sequence with strong similarity to protein ref: NP_067067.1 (*H. sapiens*) Rag D protein; hypothetical GTP-binding protein DKFZp761H171 [*Homo sapiens*] |
| 637 | 1368085_at | NM_133595 | GTP cyclohydrolase I feedback regulatory protein |
| 638 | 1369103_at | NM_012755 | Fyn proto-oncogene |
| 639 | 1389456_at | BI296591 | *Rattus norvegicus* transcribed sequences |
| 640 | 1370904_at | BI301490 | *R. norvegicus* mRNA for RT1.Ma |
| 641 | 1371499_at | AI227627 | CD9 antigen (p24) |
| 642 | 1371362_at | BI285402 | *Rattus norvegicus* transcribed sequence with strong similarity to protein sp: Q92841 (*H. sapiens*) DD17_HUMAN Probable RNA-dependent helicase p72 (DEAD-box protein p72) (DEAD-box protein 17) |

TABLE 5-continued

Genes differentially expressed in CNI1493-treated colon

| No. | Identifier | Acce. No. | Description |
|---|---|---|---|
| 643 | 1388920_at | AI230985 | bone morphogenetic protein 6 |
| 644 | 1368851_at | NM_012555 | v-ets erythroblastosis virus E26 oncogene homolog 1 (avian) |
| 645 | 1373343_at | AI175820 | *Rattus norvegicus* transcribed sequences |
| 646 | 1374888_at | AI317837 | *Rattus norvegicus* transcribed sequences |
| 647 | 1376453_at | BF419074 | *Rattus norvegicus* transcribed sequences |
| 648 | 1376062_at | BG375315 | syndecan 1 |
| 649 | 1371046_at | AW920849 | "*Rattus norvegicus* beta II spectrin-short isoform mRNA, partial cds" |
| 650 | 1368080_at | NM_054008 | Rgc32 protein |
| 651 | 1371931_at | BI274753 | general transcription factor II I |
| 652 | 1388463_at | AW252660 | *Rattus norvegicus* transcribed sequence with moderate similarity to protein ref: NP_057010.1 (*H. sapiens*) putative secreted protein; similar to putative secreted protein (*H. sapiens*) [*Homo sapiens*] |
| 653 | 1388639_at | BF284148 | *Rattus norvegicus* transcribed sequence with strong similarity to protein ref: NP_060149.1 (*H. sapiens*) hypothetical protein FLJ20128 [*Homo sapiens*] |
| 654 | 1379685_at | AI502753 | CTD-binding SR-like protein rA4 |
| 655 | 1389967_at | AA892386 | "*Rattus norvegicus* ADP-ribosylation-like factor 6-interacting protein mRNA, complete cds" |
| 656 | 1368941_at | NM_032076 | prostaglandin E receptor 4 (subtype EP4) |
| 657 | 1390457_at | BM385762 | *Rattus norvegicus* transcribed sequences |
| 658 | 1390458_at | BG666849 | *Rattus norvegicus* transcribed sequences |
| 659 | 1375254_at | BE103444 | *Rattus norvegicus* transcribed sequence with strong similarity to protein pir: JC5023 (*H. sapiens*) JC5023 CMP-sialic acid transporter - human |
| 660 | 1375530_at | BG374612 | *Rattus norvegicus* transcribed sequence with strong similarity to protein ref: NP_062298.1 (*M. musculus*) glucosamine-phosphate N-acetyltransferase 1; glucosamine-6-phosphate acetyltransferase; glucosamine-phosphate N-acetyltransferase [*Mus musculus*] |

TABLE 6

Genes differentially expressed in CNI1493-treated S1 DRG

| No. | Identifier | Acce. No. | CTRL-VHL | CTRL-CNI | IBS-VHL | IBS-CNI | Description |
|---|---|---|---|---|---|---|---|
| 52 | 1373932_at | BE098739 | 1.00 | 4.46 | 1.91 | 6.75 | ESTs |
| 48 | 1370913_at | AI409634 | 1.00 | 1.70 | 0.98 | 3.44 | Best5 protein |
| 15 | 1369202_at | NM_017028 | 1.00 | 2.20 | 0.35 | 3.04 | myxovirus (influenza virus) resistance 2 |
| 62 | 1371152_a_at | Z18877 | 1.00 | 1.49 | 0.48 | 2.48 | 25 oligoadenylate synthetase |
| 53 | 1367850_at | NM_053843 | 1.00 | 1.66 | 1.01 | 2.32 | "Fc receptor, IgG, low affinity III" |
| 54 | 1389006_at | AI170394 | 1.00 | 1.53 | 1.03 | 2.28 | ESTs |
| 58 | 1383564_at | BF411036 | 1.00 | 1.34 | 0.52 | 2.26 | "ESTs, Highly similar to IRF7 MOUSE Interferon regulatory factor 7 (IRF-7) [*M. musculus*]" |
| 67 | 1389034_at | BI295179 | 1.00 | 1.49 | 0.59 | 2.24 | "ESTs, Moderately similar to UBPI_MOUSE Ubiquitin carboxyl-terminal hydrolase 18 (Ubiquitin thiolesterase 18) (Ubiquitin-specific processing protease 18) (Deubiquitinating enzyme 18) (43 kDa ubiquitin-specific protease) [*M. musculus*]" |
| 35 | 1386166_at | AA892881 | 1.00 | 1.59 | 1.43 | 2.18 | EST |
| 69 | 1388164_at | AF029241 | 1.00 | 1.52 | 0.97 | 2.09 | "*Rattus norvegicus* partial mRNA for BM1k MHC class Ib antigen, strain SHR" |
| 65 | 1370892_at | BI285347 | 1.00 | 1.66 | 0.69 | 2.05 | Complement component 4 |
| 73 | 1369186_at | D85899 | 1.00 | 1.78 | 1.10 | 2.05 | caspase 1 |
| 56 | 1372691_at | BI292558 | 1.00 | 1.34 | 0.94 | 2.02 | "ESTs, Highly similar to A57501 uridine phosphorylase (EC 2.4.2.3) I - mouse [*M. musculus*]" |

TABLE 6-continued

Genes differentially expressed in CNI1493-treated S1 DRG

| No. | Identifier | Acce. No. | CTRL-VHL | CTRL-CNI | IBS-VHL | IBS-CNI | Description |
|---|---|---|---|---|---|---|---|
| 70 | 1371015_at | X52711 | 1.00 | 1.40 | 0.81 | 1.98 | "Myxovirus (influenza) resistance, homolog of murine Mx (also interferon-inducible protein IFI78)" |
| 74 | 1376151_a_at | AI407953 | 1.00 | 1.51 | 0.92 | 1.95 | ESTs |
| 51 | 1374730_at | AI102519 | 1.00 | 1.42 | 1.11 | 1.91 | "ESTs, Highly similar to TYRO protein tyrosine kinase binding protein; killer cell activating receptor associated protein [*Mus musculus*] [*M. musculus*]" |
| 30 | 1390730_at | BM383911 | 1.00 | 1.69 | 1.33 | 1.86 | ESTs |
| 36 | 1375346_at | BI290002 | 1.00 | 1.62 | 1.43 | 1.82 | "ESTs, Weakly similar to hypothetical protein FLJ20010 [*Homo sapiens*] [*H. sapiens*]" |
| 72 | 1390738_at | BM385476 | 1.00 | 1.66 | 1.20 | 1.74 | ESTs |
| 47 | 1370186_at | AI599350 | 1.00 | 1.32 | 1.05 | 1.74 | "proteosome (prosome, macropain) subunit, beta type 9 (large multifunctional protease 2)" |
| 80 | 1389553_at | BF393825 | 1.00 | 1.16 | 0.85 | 1.73 | "ESTs, Weakly similar to RIKEN cDNA 1810046I24 [*Mus musculus*] [*M. musculus*]" |
| 77 | 1372930_at | AI411381 | 1.00 | 1.14 | 0.76 | 1.72 | "ESTs, Weakly similar to DEAF-1 related transcriptional regulator (NUDR) [*Rattus norvegicus*] [*R. norvegicus*]" |
| 59 | 1367786_at | NM_080767 | 1.00 | 1.23 | 0.73 | 1.66 | "proteasome (prosome, macropain) subunit, beta type, 8 (low molecular mass polypeptide 7)" |
| 49 | 1388071_x_at | M24024 | 1.00 | 1.28 | 1.05 | 1.66 | RT1 class Ib gene |
| 44 | 1380030_at | AW523520 | 1.00 | 1.49 | 0.96 | 1.65 | "ESTs, Highly similar to RIKEN cDNA 3110024A21 [*Mus musculus*] [*M. musculus*]" |
| 57 | 1390510_at | BI294706 | 1.00 | 1.21 | 0.83 | 1.65 | "ESTs, Weakly similar to RIKEN cDNA 1810027D10 [*Mus musculus*] [*M. musculus*]" |
| 42 | 1374944_at | BI275829 | 1.00 | 1.26 | 0.65 | 1.65 | "ESTs, Moderately similar to hypothetical protein LOC51058 [*Homo sapiens*] [*H. sapiens*]" |
| 23 | 1384446_at | BF402271 | 1.00 | 1.72 | 1.51 | 1.62 | ESTs |
| 34 | 1375988_at | AW914928 | 1.00 | 1.39 | 1.38 | 1.62 | ESTs |
| 27 | 1373403_at | AI230625 | 1.00 | 1.59 | 1.11 | 1.61 | ESTs |
| 66 | 1387995_a_at | BI285494 | 1.00 | 1.40 | 0.84 | 1.60 | interferon-inducible protein variant 10 |
| 39 | 1387969_at | U22520 | 1.00 | 1.52 | 1.06 | 1.59 | "small inducible cytokine B subfamily (Cys-X-Cys), member 10" |
| 32 | 1384167_at | AW522260 | 1.00 | 1.70 | 1.38 | 1.59 | ESTs |
| 37 | 1387566_at | NM_133551 | 1.00 | 1.42 | 1.25 | 1.59 | "phospholipase A2, group IVA (cytosolic, calcium-dependent)" |
| 55 | 1372516_at | AI317842 | 1.00 | 1.24 | 1.06 | 1.58 | "ESTs, Weakly similar to S62328 kinesin-like DNA binding protein KID - human [*H. sapiens*]" |
| 43 | 1374277_at | BI289615 | 1.00 | 1.44 | 1.01 | 1.56 | ESTs |
| 28 | 1376264_at | AW526697 | 1.00 | 1.56 | 1.51 | 1.56 | ESTs |
| 33 | 1388872_at | BI290053 | 1.00 | 1.25 | 1.19 | 1.56 | isopentenyl-diphosphate delta isomerase |
| 14 | 1390312_at | BG670441 | 1.00 | 1.45 | 0.77 | 1.55 | "ESTs, Weakly similar to hypothetical protein FLJ20073 [*Homo sapiens*] [*H. sapiens*]" |
| 64 | 1388149_at | X57523 | 1.00 | 1.15 | 0.72 | 1.52 | "Transporter 1, ABC (ATP binding cassette)" |
| 71 | 1389571_at | BG666368 | 1.00 | 1.20 | 0.95 | 1.52 | "ESTs, Weakly similar to signal transducer and activator of transcription 1 [*Rattus norvegicus*] [*R. norvegicus*]" |

TABLE 6-continued

Genes differentially expressed in CNI1493-treated S1 DRG

| No. | Identifier | Acce. No. | CTRL-VHL | CTRL-CNI | IBS-VHL | IBS-CNI | Description |
|---|---|---|---|---|---|---|---|
| 68 | 1368835_at | AW434718 | 1.00 | 1.33 | 0.87 | 1.51 | signal transducer and activator of transcription 1 |
| 60 | 1388347_at | AI233210 | 1.00 | 1.11 | 0.93 | 1.51 | "ESTs, Moderately similar to I49013 thymic shared antigen-1 - mouse [*M. musculus*]" |
| 12 | 1376693_at | AA998964 | 1.00 | 1.27 | 0.60 | 1.49 | "ESTs, Moderately similar to hypothetical protein FLJ20073 [*Homo sapiens*] [*H. sapiens*]" |
| 50 | 1373043_at | BI275923 | 1.00 | 1.36 | 1.16 | 1.49 | "ESTs, Highly similar to stromal cell-derived factor 2-like 1 [*Mus musculus*] [*M. musculus*]" |
| 24 | 1374465_at | AI237098 | 1.00 | 1.48 | 1.04 | 1.49 | "ESTs, Highly similar to ubiquitously expressed transcript [*Mus musculus*] [*M. musculus*]" |
| 63 | 1373025_at | AI411618 | 1.00 | 1.15 | 0.61 | 1.47 | "ESTs, Weakly similar to S49158 complement protein C1q beta chain precursor - rat [*R. norvegicus*]" |
| 25 | 1369962_at | NM_031014 | 1.00 | 1.58 | 1.36 | 1.47 | 5-aminoimidazole-4-carboxamide ribonucleotide formyltransferase/IMP |
| 19 | 1377117_at | BF387780 | 1.00 | 1.88 | 0.94 | 1.45 | ESTs |
| 16 | 1388754_at | AI176839 | 1.00 | 1.49 | 0.88 | 1.45 | ESTs |
| 46 | 1376056_at | BF291214 | 1.00 | 1.33 | 1.07 | 1.43 | "ESTs, Moderately similar to hypothetical protein FLJ14464 [*Homo sapiens*] [*H. sapiens*]" |
| 29 | 1399056_at | AI716436 | 1.00 | 1.57 | 1.21 | 1.43 | "ESTs, Moderately similar to candidate tumor suppressor protein [*Homo sapiens*] [*H. sapiens*]" |
| 3 | 1376751_at | AI044250 | 1.00 | 1.74 | 1.16 | 1.41 | "ESTs, Highly similar to ST19_MOUSE Serine/threonine-protein kinase 19 (RP1 protein) [*M. musculus*]" |
| 11 | 1367846_at | NM_012618 | 1.00 | 1.59 | 0.95 | 1.41 | S100 calcium-binding protein A4 |
| 45 | 1373504_at | BF287967 | 1.00 | 1.32 | 0.96 | 1.40 | "ESTs, Weakly similar to JE0204 testicular protein Tpx-1 - rat [*R. norvegicus*]" |
| 22 | 1372043_at | BI282363 | 1.00 | 1.52 | 1.16 | 1.37 | "ESTs, Moderately similar to ribosomal protein P0-like protein; 60S acidic ribosomal protein P0 [*Homo sapiens*] [*H. sapiens*]" |
| 38 | 1370214_at | AI175539 | 1.00 | 1.18 | 0.84 | 1.34 | Parvalbumin (calcium binding protein) |
| 9 | 1390655_at | BF420653 | 1.00 | 1.47 | 0.54 | 1.34 | "ESTs, Highly similar to T14155 zinc finger protein Peg3 - mouse [*M. musculus*]" |
| 26 | 1375669_at | BI285619 | 1.00 | 1.39 | 1.03 | 1.32 | "ESTs, Weakly similar to FK506 binding protein 2 (13 kDa) [*Rattus norvegicus*] [*R. norvegicus*]" |
| 21 | 1398884_at | BM384924 | 1.00 | 1.71 | 1.10 | 1.32 | "ESTs, Highly similar to prefoldin 5; EIG-1; c-myc binding protein MM-1; DNA segment, Chr 15, ERATO Doi 697, expressed [*Mus musculus*] [*M. musculus*]" |
| 1 | 1368465_at | NM_012892 | 1.00 | 1.66 | 1.12 | 1.30 | amiloride-sensitive cation channel 1 |
| 20 | 1371381_at | AI007981 | 1.00 | 1.46 | 0.99 | 1.29 | "ESTs, Moderately similar to UCRX_HUMAN Ubiquinol-cytochrome C reductase complex 7.2 kDa protein (Cytochrome C1, nonheme 7 kDa protein) (Complex III subunit X) (7.2 kDa cytochrome c1-associated protein subunit) (HSPC119) [*H. sapiens*]" |

TABLE 6-continued

Genes differentially expressed in CNI1493-treated S1 DRG

| No. | Identifier | Acce. No. | CTRL-VHL | CTRL-CNI | IBS-VHL | IBS-CNI | Description |
|---|---|---|---|---|---|---|---|
| 4 | 1372815_at | BG673028 | 1.00 | 1.70 | 1.02 | 1.29 | "ESTs, Highly similar to MGN_HUMAN Mago nashi protein homolog [*M. musculus*]" |
| 41 | 1388628_at | BI284430 | 1.00 | 1.30 | 0.84 | 1.29 | "ESTs, Weakly similar to PSD7_MOUSE 26S proteasome non-ATPase regulatory subunit 7 (26S proteasome regulatory subunit S12) (Proteasome subunit p40) (Mov34 protein) [*M. musculus*]" |
| 61 | 1373037_at | BI279216 | 1.00 | 1.07 | 0.74 | 1.26 | "ESTs, Weakly similar to ubiquitin-conjugating enzyme E2D 2 [*Rattus norvegicus*] [*R. norvegicus*]" |
| 2 | 1374950_at | BF400611 | 1.00 | 1.52 | 0.89 | 1.23 | ESTs |
| 10 | 1386425_at | H33472 | 1.00 | 1.27 | 0.73 | 1.23 | EST |
| 31 | 1390065_at | BE096685 | 1.00 | 1.53 | 0.86 | 1.22 | ESTs |
| 17 | 1390389_at | BM385936 | 1.00 | 1.21 | 0.87 | 1.20 | ESTs |
| 7 | 1369970_at | NM_031827 | 1.00 | 1.45 | 0.89 | 1.18 | vesicle-associated membrane protein 8 (endobrevin) |
| 13 | 1390562_s_at | BE102350 | 1.00 | 1.09 | 0.68 | 1.15 | ESTs |
| 8 | 1390147_at | AI549079 | 1.00 | 1.26 | 0.75 | 1.12 | "ESTs, Highly similar to T17232 hypothetical protein DKFZp434I116.1 - human (fragment) [*H. sapiens*]" |
| 95 | 1369157_at | NM_017229 | 1.00 | 1.05 | 1.77 | 1.09 | phosphodiesterase 3B |
| 78 | 1387242_at | NM_019335 | 1.00 | 0.96 | 2.62 | 0.95 | "Protein kinase, interferon-inducible double stranded RNA dependent" |
| 79 | 1377225_at | BF400628 | 1.00 | 0.76 | 3.47 | 0.85 | ESTs |
| 18 | 1372137_at | BI279854 | 1.00 | 1.13 | 0.73 | 1.03 | "ESTs, Highly similar to GC5L_MOUSE GCN5-LIKE PROTEIN 1 [*M. musculus*]" |
| 75 | 1393280_at | AA874924 | 1.00 | 1.18 | 0.28 | 1.09 | "ESTs, Moderately similar to lymphocyte antigen 86 [*Mus musculus*] [*M. musculus*]" |
| 76 | 1372604_at | BI289459 | 1.00 | 1.55 | 0.08 | 1.29 | "ESTs, Weakly similar to apolipoprotein L, 3; TNF-inducible protein CG12-1 [*Homo sapiens*] [*H. sapiens*]" |
| 102 | 1374802_at | AI010721 | 1.00 | 0.90 | 1.72 | 0.96 | "ESTs, Moderately similar to hypothetical protein FLJ20424 [*Homo sapiens*] [*H. sapiens*]" |
| 40 | 1371171_at | M10094 | 1.00 | 0.76 | 6.16 | 0.89 | RT1 class Ib gene |
| 88 | 1371725_at | BM392410 | 1.00 | 0.56 | 1.01 | 0.95 | ESTs |
| 5 | 1368316_at | NM_019158 | 1.00 | 1.22 | 0.71 | 0.91 | aquaporin 8 |
| 89 | 1375084_at | BF419780 | 1.00 | 0.64 | 1.12 | 0.90 | ESTs |
| 85 | 1398272_at | NM_022860 | 1.00 | 0.66 | 0.99 | 0.90 | beta-4N-acetylgalactosaminyltransferase |
| 81 | 1374721_at | AI178647 | 1.00 | 0.74 | 1.15 | 0.89 | ESTs |
| 90 | 1374398_at | AI178787 | 1.00 | 0.68 | 1.10 | 0.86 | "ESTs, Highly similar to suppressor of Ty 6 homolog (*S. cerevisiae*) [*Mus musculus*] [*M. musculus*]" |
| 91 | 1369999_a_at | NM_053601 | 1.00 | 0.68 | 0.95 | 0.84 | neuronatin |
| 6 | 1387658_at | U93849 | 1.00 | 1.61 | 0.43 | 0.83 | Eukaryotic elongation factor 2 kinase |
| 129 | 1387349_at | NM_013028 | 1.00 | 0.56 | 0.76 | 0.81 | Short stature homeobox 2 |
| 94 | 1390347_at | AW535909 | 1.00 | 0.72 | 1.02 | 0.80 | ESTs |
| 100 | 1376944_at | AI407163 | 1.00 | 0.94 | 1.34 | 0.79 | ESTs |
| 96 | 1369052_at | NM_133323 | 1.00 | 0.90 | 1.29 | 0.79 | zinc finger protein 111 |
| 84 | 1376410_at | BI291814 | 1.00 | 0.66 | 0.93 | 0.76 | ESTs |
| 118 | 1389193_at | BM388083 | 1.00 | 0.60 | 0.83 | 0.76 | ESTs |
| 99 | 1376537_at | AW435010 | 1.00 | 0.81 | 1.06 | 0.75 | ESTs |
| 136 | 1374655_at | BG378095 | 1.00 | 0.57 | 0.90 | 0.75 | ESTs |
| 97 | 1375983_at | AI234287 | 1.00 | 0.77 | 1.21 | 0.74 | ESTs |
| 92 | 1392890_at | BG663460 | 1.00 | 0.59 | 1.24 | 0.74 | ESTs |
| 135 | 1369061_at | NM_053906 | 1.00 | 0.25 | 0.81 | 0.74 | glutathione reductase |
| 101 | 1376610_a_at | BE109163 | 1.00 | 0.77 | 1.60 | 0.74 | "ESTs, Weakly similar to G02540 nucleobindin - human [*H. sapiens*]" |
| 103 | 1377823_at | AW531363 | 1.00 | 1.04 | 1.60 | 0.74 | ESTs |
| 82 | 1388116_at | BI285575 | 1.00 | 0.56 | 1.13 | 0.73 | "collagen, type 1, alpha 1" |

TABLE 6-continued

Genes differentially expressed in CNI1493-treated S1 DRG

| No. | Identifier | Acce. No. | CTRL-VHL | CTRL-CNI | IBS-VHL | IBS-CNI | Description |
|---|---|---|---|---|---|---|---|
| 121 | 1377070_at | BE098910 | 1.00 | 0.59 | 0.72 | 0.73 | "ESTs, Moderately similar to S3B2_HUMAN Splicing factor 3B subunit 2 (Spliceosome associated protein 145) (SAP 145) (SF3b150) (Pre-mRNA splicing factor SF3b 145 kDa subunit) [H. sapiens]" |
| 131 | 1369958_at | NM_022542 | 1.00 | 0.59 | 0.77 | 0.72 | rhoB gene |
| 130 | 1376288_at | AI408455 | 1.00 | 0.64 | 0.78 | 0.71 | ESTs |
| 132 | 1391078_at | BM391856 | 1.00 | 0.56 | 0.66 | 0.71 | "ESTs, Moderately similar to A56284 differentiation-specific element binding protein - mouse [M. musculus]" |
| 113 | 1374593_at | AA799421 | 1.00 | 0.66 | 0.74 | 0.70 | "ESTs, Highly similar to KPCE_RAT PROTEIN KINASE C, EPSILON TYPE (NPKC-EPSILON) [R. norvegicus]" |
| 112 | 1372158_at | BI295768 | 1.00 | 0.66 | 0.79 | 0.70 | LRP16 protein |
| 83 | 1370969_at | BE107303 | 1.00 | 0.58 | 1.05 | 0.69 | homeo box A5 |
| 93 | 1370583_s_at | AY082609 | 1.00 | 0.73 | 0.98 | 0.69 | P-glycoprotein/multidrug resistance 1 |
| 98 | 1370139_a_at | AB051214 | 1.00 | 0.87 | 1.16 | 0.68 | zzN/A |
| 87 | 1389919_at | BI296756 | 1.00 | 0.60 | 0.97 | 0.67 | "ESTs, Weakly similar to actopaxin [Rattus norvegicus] [R. norvegicus]" |
| 117 | 1368242_at | NM_013186 | 1.00 | 0.60 | 0.72 | 0.66 | "Potassium voltage gated channel, Shab-related subfamily, member 1" |
| 106 | 1379747_at | AA866443 | 1.00 | 0.83 | 0.97 | 0.66 | ESTs |
| 141 | 1390626_at | BF398788 | 1.00 | 0.66 | 1.04 | 0.66 | ESTs |
| 133 | 1369113_at | NM_019282 | 1.00 | 0.59 | 0.87 | 0.65 | "cysteine knot superfamily 1, BMP antagonist 1" |
| 137 | 1376320_at | BF393051 | 1.00 | 0.75 | 1.08 | 0.65 | ESTs |
| 86 | 1387588_at | NM_138890 | 1.00 | 0.47 | 1.13 | 0.65 | zzN/A |
| 148 | 1399138_at | BG672805 | 1.00 | 0.71 | 0.87 | 0.65 | ESTs |
| 105 | 1398311_a_at | AF313464 | 1.00 | 0.92 | 1.13 | 0.64 | kinase D-interacting substance of 220 kDa |
| 115 | 1375538_at | AI230737 | 1.00 | 0.66 | 0.82 | 0.63 | ESTs |
| 140 | 1376204_at | AW531412 | 1.00 | 0.71 | 0.94 | 0.63 | ESTs |
| 111 | 1390538_at | BF414192 | 1.00 | 0.64 | 0.80 | 0.63 | ESTs |
| 151 | 1374909_at | BI296626 | 1.00 | 0.69 | 0.90 | 0.62 | "ESTs, Weakly similar to Gasz [Rattus norvegicus] [R. norvegicus]" |
| 146 | 1368769_at | NM_031760 | 1.00 | 0.82 | 1.01 | 0.62 | "ATP-binding cassette, sub-family B (MDR/TAP), member 11" |
| 107 | 1387929_at | AB020504 | 1.00 | 0.76 | 0.82 | 0.61 | PMF32 protein |
| 149 | 1376464_at | BE102505 | 1.00 | 0.79 | 0.79 | 0.60 | ESTs |
| 110 | 1375705_at | AI103622 | 1.00 | 0.60 | 0.73 | 0.59 | Guanine nucleotide-binding protein beta 1 |
| 128 | 1374084_at | BE119993 | 1.00 | 0.68 | 0.64 | 0.59 | ESTs |
| 123 | 1390722_at | AW531272 | 1.00 | 0.60 | 0.70 | 0.59 | ESTs |
| 122 | 1373008_x_at | BF386649 | 1.00 | 0.44 | 0.57 | 0.58 | reticulon 4 receptor |
| 139 | 1376939_at | BI284907 | 1.00 | 0.67 | 0.85 | 0.58 | ESTs |
| 119 | 1369059_at | NM_053705 | 1.00 | 0.55 | 0.78 | 0.58 | "transient receptor potential-related protein, ChaK" |
| 126 | 1392500_at | AA957990 | 1.00 | 0.59 | 0.67 | 0.58 | ESTs |
| 152 | 1369048_at | NM_017289 | 1.00 | 0.71 | 0.64 | 0.56 | "gamma-aminobutyric acid A receptor, delta" |
| 124 | 1375508_at | BE095963 | 1.00 | 0.50 | 0.61 | 0.56 | "ESTs, Highly similar to KIF2_MOUSE KINESIN-LIKE PROTEIN KIF2 [M. musculus]" |
| 142 | 1368429_at | NM_133615 | 1.00 | 0.60 | 0.81 | 0.56 | "TAF9-like RNA polymerase II, TATA box binding protein (TBP)-associated factor, 31 kD" |
| 144 | 1373981_at | BI299720 | 1.00 | 0.62 | 0.60 | 0.55 | ESTs |
| 114 | 1369285_at | NM_031082 | 1.00 | 0.74 | 0.76 | 0.55 | geranylgeranyltransferase type I (GGTase-I) |

TABLE 6-continued

Genes differentially expressed in CNI1493-treated S1 DRG

| No. | Identifier | Acce. No. | CTRL-VHL | CTRL-CNI | IBS-VHL | IBS-CNI | Description |
|---|---|---|---|---|---|---|---|
| 108 | 1372804_at | AI175555 | 1.00 | 0.80 | 0.87 | 0.54 | "ESTs, Highly similar to hypothetical brain protein similar to X96994 BR-1 protein (*Helix pomatia*) [*Mus musculus*] [*M. musculus*]" |
| 134 | 1386299_at | AI639471 | 1.00 | 0.50 | 0.86 | 0.53 | EST |
| 138 | 1377362_at | BF390409 | 1.00 | 0.43 | 0.81 | 0.51 | ESTs |
| 125 | 1387131_at | AF193015 | 1.00 | 0.44 | 0.55 | 0.50 | "serine (or cysteine) proteinase inhibitor, clade I (neuroserpin), member 1" |
| 147 | 1373778_at | BE349670 | 1.00 | 0.83 | 0.92 | 0.46 | ESTs |
| 145 | 1377030_at | BF390550 | 1.00 | 0.59 | 0.82 | 0.45 | ESTs |
| 143 | 1389436_at | AI236615 | 1.00 | 0.75 | 0.77 | 0.45 | ESTs |
| 116 | 1386181_at | AI639056 | 1.00 | 0.51 | 0.85 | 0.44 | EST |
| 150 | 1371042_at | BG664160 | 1.00 | 0.63 | 0.70 | 0.42 | mitogen-activated protein kinase kinase kinase 3 |
| 109 | 1387453_at | NM_024489 | 1.00 | 0.49 | 0.83 | 0.39 | zinc finger protein RIN ZF |
| 127 | 1390368_at | AI716535 | 1.00 | 0.40 | 0.46 | 0.34 | ESTs |
| 104 | 1372640_at | BI277758 | 1.00 | 0.85 | 1.80 | 0.33 | ESTs |
| 120 | 1369054_at | NM_133518 | 1.00 | 0.48 | 0.60 | 0.25 | rabphilin 3A |

The human homologs of some of the rat CVHGs are provided in Table 7.

TABLE 7

Human homologs of rat CVHGs

| Gene | Locus ID | Nucleotide sequence | Amino acid sequence |
|---|---|---|---|
| desmin | 1674 | SEQ ID NO: 1 | SEQ ID NO: 34 |
| PEP-19 | 5121 | SEQ ID NO: 2 | SEQ ID NO: 35 |
| IGFBP2 | 3485 | SEQ ID NO: 3 | SEQ ID NO: 36 |
| ADAMTS1 | 9510 | SEQ ID NO: 4 | SEQ ID NO: 37 |
| ARGBP2 | 8470 | SEQ ID NO: 5 | SEQ ID NO: 38 |
| stathmin-like 2 | 11075 | SEQ ID NO: 6 | SEQ ID NO: 39 |
| myxovirus resistance 2 | 4600 | SEQ ID NO: 7 | SEQ ID NO: 40 |
| IRF7 | 3665 | SEQ ID NO: 8 | SEQ ID NO: 41 |
| GBP2 | 2634 | SEQ ID NO: 9 | SEQ ID NO: 42 |
| SLC28a2 | 9153 | SEQ ID NO: 10 | SEQ ID NO: 43 |
| BDNF | 627 | SEQ ID NO: 11 | SEQ ID NO: 44 |
| phosphodiesterase 3B | 5140 | SEQ ID NO: 12 | SEQ ID NO: 45 |
| TREK2 | 54207 | SEQ ID NO: 13 | SEQ ID NO: 46 |
| trkA | 4914 | SEQ ID NO: 14 | SEQ ID NO: 47 |
| IL1R1 | 3554 | SEQ ID NO: 15 | SEQ ID NO: 48 |
| EEF2k | 29904 | SEQ ID NO: 16 | SEQ ID NO: 49 |
| actin, gamma 2 | 72 | SEQ ID NO: 17 | SEQ ID NO: 50 |
| myosin heavy chain 11 | 4629 | SEQ ID NO: 18 | SEQ ID NO: 51 |
| MRCL3 | 10627 | SEQ ID NO: 19 | SEQ ID NO: 52 |
| MRLC2 | 103910 | SEQ ID NO: 20 | SEQ ID NO: 53 |
| Rho family GTPase 1 | 27289 | SEQ ID NO: 21 | SEQ ID NO: 54 |
| HSPB1 | 3315 | SEQ ID NO: 22 | SEQ ID NO: 55 |
| RIPK4 | 54101 | SEQ ID NO: 23 | SEQ ID NO: 56 |
| type I protein phosphatase inhibitor | 80316 | SEQ ID NO: 24 | SEQ ID NO: 57 |
| transgelin | 6876 | SEQ ID NO: 25 | SEQ ID NO: 58 |
| beta 1 integrin | 3688 | SEQ ID NO: 26 | SEQ ID NO: 59 |
| Desmuslin | 23336 | SEQ ID NO: 27 | SEQ ID NO: 60 |
| C/EBP delta | 1052 | SEQ ID NO: 28 | SEQ ID NO: 61 |
| FBXL22 | 283807 | SEQ ID NO: 29 | SEQ ID NO: 62 |
| AF427491 | | SEQ ID NO: 30 | SEQ ID NO: 63 |
| cig5 | 91543 | SEQ ID NO: 31 | SEQ ID NO: 64 |
| SAMD9 | 54809 | SEQ ID NO: 32 | SEQ ID NO: 65 |
| IFI27 | 3429 | SEQ ID NO: 33 | SEQ ID NO: 66 |

CVHGs and CVHG Products as Markers for CVH and CVH-Related Disorders

In general, Table 3 and Table 5 provide CVHGs that are differentially expressed at in the CVH colon relative to controls. These genes may be a component in the disease mechanism and can be used as markers for diagnosing and monitoring CVH and CVH-related disorders. The CVHGs of Tables 3 and 5, as well as the corresponding CVHG products (CVHPN and CVHPP) may become novel therapeutic targets for the treatment and prevention of CVH and CVH-related disorders. Furthermore, the CVHG products themselves may be used for the treatment of CVH.

Accordingly, the present invention pertains to the use of the CVHGs listed in Tables 3 and 5, the transcribed polynucleotides (CVHPNs), and the encoded polypeptides (CVHPPs) as markers for CVH and CVH-related disorders. Moreover, the use of expression profiles of these genes can indicate the presence of or a risk of CVH and CVH-related disorders. These markers are further useful to correlate differences in levels of expression with a poor or favorable prognosis of CVH and CVH-related disorders. In particular, the present invention is directed to the use of CVHGs and panels of CVHGs set forth in Tables 3 and 5 or homologs thereof. For example, panels of the CVHGs can be conveniently arrayed on solid supports, i.e., biochips, such as the GeneChipo®, for use in kits. The CVHGs can be used to assess the efficacy of a treatment or therapy of CVH and CVH-related disorders, or as a target for a treatment or therapeutic agent. The CVHGs can also be used to produce antibodies specific to CVHG products, and to construct gene therapy vectors that inhibit the development of CVH and CVH-related disorders. Therefore, without limitation as to mechanism, the invention is based in part on the principle that modulation of the expression of the CVHGs of the invention may ameliorate CVH and CVH-related disorders when they are expressed at levels similar or substantially similar to normal (non-diseased) tissue.

In one aspect, the invention provides CVHGs whose level of expression, which signifies their quantity or activity, is correlated with the presence of CVH and CVH-related disorders. In certain preferred embodiments, the invention is performed by detecting the presence of an CVHPN or a CVHPP.

In another aspect of the invention, the expression levels of the CVHGs are determined in a particular subject sample for which either diagnosis or prognosis information is desired. The level of expression of a number of CVHGs simultaneously provides an expression profile, which is essentially a "fingerprint" of the presence or activity of an CVHG or plurality of CVHGs that is unique to the state of the cell. In certain embodiments, comparison of relative levels of expression is indicative of the severity of CVH and CVH-related disorders, and as such permits for diagnostic and prognostic analysis. Moreover, by comparing relative expression profiles of CVHGs from tissue samples taken at different points in time, e.g., pre- and post-therapy and/or at different time points within a course of therapy, information regarding which genes are important in each of these stages is obtained. The identification of genes that are abnormally expressed in CVH versus normal tissue, as well as differentially expressed genes during CVH development, allows the use of this invention in a number of ways. For example, comparison of expression profiles of CVHGs at different stages of the disease progression provides a method for long-term prognosis. In another example mentioned above, the efficacy of a particular treatment regime may be evaluated, including whether a particular drug will act to improve the long-term prognosis in a particular patient.

Similarly, CVHGs listed in Tables 4, 6 and 7 can also be used as targets of CVH treatment and as markers to monitor the efficacy of CVH treatment. The gene products from CVHGs of Tables 4, 6 and 7 may also be used in the treatment of CVH and CVH-related disorders.

The discovery of these differential expression patterns for individual or panels of CVHGs allows for screening test compounds with the goal of modulating a particular expression pattern. For example, screening can be done for compounds that will convert an expression profile for a poor prognosis to one for a better prognosis. In certain embodiments, this may be done by making biochips comprising sets of the significant CVHGs, which can then be used in these screens. These methods can also be done on the protein level; that is, protein expression levels of the CVHGs can be evaluated for diagnostic and prognostic purposes or to screen test compounds. For example, in relation to these embodiments, significant CVHGs may comprise CVHGs which are determined to have modulated activity or expression in response to a therapy regime. Alternatively, the modulation of the activity or expression of a CVHG may be correlated with the diagnosis or prognosis of CVH and CVH-related disorders.

In addition, the CVHGs listed in Tables 3-8 can be administered for gene therapy purposes, including the administration of antisense nucleic acids and RNAi. The CVHG products (including CVHPPs and CVHPNs) and modulator of CVHG products (such as anti-CVHPP antibodies) can also be administered as therapeutic drugs.

For example, the CVHG desmin has significantly increased expression in CVH tissue samples, relative to control tissue samples. The presence of increased mRNA for this gene (or any other CVHGs set forth in Tables 3 and 5), and increased levels of the protein products of this gene (or any other CVHGs set forth in Tables 3 and 5) serve as markers for CVH. Accordingly, amelioration of CVH can be achieved by modulating up-regulated CVH markers, such as desmin, to normal levels.

In another embodiment of the invention, a product of CVHG, either in the form of a polynucleotide or a polypeptide, can be used as a therapeutic compound of the invention. In yet other embodiments, a modulator of CVHG expression or the activity of an CVHG product may be used as a therapeutic compound of the invention, or may be used in combination with one or more other therapeutic compositions of the invention. Formulation of such compounds into pharmaceutical compositions is described in subsections below. Administration of such a therapeutic may suppress bioactivity of CVHG product, and therefore may be used to ameliorate CVH.

Sources of CVHG Products

The CVHG products (CVHPNs and CVHPPs) of the invention may be isolated from any tissue or cell of a subject. It will be apparent to one skilled in the art that bodily fluids, such as blood or feces, may also serve as sources from which the CVHG product of the invention may be assessed. A biological sample of the invention is obtained as a blood sample, a urine or feces sample, a colon biopsy sample. A biological sample may comprise biological components such as blood plasma, serum, erythrocytes, leukocytes, blood platelets, lymphocytes, macrophages, fibroblast cells, mast cells, fat cells, neuronal cells, epithelial cells and the like. The tissue samples containing one or more of the CVHG product themselves may be useful in the methods of the invention, and one skilled in the art will be cognizant of the methods by which such samples may be conveniently obtained, stored and/or preserved.

Isolated Polynucleotides

One aspect of the invention pertains to isolated polynucleotides. Another aspect of the invention pertains to isolated polynucleotide fragments sufficient for use as hybridization probes to identify a CVHPN in a sample, as well as nucleotide fragments for use as PCR probes/primers of the amplification or mutation of the nucleic acid molecules which encode the CVHPP of the invention.

A CVHPN molecule of the present invention, e.g., a polynucleotide molecule having the nucleotide sequence of one of the CVHGs listed in Tables 3-8, or homologs thereof, or a portion thereof, can be isolated using standard molecular biology techniques and the sequence information provided herein, as well as sequence information known in the art. Using all or a portion of the polynucleotide sequence of one of the CVHGs listed Tables 3-8 (or a homolog thereof) as a hybridization probe, a CVHG of the invention or a CVHPN of the invention can be isolated using standard hybridization and cloning techniques.

A CVHPN of the invention can be amplified using cDNA, mRNA or alternatively, genomic DNA, as a template and appropriate oligonucleotide primers according to standard PCR amplification techniques. The polynucleotide so amplified can be cloned into an appropriate vector and characterized by DNA sequence analysis. Furthermore, oligonucleotides corresponding to CVHG nucleotide sequences of the invention can be prepared by standard synthetic techniques, e.g., using an automated DNA synthesizer.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using, for example, software well known in the art. Primers are preferably 22-30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR, which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591.

Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., PCR Methods Applic. 1:11-19, 1991) and walking PCR (Parker et al., Nucl. Acids. Res. 19:3055-60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

In another preferred embodiment, an isolated polynucleotide molecule of the invention comprises a polynucleotide molecule which is a complement of the nucleotide sequence of a CVHG listed in Tables 3-8, or homolog thereof, a CVHPN of the invention, or a portion of any of these nucleotide sequences. A polynucleotide molecule which is complementary to such a nucleotide sequence is one which is sufficiently complementary to the nucleotide sequence such that it can hybridize to the nucleotide sequence, thereby forming a stable duplex.

The polynucleotide molecule of the invention, moreover, can comprise only a portion of the polynucleotide sequence of a CVHG, for example, a fragment which can be used as a probe or primer. The probe/primer typically comprises a substantially purified oligonucleotide. The oligonucleotide typically comprises a region of nucleotide sequence that hybridizes under stringent conditions to at least about 7 or 15, preferably about 25, more preferably about 50, 75, 100, 125, 150, 175, 200, 225, 250, 275, 300, 325, 350, 400 or more consecutive nucleotides of a CVHG or a CVHPN of the invention.

Probes based on the nucleotide sequence of anCVHG or anCVHPN of the invention can be used to detect transcripts or genomic sequences corresponding to the CVHG or CVHPN of the invention. In preferred embodiments, the probe comprises a label group attached thereto, e.g., the label group can be a radioisotope, a fluorescent compound, an enzyme, or an enzyme co-factor. Such probes can be used as a part of a diagnostic kit for identifying cells or tissue which misexpress (e.g., over- or under-express) a CVHG, or which have greater or fewer copies of an CVHG. For example, a level of a CVHG product in a sample of cells from a subject may be determined, or the presence of mutations or deletions of a CVHG of the invention may be assessed.

The invention further encompasses polynucleotide molecules that differ from the polynucleotide sequences of the CVHGs listed in Tables 3-8 but encode the same proteins as those encoded by the genes shown in Tables 3-8 due to degeneracy of the genetic code.

The invention also specifically encompasses homologs of the CVHGs listed in Tables 3-8 of other species. Gene homologs are well understood in the art and are available using databases or search engines such as the Pubmed-Entrez database.

The invention also encompasses polynucleotide molecules which are structurally different from the molecules described above (i.e., which have a slight altered sequence), but which have substantially the same properties as the molecules above (e.g., encoded amino acid sequences, or which are changed only in non-essential amino acid residues). Such molecules include allelic variants, and are described in greater detail in subsections herein.

In addition to the nucleotide sequences of the CVHGs listed in Tables 3-8, it will be appreciated by those skilled in the art that DNA sequence polymorphisms that lead to changes in the amino acid sequences of the proteins encoded by the CVHGs listed in Tables 3-8 may exist within a population (e.g., the human population). Such genetic polymorphism in the CVHGs listed in Tables 3-8 may exist among individuals within a population due to natural allelic variation. An allele is one of a group of genes which occur alternatively at a given genetic locus. In addition it will be appreciated that DNA polymorphisms that affect RNA expression levels can also exist that may affect the overall expression level of that gene (e.g., by affecting regulation or degradation). As used herein, the phrase "allelic variant" includes a nucleotide sequence which occurs at a given locus or to a polypeptide encoded by the nucleotide sequence.

Polynucleotide molecules corresponding to natural allelic variants and homologs of the CVHGs can be isolated based on their homology to the CVHGs listed in Tables 3-8, using the cDNAs disclosed herein, or a portion thereof, as a hybridization probe according to standard hybridization techniques under stringent hybridization conditions. Polynucleotide molecules corresponding to natural allelic variants and homologs of the CVHGs of the invention can further be isolated by mapping to the same chromosome or locus as the CVHGs of the invention.

In another embodiment, an isolated polynucleotide molecule of the invention is at least 15, 20, 25, 30, 50, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000 or more nucleotides in length and hybridizes under stringent conditions to a polynucleotide molecule corresponding to a nucleotide sequence of an CVHG of the invention. Preferably, the isolated polynucleotide molecule of the invention hybridizes under stringent conditions to the sequence of one of the CVHGs set forth in Tables 3-8, or corresponds to a naturally-occurring polynucleotide molecule.

In addition to naturally-occurring allelic variants of the CVHG of the invention that may exist in the population, the skilled artisan will further appreciate that changes can be introduced by mutation into the nucleotide sequences of the CVHGs of the invention, thereby leading to changes in the amino acid sequence of the encoded proteins, without altering the functional activity of these proteins. For example, nucleotide substitutions leading to amino acid substitutions at "non-essential" amino acid residues can be made. A "non-essential" amino acid residue is a residue that can be altered from the wild-type sequence of a protein without altering the biological activity, whereas an "essential" amino acid residue is required for biological activity. For example, amino acid residues that are conserved among allelic variants or homologs of a gene (e.g., among homologs of a gene from different species) are predicted to be particularly unamenable to alteration.

In yet other aspects of the invention, polynucleotides of a CVHG may comprise one or more mutations. An isolated polynucleotide molecule encoding a protein with a mutation in a CVHPP of the invention can be created by introducing one or more nucleotide substitutions, additions or deletions into the nucleotide sequence of the gene encoding the CVHPP, such that one or more amino acid substitutions, additions or deletions are introduced into the encoded protein. Such techniques are well known in the art. Mutations can be introduced into the CVHG of the invention by standard techniques, such as site-directed mutagenesis and PCR-mediated mutagenesis. Preferably, conservative amino acid substitutions are made at one or more predicted non-essential amino acid residues. Alternatively, mutations can be introduced randomly along all or part of a coding sequence of a CVHG of the invention, such as by saturation mutagenesis, and the resultant mutants can be screened for biological activity to identify mutants that retain activity. Following mutagenesis, the encoded protein can be expressed recombinantly and the activity of the protein can be determined.

A polynucleotide may be further modified to increase stability in vivo. Possible modifications include, but are not limited to, the addition of flanking sequences at the 5' and/or 3' ends; the use of phosphorothioate or 2 O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Another aspect of the invention pertains to isolated polynucleotide molecules, which are antisense to the CVHGs of the invention. An "antisense" polynucleotide comprises a nucleotide sequence which is complementary to a "sense" polynucleotide encoding a protein, e.g., complementary to the coding strand of a double-stranded cDNA molecule or complementary to an mRNA sequence. Accordingly, an antisense polynucleotide can hydrogen bond to a sense polynucleotide. The antisense polynucleotide can be complementary to an entire coding strand of a gene of the invention or to only a portion thereof. In one embodiment, an antisense polynucleotide molecule is antisense to a "coding region" of the coding strand of a nucleotide sequence of the invention. The term "coding region" includes the region of the nucleotide sequence comprising codons which are translated into amino acids. In another embodiment, the antisense polynucleotide molecule is antisense to a "noncoding region" of the coding strand of a nucleotide sequence of the invention.

Antisense polynucleotides of the invention can be designed according to the rules of Watson and Crick base pairing. The antisense polynucleotide molecule can be complementary to the entire coding region of an mRNA corresponding to a gene of the invention, but more preferably is an oligonucleotide which is antisense to only a portion of the coding or noncoding region. An antisense oligonucleotide can be, for example, about 5, 10, 15, 20, 25, 30, 35, 40, 45 or 50 nucleotides in length. An antisense polynucleotide of the invention can be constructed using chemical synthesis and enzymatic ligation reactions using procedures known in the art. For example, an antisense polynucleotide can be chemically synthesized using naturally occurring nucleotides or variously modified nucleotides designed to increase the biological stability of the molecules or to increase the physical stability of the duplex formed between the antisense and sense polynucleotides, e.g., phosphorothioate derivatives and acridine substituted nucleotides can be used. Examples of modified nucleotides which can be used to generate the antisense polynucleotide include 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenosine, unacil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, (acp3)w, and 2,6-diaminopurine. Alternatively, the antisense polynucleotide can be produced biologically using an expression vector into which a polynucleotide has been subcloned in an antisense orientation (i.e., RNA transcribed from the inserted polynucleotide will be of an antisense orientation to a target polynucleotide of interest, described further in the following subsection).

The antisense polynucleotide molecules of the invention are typically administered to a subject or generated in situ such that they hybridize with or bind to cellular mRNA and/or genomic DNA encoding a CVHPP of the invention to thereby inhibit expression of the protein, e.g., by inhibiting transcription and/or translation. The hybridization can be by conventional nucleotide complementarity to form a stable duplex or, for example, in the cases of an antisense polynucleotide molecule which binds to DNA duplexes, through specific interactions in the major groove of the double helix. An example of a route of administration of antisense polynucleotide molecules of the invention include direct injection at a tissue site. Alternatively, antisense polynucleotide molecules can be modified to target selected cells and then administered systemically. For example, for systemic administration, antisense molecules can be modified such that they specifically bind to receptors or antigens expressed on a selected cell surface, e.g., by linking the antisense polynucleotide molecules to peptides or antibodies which bind to cell surface receptors or antigens. The antisense polynucleotide molecules can also be delivered to cells using the vectors described herein. To achieve sufficient intracellular concentrations of the antisense molecules, vector constructs comprising the antisense polynucleotide molecules are preferably placed under the control of a strong promoter.

In yet another embodiment, the antisense polynucleotide molecule of the invention is an α-anomeric polynucleotide molecule. An α-anomeric polynucleotide molecule forms specific double-stranded hybrids with complementary RNA in which, contrary to the usual β-units, the strands run parallel to each other. The antisense polynucleotide molecule can also comprise a 2'-o-methylribonucleotide or a chimeric RNA-DNA analogue.

In still another embodiment, an antisense polynucleotide of the invention is a ribozyme. Ribozymes are catalytic RNA molecules with ribonuclease activity which are capable of cleaving a single-stranded polynucleotide, such as an mRNA, to which they have a complementary region. Thus, ribozymes (e.g., hammerhead ribozymes) can be used to catalytically cleave mRNA transcripts of the CVHGs of the invention to thereby inhibit translation of the mRNA. A ribozyme having specificity for a CVHPN can be designed based upon the nucleotide sequence of the CVHPN. For example, a derivative of a Tetrahymena L-19 IVS RNA can be constructed in which the nucleotide sequence of the active site is complementary to the nucleotide sequence to be cleaved in a CVHG mRNA. Alternatively, mRNA transcribed from a CVHG can be used to select a catalytic RNA having a specific ribonuclease activity from a pool of RNA molecules. Alternatively, expression of a CVHG of the invention can be inhibited by targeting nucleotide sequences complementary to the regulatory region of the CVHG (e.g., the promoter and/or enhancers) to form triple helical structures that prevent transcription of the gene in target cells.

Expression of the CVHGs of the invention can also be inhibited using RNA interference ("RNA$_i$"). This is a technique for post-transcriptional gene silencing ("PTGS"), in which target gene activity is specifically abolished with cognate double-stranded RNA ("dsRNA"). RNA$_i$ resembles in many aspects PTQS in plants and has been detected in many invertebrates including the trypanosome, hydra, planaria, nematode and fruit fly (*Drosophila melanogaster*). It may be involved in the modulation of transposable element mobilization and antiviral state formation. RNA$_i$ technology is disclosed, for example, in U.S. Pat. No. 5,919,619 and PCT Publication Nos. WO99/14346 and WO01/29058. Basically, dsRNA of about 21 nucleotides, homologous to the target gene, is introduced into the cell and a sequence specific reduction in gene activity is observed.

In yet another embodiment, the polynucleotide molecules of the present invention can be modified at the base moiety, sugar moiety or phosphate backbone to improve the stability, hybridization, or solubility of the molecule. For example, the deoxyribose phosphate backbone of the polynucleotide molecules can be modified to generate peptide polynucleotides. As used herein, the terms "peptide polynucleotides" or "PNAs" refer to polynucleotide mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols.

PNAs can be used in therapeutic and diagnostic applications. For example, PNAs can be used as antisense agents for sequence-specific modulation of CVHG expression by, for example, inducing transcription or translation arrest or inhibiting replication. PNAs of the polynucleotide molecules of the invention can be used in the analysis of single base pair mutations in a gene, (e.g., by PNA-directed PCR clamping). They may also serve as artificial restriction enzymes when used in combination with other enzymes (e.g., S1 nucleases) or as probes or primers for DNA sequencing or hybridization.

In another embodiment, PNAs can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of the polynucleotide molecules of the invention can be generated which may combine the advantageous properties of PNA and DNA. Such chimeras allow DNA recognition enzymes, (e.g., DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation. The synthesis of PNA-DNA chimeras can be performed. For example, a DNA chain can be synthesized on a solid support using standard phosphoramidite coupling chemistry. Modified nucleoside analogs, such as 5'-(4-methoxytrityl)amino-5'-deoxy-thymidine phosphoramidite, can be used as a spacer between the PNA and the 5' end of DNA. PNA monomers are then coupled in a stepwise manner to produce a chimeric molecule with a 5' PNA segment and a 3' DNA segment. Alternatively, chimeric molecules can be synthesized with a 5' DNA segment and a 3' PNA segment.

In other embodiments, the oligonucleotide may include other appended groups such as peptides (e.g., for targeting host cell receptors in vivo), or agents facilitating transport across the cell membrane or the blood-kidney barrier (see, e.g. PCT Publication No. W089/10134). In addition, oligonucleotides can be modified with hybridization-triggered cleavage agents or intercalating agents. To this end, the oligonucleotide may be conjugated to another molecule (e.g., a peptide, hybridization triggered cross-linking agent, transport agent, or hybridization-triggered cleavage agent). Finally, the oligonucleotide may be detectably labeled, either such that the label is detected by the addition of another reagent (e.g., a substrate for an enzymatic label), or is detectable immediately upon hybridization of the nucleotide (e.g., a radioactive label or a fluorescent label).

Isolated Polypeptides

Several aspects of the invention pertain to isolated CVHPPs, and biologically active portions thereof, as well as polypeptide fragments suitable for use as immunogens to raise anti-CVHPP antibodies. In one embodiment, native CVHPPs can be isolated from cells or tissue sources by an appropriate purification scheme using standard protein purification techniques. Standard purification methods include electrophoretic, molecular, immunological and chromatographic techniques, including ion exchange, hydrophobic, affinity, and reverse-phase HPLC chromatography, and chromatofocusing. For example, a CVHPP may be purified using a standard anti-CVHPP antibody column. Ultrafiltration and diafiltration techniques, in conjunction with protein concentration, are also useful. The degree of purification necessary will vary depending on the use of the CVHPP. In some instances no purification will be necessary.

In another embodiment, CVHPPs or mutated CVHPPs are produced by recombinant DNA techniques. Alternative to recombinant expression, a CVHPP or mutated CVHPP can be synthesized chemically using standard peptide synthesis techniques.

The invention also provides variants of CVHPPs. The variant of a CVHPP is substantially homologous to the native CVHPP encoded by an CVHG listed in Table 4, and retains the functional activity of the native CVHPP, yet differs in amino acid sequence due to natural allelic variation or mutagenesis, as described in detail above. Accordingly, in another embodiment, the variant of a CVHPP is a protein which comprises an amino acid sequence at least about 60%, 65%, 70%, 75%, 80%, 85%, 90%, 95%, 98% or more homologous to the amino acid sequence of the original CVHPP.

In a non-limiting example, as used herein, proteins are referred to as "homologs" and "homologous" where a first protein region and a second protein region are compared in terms of identity. To determine the percent identity of two amino acid sequences or of two polynucleotide sequences, the sequences are aligned for optimal comparison purposes (e.g., gaps can be introduced in one or both of a first and a second amino acid or polynucleotide sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleotide "identity" is equivalent to amino acid or nucleotide "homology"). The percent identity between the two sequences is a function of the number of identical positions shared by the sequences, taking into account the number of gaps and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (J. Mol. Biol. 48:444-453, 1970) algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6, In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6.

The polynucleotide and protein sequences of the present invention can further be used as a "query sequence" to perform a search against public databases to, for example, identify other family members or related sequences. Such searches can be performed using BLAST programs available at the BLAST website maintained by the National Center of biotechnology Information (NCBI), National Library of Medicine, Washington D.C. USA.

The invention also provides chimeric or fusion CVHPPs. Within a fusion CVHPP the polypeptide can correspond to all or a portion of a CVHPP. In a preferred embodiment, a fusion CVHPP comprises at least one biologically active portion of a CVHPP. Within the fusion protein, the term "operatively linked" is intended to indicate that the CVHPP-related polypeptide and the non-CVHPP-related polypeptide are fused in-frame to each other. The non-CVHPP-related polypeptide can be fused to the N-terminus or C-terminus of the CVHPP-related polypeptide.

A peptide linker sequence may be employed to separate the CVHPP-related polypeptide from non-CVHPP-related polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the CVHPP-related polypeptide and non-CVHPP-related polypeptide; and (3) the lack of hydrophobic or charged residues that might react with the polypeptide functional epitopes. Preferred peptide linker sequences contain gly, asn and ser residues. Other near neutral amino acids, such as thr and ala may also be used in the linker sequence. Amino acid sequences which may be used as linkers are well known in the art. The linker sequence may generally be from 1 to about 50 amino acids in length. Linker sequences are not required when the CVHPP-related polypeptide and non-CVHPP-related polypeptide have non-essential N-terminal amino acid regions that can be used to separate the functional domains and prevent steric interference.

For example, in one embodiment, the fusion protein is a glutathione S-transferase (GST)-CVHPP fusion protein in which the CVHPP sequences are fused to the C-terminus of the GST sequences. Such fusion proteins can facilitate the purification of recombinant CVHPPs.

The CVHPP-fusion proteins of the invention can be incorporated into pharmaceutical compositions and administered to a subject in vivo, as described herein. The CVHPP-fusion proteins can be used to affect the bioavailability of a CVHPP substrate. CVHPP-fusion proteins may be useful therapeutically for the treatment of, or prevention of, damages caused by, for example, (i) aberrant modification or mutation of a CVHG; (ii) mis-regulation of a CVHG; and (iii) aberrant post-translational modification of a CVHPP.

Moreover, the CVHPP-fusion proteins of the invention can be used as immunogens to produce anti-CVHPP antibodies in a subject, to purify CVHPP ligands, and to identify molecules which inhibit the interaction of a CVHPP with a CVHPP substrate in screening assays.

Preferably, a CVHPP-chimeric or fusion protein of the invention is produced by standard recombinant DNA techniques. For example, DNA fragments coding for the different polypeptide sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence. Moreover, many expression vectors are commercially available that already encode a fusion moiety (e.g., a GST polypeptide). A CVHPP-encoding polynucleotide can be cloned into such an expression vector such that the fusion moiety is linked in-frame to the CVHPP.

A signal sequence can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to polypeptides from which the signal sequence has been proteolytically cleaved (i.e., the cleavage products). In one embodiment, a polynucleotide sequence encoding a signal sequence can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present invention also pertains to variants of the CVHPPs of the invention which function as either agonists or as antagonists to the CVHPPs. In one embodiment, antagonists or agonists of CVHPPs are used as therapeutic agents. For example, antagonists of an up-regulated CVHG that can decrease the activity or expression of such a gene and therefore ameliorate CVH in a subject wherein the CVHG is abnormally increased in level or activity. In this embodiment, treatment of such a subject may comprise administering an antagonist wherein the antagonist provides decreased activity or expression of the targeted CVHG.

In certain embodiments, an agonist of the CVHPPs can retain substantially the same, or a subset, of the biological activities of the naturally occurring form of a CVHPP or may enhance an activity of a CVHPP. In certain embodiments, an antagonist of a CVHPP can inhibit one or more of the activities of the naturally occurring form of the CVHPP by, for example, competitively modulating an activity of a CVHPP. Thus, specific biological effects can be elicited by treatment with a variant of limited function. In one embodiment, treatment of a subject with a variant having a subset of the biological activities of the naturally occurring forth of the protein has fewer side effects in a subject relative to treatment with the naturally occurring form of the CVHPP.

Mutants of a CVHPP which function as either CVHPP agonists or as CVHPP antagonists can be identified by screening combinatorial libraries of mutants, e.g., truncation mutants, of a CVHPP for CVHPP agonist or antagonist activity. In certain embodiments, such mutants may be used, for example, as a therapeutic protein of the invention. A diverse library of CVHPP mutants can be produced by, for example, enzymatically ligating a mixture of synthetic oligonucleotides into gene sequences such that a degenerate set of potential CVHPP sequences is expressible as individual polypeptides, or alternatively, as a set of larger fusion proteins (e.g., for phage display) containing the set of CVHPP sequences therein. There are a variety of methods which can be used to produce libraries of potential CVHPP variants from a degenerate oligonucleotide sequence. Chemical synthesis of a degenerate gene sequence can be performed in an automatic DNA synthesizer, and the synthetic gene is then ligated into an appropriate expression vector. Use of a degenerate set of genes allows for the provision, in one mixture, of all of the sequences encoding the desired set of potential CVHPP sequences. Methods for synthesizing degenerate oligonucleotides are known in the art.

In addition, libraries of fragments of a protein coding sequence corresponding to a CVHPP of the invention can be used to generate a diverse or heterogenous population of CVHPP fragments for screening and subsequent selection of variants of a CVHPP. In one embodiment, a library of coding sequence fragments can be generated by treating a double-stranded PCR fragment of a CVHPP coding sequence with a nuclease under conditions wherein nicking occurs only about once per molecule, denaturing the double-stranded DNA, renaturing the DNA to form double-stranded DNA which can include sense/antisense pairs from different nicked products, removing single-stranded portions from reformed duplexes by treatment with S1 nuclease, and ligating the resulting fragment library into an expression vector. By this method, an expression library can be derived which encodes N-terminal, C-terminal and internal fragments of various sizes of the CVHPP.

Several techniques are known in the art for screening gene products of combinatorial libraries made by point mutations or truncation, and for screening cDNA libraries for gene products having a selected property. The most widely used techniques, which are amenable to high-throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify CVHPP variants (Delgrave et al. Protein Engineering 6:327-331, 1993).

Portions of a CVHPP or variants of a CVHPP having less than about 100 amino acids, and generally less than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. Equipment for automated synthesis of polypeptides is commercially available from suppliers such as Perkin Elmer/ Applied BioSystems Division (Foster City, Calif.), and may be operated according to the manufacturer's instructions.

Methods and compositions for screening for protein inhibitors or activators are known in the art (see U.S. Pat. Nos. 4,980,281, 5,266,464, 5,688,635, and 5,877,007, which are incorporated herein by reference).

It is contemplated in the present invention that CVHPPs are cleaved into fragments for use in further structural or functional analysis, or in the generation of reagents such as CVHPP and CVHPP-specific antibodies. This can be accomplished by treating purified or unpurified polypeptide with a proteolytic enzyme (i.e., a proteinase) including, but not limited to, serine proteinases (e.g., chymotrypsin, trypsin, plasmin, elastase, thrombin, substilin) metal proteinases (e.g., carboxypeptidase A, carboxypeptidase B, leucine aminopeptidase, thermolysin, collagenase), thiol proteinases (e.g., papain, bromelain, Streptococcal proteinase, clostripain) and/or acid proteinases (e.g., pepsin, gastricsin, trypsinogen). Polypeptide fragments are also generated using chemical means such as treatment of the polypeptide with cyanogen bromide (CNBr), 2-nitro-5-thiocyanobenzoic acid, isobenzoic acid, BNPA-skatole, hydroxylamine or a dilute acid solution. Recombinant techniques are also used to produce specific fragments of a CVHPP.

In addition, the invention also contemplates that compounds sterically similar to a particular CVHPP may be formulated to mimic the key portions of the peptide structure, called peptidomimetics or peptide mimetics. Mimetics are peptide-containing molecules which mimic elements of polypeptide secondary structure. See, for example, U.S. Pat. No. 5,817,879 (incorporated by reference hereinafter in its entirety). The underlying rationale behind the use of peptide mimetics is that the peptide backbone of pplypeptides exists chiefly to orient amino acid side chains in such a way as to facilitate molecular interactions, such as those of receptor and ligand. Recently, peptide and glycoprotein mimetic antigens have been described which elicit protective antibody to Neisseria meningitidis serogroup B, thereby demonstrating the utility of mimetic applications (Moe et al., Int. Rev. Immunol. 20:201-20, 2001; Berezin et al., J Mol Neurosci. 22:33-39, 2004). Successful applications of the peptide mimetic concept have thus far focused on mimetics of β-turns within polypeptides. Likely β-turn structures within a CVHPP can be predicted by computer-based algorithms. For example, U.S. Pat. No. 5,933,819, incorporated by reference hereinafter in its entirety, describes a neural network based method and system for identifying relative peptide binding motifs from limited experimental data. In particular, an artificial neural network (ANN) is trained with peptides with known sequence and function (i.e., binding strength) identified from a phage display library. The ANN is then challenged with unknown peptides, and predicts relative binding motifs. Analysis of the unknown peptides validate the predictive capability of the ANN. Once the component amino acids of the turn are determined, mimetics can be constructed to achieve a similar spatial orientation of the essential elements of the amino acid side chains, as discussed in U.S. Pat. No. 6,420119 and U.S. Pat. No. 5,817,879, and in Kyte and Doolittle, J. Mol. Biol., 157:105-132, 1982; Moe and Granoff, Int. Rev. Immunol., 20(2):201-20, 2001; Granoff et al., J. Immunol., 167(11):6487-96, 2001 (each incorporated by reference hereinafter in its entirety).

Antibodies

In another aspect, the invention includes antibodies that are specific to CVHPPs of the invention or their variants. Preferably the antibodies are monoclonal, and most preferably, the antibodies are humanized, as per the description of antibodies described below.

An isolated CVHPP, or a portion or fragment thereof, can be used as an immunogen to generate antibodies that bind the CVHPP using standard techniques for polyclonal and monoclonal antibody preparation. A full-length CVHPP can be used or, alternatively, the invention provides antigenic peptide fragments of the CVHPP for use as immunogens. The antigenic peptide of a CVHPP comprises at least 8 amino acid residues of an amino acid sequence encoded by an CVHG set forth in Tables 3-8 or a homolog thereof, and encompasses an epitope of a CVHPP such that an antibody raised against the peptide forms a specific immune complex with the CVHPP. Preferably, the antigenic peptide comprises at least 8 amino acid residues, more preferably at least 12 amino acid residues, even more preferably at least 16 amino acid residues, and most preferably at least 20 amino acid residues.

Immunogenic portions (epitopes) may generally be identified using well known techniques. Such techniques include screening polypeptides for the ability to react with antigen-specific antibodies, antisera and/or T-cell lines or clones. As used herein, antisera and antibodies are "antigen-specific" if they bind to an antigen with a binding affinity equal to, or greater than $10^5$ $M^{-1}$. Such antisera and antibodies may be prepared as described herein, and using well known techniques. An epitope of a CVHPP is a portion that reacts with such antisera and/or T-cells at a level that is not substantially less than the reactivity of the full length polypeptide (e.g., in an ELISA and/or T-cell reactivity assay). Such epitopes may react within such assays at a level that is similar to or greater than the reactivity of the full length polypeptide. Such screens may generally be performed using methods well known to those of ordinary skill in the art. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

Preferred epitopes encompassed by the antigenic peptide are regions of the CVHPP that are located on the surface of the protein, e.g., hydrophilic regions, as well as regions with high antigenicity.

A CVHPP immunogen typically is used to prepare antibodies by immunizing a suitable subject, (e.g., rabbit, goat, mouse or other mammal) with the immunogen. An appropriate immunogenic preparation can contain, for example, recombinantly expressed CVHPP or a chemically synthesized CVHPP. The preparation can further include an adjuvant, such as Freund's complete or incomplete adjuvant, or a similar immunostimulatory agent. Immunization of a suitable subject with an immunogenic CVHPP preparation induces a polyclonal anti-CVHPP antibody response. Techniques for preparing, isolating and using antibodies are well known in the art.

Accordingly, another aspect of the invention pertains to monoclonal or polyclonal anti-CVHPP antibodies and immunologically active portions of the antibody molecules, including F(ab) and F(ab')$_2$ fragments which can be generated by treating the antibody with an enzyme such as pepsin.

Polyclonal anti-CVHPP antibodies can be prepared as described above by immunizing a suitable subject with a CVHPP. The anti-CVHPP antibody titer in the immunized subject can be monitored over time by standard techniques, such as with an enzyme linked immunosorbent assay (ELISA) using immobilized CVHPP. If desired, the antibody molecules directed against CVHPPs can be isolated from the subject (e.g., from the blood) and further purified by well known techniques, such as protein A chromatography, to obtain the IgG fraction. At an appropriate time after immunization, e.g., when the anti-CVHPP antibody titers are highest, antibody-producing cells can be obtained from the subject and used to prepare monoclonal antibodies by standard techniques, such as the hybridoma technique, human B cell hybridoma technique, the EBV-hybridoma technique, or trioma techniques. The technology for producing monoclonal antibody hybridomas is well known. Briefly, an immortal cell line (typically a myeloma) is fused to lymphocytes (typically splenocytes) from a mammal immunized with a CVHPP immunogen as described above, and the culture supernatants of the resulting hybridoma cells are screened to identify a hybridoma producing a monoclonal antibody that binds to a CVHPP of the invention.

Any of the many well known protocols used for fusing lymphocytes and immortalized cell lines can be applied for the purpose of generating an anti-CVHPP monoclonal antibody. Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp210-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind to a CVHPP, e.g., using a standard ELISA assay.

Alternative to preparing monoclonal antibody-secreting hybridomas, a monoclonal anti-CVHPP antibody can be identified and isolated by screening a recombinant combinatorial immunoglobulin library (e.g., an antibody phage display library) with CVHPP to thereby isolate immunoglobulin library members that bind to a CVHPP. Kits for generating and screening phage display libraries are commercially available.

The anti-CVHPP antibodies also include "Single-chain Fv" or "scFv" antibody fragments. The scFv fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the scFv to form the desired structure for antigen binding.

Additionally, recombinant anti-CVHPP antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art.

Humanized antibodies are particularly desirable for therapeutic treatment of human subjects. Humanized forms of non-human (e.g., murine) antibodies are chimeric molecules of immunoglobulins, immunoglobulin chains or fragments thereof (such as Fv, Fab, Fab', F(ab')$_2$ or other antigen-binding subsequences of antibodies), which contain minimal sequence derived from non-human immunoglobulin. Humanized antibodies include human immunoglobulins (recipient antibody) in which residues forming a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the constant regions being those of a human immunoglobulin consensus sequence. The humanized antibody will preferably also comprise at least a portion of an immunoglobulin constant region (Fc), typically that of a human immunoglobulin.

Such humanized antibodies can be produced using transgenic mice which are incapable of expressing endogenous immunoglobulin heavy and light chain genes, but which can express human heavy and light chain genes. The transgenic mice are immunized in the normal fashion with a selected antigen, e.g., all or a portion of a polypeptide corresponding to a CVHPP of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies.

Humanized antibodies which recognize a selected epitope can be generated using a technique referred to as "guided selection." In this approach a selected non-human monoclonal antibody, e.g., a murine antibody, is used to guide the selection of a humanized antibody recognizing the same epitope.

In a preferred embodiment, the antibodies to CVHPP are capable of reducing or eliminating the biological function of CVHPP, as is described below. That is, the addition of anti-CVHPP antibodies (either polyclonal or preferably monoclonal) to CVHPP (or cells containing CVHPP) may reduce or eliminate the CVHPP activity. Generally, at least a 25% decrease in activity is preferred, with at least about 50% being particularly preferred and about a 95-100% decrease being especially preferred.

An anti-CVHPP antibody can be used to isolate a CVHPP of the invention by standard techniques, such as affinity chromatography or immunoprecipitation. An anti-CVHPP antibody can facilitate the purification of natural CVHPPs from cells and of recombinantly produced CVHPPs expressed in host cells. Moreover, an anti-CVHPP antibody can be used to detect a CVHPP (e.g., in a cellular lysate or cell supernatant on the cell surface) in order to evaluate the abundance and pattern of expression of the CVHPP. Anti-CVHPP antibodies can be used diagnostically to monitor protein levels in tissue as part of a clinical testing procedure, for example, to determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive materials include $^{125}$I, $^{131}$I, $^{35}$S or $^3$H.

Anti-CVHPP antibodies of the invention are also useful for targeting a therapeutic to a cell or tissue comprising the antigen of the anti-CVHPP antibody. For example, a therapeutic, such as a small molecule, can be linked to the anti-CVHPP antibody in order to target the therapeutic to the cell or tissue comprising the CVHPP antigen. The method is particularly useful in connection with CVHPPs which are surface markers.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional, may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule. Alternatively, linkers that provide multiple sites for attachment can be used.

As is well known in the art, a given polypeptide or polynucleotide may vary in its immunogenicity. It is often necessary therefore to couple the immunogen (e.g., a polypeptide or polynucleotide) of the present invention with a carrier. Exemplary and preferred carriers are CRM197, E coli (LT) toxin, V. cholera (CT) toxin, keyhole limpet hemocyanin (KLH) and bovine serum albumin (BSA). Other albumins such as ovalbumin, mouse serum albumin or rabbit serum albumin can also be used as carriers.

Where a CVHPP (or a fragment thereof) and a carrier protein are conjugated (i.e., covalently associated), conjugation may be any chemical method, process or genetic technique commonly used in the art. For example, a CVHPP (or a fragment thereof) and a carrier protein, may be conjugated by techniques, including, but not limited to: (1) direct coupling via protein functional groups (e.g., thiol-thiol linkage, amine-carboxyl linkage, amine-aldehyde linkage; enzyme direct coupling); (2) homobifunctional coupling of amines (e.g., using bis-aldehydes); (3) homobifunctional coupling of thiols (e.g., using bis-maleimides); (4) homobifunctional coupling via photoactivated reagents (5) heterobifunctional coupling of amines to thiols (e.g., using maleimides); (6) heterobifunctional coupling via photoactivated reagents (e.g., the β-carbonyldiazo family); (7) introducing amine-reactive groups into a poly- or oligosaccharide via cyanogen bromide activation or carboxymethylation; (8) introducing thiol-reactive groups into a poly- or oligosaccharide via a heterobifunctional compound such as maleimido-hydrazide; (9) protein-lipid conjugation via introducing a hydrophobic group into the protein and (10) protein-lipid conjugation via incorporating a reactive group into the lipid. Also, contemplated are heterobifunctional "non-covalent coupling" techniques such the Biotin-Avidin interaction. For a comprehensive review of conjugation techniques, see Aslam and Dent (Aslam and Dent, "Bioconjugation: Protein Coupling Techniques for the Biomedical Sciences," Macmillan Reference Ltd., London, England, 1998), incorporated hereinafter by reference in its entirety.

In a specific embodiment, antibodies to a CVHPP may be used to eliminate the CVHPP in vivo by activating the complement system or mediating antibody-dependent cellular cytotoxicity (ADCC), or cause uptake of the antibody coated cells by the receptor-mediated endocytosis (RE) system.

Vectors

Another aspect of the invention pertains to vectors containing a polynucleotide encoding a CVHPP, a variant of a CVHPP, or a portion thereof. One type of vector is a "plasmid," which includes a circular double-stranded DNA loop into which additional DNA segments can be ligated. In the present specification, "plasmid" and "vector" can be used interchangeably as the plasmid is the most commonly used form of vector. Vectors also include expression vectors and gene delivery vectors.

The expression vectors of the invention comprise a polynucleotide encoding a CVHPP or a portion thereof in a form suitable for expression of the polynucleotide in a host cell, which means that the expression vectors include one or more regulatory sequences, selected on the basis of the host cells to be used for expression, and operatively linked to the polynucleotide sequence to be expressed. It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, such as CVHPPs, mutant forms of CVHPPs, CVHPP-fusion proteins, and the like.

The expression vectors of the invention can be designed for expression of CVHPPs in prokaryotic or eukaryotic cells. For example, CVHPPs can be expressed in bacterial cells such as E. coli, insect cells (using baculovirus expression vectors), yeast cells or mammalian cells. Alternatively, the expression vector can be transcribed and translated in vitro, for example using T7 promoter regulatory sequences and T7 polymerase.

The expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of the recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia, Piscataway, N.J.), pMAL (New England Biolabs, Beverly, Mass.) and pRITS (Pharmacia, Piscataway, N.J.) which fuse glutathione S transferase (GST), maltose E binding protein, and protein A, respectively, to the target recombinant protein.

Purified fusion proteins can be utilized in CVHPP activity assays, (e.g., direct assays or competitive assays described in detail below), or to generate antibodies specific for CVHPPs.

One strategy to maximize recombinant protein expression in E. coli is to express the protein in a host bacteria with an impaired capacity to proteolytically cleave the recombinant protein. Another strategy is to alter the polynucleotide sequence of the polynucleotide to be inserted into an expression vector so that the individual codons for each amino acid are those preferentially utilized in E. coli, Such alteration of polynucleotide sequences of the invention can be carried out by standard DNA synthesis techniques.

In another embodiment, the CVHPP expression vector is a yeast expression vector. Examples of vectors for expression in yeast S. cerevisiae include pYepSec1, pMFa, pJRY88, pYES2 and picZ (Invitrogen Corp, San Diego, Calif.).

Alternatively, CVHPPs of the invention can be expressed in insect cells using baculovirus expression vectors. Baculovirus vectors available for expression of proteins in cultured insect cells (e.g., Sf9 cells) include the pAc series and the pVL series.

In yet another embodiment, a polynucleotide of the invention is expressed in mammalian cells using a mammalian expression vector. Examples of mammalian expression vectors include pCDM8 and pMT2PC. When used in mammalian cells, the expression vector's control functions are often provided by viral regulatory elements. For example, commonly used promoters are derived from polyoma, adenovirus 2 and 5, cytomegalovirus and Simian Virus 40, Target gene expression from the pTrc vector relies on host RNA polymerase transcription from a hybrid trp-lac fusion promoter. Target gene expression from the pET 1 d vector relies on transcription from a T7 gn10-lac fusion promoter mediated by a coexpressed viral RNA polymerase (T7 gn1). This viral polymerase is supplied by host strains BL21 (DE3) or HSLE174(DE3) from a resident prophage harboring a T7 gn1 gene under the transcriptional control of the lacUV 5 promoter.

In another embodiment, the mammalian expression vector is capable of directing expression of the polynucleotide preferentially in a particular cell type (e.g., tissue-specific regulatory elements are used to express the polynucleotide). Tissue-specific regulatory elements are known in the art and may include epithelial cell-specific promoters. Other non-limiting examples of suitable tissue-specific promoters include the liver-specific promoter (e.g., albumin promoter), lymphoid-specific promoters, promoters of T cell receptors and immunoglobulins, neuron-specific promoters (e.g., the neurofilament promoter), pancreas-specific promoters (e.g., insulin promoter), and mammary gland-specific promoters (e.g., milk whey promoter). Developmentally-regulated promoters (e.g., the α-fetoprotein promoter) are also encompassed.

The invention provides a recombinant expression vector comprising a polynucleotide encoding a CVHPP cloned into the expression vector in an antisense orientation. That is, the DNA molecule is operatively linked to a regulatory sequence in a manner which allows for expression (by transcription of the DNA molecule) of an RNA molecule which is antisense to mRNA corresponding to a CVHG of the invention. Regulatory sequences operatively linked to a polynucleotide cloned in the antisense orientation can be chosen which direct the continuous expression of the antisense RNA molecule in a variety of cell types, for instance, viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense polynucleotides are produced under the control of a high efficiency regulatory region, the activity of which can be determined by the cell type into which the vector is introduced.

The invention further provides gene delivery vehicles for delivery of polynucleotides to cells, tissues, or a mammal for expression. For example, a polynucleotide sequence of the invention can be administered either locally or systemically in a gene delivery vehicle. These constructs can utilize viral or non-viral vector approaches in in vivo or ex vivo modality. Expression of the coding sequence can be induced using endogenous mammalian or heterologous promoters. Expression of the coding sequence in vivo can be either constituted or regulated. The invention includes gene delivery vehicles capable of expressing the contemplated polynucleotides. The gene delivery vehicle is preferably a viral vector and, more preferably, a retroviral, lentiviral, adenoviral, adeno-associated viral (AAV), herpes viral, or alphavirus vector. The viral vector can also be an astrovirus, coronavirus, orthomyxovirus, papovavirus, paramyxovirus, parvovirus, picomavirus, poxvirus, togavirus viral vector.

The delivery of gene therapy constructs of this invention into cells is not limited to the above mentioned viral vectors. Other delivery methods and media may be employed such as, for example, nucleic acid expression vectors, polycationic condensed DNA linked or unlinked to killed adenovirus alone, ligand linked DNA, liposomes, eukaryotic cell delivery vehicles cells, deposition of photopolymerized hydrogel materials, handheld gene transfer particle gun, ionizing radiation, nucleic charge neutralization or fusion with cell membranes. Particle mediated gene transfer may be employed. Briefly, DNA sequence can be inserted into conventional vectors that contain conventional control sequences for high level expression, and then be incubated with synthetic gene transfer molecules such as polymeric DNA-binding cations like polylysine, protamine, and albumin, linked to cell targeting ligands such as asialoorosomucoid, insulin, galactose, lactose or transferrin. Naked DNA may also be employed. Uptake efficiency of naked DNA may be improved using biodegradable latex beads. The method may be improved further by treatment of the beads to increase hydrophobicity and thereby facilitate disruption of the endosome and release of the DNA into the cytoplasm.

Another aspect of the invention pertains to the expression of CVHPPs using a regulatable expression system. Systems to regulate expression of therapeutic genes have been developed and incorporated into the current viral and nonviral gene delivery vectors. These systems are briefly described below:

Tet-on/off system. The Tet-system is based on two regulatory elements derived from the tetracycline-resistance operon of the *E. coli* Tn10 transposon: the tet repressor protein (TetR) and the Tet operator DNA sequence (tetO) to which TetR binds. The system consists of two components, a "regulator" and a "reporter" plasmid. The "regulator" plasmid encodes a hybrid protein containing a mutated Tet repressor (rtetR) fused to the VP16 activation domain of herpes simplex virus. The "reporter" plasmid contains a tet-responsive element (TRE), which controls the "reporter" gene of choice. The rtetR-VP 16 fusion protein can only bind to the TRE, therefore activates the transcription of the "reporter" gene, in the presence of tetracycline. The system has been incorporated into a number of viral vectors including retrovirus, adenovirus and AAV.

Ecdysone system. The ecdysone system is based on the molting induction system found in *Drosophila*, but modified for inducible expression in mammalian cells. The system uses an analog of the *drosophila* steroid hormone ecdysone, muristerone A, to activate expression of the gene of interest via a heterodimeric nuclear receptor. Expression levels have been reported to exceed 200-fold over basal levels with no effect on mammalian cell physiology.

Progesterone system. The progesterone receptor is normally stimulated to bind to a specific DNA sequence and to activate transcription through an interaction with its hormone ligand. Conversely, the progesterone antagonist mifepristone (RU486) is able to block hormone-induced nuclear transport and subsequent DNA binding. A mutant form of the progesterone receptor that can be stimulated to bind through an interaction with RU486 has been generated. To generate a specific, regulatable transcription factor, the RU486-binding domain of the progesterone receptor has been fused to the DNA-binding domain of the yeast transcription factor GAL4 and the transactivation domain of the HSV protein VP16, The chimeric factor is inactive in the absence of RU486, The addition of hormone, however, induces a conformational change in the chimeric protein, and this change allows binding to a GAL4-binding site and the activation of transcription from promoters containing the GAL4-binding site.

Rapamycin system. Immunosuppressive agents, such as FK506 and rapamycin, act by binding to specific cellular proteins and facilitating their dimerization. For example, the binding of rapamycin to FK506-binding protein (FKBP) results in its heterodimerization with another rapamycin binding protein FRAP, which can be reversed by removal of the drug. The ability to bring two proteins together by addition of a drug potentiates the regulation of a number of biological processes, including transcription. A chimeric DNA-binding domain has been fused to the FKBP, which enables binding of the fusion protein to a specific DNA-binding sequence. A transcriptional activation domain also has been fused to FRAP. When these two fusion proteins are co-expressed in the same cell, a fully functional transcription factor can be formed by heterodimerization mediated by addition of rapamycin. The dimerized chimeric transcription factor can then bind to a synthetic promoter sequence containing copies of the synthetic DNA-binding sequence. This system has been successfully integrated into adenoviral and AAV vectors. Long term regulatable gene expression has been achieved in both mice and baboons.

Immunogens and Immunogenic Compositions

Within certain aspects, CVHPP, CVHPN, CVHPP-specific T cell, CVHPP-presenting APC, CVHG-containing vectors, including but are not limited to expression vectors and gene delivery vectors, may be utilized as vaccines for CVH. Vaccines may comprise one or more such compounds/cells and an immunostimulant. An immunostimulant may be any substance that enhances or potentiates an immune response (antibody and/or cell-mediated) to an exogenous antigen. Examples of immunostimulants include adjuvants, biodegradable microspheres (e.g., polylactic galactide) and liposomes (into which the compound is incorporated). Vaccines within the scope of the present invention may also contain other compounds, which may be biologically active or inactive. For example, one or more immunogenic portions of other antigens may be present, either incorporated into a fusion polypeptide or as a separate compound, within the composition of vaccine.

A vaccine may contain DNA encoding one or more CVHPP or portion of CVHPP, such that the polypeptide is generated in situ. As noted above, the DNA may be present within any of a variety of delivery systems known to those of ordinary skill in the art, including nucleic acid expression vectors, gene delivery vectors, and bacteria expression systems. Numerous gene delivery techniques are well known in the art. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface or secretes such an epitope. In a preferred embodiment, the DNA may be introduced using a viral expression system (e.g., vaccinia or other pox virus, retrovirus, or adenovirus), which may involve the use of a non-pathogenic (defective), replication competent virus. Techniques for incorporating DNA into such expression systems are well known to those of ordinary skill in the art. The DNA may also be "naked," as described, for example, in Ulmer et al., Science 259:1745-1749, 1993 and reviewed by Cohen, Science 259:1691-1692, 1993, The uptake of naked DNA may be increased by coating the DNA onto biodegradable beads, which are efficiently transported into the cells. It will be apparent that a vaccine may comprise both a polynucleotide and a polypeptide component. Such vaccines may provide for an enhanced immune response.

It will be apparent that a vaccine may contain pharmaceutically acceptable salts of the polynucleotides and polypeptides provided herein. Such salts may be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

Any of a variety of immunostimulants may be employed in the vaccines of this invention. For example, an adjuvant may be included. As defined previously, an "adjuvant" is a substance that serves to enhance the immunogenicity of an antigen. Thus, adjuvants are often given to boost the immune response and are well known to the skilled artisan. Examples of adjuvants contemplated in the present invention include, but are not limited to, aluminum salts (alum) such as aluminum phosphate and aluminum hydroxide, *Mycobacterium tuberculosis, Bordetella pertussis*, bacterial lipopolysaccharides, aminoalkyl glucosamine phosphate compounds (AGP), or derivatives or analogs thereof, which are available from Corixa (Hamilton, Mont.), and which are described in U.S. Pat No. 6,113,918; one such AGP is 2-[(R)-3-Tetradecanoyloxytetradecanoylamino]ethyl 2-Deoxy-4-O-phosphono-3-O-[(R)-3-tetradecanoyoxytetradecanoyl]-2-[(R)-3-tetradecanoyoxytetradecanoylamino]-b-D-glucopyranoside, which is also known as 529 (formerly known as RC529), which is formulated as an aqueous form or as a stable emulsion, MPL™ (3-O-deacylated monophosphoryl lipid A) (Corixa) described in U.S. Pat. No. 4,912,094, synthetic polynucleotides such as oligonucleotides containing a CpG motif (U.S. Pat. No. 6,207,646), polypeptides, saponins such as Quil A or STIMULON™ QS-21 (Antigenics, Framingham, Mass.), described in U.S. Pat. No. 5,057,540, a pertussis toxin (PT), or an *E. coli* heat-labile toxin (LT), particularly LT-K63, LT-R72, CT-S109, PT-K9/G129; see, e.g., International Patent Publication Nos. WO 93/13302 and WO 92/19265, cholera toxin (either in a wild-type or mutant form, e.g., wherein the glutamic acid at amino acid position 29 is replaced by another amino acid, preferably a histidine, in accordance with published International Patent Application number WO 00/18434). Various cytokines and lymphokines are suitable for use as adjuvants. One such adjuvant is granulocyte-macrophage colony stimulating factor (GM-CSF), which has a nucleotide sequence as described in U.S. Pat. No. 5,078,996. A plasmid containing GM-CSF cDNA has been transformed into *E. coli* and has been deposited with the American Type Culture Collection (ATCC), 1081 University Boulevard, Manassas, Va. 20110-2209, under Accession Number 39900. The cytokine EL-12 is another adjuvant which is described in U.S. Pat. No. 5,723,127. Other cytokines or lymphokines have been shown to have immune modulating activity, including, but not limited to, the interleukins 1-alpha, 1-beta, 2, 4, 5,6, 7, 8, 10, 13, 14, 15, 16, 17 and 18, the interferons-alpha, beta and gamma, granulocyte colony stimulating factor, and the tumor necrosis factors alpha and beta, and are suitable for use as adjuvants.

Any vaccine provided herein may be prepared using well known methods that result in a combination of antigen, immune response enhancer and a suitable carrier or excipient. The compositions described herein may be administered as part of a sustained release formulation (i.e., a formulation such as a capsule, sponge or gel (composed of polysaccharides, for example) that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane.

Carriers for use within such formulations are biocompatible, and may also be biodegradable; preferably the formulation provides a relatively constant level of active component release. Such carriers include microparticles of poly(lactide-co-glycolide), as well as polyacrylate, latex, starch, cellulose and dextran. Other delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

Any of a variety of delivery vehicles may be employed within vaccines to facilitate production of an antigen-specific immune response that targets cancer cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-CVH effects per se and/or to be immunologically compatible with the receiver (i.e., matched HLA haplotype). APCs may generally be isolated from any of a variety of biological fluids and organs, and may be autologous, allogeneic, syngeneic or xenogenic cells.

Certain preferred embodiments of the present invention use dendritic cells or progenitors thereof as APCs. Dendritic cells are highly potent APCs and have been shown to be effective as a physiological adjuvant for eliciting prophylactic or therapeutic anti-CVH immunity. In general, dendritic cells may be identified based on their typical shape (stellate in situ, with marked cytoplasmic processes (dendrites) visible in vitro), their ability to take up, process and present antigens with high efficiency and their ability to activate naive T cell responses. Dendritic cells may, of course, be engineered to express specific cell-surface receptors or ligands that are not commonly found on dendritic cells in vivo, and such modified dendritic cells are contemplated by the present invention. As an alternative to dendritic cells, secreted vesicles antigen-loaded dendritic cells (called exosomes) may be used within a vaccine (see Zitvogel et al., Nature Med. 4:594-600, 1998).

Dendritic cells and progenitors may be obtained from peripheral blood, bone marrow, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide encoding a CVHPP (or portion or other variant thereof) such that the CVHPP, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., Immunology and cell Biology 75:456-460, 1997. Antigen loading of dendritic cells may be achieved by incubating dendritic cells or progenitor cells with the CVHPP, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Vaccines may be presented in unit-dose or multi-dose containers, such as sealed ampoules or vials. Such containers are preferably hermetically sealed to preserve sterility of the formulation until use. In general, formulations may be stored as suspensions, solutions or emulsions in oily or aqueous vehicles. Alternatively, a vaccine may be stored in a freeze-dried condition requiring only the addition of a sterile liquid carrier immediately prior to use.

Detection Methods

As discussed earlier, expression level of CVHGs may be used as a marker for CVH and CVH-related disorders. Detection and measurement of the relative amount of a CVHG product (polynucleotide or polypeptide) of the invention can be by any method known in the art. Typical methodologies for detection of a transcribed polynucleotide include RNA extraction from a cell or tissue sample, followed by hybridization of a labeled probe (i.e., a complementary polynucleotide molecule) specific for the target RNA to the extracted RNA and detection of the probe (i.e., Northern blotting).

Typical methodologies for peptide detection include protein extraction from a cell or tissue sample, followed by binding of an antibody specific for the target protein to the protein sample, and detection of the antibody. For example, detection of desmin may be accomplished using polyclonal antibody anti-desmin. Antibodies are generally detected by the use of a labeled secondary antibody. The label can be a radioisotope, a fluorescent compound, an enzyme, an enzyme co-factor, or ligand. Such methods are well understood in the art.

In certain embodiments, the CVHGs themselves (i.e., the DNA or cDNA) may serve as markers for CVH. For example, an increase of genomic copies of a CVHG, such as by duplication of the gene, may also be correlated with CVH and CVH-assoicated disorders.

Detection of specific polynucleotide molecules may also be assessed by gel electrophoresis, column chromatography, or direct sequencing, quantitative PCR (in the case of polynucleotide molecules), RT-PCR, or nested-PCR among many other techniques well known to those skilled in the art.

Detection of the presence or number of copies of all or a part of an CVHG of the invention may be performed using any method known in the art. Typically, it is convenient to assess the presence and/or quantity of a DNA or cDNA by Southern analysis, in which total DNA from a cell or tissue sample is extracted and hybridized with a labeled probe (i.e., a complementary DNA molecules). The probe is then detected and quantified. The label group can be a radioisotope, a fluorescent compound, an enzyme, or an enzyme co-factor. Other useful methods of DNA detection and/or quantification include direct sequencing, gel electrophoresis, column chromatography, and quantitative PCR, as is known by one skilled in the art.

In certain embodiments, CVHPPs may serve as markers for CVH. Detection of specific polypeptide molecules may be assessed by gel electrophoresis, Western blot, column chromatography, or direct sequencing, among many other techniques well known to those skilled in the art.

Panels of CVHGs

The expression level of each CVHG may be considered individually, although it is within the scope of the invention to provide combinations of two or more CVHGs for use in the methods and compositions of the invention to increase the confidence of the analysis. In another aspect, the invention provides panels of the CVHGs of the invention. A panel of CVHGs comprises two or more CVHGs. A panel may also comprise 2-5, 5-15, 15-35, 35-50, or more than 50 CVHGs. In a preferred embodiment, these panels of CVHGs are selected such that the CVHGs within any one panel share certain features. For example, the CVHGs of a first panel may all relate to myelination in a CVH sample. Alternatively, CVHGs of a second panel may each exhibit differential regulation as compared to a first panel. Similarly, different panels of CVHGs may be composed of CVHGs representing different stages of CVH. Panels of the CVHGs of the invention may be made by independently selecting CVHGs from Tables 3-8, and may further be provided on biochips, as discussed below.

Screening Methods

The invention also provides methods (also referred to herein as "screening assays") for identifying modulators, i.e., candidate or test compounds or agents comprising therapeutic moieties (e.g., peptides, peptidomimetics, peptoids, polynucleotides, small molecules or other drugs) which (a) bind to a CVHPP, or (b) have a modulatory (e.g., stimulatory or inhibitory) effect on the activity of a CVHPP or, more specifically, (c) have a modulatory effect on the interactions of the CVHPP with one or more of its natural substrates (e.g., peptide, protein, hormone, co-factor, or polynucleotide), or (d) have a modulatory effect on the expression of the CVHPPs. Such assays typically comprise a reaction between the CVHPP and one or more assay components. The other components may be either the test compound itself, or a combination of the test compound and a binding partner of the CVHPP.

To screen for compounds which interfere with binding of two proteins e.g., a CVHPP and its binding partner, a Scintillation Proximity Assay can used. In this assay, the CVHPP is labeled with an isotope such as $^{251}$I. The binding partner is labeled with a scintillant, which emits light when proximal to radioactive decay (i.e., when the CVHPP is bound to its binding partner). A reduction in light emission will indicate that a compound has interfered with the binding of the two proteins.

Alternatively a Fluorescence Energy Transfer (FRET) assay could be used. In a FRET assay of the invention, a fluorescence energy donor is comprised on one protein (e.g., a CVHPP) and a fluorescence energy acceptor is comprised on a second protein (e.g., a binding partner of the CVHPP). If the absorption spectrum of the acceptor molecule overlaps with the emission spectrum of the donor fluorophore, the fluorescent light emitted by the donor is absorbed by the acceptor. The donor molecule can be a fluorescent residue on the protein (e.g., intrinsic fluorescence such as a tryptophan or tyrosine residue), or a fluorophore which is covalently conjugated to the protein (e.g., fluorescein isothiocyanate, FITC). An appropriate donor molecule is then selected with the above acceptor/donor spectral requirements in mind.

Thus, in this example, a CVHPP is labeled with a fluorescent molecule (i.e., a donor fluorophore) and its binding partner is labeled with a quenching molecule (i.e., an acceptor). When the CVHPP and its binding partner are bound, fluorescence emission will be quenched or reduced relative the CVHPP alone. Similarly, a compound which can dissociate the interaction of the CVHPP-partner complex, will result in an increase in fluorescence emission, which indicates the compound has interfered with the binding of the CVHPP to its binding partner.

Another assay to detect binding or dissociation of two proteins is fluorescence polarization or anisotropy. In this assay, the investigated protein (e.g., a CVHPP) is labeled with a fluorophore with an appropriate fluorescence lifetime. The protein sample is then excited with vertically polarized light. The value of anisotropy is then calculated by determining the intensity of the horizontally and vertically polarized emission light. Next, the labeled protein (CVHPP) is mixed with a CVHPP binding partner and the anisotropy measured again. Because fluorescence anisotropy intensity is related to the rotational freedom of the labeled protein, the more rapidly a protein rotates in solution, the smaller the anisotropy value. Thus, if the labeled CVHPP is part of a complex (e.g., CVHPP-partner), the CVHPP rotates more slowly in solution (relative to free, unbound CVHPP) and the anisotropy intensity increases. Subsequently, a compound which can dissociate the interaction of the CVHPP-partner complex, will result in a decrease in anisotropy (i.e., the labeled CVHPP rotates more rapidly), which indicates the compound has interfered with the binding of CVHPP to its binding partner.

A more traditional assay would involve labeling the CVHPP binding partner with an isotope such as $^{125}$I, incubating with the CVHPP, then immunoprecipitating of the CVHPP. Compounds that increase the free CVHPP will decrease the precipitated counts. To avoid using radioactivity, the CVHPP binding partner could be labeled with an enzyme-conjugated antibody instead.

Alternatively, the CVHPP binding partner could be immobilized on the surface of an assay plate and the CVHPP could be labeled with a radioactive tag. A rise in the number of counts would identify compounds that had interfered with binding of the CVHPP and its binding partner.

Evaluation of binding interactions may further be performed using Biacore technology, wherein the CVHPP or its binding partner is bound to a micro chip, either directly by chemical modification or tethered via antibody-epitope association (e.g., antibody to the CVHPP), antibody directed to an epitope tag (e.g., His tagged) or fusion protein (e.g., GST). A second protein or proteins is/are then applied via flow over the "chip" and the change in signal is detected. Finally, test compounds are applied via flow over the "chip" and the change in signal is detected.

Once a series of potential compounds has been identified for a combination of CVHPP, CVHPP binding partner and ALS, a bioassay can be used to select the most promising candidates. For example, a cellular assay that measures cell proliferation in presence of the CVHPP and the CVHPP binding partner was described above. This assay could be modified to test the effectiveness of small molecules that interfere with binding of a CVHPP and its binding partner in enhancing cellular proliferation. An increase in cell proliferation would correlate with a compound's potency.

The test compounds of the present invention are generally either small molecules or biomolecules. Small molecules include, but are not limited to, inorganic molecules and small organic molecules. Biomolecules include, but are not limited to, naturally-occurring and synthetic compounds that have a bioactivity in mammals, such as lipids, steroids, polypeptides, polysaccharides, and polynucleotides. In one preferred embodiment, the test compound is a small molecule. In another preferred embodiment, the test compound is a biomolecule. One skilled in the art will appreciate that the nature of the test compound may vary depending on the nature of the CVHPP. For example, if the CVHPP is an orphan receptor having an unknown ligand, the test compound may be any of a number of biomolecules which may act as cognate ligand, including but not limited to, cytokines, lipid-derived mediators, small biogenic amines, hormones, neuropeptides, or proteases.

The test compounds of the present invention may be obtained from any available source, including systematic libraries of natural and/or synthetic compounds. Test compounds may also be obtained by any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds. As used herein, the term "binding partner" refers to a molecule which serves as either a substrate for a CVHPP, or alternatively, as a ligand having binding affinity to the CVHPP.

Screening for Inhibitors of CVHPP

The invention provides methods of screening test compounds for inhibitors of CVHPP. The method of screening comprises obtaining samples from subjects diagnosed with or suspected of having CVH, contacting each separate aliquot of the samples with one of a plurality of test compounds, and comparing expression of one or more CVHGs in each of the aliquots to determine whether any of the test compounds provides a substantially altered level of expression or activity of an CVHG relative to samples with other test compounds or relative to an untreated sample or control sample. In addition, methods of screening may be devised by combining a test compound with a protein and thereby determining the effect of the test compound on the protein.

In addition, the invention is further directed to a method of screening for test compounds capable of modulating with the binding of a CVHPP and a binding partner, by combining the test compound, CVHPP, and binding partner together and determining whether binding of the binding partner and CVHPP occurs. The test compound may be either small molecules or a bioactive agent. As discussed below, test compounds may be provided from a variety of libraries well known in the art.

Modulators of CVHG expression, activity or binding ability are useful as therapeutic compositions of the invention. Such modulators (e.g., antagonists or agonists) may be formulated as pharmaceutical compositions, as described herein below. Such modulators may also be used in the methods of the invention, for example, to diagnose, treat, or prognose CVH.

High-Throughput Screening Assays

The invention provides methods of conducting high-throughput screening for test compounds capable of inhibiting activity or expression of a CVHPP of the present invention. In one embodiment, the method of high-throughput screening involves combining test compounds and the CVHPP and detecting the effect of the test compound on the CVHPP.

A variety of high-throughput functional assays well-known in the art may be used in combination to screen and/or study the reactivity of different types of activating test compounds. Since the coupling system is often difficult to predict, a number of assays may need to be configured to detect a wide range of coupling mechanisms. A variety of fluorescence-based techniques are well-known in the art and are capable of high-throughput and ultra high throughput screening for activity, including but not limited to BRET® or FRET® (both by Packard Instrument Co., Meriden, Conn.). The ability to screen a large volume and a variety of test compounds with great sensitivity permits analysis of the therapeutic targets of the invention to further provide potential inhibitors of CVH. For example, where the CVHG encodes an orphan receptor with an unidentified ligand, high-throughput assays may be utilized to identify the ligand, and to further identify test compounds which prevent binding of the receptor to the ligand. The BIACORE® system may also be manipulated to detect binding of test compounds with individual components of the therapeutic target, to detect binding to either the encoded protein or to the ligand.

By combining test compounds with CVHPPs of the invention and determining the binding activity between them, diagnostic analysis can be performed to elucidate the coupling systems. Generic assays using cytosensor microphysiometer may also be used to measure metabolic activation, while changes in calcium mobilization can be detected by using the fluorescence-based techniques such as FLIPR® (Molecular Devices Corp, Sunnyvale, Calif.). In addition, the presence of apoptotic cells may be determined by TUNEL assay, which utilizes flow cytometry to detect free 3-OH termini resulting from cleavage of genomic DNA during apoptosis. As mentioned above, a variety of functional assays well-known in the art may be used in combination to screen and/or study the reactivity of different types of activating test compounds. Preferably, the high-throughput screening assay of the present invention utilizes label-free plasmon resonance technology as provided by BIACORE® systems (Biacore International AB, Uppsala, Sweden). Plasmon free resonance occurs when surface plasmon waves are excited at a metal/liquid interface. By reflecting directed light from the surface as a result of contact with a sample, the surface plasmon resonance causes a change in the refractive index at the surface layer. The refractive index change for a given change of mass concentration at the surface layer is similar for many bioactive agents (including proteins, peptides, lipids and polynucleotides), and since the BIACORE® sensor surface can be functionalized to bind a variety of these bioactive agents, detection of a wide selection of test compounds can thus be accomplished.

Therefore, the invention provides for high-throughput screening of test compounds for the ability to inhibit activity of a protein encoded by the CVHGs listed in Table 4, by combining the test compounds and the protein in high-throughput assays such as BIACORE®, or in fluorescence-based assays such as BRET®. In addition, high-throughput assays may be utilized to identify specific factors which bind to the encoded proteins, or alternatively, to identify test compounds which prevent binding of the receptor to the binding partner. In the case of orphan receptors, the binding partner may be the natural ligand for the receptor. Moreover, the high-throughput screening assays may be modified to determine whether test compounds can bind to either the encoded protein or to the binding partner (e.g., substrate or ligand) which binds to the protein.

Predictive Medicine

The present invention pertains to the field of predictive medicine in which diagnostic assays, prognostic assays, pharmacogenetics and monitoring clinical trials are used for prognostic (predictive) purpose to thereby treat an individual prophylactically. Accordingly, one aspect of the present invention relates to diagnostic assays for determining CVHG expression and/or activity, in the context of a biological sample (e.g., blood, urine, feces, serum, cells, tissue) to thereby determine whether an individual is at risk for developing CVH associated with altered CVHG expression or activity. The invention also provides for prognostic (or predictive) assays for determining whether an individual is at risk of developing CVH associated with aberrant CVHG expression or activity.

For example, the number of copies of an CVHG can be assayed in a biological sample. Such assays can be used for prognostic or predictive purposes to thereby prophylactically treat an individual prior to the onset of CVH associated with aberrant CVHG protein, polynucleotide expression or activity.

Another aspect of the invention pertains to monitoring the influence of agents (e.g., drugs, compounds) on the expression or activity of CVHGs in clinical trials.

Diagnostic Assays

An exemplary method for detecting the presence or absence of a CVHPP or CVHPN in a biological sample involves contacting a biological sample with a compound or an agent capable of detecting the CVHPP or CVHPN (e.g., mRNA, genomic DNA). A preferred agent for detecting mRNA or genomic DNA corresponding to an CVHG or CVHPP of the invention is a labeled polynucleotide probe capable of hybridizing to a mRNA or genomic DNA of the invention. In a most preferred embodiment, the polynucleotides to be screened are arranged on a GeneChip®. Suitable probes for use in the diagnostic assays of the invention are described herein. A preferred agent for detecting a CVHPP of the invention is an antibody which specifically recognizes the CVHPP.

The diagnostic assays may also be used to quantify the amount of expression or activity of a CVHG in a biological sample. Such quantification is useful, for example, to determine the progression or severity of CVH and CVH-related disorders. Such quantification is also useful, for example, to determine the severity of CVH following treatment.

Determining Severity of CVH and CVH-related diseases

In the field of diagnostic assays, the invention also provides methods for determining the severity of CVH by isolating a sample from a subject (e.g., a colon biopsy), and detecting the presence, quantity and/or activity of one or more CVHG products in the sample relative to a second sample from a normal sample or control sample. In one embodiment, the expression levels of CVHGs in the two samples are compared, and a modulation in one or more CVHGs in the test sample indicates CVH. In other embodiments the modulation of 2, 3, 4 or more CVHGs indicates a severe case of CVH.

In another aspect, the invention provides CVHG products whose quantity or activity is correlated with the severity of CVH. The subsequent level of expression may further be compared to different expression profiles of various stages of the disease to confirm whether the subject has a matching profile. In yet another aspect, the invention provides CVHGs whose quantity or activity is correlated with a risk in a subject for developing CVH.

A preferred agent for detecting a CVHPP is an antibody capable of binding to the CVHPP, preferably an antibody with a detectable label. Antibodies can be polyclonal or more preferably, monoclonal. An intact antibody, or a fragment thereof (e.g., Fab or F(ab')$_2$) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect CVHG mRNA, protein or genomic DNA in a biological sample in vitro as well as in vivo. For example, in vitro techniques for detection of CVHG mRNA include Northern hybridizations and in situ hybridizations. In vitro techniques for detection of CVHPP include enzyme linked immunosorbent assays (ELISAs), Western blots, immunoprecipitations and immunofluorescence. In vitro techniques for detection of CVHG genomic DNA include Southern hybridizations. Furthermore, in vivo techniques for detection of CVHPP include introducing into a subject a labeled anti-CVHPP antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a tissue or serum sample isolated by conventional means from a subject, e.g., a biopsy or blood draw.

Prognostic Assays

The diagnostic method described herein can be utilized to identify subjects having or at risk of developing CVH associated with aberrant CVHG expression or activity.

The assays described herein, such as the preceding or following assays, can be utilized to identify a subject having CVH associated with an aberrant level of CVHG activity or expression. Alternatively, the prognostic assays can be utilized to identify a subject at risk for developing CVH associated with aberrant levels of CVHG protein activity or polynucleotide expression. Thus, the present invention provides a method for identifying CVH associated with aberrant CVHCG expression or activity in which a test sample is obtained from a subject and CVHPP or CVHPN (e.g., mRNA or genomic DNA) is detected, wherein the presence of CVHPP or CVHPN is diagnostic or prognostic for a subject having or at risk of developing CVH with aberrant CVHG expression or activity.

Furthermore, the prognostic assays described herein can be used to determine whether a subject can be administered an agent (e.g., an agonist, antagonist, peptidomimetic, protein, peptide, polynucleotide, small molecule, or other drug candidate) to treat or prevent CVH associated with aberrant CVHG expression or activity, such as, for example, a cytokine. For example, such methods can be used to determine whether a subject can be effectively treated with an agent to inhibit CVH. Thus, the present invention provides methods for determining whether a subject can be effectively treated with an agent for CVH associated with aberrant CVHG expression or activity.

Prognostic assays can be devised to determine whether a subject undergoing treatment for CVH has a poor outlook for disease progression. In a preferred embodiment, prognosis can be determined shortly after diagnosis, i.e., within a few days. By establishing expression profiles of different stages of CVHGs, from onset to later stages, an expression pattern may emerge to correlate a particular expression profile to increased likelihood of a poor prognosis. The prognosis may then be used to devise a more aggressive treatment program and enhance the likelihood of success.

The methods of the invention can also be used to detect genetic alterations in a CVHG, thereby determining if a subject with the altered gene is at risk for damage characterized by aberrant regulation in CVHG expression or activity. In preferred embodiments, the methods include detecting, in a sample of cells from the subject, the presence or absence of a genetic alteration characterized by at least one alteration affecting the integrity of a CVHG, or the aberrant expression of the CVHG. For example, such genetic alterations can be detected by ascertaining the existence of at least one of the following: 1) deletion of one or more nucleotides from a CVHG; 2) addition of one or more nucleotides to a CVHG; 3) substitution of one or more nucleotides of a CVHG, 4) a chromosomal rearrangement of a CVHG; 5) alteration in the level of a messenger RNA transcript of a CVHG, 6) aberrant modification of a CVHG, such as of the methylation pattern of the genomic DNA, 7) the presence of a non-wild type splicing pattern of a messenger RNA transcript of a CVHG, 8) non-wild type level of a CVHPP, 9) allelic loss of a CVHG, and 10) inappropriate post-translational modification of a CVHPP. As described herein, there are a large number of assays known in the art, which can be used for detecting alterations in a CVHG or a CVHG product. A preferred biological sample is a blood sample isolated by conventional means from a subject.

In certain embodiments, detection of the alteration involves the use of a probe/primer in a polymerase chain reaction (PCR), such as anchor PCR or RACE PCR, or, alternatively, in a ligation chain reaction (LCR), the latter of which can be particularly useful for detecting point mutations in the CVHG. This method can include the steps of collecting a sample of cells from a subject, isolating a polynucleotide sample (e.g., genomic, mRNA or both) from the cells of the sample, contacting the polynucleotide sample with one or more primers which specifically hybridize to a CVHG under conditions such that hybridization and amplification of the CVHG (if present) occurs, and detecting the presence or absence of an amplification product, or detecting the size of the amplification product and comparing the length to a control sample. It is understood that PCR and/or LCR may be desirable to be used as a preliminary amplification step in conjunction with any of the techniques used for detecting mutations described herein.

Alternative amplification methods include: self-sustained sequence replication, transcriptional amplification system, Q-Beta Replicase, or any other polynucleotide amplification method, followed by the detection of the amplified molecules using techniques well known to those of skill in the art. These detection schemes are especially useful for the detection of polynucleotide molecules if such molecules are present in very low numbers.

In an alternative embodiment, mutations in an CVHG from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicate mutations in the sample DNA. Moreover, sequence specific ribozymes (see, for example, U.S. Pat. No. 5,498,531) can be used to score for the presence of specific mutations by development or loss of a ribozyme cleavage site.

In other embodiments, genetic mutations in a CVHG can be identified by hybridizing sample and control polynucleotides, e.g., DNA or RNA, to high density arrays containing hundreds or thousands of oligonucleotides probes. For example, genetic mutations in a CVHG can be identified in two dimensional arrays containing light generated DNA probes. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the CVHG and detect mutations by comparing the sequence of the sample CVHG with the corresponding wild-type (control) sequence. It is also contemplated that any of a variety of automated sequencing procedures can be utilized when performing the diagnostic assays, including sequencing by mass spectrometry.

Other methods for detecting mutations in a CVHG include methods in which protection from cleavage agents is used to detect mismatched bases in RNA/RNA or RNA/DNA heteroduplexes. In general, the art technique of "mismatch cleavage" starts by providing heteroduplexes by hybridizing (labeled) RNA or DNA containing the wild-type CVHG sequence with potentially mutant RNA or DNA obtained from a tissue sample. The double-stranded duplexes are treated with an agent which cleaves single-stranded regions of the duplex, which will exist due to basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in CVHG cDNAs obtained from samples of cells. For example, the mutY enzyme of E. coli cleaves A at G/A mismatches and the thymidine DNA glycosylase from HeLa cells cleaves T at G/T mismatches. According to an exemplary embodiment, a probe based on an CVHG sequence, e.g., a wild-type CVHG sequence, is hybridized to cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in CVHGs. For example, single-strand conformation polymorphism (SSCP) may be used to detect differences in electrophoretic mobility between mutant and wild type polynucleotides. Single-stranded DNA fragments of sample and control CVHG polynucleotides will be denatured and allowed to renature. The secondary structure of single-stranded polynucleotides varies according to sequence. The resulting alteration in electrophoretic mobility enables the detection of even a single base change. The DNA fragments may be labeled or detected with labeled probes. The sensitivity of the assay may be enhanced by using RNA (rather than DNA) in which the secondary structure is more sensitive to a change in sequence. In a preferred embodiment, the subject method utilizes heteroduplex analysis to separate double-stranded heteroduplex molecules on the basis of changes in electrophoretic mobility (Keen et al. Trends Genet 7:5, 1991).

In yet another embodiment the movement of mutant or wild-type fragments in polyacrylamide gels containing a gradient of denaturant is assayed using denaturing gradient gel electrophoresis (DGGE). When DGGE is used as the method of analysis, DNA will be modified to insure that it does not completely denature, for example, by adding a GC clamp of approximately 40bp of high-melting GC-rich DNA by PCR. In a further embodiment, a temperature gradient is used in place of a denaturing gradient to identify differences in the mobility of control and sample DNA (Rosenbaum and Reissner Biophys Chem 265:12753, 1987).

Examples of other techniques for detecting point mutations include, but are not limited to, selective oligonucleotide hybridization, selective amplification, and selective primer extension. For example, oligonucleotide primers may be prepared in which the known mutation is placed centrally and then hybridized to target DNA under conditions which permit hybridization only if a perfect match is found (Saiki et al. Proc. Natl. Acad. Sci USA 86:6230, 1989). Such allele specific oligonucleotides are hybridized to PCR amplified target or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) or at the extreme 3' end of one primer where, under appropriate conditions, mismatch can prevent or reduce polymerase extension. In addition, it may be desirable to introduce a novel restriction site in the region of the mutation to create cleavage-based detection. It is anticipated that, in certain embodiments, amplification may also be performed using Taq ligase for amplification. In such cases, ligation will occur only if there is a perfect match at the 3' end of the 5' sequence, thus making it possible to detect the presence of a known mutation at a specific site by looking for the presence or absence of amplification.

The methods described herein may be performed, for example, by utilizing prepackaged diagnostic kits comprising at least one probe polynucleotide or antibody reagent described herein, which may be conveniently used, e.g., in clinical settings to diagnose subjects exhibiting symptoms or family history of a disease or illness involving a CVHG.

Furthermore, any cell type or tissue in which a CVHG is expressed may be utilized in the prognostic or diagnostic assays described herein.

Monitoring Effects During Clinical Trials

Monitoring the influence of agents (e.g., drugs, small molecules, proteins, nucleotides) on the expression or activity of a CVHPP can be applied not only in basic drug screening, but also in clinical trials. For example, the effectiveness of an agent determined by a screening assay, as described herein to decrease CVHG expression or activity, can be monitored in clinical trials of subjects exhibiting increased CVHG expression or activity. In such clinical trials, the expression or activity of an CVHG can be used as a "read-out" of the phenotype of a particular tissue.

For example, and not by way of limitation, CVHGs that are modulated in tissues by treatment with an agent can be identified. Thus, to study the effect of agents on the CVHPP in a clinical trial, cells can be isolated and RNA prepared and analyzed for the levels of expression of an CVHG. The levels of gene expression or a gene expression pattern can be quantified by Northern blot analysis, RT-PCR or GeneChip® as described herein, or alternatively by measuring the amount of protein produced, by one of the methods as described herein, or by measuring the levels of activity of CVHPP. In this way, the gene expression pattern can serve as a read-out, indicative of the physiological response of the cells to the agent. Accordingly, this response state may be determined before treatment and at various points during treatment of the individual with the agent.

In a preferred embodiment, the present invention provides a method for monitoring the effectiveness of treatment of a subject with an agent (e.g., an agonist, antagonist, peptidomimetic, protein, peptide, polynucleotide, small molecule, or other drug candidate identified by the screening assays described herein) including the steps of (i) obtaining a pre-administration sample from a subject prior to administration of the agent; (ii) detecting the level of expression of a CVHG protein or mRNA in the pre-administration sample; (iii) obtaining one or more post-administration samples from the subject; (iv) detecting the level of expression or activity of the CVHG protein or mRNA in the post-administration samples; (v) comparing the level of expression or activity of the CVHG protein or mRNA in the pre-administration sample with the CVHG protein or mRNA the post administration sample or samples; and (vi) altering the administration of the agent to the subject accordingly. According to such an embodiment, CVHG expression or activity may be used as an indicator of the effectiveness of an agent, even in the absence of an observable phenotypic response.

Methods of Treatment

The present invention provides for both prophylactic and therapeutic methods of treating a subject at risk for, susceptible to or diagnosed with CVH. With regard to both prophylactic and therapeutic methods of treatment, such treatments may be specifically tailored or modified, based on knowledge obtained from the field of pharmacogenomics. "Pharmacogenomics," as used herein, includes the application of genomics technologies such as gene sequencing, statistical genetics, and gene expression analysis to drugs in clinical development and on the market. More specifically, the term refers the study of how a subject's genes determine his or her response to a drug (e.g., a subject's "drug response phenotype" or "drug response genotype"). Thus, another aspect of the invention provides methods for tailoring an individual's prophylactic or therapeutic treatment with either the CVHPP molecules of the present invention or CVHPP modulators (e.g., agonists or antagonists) according to that individual's drug response. Pharmacogenomics allows a clinician or physician to target prophylactic or therapeutic treatments to subjects who will most benefit from the treatment and to avoid treatment of subjects who will experience toxic drug-related side effects.

Prophylactic Methods

In one aspect, the invention provides a method for preventing in a subject CVH associated with aberrant CVHG expression or activity, by administering to the subject anCVHG product or an agent which modulates CVHG protein expression or activity.

Subjects at risk for CVH which is caused or contributed to by aberrant CVHG expression or activity can be identified by, for example, any or a combination of diagnostic or prognostic assays as described herein.

Administration of a prophylactic agent can occur prior to the manifestation of symptoms characteristic of the differential CVHG protein expression, such that CVH is prevented or, alternatively, delayed in its progression. Depending on the type of CVHG aberrancy (e.g., typically a modulation outside the normal standard deviation), for example, a CVHG product, CVHG agonist or antagonist agent can be used for treating the subject. The appropriate agent can be determined based on screening assays described herein.

Therapeutic Methods

Another aspect of the invention pertains to methods of modulating CVHG protein expression or activity for therapeutic purposes. Accordingly, in an exemplary embodiment, the modulatory method of the invention involves contacting a cell with an agent that modulates one or more of the activities of a CVHG product activity associated with the cell. An agent that modulates CVHG product activity can be an agent as described herein, such as a polynucleotide (e.g., an antisense molecule) or a polypeptide (e.g., a dominant-negative mutant of a CVHPP), a naturally-occurring target molecule of a CVHPP (e.g., a CVHPP substrate), an anti-CVHPP antibody, a CVHG modulator (e.g., agonist or antagonist), a peptidomimetic of a CVHG protein agonist or antagonist, or other small molecules.

The invention further provides methods of modulating a level of expression of a CVHG of the invention, comprising administration to a subject having CVH, a variety of compositions which correspond to the CVHGs of Tables 3-8, including proteins or antisense oligonucleotides. The protein may be provided by further providing a vector comprising a polynucleotide encoding the protein to the cells. Alternatively, the expression levels of the CVHGs of the invention may be modulated by providing an antibody, a plurality of antibodies or an antibody conjugated to a therapeutic moiety. Treatment with the antibody may further be localized to the tissue comprising CVH. In another aspect, the invention provides methods for localizing a therapeutic moiety to CVH tissue or cells comprising exposing the tissue or cells to an antibody which is specific to a protein encoded by the CVHGs of the invention. This method may therefore provide a means to inhibit expression of a specific gene corresponding to a CVHG listed in Tables 3-8.

Determining Efficacy of a Test Compound or Therapy

The invention also provides methods of assessing the efficacy of a test compound or therapy for inhibiting CVH in a subject. These methods involve isolating samples from a subject suffering from CVH, who is undergoing treatment or therapy, and detecting the presence, quantity, and/or activity of one or more CVHGs of the invention in the first sample relative to a second sample. Where the efficacy of a test compound is determined, the first and second samples are preferably sub-portions of a single sample taken from the subject, wherein the first portion is exposed to the test compound and the second portion is not. In one aspect of this embodiment, the CVHG is expressed at a substantially decreased level in the first sample, relative to the second. Most preferably, the level of expression in the first sample approximates (i.e., is less than the standard deviation for normal samples) the level of expression in a third control sample, taken from a control sample of normal tissue. This result suggests that the test compound inhibits the expression of the CVHG in the sample. In another aspect of this embodiment, the CVHG is expressed at a substantially increased level in the first sample, relative to the second. Most preferably, the level of expression in the first sample approximates (i.e., is less than the standard deviation for normal samples) the level of expression in a third control sample, taken from a control sample of normal tissue. This result suggests that the test compound augments the expression of the CVHG in the sample.

Where the efficacy of a therapy is being assessed, the first sample obtained from the subject is preferably obtained prior to provision of at least a portion of the therapy, whereas the second sample is obtained following provision of the portion of the therapy. The levels of CVHG product in the samples are compared, preferably against a third control sample as well, and correlated with the presence, or risk of presence, of CVH. Most preferably, the level of CVHG product in the second sample approximates the level of expression of a third control sample. In the present invention, a substantially decreased level of expression of a CVHG indicates that the therapy is efficacious for treating CVH.

Pharmacogenomics

The CVHG protein and polynucleotide molecules of the present invention, as well as agents, inhibitors or modulators which have a stimulatory or inhibitory effect on CVHG expression or activity as identified by a screening assay described herein, can be administered to individuals to treat (prophylactically or therapeutically) CVH associated with aberrant CVHG activity.

In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a CVHG product (polynucleotide or polypeptide) or CVHG modulator as well as tailoring the dosage and/or therapeutic regimen of treatment with a CVHG product or CVHG modulator.

Pharmacogenomics deals with clinically significant hereditary variations in the response to drugs due to altered drug disposition and abnormal action in affected persons. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is hemolysis after ingestion of oxidant drugs (anti-malarials, sulfonamides, analgesics, nitrofurans) and consumption of fava beans.

One pharmacogenomics approach to identifying genes that predict drug response, known as "a genome-wide association," relies primarily on a high-resolution map of the human genome consisting of already known gene-related sites (e.g., a "bi-allelic" gene marker map which consists of 60,000-100,000 polymorphic or variable sites on the human genome, each of which has two variants). Such a high-resolution genetic map can be compared to a map of the genome of each of a statistically substantial number of subjects taking part in a Phase II/III drug trial to identify genes associated with a particular observed drug response or side effect. Alternatively, such a high resolution map can be generated from a combination of some ten-million known single nucleotide polymorphisms (SNPs) in the human genome. As used herein, an "SNP" is a common alteration that occurs in a single nucleotide base in a stretch of DNA. For example, an SNP may occur once per every 1,000 bases of DNA. An SNP may be involved in a disease process. However, the vast majority of SNPs may not be disease associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals. Thus, mapping of the CVHGs of the invention to SNP maps of CVH patients may allow easier identification of these genes according to the genetic methods described herein.

Alternatively, a method termed the "candidate gene approach," can be utilized to identify genes that predict drug response. According to this method, if a gene that encodes a drug target is known (e.g., a CVHG of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYPZC19) has provided an explanation as to why some subjects do not obtain the expected drug effects or show exaggerated drug response and serious toxicity after taking the standard and safe dose of a drug. These polymorphisms are expressed in two phenotypes in the population, the extensive metabolizer and poor metabolizer. The prevalence of poor metabolizer phenotypes is different among different populations. For example, the gene coding for CYP2D6 is highly polymorphic and several mutations have been identified in poor metabolizers, which all lead to the absence of functional CYP2D6. Poor metabolizers of CYP2D6 and CYP2C19 quite frequently experience exaggerated drug response and side effects when they receive standard doses. If a metabolite is the active therapeutic moiety, poor metabolizers show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling" can be utilized to identify genes that predict drug response. For example, the gene expression of an animal dosed with a drug (e.g., CVHG expression in response to a CVHG modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a CVHG product or CVHG modulator, such as a modulator identified by one of the exemplary screening assays described herein.

Pharmaceutical Compositions

The invention is further directed to pharmaceutical compositions comprising the test compound, or bioactive agent, or an CVHG modulator (i.e., agonist or antagonist), which may further include a CVHG product, and can be formulated as described herein. Alternatively, these compositions may include an antibody which specifically binds to a CVHG protein of the invention and/or an antisense polynucleotide molecule which is complementary to a CVHG polynucleotide of the invention and can be formulated as described herein.

One or more of the CVHGs of the invention, fragments of CVHGs, CVHG products, fragments of CVHG products, CVHG modulators, or anti-CVHPP antibodies of the invention can be incorporated into pharmaceutical compositions suitable for administration.

As used herein the language "pharmaceutically acceptable carrier" is intended to include any and all solvents, solubilizers, fillers, stabilizers, binders, absorbents, bases, buffering agents, lubricants, controlled release vehicles, diluents, emulsifying agents, humectants, lubricants, dispersion media, coatings, antibacterial or antifungal agents, isotonic and absorption delaying agents, and the like, compatible with pharmaceutical administration. The use of such media and agents for pharmaceutically active substances is well-known in the art. Except insofar as any conventional media or agent is incompatible with the active compound, use thereof in the compositions is contemplated. Supplementary agents can also be incorporated into the compositions.

The invention includes methods for preparing pharmaceutical compositions for modulating the expression or activity of a polypeptide or polynucleotide corresponding to a CVHG of the invention. Such methods comprise formulating a pharmaceutically acceptable carrier with an agent which modulates expression or activity of a CVHG. Such compositions can further include additional active agents. Thus, the invention further includes methods for preparing a pharmaceutical composition by formulating a pharmaceutically acceptable carrier with an agent which modulates expression or activity of a CVHG and one or more additional bioactive agents.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), intraperitoneal, transmucosal, and rectal administration. Solutions or suspensions used for parenteral, intradermal, or subcutaneous application can include the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the requited particle size in the case of dispersion and by the use of surfactants. Prevention of the action of microorganisms can be achieved by various antibacterial and antifingal agents, for example, parabens, chlorobutanol, phenol, ascorbic acid, thimerosal, and the like. In many cases, it will be preferable to include isotonic agents, for example, sugars, polyalcohols such as manitol, sorbitol, sodium, chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of a CVHPP or an anti-CVHPP antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and filsidic acid derivatives. Transmucosal administration can be accomplished through the use of nasal sprays or suppositories. For transdermal administration, the bioactive compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the therapeutic moieties, which may contain a bioactive compound, are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from e.g. Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art.

It is especially advantageous to formulate oral or parenteral compositions in dosage unit form for ease of administration and uniformity of dosage. Dosage unit form, as used herein, includes physically discrete units suited as unitary dosages for the subject to be treated; each unit contains a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that includes the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The CVHGs of the invention can be inserted into gene delivery vectors and used as gene therapy vectors. Gene therapy vectors can be delivered to a subject by, for example, intravenous administration, intraportal administration, intra-biliary administration, intra-arterial administration, direct injection into the liver parenchyma, by intramusclular injection, by inhalation, by perfusion, or by stereotactic injection. The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Kits

The invention also encompasses kits for detecting the presence of a CVHG product in a biological sample, the kit comprising reagents for assessing expression of the CVHGs of the invention. Preferably, the reagents may be an antibody or fragment thereof, wherein the antibody or fragment thereof specifically binds with a protein corresponding to a CVHG from Table 4. For example, antibodies of interest may be prepared by methods known in the art. Optionally, the kits may comprise a polynucleotide probe wherein the probe specifically binds with a transcribed polynucleotide corresponding to a CVHG selected from the group consisting of the CVHGs listed in Tables 3-8. The kits may also include an array of CVHGs arranged on a biochip, such as, for example, a GeneChip®. The kit may contain means for determining the amount of the CVHG protein or mRNA in the sample; and means for comparing the amount of the CVHG protein or mRNA in the sample with a control or standard. The compound or agent can be packaged in a suitable container. The kit can further comprise instructions for using the kit to detect CVHG protein or polynucleotide The invention further provides kits for assessing the suitability of each of a plurality of compounds for inhibiting CVH in a subject. Such kits include a plurality of compounds to be tested, and a reagent (i.e., antibody specific to corresponding proteins, or a probe or primer specific to corresponding polynucleotides) for assessing expression of a CVHG listed in Tables 3-8.

Arrays and Biochips

The invention also includes an array comprising a panel of CVHGs of the present invention. The array can be used to assay expression of one or more genes in the array.

It will be appreciated by one skilled in the art that the panels of CVHGs of the invention may conveniently be provided on solid supports, such as a biochip. For example, polynucleotides may be coupled to an array (e.g., a biochip using GeneChip® for hybridization analysis), to a resin (e.g., a resin which can be packed into a column for column chromatography), or a matrix (e.g., a nitrocellulose matrix for Northern blot analysis). The immobilization of molecules complementary to the CVHG(s), either covalently or noncovalently, permits a discrete analysis of the presence or activity of each CVHG in a sample. In an array, for example, polynucleotides complementary to each member of a panel of CVHGs may individually be attached to different, known locations on the array. The array may be hybridized with, for example, polynucleotides extracted from a blood or colon sample from a subject. The hybridization of polynucleotides from the sample with the array at any location on the array can be detected, and thus the presence or quantity of the CVHG and CVHG transcripts in the sample can be ascertained. In a preferred embodiment, an array based on a biochip is employed. Similarly, Western analyses may be performed on immobilized antibodies specific for CVHPPs hybridized to a protein sample from a subject.

It will also be apparent to one skilled in the art that the entire CVHG product (protein or polynucleotide) molecule need not be conjugated to the biochip support; a portion of the CVHG product or sufficient length for detection purposes (i.e., for hybridization), for example a portion of the CVHG product which is 7, 10, 15, 20, 25, 30, 35, 40, 45, 50, 55, 60, 65, 70, 75, 100 or more nucleotides or amino acids in length may be sufficient for detection purposes.

In one embodiment, the array can be used to assay gene expression in a tissue to ascertain tissue specificity of genes in the array. In this manner, a large number of genes can be simultaneously assayed for expression. This allows an expression profile to be developed showing a battery of genes specifically expressed in one or more tissues at a given point in time. In one embodiment the invention provides a kit comprising a brochure which comprises at least 5, more preferably 10, more preferably or more CVHGs, and the same CVHGs in computer readable form.

In addition to such qualitative determination, the invention allows the quantitation of gene expression in the biochip. Thus, not only tissue specificity, but also the level of expression of a battery of CVHGs in the tissue is ascertainable. Thus, CVHGs can be grouped on the basis of their tissue expression per se and level of expression in that tissue. As used herein, a "normal level of expression" refers to the level of expression of a gene provided in a control sample, typically the control is taken from either a non-diseased animal or from a subject who has not suffered from CVH. The determination of normal levels of expression is useful, for example, in ascertaining the relationship of gene expression between or among tissues. Thus, one tissue or cell type can be perturbed and the effect on gene expression in a second tissue or cell type can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the arrays can be used to monitor the time course of expression of one or more genes in the array. This can occur in various biological contexts, as disclosed herein, for example development and differentiation, disease progression, in vitro processes, such as cellular transformation and activation.

The array is also useful for ascertaining the effect of the expression of a gene on the expression of other genes in the same cell or in different cells. This provides, for example, for a selection of alternate molecular targets for therapeutic intervention if the ultimate or downstream target cannot be regulated.

Importantly, the invention provides arrays useful for ascertaining differential expression patterns of one or more genes identified in diseased tissue versus non-diseased tissue. This provides a battery of genes that serve as a molecular target for diagnosis or therapeutic intervention. In particular, biochips can be made comprising arrays not only of the CVHGs listed in Tables 3-8, but of CVHGs specific to subjects suffering from specific manifestations or stages of the disease.

In general, the probes are attached to the biochip in a wide variety of ways, as will be appreciated by those in the art. As described herein, the nucleic acids can either be synthesized first, with subsequent attachment to the biochip, or can be directly synthesized on the biochip.

The biochip comprises a suitable solid substrate. By "substrate" or "solid support" or other grammatical equivalents herein is meant any material that can be modified to contain discrete individual sites appropriate for the attachment or association of the nucleic acid probes and is amenable to at least one detection method. As will be appreciated by those in the art, the number of possible substrates are very large, and include, but are not limited to, glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses, plastics, etc.

Generally the substrate is planar, although as will be appreciated by those in the art, other configurations of substrates may be used as well. For example, the probes may be placed on the inside surface of a tube, for flow-through sample analysis to minimize sample volume. Similarly, the substrate may be flexible, such as a flexible foam, including closed cell foams made of particular plastics.

In a preferred embodiment, the surface of the biochip and the probe may be derivatized with chemical functional groups for subsequent attachment of the two. Thus, for example, the biochip is derivatized with a chemical functional group including, but not limited to, amino groups, carboxy groups, oxo groups and thiol groups, with amino groups being particularly preferred. Using these functional groups, the probes can be attached using functional groups on the probes. For example, nucleic acids containing amino groups can be attached to surfaces comprising amino groups. Linkers, such as homo-or hetero-bifunctional linkers, may also be used.

In an embodiment, the oligonucleotides are synthesized as is known in the art, and then attached to the surface of the solid support. As will be appreciated by those skilled in the art, either the 5' or 3' terminus may be attached to the solid support, or attachment may be via an internal nucleoside.

In an additional embodiment, the immobilization to the solid support may be very strong, yet non-covalent. For example, biotinylated oligonucleotides can be made, which bind to surfaces covalently coated with streptavidin, resulting in attachment.

Alternatively, the oligonucleotides may be synthesized on the surface, as is known in the art. For example, photoactivation techniques utilizing photopolymerization compounds and techniques are used. In a preferred embodiment, the nucleic acids can be synthesized in situ, using well known photolithographic techniques.

Modifications to the above-described compositions and methods of the invention, according to standard techniques, will be readily apparent to one skilled in the art and are meant to be encompassed by the invention.

This invention is further illustrated by the following examples which should not be construed as limiting. The contents of all references, patents and published patent applications cited throughout this application, as well as the Figures and Tables are incorporated herein by reference.

EXAMPLES

Example 1

Methods (a) Visceral Sensitization Model

New born rats were sensitized by infusion of 0.2 mls of 0.5% acetic acid into the colon at P10, control animals received saline.

(b) CNI1493 Treatment:

At eight weeks of age, rats in four treatment groups: control+vehicle (n=3), control+cni-1493 (n=3), sensitized+vehicle (n=8), sensitized+cni-1493 (n=8) were tested after administration of drug (dissolved in 2.5% mannitol, injected i.p. at 5mg/kg for four days) for sensitivity to colorectal distention (CRD). Vehicle injected animals received 2.5% mannitol in water.

(c) CRD protocol for Measuring Colonic Sensitivity in Adult Rats

For electromyographic (EMG) measurements of visceromotor responses, under anesthesia (Nembutal, 50 mg/kg i.p.), two electrodes were implanted in the abdominal wall muscles and externalized behind the head. Rats were allowed a one week recovery time from this surgery. Under mild sedation (Brevital, 5 ml of 1% ip), a 7 cm flexible balloon constructed from a surgical glove finger attached to tygon tubing was inserted into the descending colon and rectum via the anus and held in place by taping the tubing to the tail. Rats were housed in small Lucite cubicles (20×8×8 cm) and were allowed to adapt for one hour. CRD was performed by rapidly inflating the balloon to constant pressure. Pressure was measured using a sphygmomanometer connected to a pressure transducer. Rats were given graded CRD (20, 40, 60, 80 mm Hg) applied for 20 seconds every 4 minutes.

The behavioral measurements consisted of visual observation of the abdominal withdrawal reflex (AWR) by blinded observers and the assignment of an AWR score:

0, no response;
1, brief head movement followed by immobility;
2, contraction of abdominal muscles;
3, lifting of abdomen;
4, body arching and lifting of pelvic structures.

(d) Evaluation of the Colon for Inflammation/Damage

Descending colons were placed in 10% buffered formalin and portions were frozen for myeloperoxidase (MPO) assays. Haematoxilin & Eosin stained parafin sections will be scored for inflammation by a pathologist.

(e) Tissue Isolation and RNA Preparation

Colons and S1 dorsal root ganglia were snap frozen in liquid nitrogen. Colon tissue RNA and S1 dorsal root ganglia RNA was prepared using RNAzol.

(f) Target Labeling and Gene Chip Array Analysis

An in vitro transcription reaction was performed using 500 ng cDNA which contained a T7 RNA polymerase promoter incorporated during RNA amplification. The cRNA or Target RNAs produced during this in vitro transcription reaction were labeled with biotin. Biotin-labeled Target RNAs were fragmented to a mean size of 200 bases to facilitate their hybridization to probe sequences on the Gene Chip (Affymetrix) array. Each Target RNA sample was initially hybridized to a test array. This array contains a set of probes representing genes that are commonly expressed in the majority of cells (example Rat: actin, GAPDH, hexokinase, 5S rRNA, and B1/B2 repetitive elements). Test arrays confirmed the successful labeling of the target RNAs and prevented the use of degraded or non-representative target RNA samples. Success and consistency of RNA amplification between samples were also confirmed with these test arrays.

Hybridization of Gene Chip (Affymetrix) arrays was performed at 45° C. for 16 hours in 0.1 M MES pH6.6, 1 M sodium chloride, 0.02 M EDTA and 0.01% Tween 20. Four prokaryotic genes (bio B, bio C and bio D from the $E.\ coli$ biotin synthesis pathway and the cre recombinase gene from P1 bacteriophage) were added to the hybridization cocktail as internal controls. These control RNAs were used to normalize expression levels between experiments. Because the control RNAs were added at varying copy number (Bio B, 1.5 pM; Bio C, 5 pM; Bio D, 25 pM and cre, 100 pM) they were also used in estimating relative abundance of RNA transcripts in the sample. Arrays were washed using both non-stringent (1 M NaCl, 25° C.) and stringent (1 M NaCl, 50° C.) conditions prior to staining with phycoerythrin streptavidin (10 ug/ml final). Gene Chip arrays were scanned using a Gene Array Scanner (Hewlett Packard) and analyzed using the Affymetric Gene Chip Analysis Suite 5.0 software.

Gene expression profiles were produced from Affymetrix rat genome 230A chips.

Single array analysis for each chip was performed by Affymetrix Microarray Suite (MAS) software to produce a detection call, present, absent or marginal and a signal intensity value for each gene that is a relative measure of abundance of the transcript. For comparison of signal intensity values between chips, all chips were scaled to an average intensity of 500. Genes called "Absent" across all chips and genes without a |Fold change|≧2.0 in at least one of the pairwise comparisons of chips from different treatment groups were excluded. The probe sets with absolute call "Absent" across all chips and |Fold change|<2.0 in all of the possible pairwise comparisons were filtered out. These filters were applied as the first level filters to reduce the noise from the dataset. ANOVA was performed on the filtered dataset. Significant changes in gene expression were detected by analyzing signal intensity values by two-way ANOVA with 99% confidence limits. Genes were subjected to cluster analysis to identify genes associated with sensitization and treatment.

(g) Quantitative RT-PCR

Primer or primer/probe sets were designed using Primer Express software (Applied Biosystems, Foster City, Calif.) such that the amplimer spanned an intron/exon boundary where possible. Where ESTs were homologous to known genes, the sequence of the known gene was used. RT-PCR was performed using Applied Biosystems reagents and kits: Taqman Reverse Transcription Reagents N8080234 and Taqman PCR Core Reagents N8080228. PCR was performed on a GeneAmp 5700 Sequence Detection System (Applied Biosystems). Machine default PCR program was used: 2 min at 50° C., 10 min at 95° C., 45 cycles: 95° C. 15 sec, 60° C. 1 min. Fold change was calculated using delta Ct and/or relative standard curve procedures using GAPDH or b-actin as normalizers for colon genes and PGP9.5 for DRG. Data is expressed as fold change relative to control, vehicle treated values.

Primer Probe Sequences (RAT):

```
Desmin NM_022531
Forward primer (FP)
GTGGAGCGTGACAACCTGATAG

Reverse primer (RP)
TGCGCTCTAGGTCAATTCGA

CEBP/delta NM_013154 Mar. 3, 2004 SYBR green
FP
CCGCCCGAATTGCTACAGT

RP
AGTCTGTCGGAAAAGTCTTTTCTACAA

EST homologous to F-box proteins
FP
CCGTGTGCAAGTGTGTAGCAT

RP
GCCGCAGCCCGAAAG

PEP 19
FP
GCTGGAGCAACCAATGGAAA

RP
TCTGTCTCTGGTGCATCCATGT

Probe
TCT TCT TGG ACC TTC TT CTG CCC ATC ATT

Insulin-like growth factor binding protein 2 Colon
71 NM_013122
FP 1001-1022
CAACCTCAAACAGTGCAAGATG

RP 1182-1163
TGGTTTACTGCACCCTTTGG

Metalloproteinase ADAMTS-1
FP
AGGGACCGGAAGTTACTTCCA

RP
CAGGTGTGGGAGCCACATAA

Tubulin, beta 3
FP
GGGCCTTTGGACACCTATTCA

RP
GCCCTTTGGCCCAGTTGT

PROBE
C ACC ACT CTG ACC GAA GAT AAA GTT GTC AGG
```

```
Arg1b NM_053770 Feb. 19, 2004
FP
GAATCCCCACAGCCATTAGAAC

RP
GCGAGTTGTACAGACCTGCATT

Probe
ACA TGT CTG TGT CCT CAT CCG GCT TGT

Stathmin-like 2 (scgn10)
FP
TCGGAAGCTCCACGAACTCT

RP
CTCGCTCGTGCTCCCTCTT
```

(f) MPO Assay

Myeloperoxidase (MPO) assays were performed as described (Bhatia et al., Proc Natl Acad Sci USA 95:4760-4756, 1998). Frozen colon was homogenized in 20 mM phosphate buffer pH 7.4 and cetrifuged at 10,000× g for 10 minutes at 4° C. Pellet was resuspended in 50 mM phosphate buffer, pH 6.0 containing 0.5% hexadecyltrimethylammonium bromide. Samples were subjected to one cycle of freeze thawing, were incubated at 6° C. for 2 hrs and cetrifuged at 10,000× g for 5 min at 4° C. Change in absorbance at 655 nM was measured in reaction mix containing 1.6 mM TMB (Sigma) and 0.3 mM $H_2O_2$ on a Beckman DU-64 spectrophotometer. Activity was normalized to protein as measured in the extracts. Protein was measured by the BCA method (Pierce, Rockford, Ill.). Activity was expressed as the change in absorbance/min/mg protein.

Example 2

Chemical Treatment of Colon of P10 Rats Produces CVH

Previous studies showed that either mechanical irritation or treatment with mustard oil of the colons of young rats between P7 and P12 produced chronic visceral hyperalgesia (ref). To determine whether treatment of the colon of young rats with acetic acid would produce visceral hyperalgesia in adults, the colon of P10 rats was infused with 0.5% acetic acid; control littermates received saline. Rats were tested at 8 weeks of age for sensitivity to CRD and colons were examined for histopathological evidence of inflammation. Adult rats treated with acetic acid on P10 exhibited increased sensitivity to CRD compared to controls (FIG. 1). Data was analyzed by two-way repeated measures ANOVA with distention pressure as the repeated factor and P10 treatment as a between group factor. There was a significant effect of P10 treatment ($F\ 1$, 12.98) $p<0.003$, of distention pressure ($F\ 7$, 89.9) $p<0.001$, and there was a significant interaction between distention pressure and P10 treatment ($F\ 7$, 4.04) $p<0.001$. Means were compared with a Tukey test. Significant differences between AA treated and controls were found at distention pressures of 30 ($p=0.004$), 40 ($p<0.001$), 50 ($p<0.001$), 60 ($p=0.001$) and 70 ($p=0.035$) mm Hg. Chemical treatment of colon of P10 rats produces chronic visceral hypersensitivity.

Example 3

Effect of CNI1493 on Visceral Hypersensitivity

Figure 2:
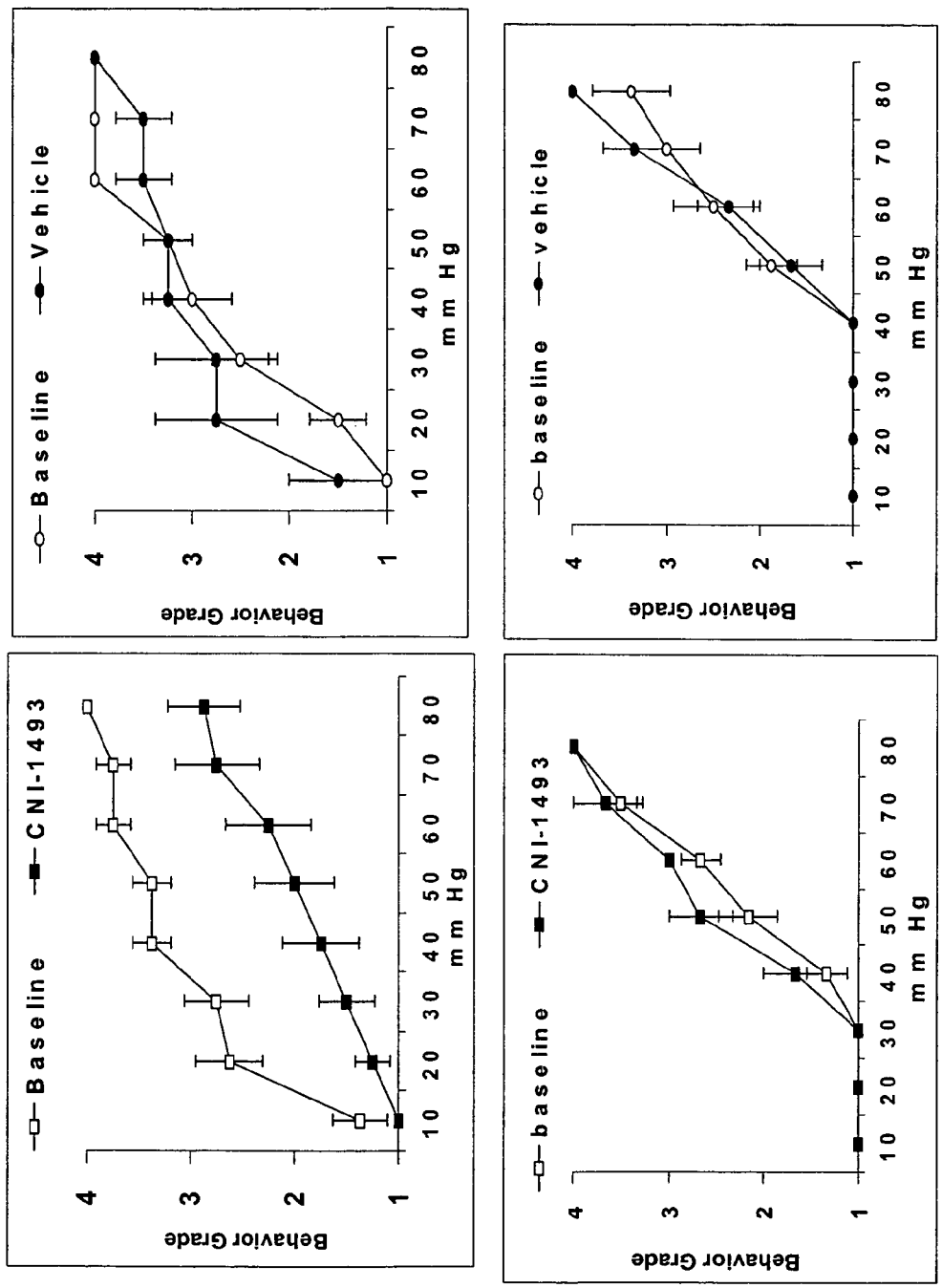
FIG. 2. Effect of CNI-1493 on the response of sensitized rats to graded CRD (n=8). Data was analyzed by two-way repeated measures ANOVA with distention pressure as the repeated factor and drug treatment as a between group factor. There was a significant effect of CNI1493 treatment (F 1, 16.96) p=0.001, of distention pressure (F 7, 28.55) p<0.001, but there was no significant interaction between distention pressure and CNI1493 treatment (F 7, 1.94) p=0.071, Means were compared with a Tukey test. Significant differences between CNI-1493 treated and controls were found at distention pressures of 20 (P=0.001), 30 (p=0.003), 40 (p<0.001), 50 (p=0.001), 60 (p<0.001) and 70 (p=0.015) and 80 (p=0.007) mm Hg.

Rats were treated for 4 days with CNI1493 and sensitivity to CRD was measured after treatment. Sensitivity to CRD was significantly reduced by drug treatment $F(1,5.46)\ p=0.05$ (FIG. 2) but was unchanged in vehicle treated rats. Data was analyzed by two-way repeated measures ANOVA with distention pressure as the repeated factor and drug treatment as a between group factor. There was a significant effect of CNI1493 treatment ($F\ 1$, 16.96) $p=0.001$, of distention pressure ($F\ 7$, 28.55) $p<0.001$, but there was no significant interaction between distention pressure and CNI-1493 treatment ($F\ 7$, 1.94) $p=0.071$. Means were compared with a Tukey test. Significant differences between CNI-1493 treated and controls were found at distention pressures of 20 ($P=0.001$), 30 ($p=0.003$), 40 ($p<0.001$), 50 ($p=0.001$), 60 ($p<0.001$) and 70 ($p=0.015$) and 80 ($p=0.007$) mm Hg.

Figure 3:
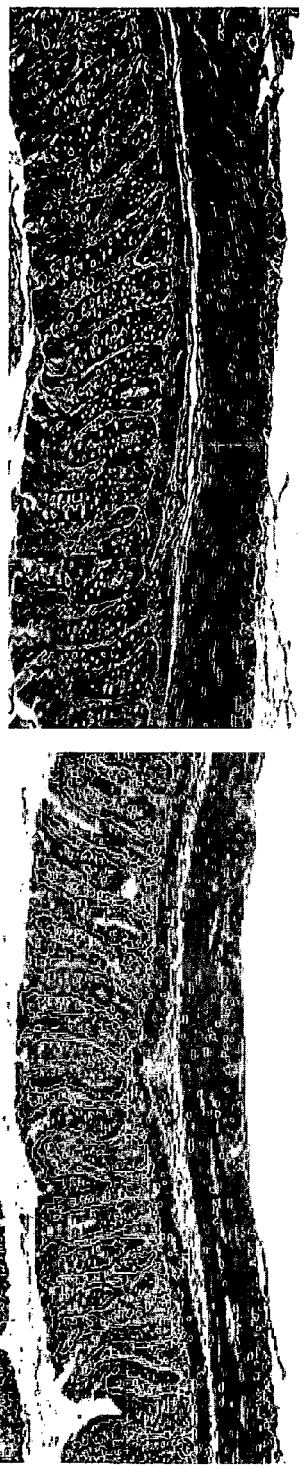
FIG. 3. Colon histology and MPO activity. H&E stained colon sections from control, vehicle (A); control, cni-1493 (B); sensitized, vehicle (C); and sensitized, CNI1493 (D). Histogram showing MPO activity in colons (E).
Figure 3:
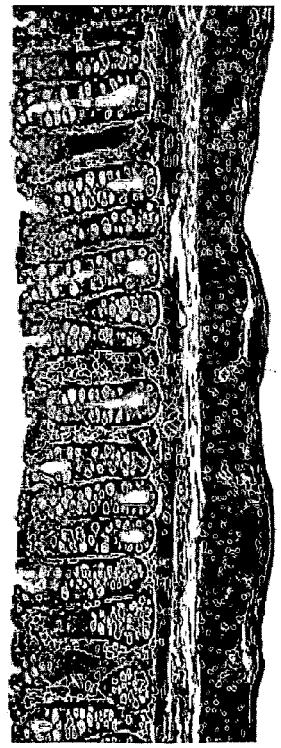
Figure 3:
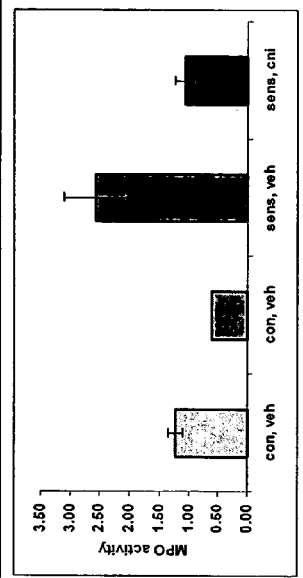

To determine whether P10 colon irritation produced chronic inflammation, H&E stained colon sections were examined for signs of inflammation and MPO activity in colon extracts was examined. No differences in appearance of the sections were noted between treatment groups and no overt signs of inflammation were observed. Mucosal architecture was normal, there was no cellular infiltrate, and there was no depletion of goblet cells. No differences were observed in colon histopathology (FIG. 3A-3D). There was a significant increase in MPO activity in the sensitized rats compared to controls (FIG. 3E). CNI-1493 treatment significantly lowered MPO activity in sensitized rats. These findings suggest that there was a low grade inflammation or increased lymphocytes present in sensitized rats.

Example 4

Gene Expression Profiles in Colon and S1 DRG

To determine the long term effects of P10 colon irritation and of subsequent CNI1493 treatment on gene expression in the colon, gene expression profiles of rat colons from each treatment group derived from Affymetrix rat genome 230A chips were subjected to cluster analysis to identify genes associated with sensitization and treatment. The analysis revealed that 114 genes were differentially expressed in sensitized/CVH colon (Table 3), 76 genes were differentially expressed in sensitized/CVH S1 DRG (Table 4), 660 genes were differentially expressed in CNI1493-treated colon (Table 5), and 137 genes were differentially expressed in CNI1493-treated S1 DRG (Table 6). Since CNI1493 treatment ameliorates CVH in the sensitized animals, genes differentially regulated by CNI1493 may also be related to the etiology of CVH. Accordingly, genes listed in Tables 3-8 are designated as CVH-related genes (CVHGs). Expression levels of a subset of genes from each group were confirmed by quantitative RT-PCR (Table 8).

TABLE 8

Comparison of chip results with RT-PCR

| | Gene | | | |
|---|---|---|---|---|
| | sen + veh Chip | sen + veh RT-PCR | sen + CNI Chip | sen + CNI RT-PCR |
| desmin | 2.6 | 1.7 | 1.3 | 0.8 |
| CCAAT/enhancerbinding (C/EBP) delta | 2.4 | 2.2 | 2.3 | 1.6 |
| EST similar to F-box proteins | 2.4 | 1.9 | 1.2 | 0.6 |
| neuron specific protein PEP-19 | 2.3 | 2.1 | 1.1 | 1.1 |
| Insulin-like growth factor binding protein 2 | 2.2 | 2.6 | 0.9 | 0.7 |

TABLE 8-continued

Comparison of chip results with RT-PCR

| Gene | sen + veh Chip | sen + veh RT-PCR | sen + CNI Chip | sen + CNI RT-PCR |
|---|---|---|---|---|
| ADAMTS1 | 2.1 | 2.0 | 1.1 | 0.8 |
| tubulin, beta 3 | 2.1 | 2.9 | 1.5 | 1.3 |
| ArgBP2 | 1.7 | 2.9 | 0.8 | 1.8 |
| scgn10 | 1.5 | 1.3 | 1.1 | 0.4 |
| BDNF | 1.7 | 1.9 | 1.7 | 2.1 |
| phosphodiesterase 3B | 1.8 | 1.6 | 1.1 | 1.2 |
| Trek2 | 2.1 | 1.5 | 1.7 | 0.9 |
| TrkA precursor | 0.7 | 0.8 | 0.7 | 0.7 |
| interleukin 1 receptor, type 1 | 0.5 | 1.1 | 0.6 | 0.8 |
| elongation factor 2 kinase | 0.4 | 1.6 | 0.8 | 1.5 |

What is claimed is:

1. A method of treating Irritable Bowel Syndrome (IBS) in a subject, in need thereof said method consisting of:
administering to said subject an amount of N,N'-bis[3,5-diacetylphenyl] decanediamidetetrakis[amidinohydrazone] tetrahydrochloride (CNI-1493) effective to differentially regulate the expression of genes related to IBS thereby treating the IBS in the subject.

* * * * *